(12) United States Patent
Oikawa

(10) Patent No.: US 12,203,084 B2
(45) Date of Patent: Jan. 21, 2025

(54) COMPOSITIONS AND METHODS FOR INCREASING PLANT GROWTH AND IMPROVING MULTIPLE YIELD-RELATED TRAITS

(71) Applicant: AFINGEN, INC., Emeryville, CA (US)

(72) Inventor: Ai Oikawa, Emeryville, CA (US)

(73) Assignee: AFINGEN, INC., Emeryville, CA (US)

( * ) Notice: Subject to any disclaimer, the term of this patent is extended or adjusted under 35 U.S.C. 154(b) by 0 days.

(21) Appl. No.: 18/172,699

(22) Filed: Feb. 22, 2023

(65) Prior Publication Data

US 2023/0287443 A1 Sep. 14, 2023

Related U.S. Application Data

(63) Continuation of application No. 16/965,809, filed as application No. PCT/US2019/015688 on Jan. 29, 2019, now Pat. No. 11,613,760.

(60) Provisional application No. 62/623,279, filed on Jan. 29, 2018.

(51) Int. Cl.
  *C12N 15/82* (2006.01)
  *C07K 14/47* (2006.01)

(52) U.S. Cl.
  CPC .......... *C12N 15/8223* (2013.01); *C07K 14/47* (2013.01)

(58) Field of Classification Search
  None
  See application file for complete search history.

(56) References Cited

U.S. PATENT DOCUMENTS

| | | | |
|---|---|---|---|
| 4,237,224 | A | 12/1980 | Cohen et al. |
| 4,945,050 | A | 7/1990 | Sanford et al. |
| 5,100,792 | A | 3/1992 | Sanford et al. |
| 2004/0019927 | A1* | 1/2004 | Sherman ............ C12N 15/8273 800/278 |
| 2012/0272406 | A1 | 10/2012 | Guan et al. |
| 2012/0322122 | A1 | 12/2012 | Shen et al. |
| 2013/0298282 | A1 | 11/2013 | Rouster et al. |
| 2014/0007287 | A1 | 1/2014 | Martin et al. |
| 2017/0298375 | A1 | 10/2017 | Han et al. |

FOREIGN PATENT DOCUMENTS

| | | |
|---|---|---|
| JP | 5403206 B2 | 1/2014 |
| WO | 2005/080580 A2 | 9/2005 |
| WO | 2005/120215 A1 | 12/2005 |
| WO | 2007141705 A2 | 12/2007 |
| WO | 2012/103555 A2 | 8/2012 |

OTHER PUBLICATIONS

Kotani et al. (GenBank Sequence Accession No. AB006703; Published Feb. 14, 2004).*
Bevan, "Binary Agrobacterium Vectors for Plant Transformation," Nucleic Acids Res. 12:8711-8721 (1984).
Frisch et al., "Complete Sequence of the Binary Vector Bin19," Plant Mol. Biol. 27:405-409 (1995).
Gaj et al., "ZFN, TALEN, and CRISPR/Cas-based Methods for Genome Engineering," Cell 31(7):397-405 (2013).
ESAU, Anatomy of Seed Plants (1977).
Meylan and Butterfield, Three-Dimensional Structure of Wood (1972).
Stratagene Cloning Systems Catalog (1993) from Stratagene, La Jolla, CA.
Evans et al., Handbook of Plant Cell Cultures, vol. 1, New York, New York: MacMillan Publishing Co. (1983).
Vasil, ed., Cell Culture and Somatic Cell Genetics of Plants, vol. I (1984) and vol. III (1986).
Emerschad et al., "Somatic Embryogenesis and Plant Development from Immature Zygotic Embryos of Seedless Grapes (*Vitis vinifera*)," Plant Cell Reports 14:6-12 (1995).
Senior, "Uses of Plant Gene Silencing," Biotechnology and Genetic Engineering Reviews 15:79-119 (1998).
Urnov et al., "Genome Editing with Engineered Zinc Finger Nucleases," Nat Rev Genet. 11: 636-646 (2010).
Ausubel et al., Current Protocols in Molecular Biology, New York, N.Y.:John Wiley & Sons (1989).
1 International Search Report of PCT/US2019/015688 mailing date Apr. 15, 2019, 2 pages.
ESAU, Plant Anatomy (1965).
Cong et al., "Multiplex Genome Engineering Using CRISPR/Cas Systems," Science 339(6121): 819-23 (2013).
Wiedenheft et al., "RNA-Guided Genetic Silencing Systems in Bacteria and Archaea," Nat 482:331-338 (2012).
Turner and Somerville, "Collapsed Xylem Phenotype of *Arabidopsis* Identifies Mutants Deficient in Cellulose Deposition in the Secondary Cell Wall," Plant Cell 9(5):689-701 (1997).
Brown et al., "Identification of Novel Genes in Arabidopsis Involved in Secondary Cell Wall Formation Using Expression Profiling and Reverse Genetics," Plant Cell 17(8):2281-95 (2005).
Oikawa et al., "An Integrative Approach to the Identification of Arabidopsis and Rice Genes Involved in Xylan and Secondary Wall Development," PLoS ONE 5(11):e15481 (2010).
Hirano et al., "Survey of Genes Involved in Rice Secondary Cell Wall Formation Through a Co-Expression Network," Plant Cell Physiol. 54(1):1803-21 (2013).
Hao and Mohnen, "A Review of Xylan and Lignin Biosynthesis: Foundation for Studying *Arabidopsis* Irregular Xylem Mutants with Pleiotropic Phenotypes," Crit. Rev. Biochem. Mol. Biol. 49(3):212-41 (2014).
The Bio-Analytic Resource for Plant Biology, available online at http://bar.utoronto.ca/ and described in Toufighi et al., "The Botany Array Resource: e-Northerns, Expression Angling, and Promoter Analyses," The Plant Journal 43:153-63 (2005).

(Continued)

*Primary Examiner* — Vinod Kumar
(74) *Attorney, Agent, or Firm* — Brooks Kushman P.C.

(57) ABSTRACT

The present invention provides compositions and methods for generating transgenic plants with increased plant growth and improved multiple yield-related traits, which comprise vascular xylem tissue-targeting overexpression of transcription factors (TFs) involved in vascular xylem cell development.

7 Claims, 29 Drawing Sheets

Specification includes a Sequence Listing.

(56) References Cited

OTHER PUBLICATIONS

Oikawa et al., "Golgi-Localized Enzyme Complexes for Plant Cell Wall Biosynthesis," Trends Plant Sci. 18:49-58, (2013).
Jefferson et al., "GUS Fusions: b Glucuronidase as a Sensitive and Versatile Gene Fusion Marker in Higher Plants," EMBO J. 6:3901-3907 (1987).
Fan et al., "AtCesA8-driven OsSUS3 Expression Leads to Largely Enhanced Biomass Saccharification and Lodging Resistance by Distinctively Altering Lignocellulose Features in Rice,"Biotechnol. Biofuels 10:221 (2017).
Yang et al., "Engineering Secondary Cell Wall Deposition in Plants," Plant Biotechnol. J. 11(3):325-35 (2013).
Tak et al., "Overexpression of MusaMYB31, a R2R3 type MYB Transcription Factor Gene Indicate its Role as a Negative Regulator of Lignin Biosynthesis in Banana," PLoS ONE 12(2):e0172695 (2017).
Agarwal et al., "MYB31/MYB42 Syntelogs Exhibit Divergent Regulation of Phenylpropanoid Genes in Maize, Sorghum and Rice," Sci. Rep. 6:28502 (2016).
Poovaiah et al., "Sugarcane Transgenics Expression MYB Transcription Factors Show Improved Glucose Release," Biotechnol Biofuels 9:143 (2016).
Zhou et al., "Changing a Conserved Amino Acid in R2R3-MYB Transcription Repressors Results in Cytoplasmic Accumulation and Abolishes Their Repressive Activity in Arabidopsis," Plant J. 84(2):395-403 (2015).
Handakumbura and Hazen, "Transcriptional Regulation of Grass Secondary Cell Wall Biosynthesis: Playing Catch-Up With *Arabidopsis thaliana*," Front. Plant Sci. 3:74 (2012).
Shen et al., "Functional Characterization of the Switchgrass (*Panicum virgatum*) R2R3-MYB Transcription Factor PvMYB4 for Improvement of Lignocellulosic Feedstocks," New Phytol. 193:121-36 (2012).
Wang and Dixon, "On-Off Switches for Secondary Cell Wall Biosynthesis," Mol. Plant. 5(2):297-303 (2012).
Bedon et al., "Subgroup 4 R2R3-MYBs in Conifer Trees: Gene Family Expansion and Contribution to the Isoprenoid- and Flavonoid-Oriented Responses," Journal of Experimental Botany 61(14):3847-3864 (2010).
Fornalé et al., "ZmMYB31 Directly Represses Maize Lignin Genes and Redirects the Phenylpropanoid Metabolic Flux," Plant J. 64(4):633-44 (2010).
Sonbol et al., "The Maize ZmMYB42 Represses the Phenylpropanoid Pathway and Affects the Cell Wall Structure, Composition and Degradability in *Arabidopsis thaliana*," Plant Mol. Biol. 70:283-96 (2009).
Legay et al., "Molecular Characterization of EgMYB1, a Putative Transcriptional Repressor of the Lignin Biosynthetic Pathway," Plant Sci. 173:542-9 (2007).
Fornalé et al., "Down-Regulation of the Maize and *Arabidopsis thaliana* Caffeic Acid O-methyl-transferase Genes by Two New Maize R2R3-MYB Transcription Factors," Plant Mol. Biol. 62(6):809-23 (2006).
Preston et al., "AtMYB32 is Required for Normal Pollen Development in *Arabidopsis thaliana*," Plant J. 40(6):979-95 (2004).
Xu et al., "Overexpression of the Transcription Factors GmSHN1 and GmSHN9 Differentially Regulates Wax and Cutin Biosynthesis, Alters Cuticle Properties, and Changes Leaf Phenotypes in Arabidopsis," Int. J. Mol. Sci. 17(4):E587 (2016).
Djemal and Khoudi, Isolation and Molecular Characterization of a Novel WIN/SHN1 Ethylene-Responsive Transcription Factor TdSHN1 From Durum Wheat (*Triticum turgidum* L. subsp. *durum*) Protoplasma 252(6):1461-73 (2015).
Al-Abdallat et al., "Over-Expression of SlSHN1 Gene Improves Drought Tolerance by Increasing Cuticular Wax Accumulation in Tomato," Int. J. Mol. Sci. 15(11):19499-515 (2014).
Sela et al., "Overexpression of AtSHN1/WIN1 provokes Unique Defense Responses," PLoS One 8(7):e70146 (2013).

Wang et al., "An Ethylene Response Factor OsWR1 Responsive to Drought Stress Transcriptionally Activate Wax Synthesis Related Genes and Increases Wax Production in Rice," Plant Mol Biol. 78(3):275-88 (2012).
Shi et al., "SHINE Transcription Factors Act Redundantly to Pattern the Archetypal Surface of *Arabidopsis* Flower Organs," PLoS Genet. 7(5):e1001388 (2011).
Kannangara et al., "The Transcription Factor WIN1/SHN1 Regulates Cutin Biosynthesis in *Arabidopsis thaliana*," Plant Cell 19(4):1278-94 (2007).
Fromm et al., "Expression of Genes Transferred into Monocot and Dicot Plant Cells by Electroporation," Proc. Natl. Acad. Sci. USA 82:5824 (1985).
Aharoni et al., "The SHINE clade of AP2 Domain Transcription Factors Activates Wax Biosynthesis, Alters Cuticle Properties, and Confers Drought Tolerance When Overexpressed in *Arabidopsis*," Plant Cell 16(9):2463-80 (2004).
Hussey et al., "Navigating the Transcriptional Roadmap Regulating Plant Secondary Cell Wall Deposition," Front. Plant Sci. 4:325 (2013).
Yang and Wang, "Molecular Mechanisms for Vascular Development and Secondary Cell wall Formation," Front. Plant Sci. 7:356 (2016).
Ambavaram et al., "Coordinated Activation of Cellulose and Repression of Lignin Biosynthesis Pathways in Rice," Plant Physiol. 155(2):916-31 (2011).
Legay et al., "EgMYB1, an R2R3 MYB Transcription Factor from Eucalyptus Negatively Regulates Secondary Cell Wall Formation in Arabidopsis and Poplar," New Phytol. 188(3):774-86 (2010).
Wang et al., "Mutation of WRKY Transcription Factors Initiates Pith Secondary Wall Formation and Increases Stem Biomass in Dicotyledonous Plants," Proc. Natl. Acad. Sci. U. S. A. 107(51):22338-43 (2010).
Yang et al., "PtrWRKY19, a Novel WRKY Transcription Factor, Contributes to the Regulation of Pith Secondary Wall Formation in Populus trichocarpa," Sci. Rep. 6:18643 (2016).
Bourouis et al., "Vectors Containing a Prokaryotic Dihydrofolate Reductase Gene Transform Drosophila Cells to Methotrexate-resistance," EMBO J. 2:1099-1104 (1983).
Fraley et al., "Expression of Bacterial Genes in Plant Cells," Proc. Nat'l Acad. Sci. USA 80:4803-4807 (1983).
Odell et al., "Identification of DNA Sequences Required for Activity of the Cauliflower Mosaic Virus 35S Promoter," Nature 313(6005):810-812 (1985).
Coruzzi et al., "Tissue-specific and light-regulated expression of a pea nuclear gene encoding the small subunit of ibulose-1,5-bisphosphate carboxylase," EMBO J. 3(8):1671-1679 (1984).
Joung & Sander, "TALENs: A Widely Applicable Technology for Targeted Genome Editing," Nat Rev Mol Cell Biol. 14: 49-55 (2013).
Studier et al., "Use of T7 RNA Polymerase to Direct Expression of Cloned Genes," Gene Expression Technology vol. 185 (1990).
Sambrook et al., Molecular Cloning: A Laboratory Manual, Second Edition, Cold Spring Harbor, NY:Cold Spring Harbor Press (1989).
Orlando: Acad. Press; and Fitch et al., "Somatic Embryogenesis and Plant Regeneration from Immature Zygotic Embryos of Papaya (*Carica papaya* L.)," Plant Cell Rep. 9:320 (1990).
Fraley et al., "Liposome-mediated Delivery of Tobacco Mosaic Virus RNA Into Tobacco Protoplasts: A Sensitive Assay for Monitoring Liposome-protoplast Interactions," Proc. Natl. Acad. Sci. USA 79:1859-63 (1982).
Sequence Accession ADH50116, Oct. 16, 2008, sequence alignment attached at the end of the Non final office action, Issued by the USPTO in U.S. Appl. No. 16/965,809, dated May 19, 2022. (Year: 2008).
Sequence Accession AD236916, Jun. 30, 2005, sequence alignment attached at the end of the Non final office action, issued by the USPTO in U.S. Appl. No. 16/965,809, dated May 19, 2022. (Year: 2005).

\* cited by examiner

001 pAtCTL2-AtMYB32-tRBS V2
2496 bp

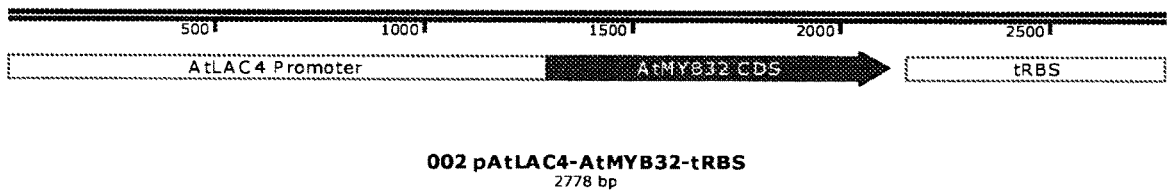

002 pAtLAC4-AtMYB32-tRBS
2778 bp

```
atacatgtcatgatttttataattatgtatatataaatactaattgatgtatgaagtacgtagataatgttacgat
ctattaatctatttacattaacttttaattagtgttgagtagggaaaattaacatataaacctttagcagttggt
tgtattattaaaaataatttgaacttaaaatccaccttcgaaaagataaatcaaacaagtataaaaaatgctata
aatccagaatatttacctaaggttttttattcttctacttaataatgtaagataaaaccggcacaatacttgttac
gtatgcatggtaggtaccgcaattgtgtaagcaaatcggcacaatactaaggttacatatactaactaaataaaa
caatctgatttcagtgacaccgtatatctaacctttattcaaatccaagggaacatgacttgacttcttctgttg
gaactaactcgatccctcaaccatctccagggatagaagagttagtaaaatcaaacttgaagtgaggaagtaagc
agtttaacgactccatatgactacagttatatacaaagttgggcacaaagtacaagtactaaatactcaaagtca
gataataattttaataagtacaaactatatatatgcagtacaattattgagtatatataaacgagactggtgatt
tggggcattgtccaccagggtgttatatcccaattgaaatttgaaaatttaagtgtgtgagtgttacgacaaaaa
aaagtgtgtgaattgtaggcgcggtgaaaaggtaaattaagattggaactagaaaaatagttgaatatcctttac
taaaagttgtcaattccggttttagtaaaaaaaaatttaaaatagaaatttatccaaaagacttcaaacacac
atattcgcatatataacataagatatcattttttgtaaacagttaaaaagaaaaacacatgtttttttttttaat
ttagaaaaaaacatgttattatacaaaacagagttttgcccacttttaatatgttatgaaaagaaaaatgatttt
cttgggtttggtcagagagattggttgtggtaagaatgggaatcttaattacaaagaattggattttgggtcgac
ctaccacctaaaacgacgtcgcctccatctctggtttccaaatctctttctcctctcccttataagcttgcgtt
ggccagtcgctcatctcgaaaacagagagaaaaagactaaaaacacagtttaagaagaaggagagatagagagag
aagagaaagatagagagggag[shaded region containing AtMYB32 CDS sequence]
```

(The CDS portion is shown as a shaded block representing the AtMYB32 coding sequence.)

```
agcactttggaaatgaaatgacacgtgtgaattacaggtgaccagctcgaatttccccgatagctttcgttcgta
tcatcggtttcgacaacgttcgtcaagttcaatgcatcagtttcattgcgcacacaccagaatcctactgagttc
gagtattatggcatgggaaacatgtttttcttgtaccattgttgtgcttgtaatttactgtgttttttattcg
gtttcgctatcgaactgtgaaatggaaatggatggagaagagttaatgaatgatatggtcctttgttcattct
caaattaatattatttgttttttctcttatttgttgtgtgttgaatttgaaaatataagagatatgcaaacattt
tgttttgagtaaaaatgtgtcaaatcgtggcctctaatgaccgaagttaatatgaggagtaaaacacttgtagtt
gtaccattatgcttattcactaggcaacaaatatattttcagacctagaaaagctgcaaatgttactgaatacaa
gtatgtcctcttgtgtttttagacatttatgaactttcctttatgtaattttccagaatccttgtcagattctaat
cattgctttataattatagttatactcatggatttgtagttgagtatgaaaatattttttaatgcattttatgac
ttg    2778
```

FIG. 2

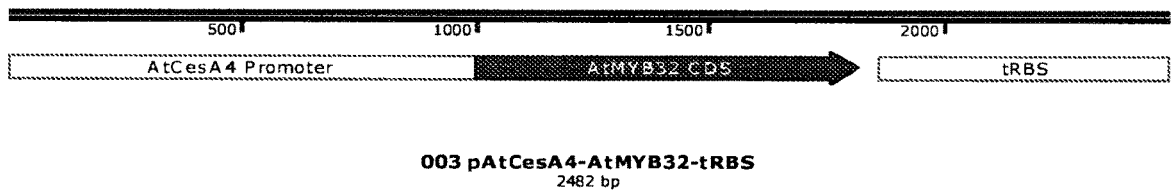

003 pAtCesA4-AtMYB32-tRBS
2482 bp

```
aactagaacacttcagataaatttgtcgttctgttgacttcatttattctctaaacacaaagaactatagacca
taatcgaaataaaaaccctaaaaaaccaaatttatctatttaaaacaaacattagctatttgagtttcttttaggt
aagttatttaaggttttggagactttaagatgttttcagcatttatggttgtgtcattaatttgtttagtttagt
aaagaaagaaaagatagtaattaaagagttggttgtgaaatcatatttaaaacattaataggtatttatgtctaa
tttggggacaaaatagtggaattctttatcatatctagctagttcttatcgagtttgaactcgggttatgattat
gttacatgcattggtccatataaatctatgagcaatcaatataattcgagcattttggtataacataatgagcca
agtataacaaaagtatcaaacctatgcaggggagaagatgatgaaaagaagagtgtgagccaatacaaagcagat
ttgaggacatggcttacaagtcttgggtacagagtttggggagtgatgggtgcacaatggaacagcttctctggt
tgtccagttcccaagagaaccttcaagctccctaactccatctactatgtcgcctgattaaatcttatttactaa
caaaacaataagatcagagtttcattctgattcttgagtcttttttttctctctcccctcttttcatttctggttt
atataaccaattcaaatgcttatgatccatgcatgaaccatgatcatctttgtgtttttttttccttctgtatta
ccattttgggcctttgtgaaattgattttgggcttttgttatataatctcctctttctctttctctacctgattg
gattcaagaacatagccagatttggtaaagtttataagatacaaaatattaagtaagactaaagtagaaatacat
aataacttgaaagctactctaagttatggcaaggtctccttgctgtgagaaagaccacacaaacaaaggagcttg
gactaaggaagaagacgataagctcatctcttacatcaaagctcacggtgaaggttgttggcgttctcttcctag
atccgccggtcttcaacgttgcggaaaaagctgtcgtctccgatggatlaactatctccgacctgatctcaagag
gggtaacttcaccctcgaagaagatgatctcatcatcaaactacatagccttctcggtaacaagtggtctcttat
tgcgacgagattaccaggaagaacagataacgagattaagaattactggaacacacatgttaagaggaagctatt
aagaaagggattgatccggcgactcatcgacctatcaacgagaccaaaacttctcaagattcgtctgattctag
taaaacagaggacccctcttgtcaagattctctctctttggtcctcagctggagaaaatagcaaatttcggggacga
gagaattcaaaagagagttgagtactcagttgttgaagaagatgtctggactgaatcttgagcttaggatgag
tccaccatggcaagacaagctccatgatgagaggaaactaaggtttgggagagtgaagtataggtgcagtgcotg
ccgtttggattcgggaacggcaaggagtgtagctgtaataatgtgaaatgtcaaacagaggacgtagtagcag
cagttattcttcaacgacattagtagtagcattggttatgacttcttgggtctaaacaacactagggtttgga
tttagcactttggaaatgaaatgacacgtgtgaattacaggtgaccagctcgaatttccccgatagctttcgtt
cgtatcatcggtttcgacaacgttcgtcaagttcaatgcatcagtttcattgcgcacacaccagaatcctactga
gttcgagtattatggcattgggaaacatgttttcttgtaccatttgttgtgcttgtaattactgtgttttta
ttcggttttcgctatcgaactgtgaaatggaaatggatggagaagagttaatgaatgatatggtccttttgttca
ttctcaaattaatattatttgtttttctcttatttgttgtgtgttgaatttgaaaatataagagatatgcaaac
atttgtttgagtaaaaatgtgtcaaatcgtggcctctaatgaccgaagttaatatgaggagtaaaacacttgt
agttgtaccattatgcttattcactaggcaacaaatatttcagacctagaaaagctgcaaatgttactgaat
acaagtatgtcctcttgtgttttagacatttatgaactttcctttatgtaattttccagaatccttgtcagattc
taatcattgctttataattatagttatactcatggatttgtagttgagtatgaaaatatttttaatgcatttta
tgacttg       2482
```

FIG. 3

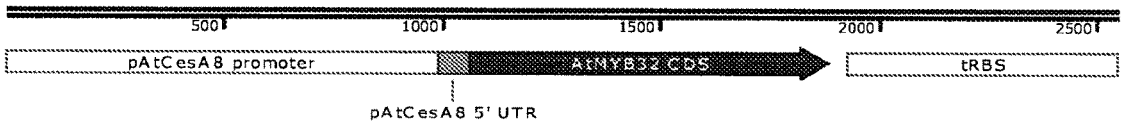

004 pAtCesA8-AtMYB32-tRBS
2546 bp

```
aacccataactttagtattcttcaacccttacaacttatctgagcaaaatcagaaggtcgaatttgatggatggt
tttgctgtatttggtcaacggttttatttgagacagtagaccagaggaaactcagatgtgatgatgcaaagactg
aattggttaagagtgtagattgatttgttctaacattgcaaatgtagagtagaattatgcaaaaaacgttaatga
acagagaagtgattaagcagaaacaaaattagagaagtgatattatatctcaaaaatttattttttggtacagctaa
agctcaaattgttatagagattagagatattaaaccaaatgacgagtgttttctttagtagtaaacggtgaaaat
tctcttctgacaaagacaattaaaatttaggtttaagacttaatatttgtcacaaattgtcatttacctaaat
aaaaaaaaactaaatattttttttagatacatatgtgtcttataatttaactataaatttaattttatgtct
taaataattgtttacactataaatttaaatattttaatgctaaaattaatttgattcaaaaagtgattttaatt
cttattttttcttatagaaagttggtgattgaaaagatttacttaaaaattataacaacttcaatggtgaataacc
cgacccgaataaaccggatataacaacttcaatgttagcttgatatagaaagtacggtgacgcttaggaggcaag
caagctagtatctgccgctggttagagacaaagaacatgtgtcactcctctcaactaaaactttccttcacttt
ccgcaaaatcatttcaaaaaagctccaaatttagcttacccatcagctttctcagaaaaccagtgaaagaaactt
ctcaacttccgattttcacaatccaccaaacttttttttaataactttttttcctcttattacaaaacctccact
ctcatggcttctcaaactgttatccatccaaatctcaatccctaattagggttcatttctctgtttctccaaac
agggaattcgaagatggcaaggtctccttgctgtgagaaagaccacacaaacaaaggagcttgaactaaggaag
aagacgataagctcatctcttacatcaaagctcacggtgaaggttgttggcgttctcttcctagatccgccggtc
ttcaacgttgcggaaaaagctgtcgtctccgatggattaactatctccgacctgatctcaagaggggtaacttca
ccctcgaagaagatgatctcatcatcaaactacatagccttctcggtaacaagtggtctcttattgcgacgagat
taccaggaagaacagataacgagattaagaattactggaacacacatgttaagnagaaagctattaagaaaaggga
ttgatccggcgactcatcgacctatcaacgagaccaaaactctctcaagattcgtctgattctagtaaaacagagg
accttcttgtcaagattctctctttgtcctcagctggagaaaatagcaaatttcggggacgagagaattcaaa
agagagttgagtactcagttgttgaagaaagatgtctggacttgaatcttgagcttaggatcagtccaccatggc
aagacaagctccatgatgagaggaacctaaggtttggggagagtgaagtatagtgcagtgcgtgcgttttggat
cgggaacgccaaggagtgtagctgtaataatgtgaaagtcaaacaggggacagtagtagcagcagttattctt
caacgacattagtagtagcattggttatgacttcttgggtctaaacaaacataggggttttggattttagcactt
tggaaatgaaatgacacgtgtgaattacaggtgaccagctcgaatttccccgatagctttcgttcgtatcatcgg
tttcgacaacgttcgtcaagttcaatgcatcagtttcattgcgcacacaccagaatcctactgagttcgagtatt
atggcattgggaaacatgtttttcttgtaccatttgttgtgcttgtaatttactgtgttttttattcggttttcg
ctatcgaactgtgaaatggaaatggatgggagaagagttaatgaatgatatggtccttttgttcattctcaaatta
atattatttgttttttctcttatttgttgtgtgttgaatttgaaaatataagagatatgcaaacattttgttttg
agtaaaaatgtgtcaaatcgtggcctctaatgaccgaagttaatatgaggagtaaaacacttgtagttgtaccat
tatgcttattcactaggcaacaaatatattttcagacctagaaaagctgcaaatgttactgaatacaagtatgtc
ctcttgtgttttagacatttatgaacttttcctttatgtaattttccagaatccttgtcagattctaatcattgct
ttataattatagttatactcatggatttgtagttgagtatgaaaatatttttttaatgcatttttatgacttg
```
2546

FIG. 4

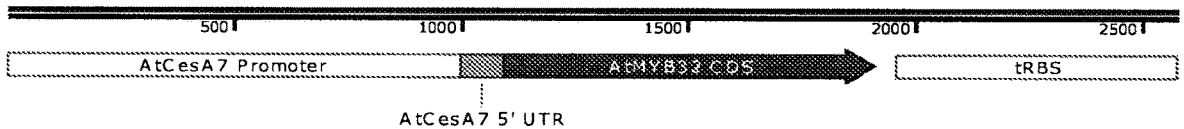

006 pAtCesA7-AtMYB32-tRBS
2575 bp

```
tgcgaacagtttgattctgttttctttttcctttttttgggtaattttcttataacttttttcatagtttcgat
tatttggataaaattttcagattgaggatcatttatttatttattagtgtagtctaatttagttgtataactat
aaaattgttgtttgtttccgaatcataagtttttttttttttggttttgtattgataggtgcaagagactcaaa
attctggtttcgatgttaacagaattcaagtagctgcccacttgattcgatttgttttgtatttggaaacaacca
tggctggtcaaggcccagcccgttgtgcttctgaacctgcctagtcccatggactagatctttatccgcagactc
caaaagaaaaggattggcgcagaggaattgtcatggaaacagaatgaacaagaaagggtgaagaagatcaaagg
catatatgatctttacattctctttagcttatgtatgcagaaaattcacctaattaaggacagggaacgtaactt
ggcttgcactcctctcaccaaaccttaccccctaactaattttaattcaaaattactagtatttggccgatcac
tttatataataagataccagatttattatatttacgaattatcagcatgcatatactgtatatagttttttttt
gttaaagggtaaaataataggatccttttgaataaaatgaacatatataattagtataatgaaaacagaaggaaa
tgagattaggacagtaagtaaaatgagagacctgcaaaggataaaaaagagaagcttaaggaaaccgcgacga
tgaaagaaagacatgtcatcagctgatggatgtgagtgatgagtttgttgcagttgtgtagaaattttactaaa
acagttgttttacaaaaagaaataatataaaacgaaagcttagcttgaaggcaatggagactctacaacaaac
tatgtaccatacagagagagaaactaaaagcttttcacacatataaaaccaaacttattcgtctctcattgatcac
cgttttgttctctcaagatcgctgctaatctccggccgtccctatggcaaggtctccttgctgtgagaagacca
cacaaacaaaggagcttggactaaggaagaagatgataagctcatctcttacatcaaagctcacggtgaaggttg
ttggcgttctctcctagatccgccggtcttcaacgttgcgaaaagctgtcgtctccgatggattaactatct
ccgacctgatctcaagaggggtaacttcaccctcgaagaagatgatctcatcatcaaactacatagtcttctcgg
taacaagtggtctcttattgcgacgagattaccaggaagaacagataacgagattaagaattactggaacacaca
tgttaagaggaagctattaagaaaaggattgatccggcgactcatcgacctatcaacgagaccaaaacttctca
agattcgtctgattctagtaaaacagaggacctcttgtcaagattctctcttttggtctcagctggagaaat
agcaaattccggggacgagagaattcaaaagagagttgagtactcagttgtgaagaaagatgtctgaacttgaa
tcttgagcttaggatcagtccaccatggcaaggacaagctccatgatgagaggaacctaaggttgggagagtgaa
gtataggtgcagtgcgtgccgttttggattcggaacgtcaaggagtgtagctgtaataatgtgaatgtcaaac
agaggacagtagtagcagcagttattcttcaaccgacattagtagtagcattggttatgacttctggtctaaa
caacactagggttttggattttagcacttggaaatgaaatgacacgtgtgaattacaggtgaccagctcgaatt
tccccgatagctttcgttcgtatcatcggtttcgacaacgttcgtcaagttcaatgcatcagtttcattgcgcac
acaccagaatcctactgagttcgagtattatggcattgggaaacatgttttcttgtaccatttgttgtgcttgt
aatttactgtgttttttattcggttttcgctatcgaactgtgaaatggaaatggatgggagaagagttaatgaatg
atatggtccttttgttcattctcaaattaatattatttgtttttttctcttatttgttgtgtgttgaatttgaaaa
tataagagatatgcaaacattttgttttgagtaaaaatgtgtcaaatcgtggcctctaatgaccgaagttaatat
gaggagtaaaacacttgtagttgtaccattatgcttattcactaggcaacaaatatattttcagacctagaaaag
ctgcaaatgttactgaatacaagtatgtcctcttgtgttttagacatttatgaactttcctttatgtaatttttcc
agaatccttgtcagattctaatcattgctttataattatagttatactcatggatttgtagttgagtatgaaaat
atttttaatgcattttatgacttg     2575
```

FIG. 6

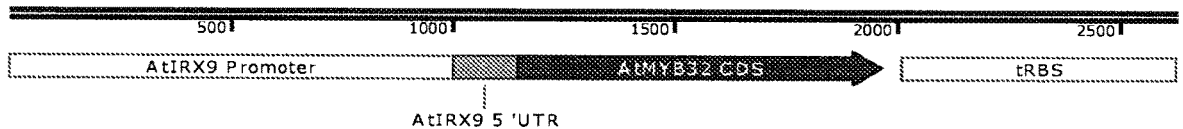

007 pAtIRX9-AtMYB32-tRBS
2628 bp

```
tctctaattgtcaagtatcttagtctagagttaattacttaaatactaaaaggctgtcgacaaaatcaagcttga
atctccttgtggtatcttcaactcttcgttgtctgcttacgagtggtttactcagtaattatctataatatgtta
ttttttttccctcatcttttagttgttgtttcattacattgaaaagcttgtaatgtcttatatggtatatatgg
atcttatgagtgaggcaagatccatgatgttttttgatcttagaatgtatatgatgatcttagaatgtatttgacc
gcccacaaattattgttcattgggattatatctctagtccaactccaagcaatcgaaatgggtcctgcttttaag
aacaacagtatatgtttaagaataataactttatatattctcgatttaagatcttttgacaaaacctccttttc
gttaggagcgtactaatttccaagtgtttgattagtggggtctccgtaaatttatttagagtttctatctattta
ttaatagctcaattaattaatctatactgtatctaaacatcaatttatatattactcttgagaccaaaactgtc
aatttataacattggatagtttcttaattcttattatatattttttcaaacactttcaagactaatctccacatt
aggtactctctctagagataaaaatatttatcaaaaacattttttatttatttattaagtagtagataaactactg
tggcaaaatcgtaaatgtctaaatgctgatgaattttttttgctgctccaatctggtttagtgctccatatacat
ccacggccaaaatgaatctatggcggcattaagattcattagtaagcaacgattatattaatataattgttttta
gcaatgattttccgtaatttcccaaatatgtttcagttaatgtgttccaatcccaacaactggttgttgcaaaag
accaccaacgcaagcaatcatcaaacatcaaaataatcttaccttagcgaacaaacaataactacacaattctca
taaagctctatatatcactaacttcacacatttgttttcacaaaaataaaaacggaactcactcaagaaacc
ttcttccttgaagagagggttatggcaaggtctccttgctgtgagaaagaccacacaaacaaaggagcttggact
aaggaagaagacgataagctcatctcttacatcaaagctcacggtgaaggttgttggcgttctcttcctagatcc
gccggtcttcaacgttgcggaaaaagctgtcgtctccgatggattaactatctccgacctgatctcaagagggt
aacttcaccctcgaagaagatgatctcatcatcaaactacatagcgttctcggtaacaagtggtctcttattgcg
acgagattaccaggaagaacagataacgagattaagaattactggaacacacatgttaagaggaagctattaaga
aaagggattgatccggcgactcatcgacctatcaacgagaccaaaacttctcaagattcgtctgattctagtaaa
acagaggaccctcttgtcaagattctctctcttttggtcctcagctggagaaaatagcaaatttcggggacgagaga
attcaaaagagagttgagtactcagttgttgaagaaagatgtctggacttgaatcttgagcttaggatcagtcca
ccatggcaagacaagctccatgatgagaggaacctaaggtttgggagagtgaagtataggtgcagtgcgtgccgt
tttggattcggaacggcaaggagtgtagctgtaataatgtgaaatgtcaaacagaggacagtagtagcagcagt
tattcttcaaccgacattagtagtagcattggttatgacttcttgggtctaaacaacactaggttttggatttt
agcactttggaaatgaaatgacacgtgtgaattacaggtgaccagctcgaatttccccgatagctttcgttcgta
tcatcggtttcgacaacgttcgtcaagttcaatgcatcagtttcattgcgcacacaccagaatcctactgagttc
gagtattatggcattgggaaacatgttttcttgtaccatttgttgtgcttgtaatttactgtgttttttattcg
gttttcgctatcgaactgtgaaatggaaatggatggagaagagttaatgaatgatatggtccttttgttcattct
caaattaatattatttgttttttctcttatttgttgtgtgttgaatttgaaaatataagagatatgcaaacattt
tgttttgagtaaaaatgtgtcaaatcgtggcctctaatgaccgaagttaatatgaggagtaaaacacttgtagtt
gtaccattatgcttattcactaggcaacaaatatattttcagacctagaaaagctgcaaatgttactgaatacaa
gtatgtcctcttgtgttttagacatttatgaactttcctttatgtaattttccagaatccttgtcagattctaat
cattgctttataattatagttatactcatggatttgtagttgagtatgaaaatatttttaatgcattttatgac
ttg      2628
```

FIG. 7

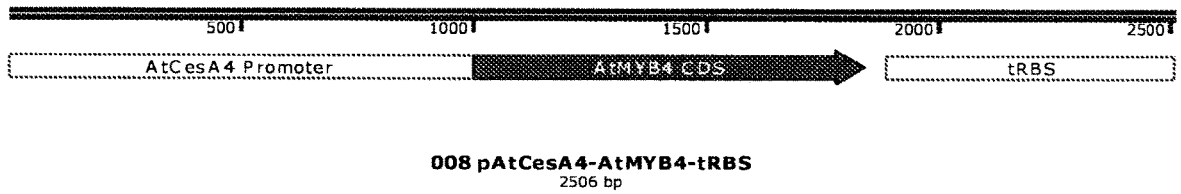

008 pAtCesA4-AtMYB4-tRBS
2506 bp

```
aactagaacacttcagataaatttttgtcgttctgttgacttcatttattctctaaacacaaagaactatagacca
taatcgaaataaaaaccctaaaaaccaaatttatctatttaaaacaaacattagctatttgagtttcttttaggt
aagttatttaaggttttggagactttaagatgttttcagcatttatggttgtgtcattaatttgtttagtttagt
aaagaaagaaaagatagtaattaaagagttggttgtgaaatcatatttaaaacattaataggtatttatgtctaa
tttggggacaaaatagtggaattctttatcatatctagctagttcttatcgagtttgaactcgggttatgattat
gttacatgcattggtccatataaatctatgagcaatcaatataattcgagcattttggtataacataatgagcca
agtataacaaaagtatcaaacctatgcagggggagaagatgatgaaaagaagagtgtgagccaatacaaagcagat
ttgaggacatggcttacaagtcttgggtacagagtttggggagtgatgggtgcacaatggaacagcttctctggt
tgtccagttcccaagagaaccttcaagctccctaactccatctactatgtcgcctgattaaatcttatttactaa
caaacaataagatcagagtttcattctgattcttgagtcttttttttctctctccctcttttttcatttctggttt
atataaccaattcaaatgcttatgatccatgcatgaaccatgatcatctttgtgttttttttccttctgtatta
ccattttgggcctttgtgaaattgattttggcttttgttatataatctcctctttctctttctctacctgattg
gattcaagaacatagccagatttggtaaagtttataagatacaaaatattaagtaagactaaagtagaaatacat
aataacttgaaagctactctaagttatgggaaggtcaccgtgctgtgagaaagctcacacaaacaaaggagcatg
gacgaaagaagaggacgagaggctcgtcgcctacattaaagctcatggagaaggctgctggagatctctcccaa
agccgccggacttcttcgctgtggcaagagctgcctccggtctggatcaactatctccggcctgaccttaagcg
tggaaacttcaccgaggaggaagacgaactcatcatcaagctcctatagccttcttggcaacaaatggtcgcttat
tgccgggagattaccgggaagaacaaataacgagataaagaactattggaacacgcatatacgaaggaaagcttat
aaacagagggattgatccaacgagtcatagaccaatccaagaatcatcagcttctcaagattctaaagctacaca
actagaaccagttacgagtaataccattaatatctcattcacttctgctccaaaggtcgaaacgttccatgaaag
tataagctttccgggaaaatcagagaaaatctcaatgcttacgtcaaagaagaaaaagatgagtgcccagttca
agaaaagttcccagatttgaatcttgagctcagaatcagtcttcctgatgatgttgatcgtcttcaagggcatgg
aaagtcaacaacgccacgttgtttcaagtgcagcttagggatgataaacggcatggagtgcagatgcagaaaaat
gagatgcgatgtagtcggaggtagcagcaaggggagtgacatgagcaatggattggattttttaggggttggcaaa
gaaagagaccacttctctttttgggctttcgaagcttggagatgaaataacacgtgtgaattacaggtgaccagct
cgaattccccgatagctttcgttcgtatcatcggtttcgacaacgttcgtcaagttcaatgcatcagtttcatt
gcgcacacaccagaatcctactgagttcgagtattatggcattgggaaacatgttttttcttgtaccatttgttgt
gcttgtaatttactgtgtttttttattcggttttcgctatcgaactgtgaaatggaaatggatggagaagagttaa
tgaatgatatggtccttttgttcattctcaaattaatattatttgtttttttctcttattgttgtgtgttgaatt
tgaaaatataagagatatgcaaacatttttgttttgagtaaaaatgtgtcaaatcgtggcctctaatgaccgaagt
taatatgaggagtaaaacacttgtagttgtaccattatgcttattcactaggcaacaaatatattttcagaccta
gaaaagctgcaaatgttactgaatacaagtatgtcctcttgtgttttagacatttatgaactttcctttatgtaa
ttttccagaatccttgtcagattctaatcattgctttataattatagttatactcatggatttgtagttgagtat
gaaaatattttttaatgcattttatgacttg     2506
```

FIG. 8

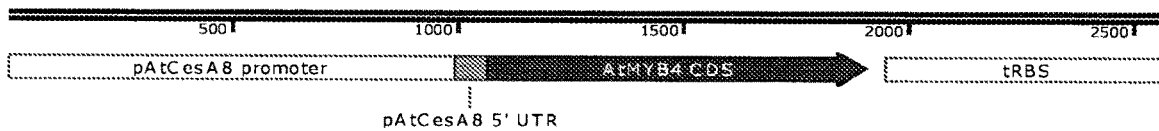

009 pAtCesA8-AtMYB4-tRBS
2570 bp

```
aacccataactttagtattcttcaaccccttacaacttatctgagcaaaatcagaaggtcgaatttgatggatggt
tttgctgtatttggtcaacggttttatttgagacagtagaccagaggaaactcagatgtgatgatgcaaagactg
aattggttaagagtgtagattgatttgttctaacattgcaaatgtagagtagaattatgcaaaaaacgttaatga
acagagaagtgattaagcagaaacaaaattagagaagtgatattatatctcaaaatttattttggtacagctaa
agctcaaattgttatagagattagagatattaaaccaaatgacgagtgttttctttagtagtaaacggtgaaaat
tctcttctgacaaagacaattaaaattttaggtttaagactttaatatttgtcacaaattgtcatttacctaaat
aaaaaaaaactaaatattttttttagatacatatgtgtcttataattttaactataaattttaattttatgtct
taaataattgtttacactataaatttaaatatttttaatgctaaaattaatttgattcaaaaaagtgattttaatt
cttattttttcttatagaaagttggtgattgaaaagatttacttaaaaattataacaacttcaatggtgaataacc
cgacccgaataaaccggatataacaacttcaatgttagcttgatatagaaagtacggtgacgcttaggaggcaag
caagctagtatctgccgctggttagagacaaagaacatgtgtcactcctctcaactaaaactttccttcactttc
ccgcaaaatcatttcaaaaaagctccaaatttagcttacccatcagctttctcagaaaaccagtgaaagaaactt
ctcaacttccgattttttcacaatccaccaaacttttttttaataacttttttttcctcttattacaaaacctccact
ctcatggcttctcaaact tgttatccatccaaatctcaatcctaattagggttcatttctctgtttctccaaac
agggaattcgaagatggaaggtcaccgtgctgtgagaaagctcacacaaacaaaggagcatggacgaaagaag
aggacgagaggctcgtcgcctacattaaagctcatggagaaggctgctggagatctctccccaaagccgccggac
ttcttcgctgtggcaagagctgccgtctctggtggattcactatctccggcctgaccttaagcgtggaaacttca
ccgaggaagaagacgaactcatcatcaagctccatagccttcttggcaacaaatggtcgcttattgccgggagat
taccgggaagaacagataacgagataaagaactattggacacgcatatacgaagaaagcttataaacagaggga
ttgatccaacgagtcatagacaatccaagaatcatcagcttctcaagattctaaactacacaactagaaccag
ttacgagtaataccattaatatctcattcacttctgctccaaaggtcgaaacgttccatgaaagtataagctttc
cgggaaaatcagagaaaatctcaatgcttacgttcaaagaagaaaagatgagtgcccagttcaagaaaagttcc
cagatttgaatcttgagctcagaatcagtcttcctgatgatgttgatcgtcttcaaggcatggaaagtcaacaa
cgccacgttgtttcaagtcagcttaggatgataaacggcatggagtgcagatgcggaagaatgagtgcgatg
tagtcggaggtagcagcaaggggagtgacatgagcaatggatttgattttttaggggtagcaaagaangagacca
cttctctttttgggctttcgaagcttggagatgaaataacacgtgtgaattacaggtgaccagctcgaattcccc
gatagctttcgttcgtatcatcggtttcgacaacgttcgtcaagttcaatgcatcagtttcattgcgcacacacc
agaatcctactgagttcgagtattatggcattgggaaacatgttttcttgtaccatttgttgtgcttgtaattt
actgtgtttttattcggttttcgctatcgaactgtgaaatggaaatggatggagaagagttaatgaatgatatg
gtccttttgttcattctcaaattaatattatttgtttttttctcttatttgttgtgtgttgaatttgaaaatataa
gagatatgcaaacattttgttttgagtaaaaatgtgtcaaatcgtggcctctaatgaccgaagttaatatgagga
gtaaaacacttgtagttgtaccattatgcttattcactaggcaacaaatatattttcagacctagaaaagctgca
aatgttactgaatacaagtatgtcctcttgtgttttagacatttatgaactttcctttatgtaatttttccagaat
ccttgtcagattctaatcattgctttataattatagttatactcatggatttgtagttgagtatgaaaatatttt
ttaatgcatttttatgacttg        2570
```

FIG. 9

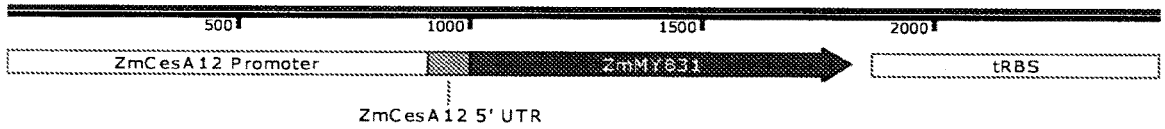

010 pZmCesA12-ZmMYB31-tRBS
2485 bp

```
aggcggggccggaggagggcaccagagaggctgctcaggagagagaaataatagaatatgtggtatagagtaaac
atgagtgcggatgattgtggtatagagtaaagaattttgctgactaggacagaatattcttttagggtagaaat
ttagagtactatgagtgcggatagcctaaggaccactttaaatttgacacaatattgaaatttgaatggttttaa
catttgaaggctgaaaaccaaaatactttgtagctaagtgttggaaacccgactcggccaataagtcgacagacc
gtaaaataaggtcaatctaaactttatgataaatattcttgtttgatagcaatagcattgcaggaccaggaccca
agggaagagaagatgccaaatcccatcgaggctaaagcaaaaacgatccaatttatgagcaaacccacactgaag
tttcaaaattgttttctgaaaaaaagtaaccagcaagttaaaaaatgagatggcgggaaagccaagtctcggtt
ggtcgaggggttggttggggcgcagcctgacaagtgacaacggcagcaggatagtagcatcaggcgcaagccagc
gcaggcggcagcgcgaggatttcgcttcacttagcggcaacggagacgctgcacccaaccaacacgagctccccc
tcacccgctgcgacgcgcgcgtcccacgagcggaagcccccgcgccgacgcgagcgcggggctcgaccgaccg
acccaacgcctccatctccaccgcgcgcaccaaatcgcactcccgtccgccccgcgatcgaacagccaccgctc
acctctcccacccgccaaaaacctccggcctcctctcatattcatatagctagcccctgccacaaggtagagcgt
cgctcacacctgcgtcgctctgcctcgcaatcgcgaatctgtcgagcactgagggggtcggaggccgagagctag
cctagcacgccggcctccgcgcgcgatggggaggtcgccgtgctgcgagaaggcgcacaccaacaaggcgcgtg
gaccaaggaggaggacgagcgcctggtcgcgcacatcacggcgcacggcgaggggtgctggcgctcgctgccaa
ggccgccggcctcctgcgctgcggcaagagctgccgcctctgctggatcaactacctcgcccgacctcaagcg
cggcaactcacggaggaagaggacgagctcatcgtcaagctgcacagcgtcctcggcaacaagtggtccctgat
cgccggaaggctgtccggcaggacggacaacgagatcaagaactactggaacacgcacatctggaggaagctgct
gagcaggggatcgacccggtgacgcactgccgcggtcacggagcaccacgcgtccaacatcaccatatcgttcga
gacggaagtggccgccgtccgtgatgataagaagggccgtcttccggttggaggatgaggaggaggaggagga
gcgcaacaaggcgacgatggtcgtcggccgacggaccggcagagccagagccacagccacagccccgccggcga
gtggggccaggggaagaggccgctcaagtgccccgacctcaacctggacctctgcatcagccgccgtgccagga
ggaggaggagatgaggagctgcgatgagagtgagaccggcggtgaagcgggaggccgggctctgcttcggctg
cagcctggggctccccaggacgcggactgcaagtgcagcagcagcagcttcctcggctcaggatcgccatgct
cgacttcagaagcctcgagatgaaatgacacgtgtgaattacaggtgaccagctcgaatttcccgatagctttc
gttcgtatcatcggtttcgacaacgttcgtcaagttcaatgcatcagtttcattgcgcacacaccagaatcctac
tgagttcgagtattatggcattgggaaacatgtttttcttgtaccatttgttgtgcttgtaatttactgtgtttt
ttattcggttttcgctatcgaactgtgaaatggaaatggatggagaagagttaatgaatgatatggtccttttgt
tcattctcaaattaatattatttgttttttctcttatttgttgtgtgttgaatttgaaaatataagagatatgca
aacattttgttttgagtaaaaatgtgtcaaatcgtggcctctaatgaccgaagttaatatgaggagtaaaacact
tgtagttgtaccattatgcttattcactaggcaacaaatatattttcagacctagaaaagctgcaaatgttactg
aatacaagtatgtcctcttgtgttttagacatttatgaactttcctttatgtaattttccagaatccttgtcaga
ttctaatcattgctttataattatagttatactcatggatttgtagttgagtatgaaatatttttaatgcatt
ttatgacttg    2485
```

FIG. 10

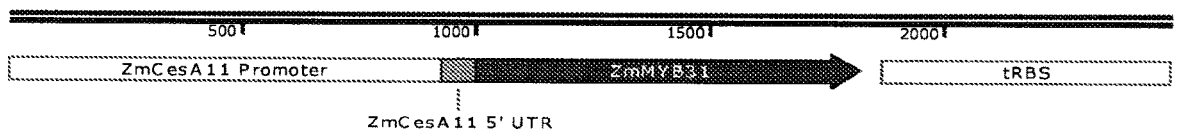

011 pZmCesA11-ZmMYB31-tRBS
2485 bp

```
atactgaacattatgttgcataacatgtagataaggacacgaaaacatagaaagtttctcagttatatttaccca
tcaacatgaaataaaaaacaacaaagatgtcatagtgatgtttgtttcaacttaccaagggtgaccatgtcgtat
ttataataatattatatatttatatcgtcaatagaatattagtgttacggtgatatttagcacaccgatttttt
atatcatactgatgtttatcgttttgtatctatattttatatttgttttataataatattagatatttatttcgt
caatagaatattaatgttatgatgatactttactatattgattttacatatgatagtgatgttactccttccgta
tctatattttatattagtttttatctcctggcaacacggtcacaacagaagagaagttttcagaccgattccag
gatcgatttttttttatatctgggctaagacatcaggtagagattgtttaacctttgcggctttccgcactgac
ggacccaccccaccgcatcaacggaacctaccaaccaccccgtgctccgaccccccatctgcccgtcttccag
gttacgccccgcgcggccgcgcgcgcggaagctgtatcaccccacccgtcgacgtcgtcttcgcttcgaaacccc
gcaaaacccgcggaaaaaacccacctgctgcacgcacgcaccccctccctctccctcccatggcgcctcccct
cacccaactctttgcttccattctttccatccaccccgccaatgcgacgccgacgcgcaactccacccaccgcct
gccagcgccacctcaccgcaccgcttccatcacccgcgatcatgggctaccgctatatcaccacgcctccaacc
tccggcacgcttagcctctctctcccattctctcacacccaacaccagctatcacaccctgatccccgaggcg
cgcgtcgggtgaggaggagggccatgggaggtcgccgtgctgcgaggaggcgcacaccaacaagggcgcgtg
gaccaaggaggaggacgagcgcctggtcgcgcacatcagggcgcacggcgaggggtgctggcgctcgctgcccaa
ggccgccggcctcctgcgctgcggcaagagctgccgcctccgctggatcaactaccttccgccccgacctcaggcg
cggcaacttcacggaggaagaggacgagctcatcgtcaagctgcacagcgtcctcggcaacaagtggtccctgat
cgccggaaggctgtctggcaggacggacaacgagatcaagaactactgaacacgacacatccggaggaagctgct
gagcaggcggatcgacccggtgacgcatccgcccggtcacggagcacgcgtccaacatcaccatatcgttcga
gacggaagtggccgccgctgccgtgatgataagaaggcgccgtcttccggttggaggacgaggaggaggagga
gcgcaacaaggcgacgatggtcgtcggccgcgatcggcagagccagagccacagccacagccacctcgccggcga
gtggggccaggggaagaggccgctcaagtgccccgacctcaacctggacctctgcatcagccgccgtgccagga
ggaggaggagatggaggagcgtgcgatgagagtgagaccggcggtgaagcggggaggccggcgtctgcttcggctg
cagcctggggctcccccaggacgcggacgtgcaagtgcaagcagcagcttcctcggggctcaggaccgccatgct
cgacttcagaagcctcgagatgaaatgacacgtgtgaattacaggtgaccagctcgaatttccccgatagctttc
gttcgtatcatcggtttcgacaacgttcgtcaagttcaatgcatcagtttcattgcgcacacaccagaatcctac
tgagttcgagtattatggcattgggaaacatgttttcttgtaccatttgttgtgcttgtaatttactgtgtttt
ttattcggttttcgctatcgaactgtgaaatggaaatggatggagaagagttaatgaatgatatggtccttttgt
tcattctcaaattaatattatttgttttttctcttatttgttgtgtgttgaatttgaaaatataagagatatgca
aacatttttgttttgagtaaaaatgtgtcaaatcgtggcctctaatgaccgaagttaatatgaggagtaaaacact
tgtagttgtaccattatgcttattcactaggcaacaaatatattttcagacctagaaaagctgcaaatgttactg
aatacaagtatgtcctcttgtgttttagacatttatgaactttcctttatgtaattttccagaatccttgtcaga
ttctaatcattgctttataattatagttatactcatggatttgtagttgagtatgaaaatatttttaatgcatt
ttatgacttg  2485
```

013 pOsCesA7-ZmMYB31-tRBS
2485 bp

```
ttcaatgcaggatgacgccaagagggagaaaccaagcagaggtggacggtacaacgtgtaagtcaccgcaaaacg
ttgcagcttggatagtggccatcgagtggtgtgccgataccggcgcctgttctttacagcctcagctagtgttgt
tgtccgaggcaattttttccgacctattgtgttgctttcctctctgatagcttatggtaaaagatacaaagatgtt
gaggagtttgtacgccacttaattttgctcgtaacatacattgacaatcaagaggagccatggcattgcgatctg
cttacacggcatattcttactggatggtgtacactacttaccctttttaatgcaagcatcaatccattgcttttc
tcactgcacacctgattcgtactgaaaacgtgaaacataaaaaaaaacaaaaatctagctgatgttggctctcgg
ggcctcgagtctagtttgtcctagatggctaacctgatatgtgttggtcacgctcacgtttgaaccgagaaagag
tgtgtgtgtgtgtgtcggcgtgctgctacaccagagcctccctgaatcgcaatgcgtgttaacgccagcatcg
caggatttcatctcacttgacaggttcagatggccttcctcctaccgtctgccatttatacacgcagtgacttaa
cgcttacacgagccggatggcccggatctcccccctgcaccatctcaccagaaaaacggtgaggcgtcaccgcaa
cccacccaccaaacacatccacgtcccttcaccgttggccttcgattttgcttcagctgcactacgaccccctcca
acacatttccctcgcgtctcgttgcgatctcaccttacgacgatctcgttccagcagcagcagcatcggcagcgg
cggcttgcttccgaagcgagcaatgcatggcgcgcgcggccgcgtgcgtgcgtgccttggcttgcgctctaatca
aaccgggacgccccaactcacggttatggggaggtcgccgtgctgcgagaaggcgcacaccaacaagggcgcgtg
gaccaaggaggaggacgagcgcctggtcgcgcacatcaggcgcacggcgaggggtgctggcgctcgctgcccaa
ggccgccggcctcctgcgctgcggcaagagctgccgcctccgctggatcaactacctccgccccgacctcaagcg
cggcaacttcacggaggaagaggacgagctcatcgtcaagctgcacagcgtcctcggcaacaagtgttcctgat
cgccggaaggctgcccggcaggacggacaacgagatcaagaactactggaacacgcacatccggaggagctgct
gagcaggggatcgaccggtgacgcaccggtgcagcaggagcaccacgcgtccaacatcaccatatcgttcga
gacggaagtggccgccgctgcccgtgatgataagaagggcgccgtcttccggttggaggacgaggaggaggaggagga
gcgcaacaaggcgacgatggtcgtcggccgcgaccggcagagccagagccacagccacagccaccccgccggcga
gtggggctaggggaagaggccgctcaagtgcctccgacctcaacctggacctctgcatcagccgccgtgccagga
ggaggaggagatggaggaggctgcgatgagagtgagccggtggtgaagcaggagccggctctgcttcggctg
cagcctgggcctccaggaccgcggactgcaagtgcagcagcagcagctccctcgggctcaggaccgcatgct
cgacttcagaagcctcgagatgaaatgacacgtgtgaattacaggtgaccagctcgaatttcccccgatagctttc
gttcgtatcatcggtttcgacaacgttcgtcaagttcaatgcatcagtttcgcgcacaccagaatcctac
tgagttcgagtattatggcattgggaaacatgttttcttgtaccattgttgtgcttgtaatttactgtgtttt
ttattcggttttcgctatcgaactgtgaaatggaaatggatggagaagagttaatgaatgatatggtcctttgt
tcattctcaaattaatattatttgttttttctcttatttgttgtgtgttgaatttgaaaatataagagatatgca
aacattttgttttgagtaaaaatgtgtcaaatcgtggcctctaatgaccgaagttaatatgaggagtaaaacact
tgtagttgtaccattatgcttattcactaggcaacaaatatattttcagacctagaaaagctgcaaatgttactg
aatacaagtatgtcctcttgtgttttagacattatgaactttcctttatgtaattttccagaatccttgtcaga
ttctaatcattgctttataattatagttatactcatggatttgtagttgagtatgaaaatattttttaatgcatt
ttatgacttg                2485
```

FIG. 13

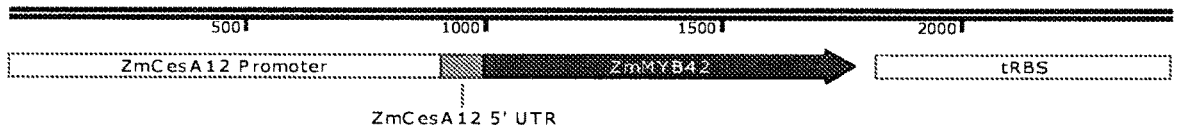

014 pZmCesA12-ZmMYB42-tRBS
2440 bp

```
aggcggggccggaggagggcaccagagaggctgctcaggagagagaaataatagaatatgtggtatagagtaaac
atgagtgcggatgattgtggtatagagtaaagaattttgctgactaggacagaatattctttttagggtagaaat
ttagagtactatgagtgcggatagcctaaggaccactttaaatttgacacaatattgaaatttgaatggttttaa
catttgaaggctgaaaaccaaaatactttgtagctaagtgttggaaacccgactcggccaataagtcgacagacc
gtaaaataaggtcaatctaaactttatgataaatattcttgtttgatagcaatagcattgcaggaccaggaccca
agggaagagaagatgccaaatcccatcgaggctaaagcaaaaacgatccaatttatgagcaaacccacactgaag
tttcaaaattgttttctgaaaaaaaagtaaccagcaagttaaaaaatgagatggcgggaaagccaagtctcggtt
ggtcgaggggttggttggggcgcagcctgacaagtgacaacggcagcaggatagtagcatcaggcgcaagccagc
gcaggcggcagcgcgaggatttcgcttcacttagcggcaacggagacgctgcacccaaccaacacgagctcccc
tcacccgctgcgacgcgcgcgtcccacgagcggaagcccccgcgccgacgcgagcgcggggctcgaccgaccg
acccaacgcctccatctccaccgcgcgcaccaaatcgcactcccgtccgccccgccgatcgaacagccaccgctc
acctctcccacccgccaaaaacctccggcctcctctcatattcatatagctagcccctgccacaaggtagagcgt
cgctcacacctgcgtcgcctgcctcgcaatcgcgaatctgtcgagcacctgaggggtcggaggccgagagctag
cctagcacgccggcctcgcgcgcgatggggcggtcgccgtgctgcgagaaggcgcacaccaacaggggcgcgtg
gaccaaggaggaggacgagcggctggtggcctacgtccgcgtgcacggcgaagggtgctggcgctcgctgcccag
ggcggcggcctgctgcgctgcggcaagagctgccgcctgcgctggatcaactacctccgccggacctcaagcg
aggcaacttcaccgccgacgaggacgacctcatcgtcgctgcacagctcctcggggaacaagtcgctcat
cgccgcgcggctcccgggacggacacaacgagatcaagaactactggaacacgacacatccggcgcaagctgct
gggcagcggcatcgaccccgtcacggcaccgccgcgtcgcgggggcgccgcgaccaccatctcgttccagcccag
ccccaactccgccgccgccgccgccgcctcagaaacagcagcgcaggcgccgatcaaggccgaggagacggcggc
cgtcaaggcgcccaggtgccccgaccctcaacctggacctctgcatcagccgccgtgccagtatgaggacgacgg
cgaggaggaggacgaggagctggaccctcaagcccgtcttcgtcaagcgggaggcgctgcaggccggccacggcca
ggccacggcctctgcctcggctgcctggggcggacagaagggagcggccgggtgcagctgcagcaacggcca
ccactccctggggctcaggaccagcgtgctcgacttcagaggcctggagatgaagtgacacgtgtgaattacagg
tgaccagctcgaatttccccgatagctttcgttcgtatcatcggtttcgacaacgttcgtcaagttcaatgcatc
agtttcattgcgcacacaccagaatcctactgagttcgagtattatggcattgggaaacatgttttcttgtacc
atttgttgtgcttgtaatttactgtgttttttattcggttttcgctatcgaactgtgaaatggaaatggatggag
aagagttaatgaatgatatggtcctttgttcattctcaaattaatatattgttttttctcttatttgttgtg
tgttgaatttgaaaatataagagatatgcaaacattttgttttgagtaaaaatgtgtcaaatcgtggcctctaat
gaccgaagttaatatgaggagtaaaacacttgtagttgtaccattatgcttattcactaggcaacaaatatattt
tcagacctagaaaagctgcaaatgttactgaatacaagtatgtcctcttgtgttttagacatttatgaactttcc
tttatgtaattttccagaatccttgtcagattctaatcattgctttataattatagttatactcatggatttgta
gttgagtatgaaaatatttttttaatgcatttatgacttg     2440
```

FIG. 14

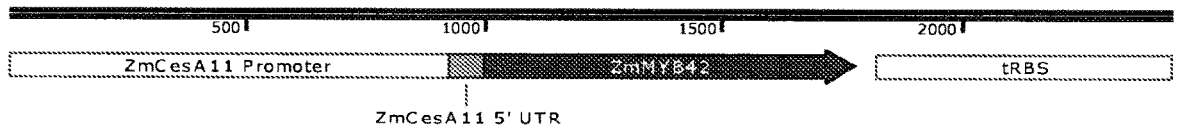

015 pZmCesA11-ZmMYB42-tRBS
2440 bp

```
atactgaacattatgttgcataacatgtagataaggacacgaaaacatagaaagtttctcagttatatttaccca
tcaacatgaaataaaaaacaacaaagatgtcatagtgatgtttgtttcaacttaccaagggtgaccatgtcgtat
ttataataatattatatatttatatcgtcaatagaatattagtgttacggtgatatttttagcacaccgatttttt
atatcatactgatgtttatcgttttgtatctatattttatatttgttttataataatattagatatttatttcgt
caatagaatattaatgttatgatgatactttactatattgatttacatatgatagtgatgttactccttccgta
tctatattttatattagtttttatctcctggcaacacggtcacaacagaagagaagttttttcagaccgattccag
gatcgattttttttttatatctgggctaagacatcaggtagagattgtttaaccttttgcggctttccgcactgac
ggacccaccccaccgcatcaacggaacctaccaaccaccccgtgctccgaccccccatctgcccgtcttccag
gttacgcccgcgcggccgcgcgcgcggaagctgtatcacccccacccgtcgacgtcgtcttcgcttcgaaacccc
gcaaaacccgcggaaaaaacccacctgctgcacgcacgcacccccctccctctccctccccatggcgcctcccct
cacccaactctttgcttccattctttccatccacccgccaatgcgacgccgacgccgcaactccacccaccgcct
gccagcgccacctcaccgcaccgcttccatcaccccgcgatcatgggctaccgctatatcaccacgcctccaacc
tccggcacgcttagcctctctctccc[attctctcacacccagctatcacaccctgatccccgaggccg]
[cgcgtcggggtgaggaggaggggccatgggcggtcgccgtgctgcgagaaggcgcacaccaacagggcgcgtg]
[gaccaaggaggaggacgagcggctggtggcctacgtccgcgcgcacggcgaaggggtgctggcgcttgctgccag]
[ggcggcgggcctgctgcgctgcggcaagagctgccgcctgtgctggatcaactaccttccgcccggacctcaagcg]
[aggcaacttcaccgccgacgaggacgaccctcatcgtcaagctgcacagcctcctcgggaacaagtggtcgctcat]
[cgccgcgcggctcccggggcggacggacaacgagatcaagaactactgggaacacgcacatccggctgcaagctgct]
[gggcagcggcatcgaccccgtcacgcaccgccgctgcgtggggcgccgcgaccaccatctcgttccagccag]
[ccccaactccgccgccccgccgccgccgcagaaacagcagcgcaggcgccgatcaaggccgaggagacggccggc]
[cgtcaaggcgccaggtgccccgacctcaacctggacctctgcatcagcccgccgtgccagcatgaggacgacgg]
[cgaggaggaggacgaggagctggacctcaagcccgccttcgtcaagcggggaggcgctgcaggccggccacggcca]
[cggccacggcctctgcctcggctgcggcctgggcggacagaagggagcggccgggtgcagctgcagcaacggcca]
[ccacttcctggggctcaggacagcgtgctcgacttcagaggctggagatgaagtga]cacgtgtgaattacagg
tgaccagctcgaatttccccgatagctttcgttcgtatcatcggtttcgacaacgttcgtcaagttcaatgcatc
agtttcattgcgcacacaccagaatcctactgagttcgagtattatggcattgggaaacatgttttcttgtacc
atttgttgtgcttgtaatttactgtgttttttattcggttttcgctatcgaactgtgaaatggaaatggatggag
aagagttaatgaatgatatggtccttttgttcattctcaaattaatattatttgttttttctcttatttgttgtg
tgttgaatttgaaaatataagagatatgcaaacattttgttttgagtaaaaatgtgtcaaatcgtggcctctaat
gaccgaagttaatatgaggagtaaaacacttgtagttgtaccattatgcttattcactaggcaacaaatatattt
tcagacctagaaaagctgcaaatgttactgaatacaagtatgtcctcttgtgttttagacatttatgaactttcc
tttatgtaattttccagaatccttgtcagattctaatcattgctttataattatactcatggatttgta
gttgagtatgaaaatatttttttaatgcatttttatgacttg            2440
```

FIG. 15

016 pOsCesA4-ZmMYB42-tRBS
2581 bp

017 pOsCesA7-ZmMYB42-tRBS
2440 bp

```
ttcaatgcaggatgacgccaagagggagaaaccaagcagaggtggacggtacaacgtgtaagtcaccgcaaaacg
ttgcagcttggatagtggccatcgagtggtgtgccgataccggcgcctgttctttacagcctcagctagtgttgt
tgtccgaggcaatttttccgacctattgtgttgcttcctctctgatagcttatggtaaaagatacaaagatgtt
gaggagtttgtacgccacttaattttgctcgtaacatacattgacaatcaagaggagccatggcattgcgatctg
cttacacggcatattcttactggatggtgtacactacttaccctttttaatgcaagcatcaatccattgcttttc
tcactgcacacctgattcgtactgaaaacgtgaaacataaaaaaaaacaaaaatctagctgatgttggctctcgg
ggcctcgagtctagtttgtcctagatggctaacctgatatgtgttggtcacgctcacgtttgaaccgagaaagag
tgtgtgtgtgtgtgtcggcgtgctgctacaccagagcctccctgaatcgcaatgcgtgttaacgccagcatcg
caggatttcatctcacttgacaggttcagatggccttcctcctaccgtctgccatttatacacgcagtgacttaa
cgcttacacgagccggatggcccggatctcccccctgcaccatctcaccagaaaaacggtgaggcgtcaccgcaa
cccacccaccaaacacatccacgtcccttcaccgttggccttcgatttttgcttcagctgcactacgacccctcca
acacatttccctcgcgtctcgttgcgatctcaccttacgacgatctcgttccagcagcagcagcatcggcagcgg
cggcttgcttccgaagcgagcaatgcatggcgcgcgcggccgcgtgcgtgcgtgccttggcttgcgctctaatca
aaccgggacgccccaactcacggttatggggcggtcgccgtgctgcgagaagcgcacaccaacaggggcgcgtg
gaccaaggaggaggacgagcggctggtggcctacgtccgcgcgcacggcgaaggtgctggcgctcgctgccag
ggcggcgggcctgctgcgctgcggcaagagctgccgcctgcgctggatcaactacctccgcccggacctcaagcg
aggcaacttcaccgctgacgaggacgacctcatcgtcaagctgcacagcctcctggggaacaacgcacatccggcgcaagtcct
cgccgcgcgtgctcccggggcggacggacaacgagatcaagagctactggaacacgcacatccggcgcaagctgct
gggcagcggcatcgactccgtcacgcaccgccgcgtcgcgggggcgccgcgaccaccatctcgttccagcccag
ccccaactccgccgccgccgccgccgcagaaacagcagcgcaggcgccgatcaaggccgaggagacggcggc
cgtcaaggcgcccaggtgcccgacctcaacctggacctctgcatcagcccgccgtgccagcatgaggacgacgg
cgaggaggaggacgaggagctggacctcaagcccgccttcgtcaagcggaggcgctgcaggccggccacggcca
cggccacggcctcggcctggcggcctggccggacagaaggggagcggccgggtgcagctgcagcaacggcca
ccattcctgggcgtcaggaccagcgtgctcgacttcagaggcttggagatgaagtgacacgtgtgaattacagg
tgaccagctcgaatttccccgatagctttcgttcgtatcatcggtttcgacaacgttcgtcaagttcaatgcatc
agtttcattgcgcacacaccagaatcctactgagttcgagtattatggcattgggaaacatgttttcttgtacc
atttgttgtgcttgtaatttactgtgttttttattcggttttcgctatcgaactgtgaaatggaaatggatggag
aagagttaatgaatgatatggtcctttgttcattctcaaattaatattatttgtttttctcttatttgttgtg
tgttgaatttgaaaatataaggagatatgcaaacattttgttttgagtaaaaatgtgtcaaatcgtggcctctaat
gaccgaagttaatatgaggagtaaaacacttgtagttgtaccattatgcttattcactaggcaacaaatatattt
tcagacctagaaaagctgcaaatgttactgaatacaagtatgtcctcttgtgttttagacatttatgaactttcc
tttatgtaattttccagaatccttgtcagattctaatcattgctttataattatagttatactcatggatttgta
gttgagtatgaaaatatttttttaatgcatttatgacttg          2440
```

FIG. 17

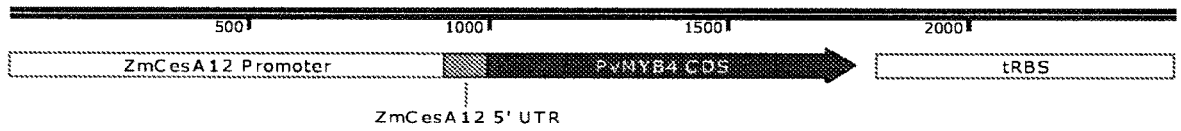

018 pZmCesA12-PvMYB4-tRBS
2428 bp

```
aggcggggccggaggagggcaccagagaggctgctcaggagagagaaataatagaatatgtggtatagagtaaac
atgagtgcggatgattgtggtatagagtaaagaattttgctgactaggacagaatattcttttagggtagaaat
ttagagtactatgagtgcggatagcctaaggaccactttaaatttgacacaatattgaaatttgaatggttttaa
catttgaaggctgaaaaccaaaatactttgtagctaagtgttggaaacccgactcggccaataagtcgacagacc
gtaaaataaggtcaatctaaactttatgataaatattcttgtttgatagcaatagcattgcaggaccaggaccca
agggaagagaagatgccaaatcccatcgaggctaaagcaaaaacgatccaatttatgagcaaacccacactgaag
tttcaaaattgttttctgaaaaaaaagtaaccagcaagttaaaaaatgagatggcgggaaagccaagtctcggtt
ggtcgaggggttggttggggcgcagcctgacaagtgacaacggcagcaggatagtagcatcaggcgcaagccagc
gcaggcggcagcgcgaggatttcgcttcacttagcggcaacggagacgctgcacccaaccaacacgagctccccc
tcacccgctgcgacgcgcgcgtcccacgagcggaagcccccgcgccgacgcgagcgcggggctcgaccgaccg
acccaacgcctccatctccaccgcgcgcaccaaatcgcactcccgtccgccccgccatcgaacagccaccgctc
acctctcccacccgccaaaaacctccggcctcctctcatattcatatagctagccctgccacaaggtagagcgt
cgctcacacctgcgtcgcctgcctcgcaatcgcgaatctgtcgagcacctgagggggtcggaggccgagagctag
cctagcacgccggcctccgcgcgcgatggggcgatcgccgtgctgcgagaaggcgcacacgaacaagggcgcctg
gaccaaggaggaggacgaccgcctcgttgcctacatccgggcgcacggcgaggggtgctggcgctccctccccaa
ggccgcggcctgctgcgctgcggcaagngctgccgcctgcgctggatcaactacctccgccggacctcaagcg
cggcaacttcaccgccgacgaggacgaccctcatcgtcaagctccacagcctcctcggcaacaagtggtcgcttcat
cgccgcgcgcctccccggccgcaccgacaacgagatcaagaactactggaacacgcacatcaagcgcaagttcct
cagccgcggcatcgaccgcggtcatcacaccgcgtccatcgccgacagcagcagcagaaacgtcaccatcttccttccagcc
cgacgcgccgtcgcagcagcagctcagcgacgacgccgagcgcgcgcgccgccgccgccgcagcagcagcagca
gctcaagccgccgccaggtgccccgacctcaatctcgacctctgcatcagccgccctgccacaaggaagagga
ggaccaggagctcgtcaagccgccgccgtcaagcgcgagatgctgcaggccggccacggcactctaggactctg
cttcggctgcagcctggcctccagaagggcgccgctcggntgcacctgcagcagcaacagccacttcctgguugct
cagggtcggcatgctcctcgacttcagagggcctcgagatgaagtgacacgtgtgaattacaggtgaccagctcga
atttccccgatagctttcgttcgtatcatcggtttcgacaacgttcgtcaagttcaatgcatcagtttcattgcg
cacacaccagaatcctactgagttcgagtattatggcattgggaaacatgttttcttgtaccatttgttgtgct
tgtaatttactgtgtttttattcggttttcgctatcgaactgtgaaatggaaatggatggagaagagttaatga
atgatatggtcctttgttcattctcaaattaatattatttgttttttctcttatttgttgtgtgttgaatttga
aaatataagagatatgcaaacattttgttttgagtaaaaatgtgtcaaatcgtggcctctaatgaccgaagttaa
tatgaggagtaaaacacttgtagttgtaccattatgcttattcactaggcaacaaatatattttcagacctagaa
aagctgcaaatgttactgaatacaagtatgtcctcttgtgttttagacattttatgaactttcctttatgtaattt
tccagaatccttgtcagattctaatcattgctttataattatagttatactcatggatttgtagttgagtatgaa
aatattttttaatgcatttatgacttg                    2428
```

FIG. 18

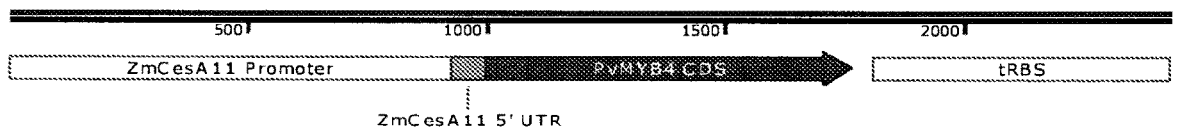

019 pZmCesA11-PvMYB4-tRBS
2428 bp

```
atactgaacattatgttgcataacatgtagataaggacacgaaaacatagaaagtttctcagttatatttaccca
tcaacatgaaataaaaaacaacaaagatgtcatagtgatgtttgtttcaacttaccaagggtgaccatgtcgtat
ttataataatattatatatttatatcgtcaatagaatattagtgttacggtgatattttagcacaccgattttt
atatcatactgatgtttatcgttttgtatctatatttatatttgttttataataatattagatatttatttcgt
caatagaatattaatgttatgatgatacttta  ctatattgattttacatatgatagtgatgttactccttccgta
tctatattttatattagttttta  tctcctggcaacacggtcacaacagaagagaagttttt  cagaccgattccag
gatcgatttttttttta  tatctgggctaagacatcaggtagagattgtttaaccttt gcggctttccgcactgac
ggacccaccccaccgcatcaacggaacctaccaaccaccccgtgctccgaccccc  atctgccc  gtcttccag
gttacgccccgcgcggccgcgcgcgcggaagctgtatcaccccaccc  gtcgacgtc gtcttcgcttcgaaacccc
gcaaaaccccgcggaaaaaacccacctgctgcacgcacgcacccc  ctccctctccctcccatggcgcctcccct
cacccaactctttgcttccattcttt ccatccaccc  gccaat gcgacgccgacgccgcaactccacccaccgcct
gccagcgccacctcaccgcaccgcttccatcac cccgc gatcatgggctaccgctatatcaccacgcctccaacc
tccggcacgcttagcctctctctccc attctctcacacccaacacccagctatcacacc ctgatccccgaggccg
tgcgtcggggtgaggaggagggggccatggggcgatcgccgtgctgcgagaaggcgcacacgaacaggg cgcctg
gaccaaggaggaggacgaccgcctcgttgcctacatccggg cgcacggcgaggggtgctggcgctccctcccc aa
ggcgcgggcctgctgctgggcaagagctgccgcctgcgctggatcaactacctccgccggacctcaagcg
cgccaacttcaccgccgacgaggacgacctcatcgtcaagctccaca gcctcctcggcaacaagtggtcgctcat
cgccgcgcgcctccccggccgcaccgacaacgagatcaagaactactggaacacgcacatcaagcgcaagctcct
cagctgcggcatcgaccccgttcacacaccgccccatcgccgacgcagccagaaagtcactatctccttccagcc
cgacgcgccgtcgcagcagcagctcagcgacgacgcgagg cgccgccgccgccgccgcagcagcagcagca
gctcaagccgccgccaggtgccccgacctcaatctcgacct cgtcgcatcagcccgccctgccacaaggaggaaga
ggaccaggagctcgtcaagccgccgccgctcaagcgcgagatgctgcaggccgcacggcactctaggactctg
cttcggctgcagcctggcctccagaaggcgccgccgggtgtacctgcagcagcaacagccacttcctgggct
cagggtcggcatgctcctcgacttcagaggcctcgagatgaagtgacacgtgtgaattacaggtgaccagctcga
atttccccgatagctttcgttcgtatcatcggtttcgacaacgttcgtcaagttcaatgcatcagtttcattgcg
cacacaccagaatcctactgagttcgagtattatggcattgggaaacatgttttt cttgtaccatttgttgtgct
tgtaatttactgtgtttttta  ttcggttttcgctatcgaactgtgaaatggaaatggatggagaagagttaatga
atgatatggtcctttttgttcattctcaaattaatatta  tttgttttttctcttatttgttgtgtgttgaatttga
aaatataagagatatgcaaacattttgttttgagtaaaaatgtgtcaaatcgtggcctctaatgaccgaagttaa
tatgaggagtaaaacacttgtagttgtaccattatgcttattcactaggcaacaaatatattttcagacctagaa
aagctgcaaatgttactgaatacaagtatgtcctcttgtgttttagacatttatgaactttcctttatgtaattt
tccagaatccttgtcagattctaatcattgctttataattatagttatactcatggatttgtagttgagtatgaa
aatattttttaatgcatttt atgacttg       2428
```

FIG. 19

021 pOsCesA7-PvMYB4-tRBS
2428 bp

```
ttcaatgcaggatgacgccaagagggagaaaccaagcagaggtggacggtacaacgtgtaagtcaccgcaaaacg
ttgcagcttggatagtggccatcgagtggtgtgccgataccggcgcctgttctttacagcctcagctagtgttgt
tgtccgaggcaattttttccgacctattgtgttgctttcctctctgatagcttatggtaaaagatacaaagatgtt
gaggagtttgtacgccacttaattttgctcgtaacatacattgacaatcaagaggagccatggcattgcgatctg
cttacacggcatattcttactggatggtgtacactacttacccttttttaatgcaagcatcaatccattgcttttc
tcactgcacacctgattcgtactgaaaacgtgaaacataaaaaaaaaacaaaaatctagctgatgttggctctcgg
ggcctcgagtctagtttgtcctagatggctaacctgatatgtgttggtcacgctcacgtttgaaccgagaaagag
tgtgtgtgtgtgtgtcggcgtgctgctacaccagagcctccctgaatcgcaatgcgtgttaacgccagcatcg
caggatttcatctcacttgacaggttcagatggccttcctcctaccgtctgccatttatacacgcagtgacttaa
cgcttacacgagccggatggcccggatctccccctgcaccatctcaccagaaaaacggtgaggcgtcaccgcaa
cccacccaccaaacacatccacgtcccttcaccgttggccttcgattttgcttcagctgcactacgaccccctcca
acacatttccctcgcgtctcgttgcgatctcacttacgacgatctcgttccagcagcagcagcatcggcagcgg
cggcttgcttccgaagcgagcaatgcatggcgcgcgcggccgcgtgcgtgcgtgccttggcttgcgctctaatca
aaccgggacgccccaactcacggttatggggcgatcgccgtgctgcgagaaggcgcacacgaacaagggcgcctg
gaccaaggaggaggacgacgcctcgttgcctacatccgggcgcacggcgaggggtgctggcgctccctccccaa
ggccgcgggcctgctgcgctgcggcaagagctgccgcctgcgctggatcaactacctccgccggacctcaagcg
cggtaacttcaccgccgacgaggacgacgccctcatcgtcaagctccacagcctcctcggcaacaagtggtcgctcat
cgccgcgcgcctccccggcgcaccgacaacgagatcaagaactactggaacacgcacatcaagcgcaagctcct
cagctgcggcatcgaccccgtcacacacgcgcccatcgccgacgcagccagaaacgtcaccatctcctccagcc
cgacgcgcgtcgcagcagcagctcagcgacgacgccgaggcgccgccgccgccgccgccgcagcagcagcagca
gctcaagccgcgcccaggtgccccgacctcaatctcgacctctgcatcagcccgcctgccacaaggaagaaga
ggaccaggagctcgtccaagccgccgccgtcaagcgcggagatgctgcaggccggccacgccactctaggactctg
cttcggctgtagcctggcctccagaagggcgccgccggtgcaccctgcagcagcaacagccacttcctggggct
cagggtcggcatgctcctcgacttcagaggcctcgagatgaagtgacacgtgtgaattacaggtgaccagctcga
atttccccgatagctttcgttcgtatcatcggtttcgacaacgttcgtcaagttcaatgcatcagtttcattgcg
cacacaccagaatcctactgagttcgagtattatggcattgggaaacatgttttcttgtaccatttgttgtgct
tgtaatttactgtgttttttattcggttttcgctatcgaactgtgaaatggaaatggatggagaagagttaatga
atgatatggtcccttttgttcattctcaaattaatattatttgtttttctcttatttgttgtgtgttgaatttga
aaatataagagatatgcaaacattttgttttgagtaaaaatgtgtcaaatcgtggcctctaatgaccgaagttaa
tatgaggagtaaaacacttgtagttgtaccattatgcttattcactaggcaacaaatatattttcagacctagaa
aagctgcaaatgttactgaatacaagtatgtcctcttgtgttttagacatttatgaactttcctttatgtaattt
tccagaatccttgtcagattctaatcattgctttataattatagttatactcatggatttgtagttgagtatgaa
aatattttttaatgcatttttatgacttg            2428
```

FIG. 21

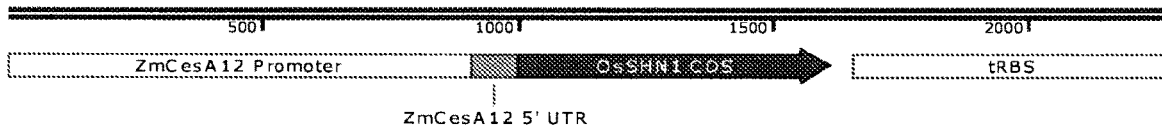

022 pZmCesA12-OsSHN1-tRBS
2275 bp

```
aggcggggccggaggagggcaccagagaggctgctcaggagagagaaataatagaatatgtggtatagagtaaac
atgagtgcggatgattgtggtatagagtaaagaattttgctgactaggacagaatattcttttagggtagaaat
ttagagtactatgagtgcggatagcctaaggaccacttaaatttgacacaatattgaaatttgaatggttttaa
catttgaaggctgaaaaccaaaatactttgtagctaagtgttggaaacccgactcggccaataagtcgacagacc
gtaaataaggtcaatctaaactttatgataaatattcttgtttgatagcaatagcattgcaggaccaggaccca
agggaagagaagatgccaaatcccatcgaggctaaagcaaaaacgatccaatttatgagcaaaccacactgaag
tttcaaaattgttttctgaaaaaaagtaaccagcaagttaaaaaatgagatggcgggaaagccaagtctcggtt
ggtcgaggggttggttggggcgcagcctgacaagtgacaacggcagcaggatagtagcatcaggcgcaagccagc
gcaggcggcagcgcgaggatttcgcttcacttagcggcaacggacgctgcacccaaccaacacgagctccccc
tcacccgctgcgacgcgcgcgtcccacgagcggaagcccccgcgccgacgcgagcgcggggctcgaccgaccg
acccaacgcctccatctccaccgcgcgcaccaaatcgcactcccgtccgccccgccatcgaacagccaccgctc
acctctcccacccgccaaaaacctccggcctcctctcatattcatatagctagccctgccacaaggtagagcgt
cgctcacacctgcgtcgcctgcctcgcaatcgcgaatctgtcgagcacctgagggtcggaggccgagagctag
cctagcacgccggcctccgcgcgcgatgctacagccaagaagaagttcgtggagtcaggcagcggcactgggg
ctcctgggtctctgagatcagacaccccctccttaaaaggagggtggctgggcaccttttgagacggccgagga
ggctgcgcgagcctacgatgaggctgctgtgctgatgagtggccgcaacgccaagaaccttccgtgcagag
gaactccaccgatgatctcgccacggccgcagaccaggacgcctgtagcaatggcggtagcaggaactcctccgc
ggcaacctgtcacagattctcagtgctaagctccgcaagtgctgcaaggcgccatctccgtcctaacctgcct
ccgcctcgaccccgagaagtccacattggcgtgtggcaaaagcgcgcaggggccgcgctgactccaactggt
gatgacggtggagctcaacaaagaggtagaaccaactgaacctgcagctcagccacatcaacagcaacagcttc
gcaagtgacaatggatgatgaggaaaagattgcgctgcaaatgatcgaggagttgctgagcaggagcagtccagc
ttcaccctcacatggagagggagagggtagctttgtcatctgacacgtgtgaattacaggtgaccagctcgaatt
tccccgatagctttcgttcgtatcatcggtttcgacaacgttcgtcaagttcaatgcatcagtttcattgcgcac
acaccagaatcctactgagttcgagtattatggcattgggaaacatgttttcttgtaccatttgttgtgcttgt
aatttactgtgttttttattcggttttcgctatcgaactgtgaaatggaaatggatggagaagagttaatgaatg
atatggtccttttgttcattctcaaattaatattatttgttttttctcttatttgttgtgtgttgaatttgaaaa
tataagagatatgcaaacattttgttttgagtaaaaatgtgtcaaatcgtggcctctaatgaccgaagttaatat
gaggagtaaaaacacttgtagttgtaccattatgcttattcactaggcaacaaatatattttcagacctagaaaag
ctgcaaatgttactgaatacaagtatgtcctcttgtgttttagacatttatgaactttcctttatgtaatttttcc
agaatccttgtcagattctaatcattgctttataattatagttatactcatggatttgtagttgagtatgaaaat
atttttttaatgcatttttatgacttg                      2275
```

FIG. 22

023 pZmCesA11-OsSHN1-tRBS
2275 bp

```
atactgaacattatgttgcataacatgtagataaggacacgaaaacatagaaagtttctcagttatatttaccca
tcaacatgaaataaaaaacaacaaagatgtcatagtgatgtttgtttcaacttaccaagggtgaccatgtcgtat
ttataataatattatatatttatatcgtcaatagaatattagtgttacggtgatattttagcacaccgattttt
atatcatactgatgtttatcgttttgtatctatattttatatttgttttataataatattagatatttatttcgt
caatagaatattaatgttatgatgatacttactatattgatttacatatgatagtgatgttactccttccgta
tctatattttatattagtttttatctcctggcaacacggtcacaacagaagagaagttttcagaccgattccag
gatcgatttttttttatatctgggctaagacatcaggtagagattgtttaacctttgcggctttccgcactgac
ggacccaccccaccgcatcaacggaacctaccaaccaccccgtgctccgaccccccatctgcccgtcttccag
gttacgccccgcgcggccgcgcgcgcggaagctgtatcaccccacccgtcgacgtcgtcttcgcttcgaaacccc
gcaaaaccccgcggaaaaaacccacctgctgcacgcacgcacccctccctctcccccatggcgcctcccct
cacccaactctttgcttccattctttccatccacccgccaatgcgacgccgacgccgcaactccacccaccgcct
gccagcgccacctcaccgcaccgcttccatcaccccgcgatcatgggctaccgctatatcaccacgcctccaacc
tccggcacgcttagcctctctctccc attctctcacacccaacaccagctatcacacctgatcccgaggccg
cgcgtcggggtgaggaggagggccatgqtacagccaaagaagaagtttcqtqqaqtcaggcaqcqqcactgggq
ctcctgggtctctgagatcagacaccccctccttaaaaggaqqqtqtggctgggcaccttqaqacgqccqaqqa
qqctqcqcaqcctacqatqaqqctqctqtqctqatqaqtqqccqcaacqccaaqaccaactccccqtqcaqaq
qaactccaccqqtqatctcqccacqqccqcaqaccaqqacqcccqtaqcaatqqcqqtaqcaqqaactcctccqc
gggcaacctgtcacagattctcagtgctaagctccgcaagtgctgcaaggcgccatctccgtccttaacctgcct
ccqccctcqaccccqaqaaqtcccacattqqcqtqtqqcaaaaqcqcqcaqqqqccqtqctqactccaactgqqt
qatqacqqtqqaqctcaacaaaqaqqtaqaaccaactqaccctqcaqctcaqcccacatcaacaqcaacaqcttc
qcaaqtqacaatqqatqatqaqqaaaaqattqcctqcaaatqatcqaqqaqttqctqaqcaqqaqcaqtccaqc
ttcaccctcacatqqaqaqqqaqaqqqtaqctttqtcatctqacacgtgtgaattacaggtgaccagctcgaatt
tccccgatagctttcgttcgtatcatcggtttcgacaacgttcgtcaagttcaatgcatcagtttcattgcgcac
acaccagaatcctactgagttcgagtattatggcatgggaaacatgttttcttgtaccatttgttgtgcttgt
aatttactgtgttttttattcggttttcgctatcgaactgtgaaatggaaatggatggagaagagttaatgaatg
atatggtccttttgttcattctcaaattaatattatttgttttttctcttatttgttgtgttgaatttgaaaa
tataagagatatgcaaacattttgttttgagtaaaaatgtgtcaaatcgtggcctctaatgaccgaagttaatat
gaggagtaaaacacttgtagttgtaccattatgcttattcactaggcaacaaatatattttcagacctagaaaag
ctgcaaatgttactgaatacaagtatgtcctcttgtgttttagacatttatgaactttcctttatgtaattttcc
agaatccttgtcagattctaatcattgctttataattatagttatactcatggatttgtagttgagtatgaaaat
atttttaatgcatttttatgacttg  2275
```

FIG. 23

024 pOsCesA4-OsSHN1-tRBS
2416 bp

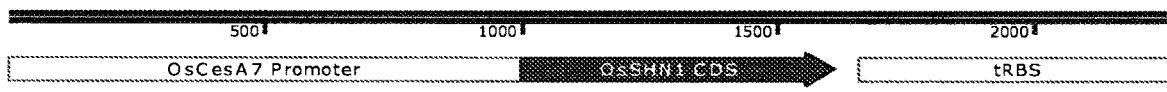

025 pOsCesA7-OsSHN1-tRBS
2275 bp

```
ttcaatgcaggatgacgccaagagggagaaaccaagcagaggtggacggtacaacgtgtaagtcaccgcaaaacg
ttgcagcttggatagtggccatcgagtggtgtgccgataccggcgcctgttctttacagcctcagctagtgttgt
tgtccgaggcaattttttccgacctattgtgttgctttcctctctgatagcttatggtaaaagatacaaagatgtt
gaggagtttgtacgccacttaattttgctcgtaacatacattgacaatcaagaggagccatggcattgcgatctg
cttacacggcatattcttactggatggtgtacactacttaccctttttaatgcaagcatcaatccattgcttttc
tcactgcacacctgattcgtactgaaaacgtgaaacataaaaaaaaacaaaaatctagctgatgttggctctcgg
ggcctcgagtctagtttgtcctagatggctaacctgatatgtgttggtcacgctcacgtttgaaccgagaaagag
tgtgtgtgtgtgtgtcggcgtgctgctacaccagagcctccctgaatcgcaatgcgtgttaacgccagcatcg
caggatttcatctcacttgacaggttcagatggccttcctcctaccgtctgccatttatacacgcagtgacttaa
cgcttacacgagccggatggcccggatctcccccctgcaccatctcaccagaaaaacggtgaggcgtcaccgcaa
cccacccaccaaacacatccacgtcccttcaccgttggccttcgattttgcttcagctgcactacgacccctcca
acacatttccctcgcgtctcgttgcgatctcaccttacgacgatctcgttccagcagcagcagcatcggcagcgg
cggcttgcttccgaagcgagcaatgcatggcgcgcgcggccgcgtgcgtgcgtgccttggcttgcgctctaatca
aaccgggacgccccaactcacggttatggtacagccaaagaagaagtttcgtggagtcaggcagcggcactgggg
ctcctgggtctctgagatcagacacccctcctaaaaggagggtgtggctggccacctttgagacggccgagga
ggctgcgcgagcctacgatgaggctgctgtgctgatgagtggccgcaacgccaagaccaaacttccccgtgcagag
gaactccatcggtgatctcgccacggccgcagacaggacgcccgtagcaatggcggtagcaggaactcctccgc
gggcaacctgtcacagattctcagtgctaagctccgcaagtgctgcaaggcgccatctccgtccttaacctgcct
ccgcctcgacccgagaagtcccacattggcgtgtgcaaaagcgcgcaggggcccgtgctgactccaactgggt
gatgacggtggagctcaacaaagaggtagaaccaactgaacctgcagctcagcccacatcaacagcaacagcttc
gcaagtgacaatggatgatgaggaaaagattgcgctgcaaatgatcgaggagttgctgagcaggagcagtccagc
ttcatcctcacatggagagggagagggtagctttgtcatctgacacgtgtgaattacaggtgaccagctcgaatt
tccccgatagctttcgttcgtatcatcggtttcgacaacgttcgtcaagttcaatgcatcagtttcattgcgcac
acaccagaatcctactgagttcgagtattatggcatgggaaacatgttttcttgtaccatttgttgtgcttgt
aatttactgtgtttttattcggttttcgctatcgaactgtgaaatggaaatggatggagaagagttaatgaatg
atatggtccttttgttcattctcaaattaatattatttgttttttctcttatttgttgtgtgttgaatttgaaaa
tataagagatatgcaaacatttgttttgagtaaaatgtgtcaaatcgtggcctctaatgaccgaagttaatat
gaggagtaaaacacttgtagttgtaccattatgcttattcactaggcaacaaatatattttcagacctagaaag
ctgcaaatgttactgaatacaagtatgtcctcttgtgttttagacatttatgaactttcctttatgtaattttcc
agaatccttgtcagattctaatcattgctttataattatagttatactcatggatttgtagttgagtatgaaaat
atttttttaatgcattttatgacttg    2275
```

FIG. 25

COMPOSITIONS AND METHODS FOR INCREASING PLANT GROWTH AND IMPROVING MULTIPLE YIELD-RELATED TRAITS

CROSS-REFERENCE TO RELATED APPLICATIONS

This application is a continuation of U.S. Ser. No. 16/965,809 filed Jul. 29, 2020 which is the U.S. national phase of PCT Application No. PCT/US2019/015688 filed on Jan. 29, 2019, which claims the benefit of U.S. Provisional patent application Ser. No. 62/623,279, filed Jan. 29, 2018, the disclosures of which are incorporated in their entirety by reference herein.

STATEMENT REGARDING FEDERALLY SPONSORED RESEARCH OR DEVELOPMENT

This invention was made with government support under Award Number 2016-33610-25368 awarded by the U.S. Department of Agriculture, Award Number NNX17CK04P awarded by the National Aeronautics and Space Administration, and Award Number DE-SC0011309 awarded by the U.S. Department of Energy. The government has certain rights in this invention.

SEQUENCE LISTING

The xml file AALB0101PUSA1.xml of size 179 KB created Apr. 24, 2023, filed herewith, is hereby incorporated by reference.

FIELD OF THE INVENTION

The present invention relates to genetic constructs and transgenic plants with vascular xylem tissue-targeting overexpression of transcription factors (TFs) involved in vascular xylem cell development, as well as their methods of use for enhancing plant growth and yield.

BACKGROUND OF THE INVENTION

Yield is commonly defined as the measurable economic value of agricultural product from a crop. This may be defined in terms of quantity or quality, or a combination of both. Yield is directly dependent on several factors, for example, the number and size of the organs, plant architecture (i.e. number of tillers or branches), seed production, nutrient content, assimilation of metabolic precursors, root development, nutrient uptake, stress tolerance, and early vigor. Optimizing the above-mentioned factors may, therefore, contribute to increasing crop and horticultural yield. Depending on the end use, the modification of certain yield traits may be favored over others. For example, for applications such as forage or wood production, or as a biofuel resource, an increase in the vegetative parts of a plant may be desirable, and for applications such as flour, starch, or oil production, an increase in seed parameters may be particularly desirable. Such plant growth and/or yield-related traits may be improved by enhancing vascular tissue meristematic activity.

In higher plants, vascular tissues are important for transporting water and nutrients throughout the plant and providing physical support for upright growth. Primary constituents of the vascular tissues, xylem and phloem, are derived from the meristematic vascular procambium and cambium (Esau, Plant Anatomy (1965); Esau, Anatomy of Seed Plants (1977)). Xylem cells are particularly important for developing secondary cell walls that form the largest part of plant lignocellulosic biomass that consists of cellulose, hemicellulose, and lignin. Histochemical studies have indicated that lignification of the secondary cell wall generally occurs after the initial deposition of the cellulosic and hemicellulosic components and that it is initiated in a spatially distinct manner, beginning with the lignification of the middle lamella. Comparative studies of the patterns of secondary cell wall deposition in xylem cells in many different vascular plants have shown that the patterning of secondary cell wall deposition in these cells is a highly conserved process across species (Esau, Plant Anatomy (1965); Meylan and Butterfield, Three-Dimensional Structure of Wood (1972)).

Traditional molecular biology approaches using mutant analysis have identified a series of enzymes involved in the formation and accumulation of secondary cell wall mass (Turner and Somerville, "Collapsed Xylem Phenotype of *Arabidopsis* Identifies Mutants Deficient in Cellulose Deposition in the Secondary Cell Wall," Plant Cell 9(5):689-701 (1997); Brown et al., "Identification of Novel Genes in *Arabidopsis* Involved in Secondary Cell Wall Formation Using Expression Profiling and Reverse Genetics," Plant Cell 17(8):2281-95 (2005); Oikawa et al., "An Integrative Approach to the Identification of *Arabidopsis* and Rice Genes Involved in Xylan and Secondary Wall Development," PLoS ONE 5(11):e15481 (2010); Hirano et al., "Survey of Genes Involved in Rice Secondary Cell Wall Formation Through a Co-Expression Network," Plant Cell Physiol. 54(1):1803-21 (2013); Hao and Mohnen, "A Review of Xylan and Lignin Biosynthesis: Foundation for Studying *Arabidopsis* Irregular Xylem Mutants with Pleiotropic Phenotypes," Crit. Rev. Biochem. Mol. Biol. 49(3):212-41 (2014)). Namely, irregular xylem (irx) mutants, which show collapsed xylem vessels in *Arabidopsis*, and brittle culm (bc) mutants, which show two-fold decrease in breaking strength compared with wild-type in rice, implicate these genes in secondary cell wall formation. The genes identified from the mutant screening were IRX1: AT4G18780 (AtCesA8), IRX2: AT5G49720 (AtKOR1), IRX3: AT5G17420 (AtCesA7), IRX4: AT1G15950 (AtCCR1), IRX5: AT5G44030 (AtCesA4), IRX6: AT5G15630 (AtCOBL4), IRX7: AT2G28110 (AtFRA8), IRX8: AT5G54690 (AtGAUT12), IRX9: AT2G37090 (glycosyltransferases family 43), IRX10: AT1G27440 (AtGUT1), IRX11: AT1G62990 (AtKNAT7), IRX12: AT2G38080 (AtLAC4), IRX13: At5G03170 (AtFLA11), IRX14: AT4G36890 (glycosyltransferases family 43), IRX15: AT3G50220 (DUF579), BC1: Os03g0416200 (OsCOBL5), BC2: (rice COBRA-like proteins), BC3: Os02g0738900 (OsDRP2B), BC6: Os09g0422500 (OsCESA9), BC7: Os01g0750300 (OsCESA4), BC10: Os05g0170000 (DUF266), BC11: Os01g0750300 (CESA4), BC12: Os09g0114500 (OsKIN4A), BC14: Os02g0614100 (OsNST1), and BC15: Os09g0494200 (OsCTL1), which mainly consist of gene members coding endomembrane enzyme/protein for the cellulose and hemicellulose deposition and/or lignification. Integrated analysis of the series of mutants and co-expression gene datasets, in particular, revealed that distinct subgroups of CesA genes and proteins involved in cellulose biosynthesis in secondary cell walls are also conserved across plant species. For example, the products of three gene sets, such as the AtCesA4 (IRX5), AtCesA7 (IRX3), and AtCesA8 (IRX1) genes in *Arabidopsis*, the OsCesA4 (BC7), OsCesA7, and OsCesA9 (BC6)

genes in rice, and the ZmCesA10, ZmCesA11, and ZmCesA12 genes in maize, appear to function non-redundantly to catalyze cellulose biosynthesis in secondary cell walls. Xylan is the most abundant hemicellulose found in the secondary cell walls of plants and is thought to function as the major cellulose cross-linking component in secondary cell walls. Several Golgi-localized glycosyltransferases, including protein members from glycosyltransferases family 43 (i.e. the above-mentioned IRX9 and IRX14), have been involved in the biosynthesis of the xylose sugar backbone in developing xylem cells. Many other orthologous genes co-expressed with the cellulose synthase and xylan synthase genes in vascular xylem tissues are found in both dicot and monocot species, which implies common biological functions (Oikawa et al., "An Integrative Approach to the Identification of *Arabidopsis* and Rice Genes Involved in Xylan and Secondary Wall Development," *PLoS ONE* 5(11):e15481 (2010)).

Since the expression amount of genes coding endomembrane enzyme/protein for the secondary cell wall cellulose/xylan deposition is specific and enormous in the vascular xylem tissues, their upstream sequence regions, namely promoters and 5'-UTR sequences, would be useful to overexpress heterogonous genes within the xylem tissues (Oikawa et al., "Golgi-Localized Enzyme Complexes for Plant Cell Wall Biosynthesis," *Trends Plant Sci.* 18:49-58, (2013); Oikawa et al., "An Integrative Approach to the Identification of *Arabidopsis* and Rice Genes Involved in Xylan and Secondary Wall Development," *PLoS ONE* 5(11):e15481 (2010)). As an example of the applications, the transgenic rice plants that expressed a sucrose synthase gene, OsSUS3, driven by the AtCesA8 (the above-mentioned IRX1) promoter maintained a normal growth with slightly increased biomass yields, and also reduced cellulose crystallinity and increased wall thickness, therefore leading to large improvements of both biomass saccharification and lodging (Fan et al., "AtCesA8-driven OsSUS3 Expression Leads to Largely Enhanced Biomass Saccharification and Lodging Resistance by Distinctively Altering Lignocellulose Features in Rice," *Biotechnol. Biofuels* 10:221 (2017)). Another recent example of the successful tailoring of biomass properties is tissue-specific overexpression of master TF (Loque and Scheller, "Spatially Modified Gene Expression in Plants," PCT Publication No. WO 2012/103555; Yang et al., "Engineering Secondary Cell Wall Deposition in Plants," *Plant Biotechnol. J.* 11(3):325-35 (2013)). Tissue-specific overexpression of TF operably linked to a heterologous promoter that induces expression of a gene that is a downstream target of the TF enabled a positive feedback manner that regulates the amplified production of the secondary cell wall production in woody tissue. To accomplish this, a tissue-specific promoter sequence such as an IRX1, IRX3, IRX5, IRX8, IRX9, IRX14, IRX7, and IRX10 promoter was linked in with NAC-MYB TFs such as NST1, NST2, SND1/NST3, SND2, SND3, MYB103, MYB85, MYB46, MYB83, MYB58, or MYB63. This strategy is, however, limited to the accumulation of specific secondary cell wall compounds such as cellulose, xylan, and lignin in xylem and fiber tissues. Overall yield and/or yield-related traits have yet to be improved since the protocol uses the series of TFs only involved in secondary cell wall development, not in the upstream process such as vascular xylem cell differentiation and/or cell development.

R2R3-MYB subfamily 4 and ERF/AP2 subfamily B-6 have been well known as TFs that modulate secondary metabolites, increase wax content, and enhance biotic/abiotic stress tolerances. For the function of R2R3-MYB subfamily 4 and its biotechnology applications, see: Tak et al., "Overexpression of MusaMYB31, a R2R3 type MYB Transcription Factor Gene Indicate its Role as a Negative Regulator of Lignin Biosynthesis in Banana," *PLoS ONE* 12(2): e0172695 (2017); Agarwal et al., "MYB31/MYB42 Syntelogs Exhibit Divergent Regulation of Phenylpropanoid Genes in Maize, Sorghum and Rice," *Sci. Rep.* 6:28502 (2016); Poovaiah et al., "Sugarcane Transgenics Expression MYB Transcription Factors Show Improved Glucose Release," *Biotechnol Biofuels* 9:143 (2016); Zhou et al., "Changing a Conserved Amino Acid in R2R3-MYB Transcription Repressors Results in Cytoplasmic Accumulation and Abolishes Their Repressive Activity in *Arabidopsis*," *Plant J.* 84(2):395-403 (2015); Martin and Butelli, "Methods for Increasing the Anthocyanin Content of Citrus Fruit," U.S. Patent Publication 20140007287; Rouster et al., "Production of Plants Having Improved Water-Deficit Tolerance," U.S. Patent Publication 20130298282; Handakumbura and Hazen, "Transcriptional Regulation of Grass Secondary Cell Wall Biosynthesis: Playing Catch-Up With *Arabidopsis thaliana*," *Front. Plant Sci.* 3:74 (2012); Guan et al., "Methods of Modifying Lignin Biosynthesis and Improving Digestibility," U.S. Patent Publication 20120272406; Shen et al., "Compositions and Methods for Improved Plant Feedstock," U.S. Patent Publication 20120322122; Shen et al., "Functional Characterization of the Switchgrass (*Panicum virgatum*) R2R3-MYB Transcription Factor PvMYB4 for Improvement of Lignocellulosic Feedstocks," *New Phytol.* 193:121-36 (2012); Wang and Dixon, "On-Off Switches for Secondary Cell Wall Biosynthesis," *Mol. Plant.* 5(2):297-303 (2012); Bedon et al., "Subgroup 4 R2R3-MYBs in Conifer Trees: Gene Family Expansion and Contribution to the Isoprenoid—and Flavonoid—Oriented Responses," *Journal of Experimental Botany* 61(14):3847-3864 (2010); Fornalé et al., "ZmMYB31 Directly Represses Maize Lignin Genes and Redirects the Phenylpropanoid Metabolic Flux," *Plant J.* 64(4):633-44 (2010); Sonbol et al., "The Maize ZmMYB42 Represses the Phenylpropanoid Pathway and Affects the Cell Wall Structure, Composition and Degradability in *Arabidopsis thaliana*," *Plant Mol. Biol.* 70:283-96 (2009); Legay et al., "Molecular Characterization of EgMYB1, a Putative Transcriptional Repressor of the Lignin Biosynthetic Pathway," *Plant Sci.* 173:542-9 (2007); Fornalé et al., "Down-Regulation of the Maize and *Arabidopsis thaliana* Caffeic Acid O-methyl-transferase Genes by Two New Maize R2R3-MYB Transcription Factors," *Plant Mol. Biol.* 62(6):809-23 (2006); Coraggio et al., "Use of the Myb4 Transcriptional Factor From Rice to Increase the Production of Secondary Metabolites by Transformed Plants," PCT Publication No. WO 2005/080580; Preston et al., "AtMYB32 is Required for Normal Pollen Development in *Arabidopsis thaliana*," *Plant J.* 40(6):979-95 (2004). For the function of ERF/AP2 subfamily B-6 and its biotechnology applications, see Xu et al., "Overexpression of the Transcription Factors GmSHN1 and GmSHN9 Differentially Regulates Wax and Cutin Biosynthesis, Alters Cuticle Properties, and Changes Leaf Phenotypes in *Arabidopsis*," *Int. J. Mol. Sci.* 17(4):E587 (2016); Djemal and Khoudi, "Isolation and Molecular Characterization of a Novel WIN/SHN1 Ethylene-Responsive Transcription Factor TdSHN1 From Durum Wheat (*Triticum turgidum* L. subsp. durum) *Protoplasma* 252(6):1461-73 (2015); Al-Abdallat et al., "Over-Expression of SlSHN1 Gene Improves Drought Tolerance by Increasing Cuticular Wax Accumulation in Tomato," *Int. J. Mol. Sci.* 15(11):19499-515 (2014); Sela et al., "Overexpression of AtSHN1/WIN1 provokes Unique Defense Responses," *PLoS One* 8(7):e70146 (2013); Loque and Scheller, "Spatially Modified Gene Expression in Plants," PCT Publication No. WO 2012/103555; Wang et al., "An Ethylene Response Factor OsWR1 Responsive to Drought Stress Transcriptionally Activate Wax Synthesis Related Genes and Increases Wax Production in Rice," *Plant Mol Biol.* 78(3):275-88 (2012); Shi et al., "SHINE Transcription Factors Act Redundantly to Pattern the Archetypal Surface of *Arabidopsis* Flower Organs," *PLoS Genet.* 7(5): e1001388 (2011); Kannangara et al., "The Transcription Factor WIN1/SHN1 Regulates Cutin Biosynthesis in *Arabidopsis thaliana,*" *Plant Cell* 19(4):1278-94 (2007); Aharoni et al., "The SHINE Clade of Transcription Factors and Their Use," PCT Publication WO 2005/120215; Aharoni et al., "The SHINE clade of AP2 Domain Transcription Factors Activates Wax Biosynthesis, Alters Cuticle Properties, and Confers Drought Tolerance When Overexpressed in *Arabidopsis,*" *Plant Cell* 16(9):2463-80 (2004). Recent overexpression studies by traditional constitutive promoters demonstrated that a series of orthologous TFs from the R2R3-MYB subfamily 4 and ERF/AP2 subfamily B-6 are also potential regulators of the secondary cell wall NAC-MYB TFs (Hussey et al., "Navigating the Transcriptional Roadmap Regulating Plant Secondary Cell Wall Deposition," *Front. Plant Sci.* 4:325 (2013); Yang and Wang, "Molecular Mechanisms for Vascular Development and Secondary Cell wall Formation," *Front. Plant Sci.* 7:356 (2016); Ambavaram et al., "Coordinated Activation of Cellulose and Repression of Lignin Biosynthesis Pathways in Rice," *Plant Physiol.* 155(2):916-31 (2011); Legay et al., "EgMYB1, an R2R3 MYB Transcription Factor from *Eucalyptus* Negatively Regulates Secondary Cell Wall Formation in *Arabidopsis* and Poplar," *New Phytol.* 188(3):774-86 (2010)).

Although gene expression of *Arabidopsis* R2R3-MYB subfamily 4, MYB4, MYB7, and MYB32, are positively regulated by secondary wall MYB TF, MYB46, they are also shown to be involved in fine-tuning the upstream transcriptional regulation of developing vascular xylem cells. Overexpression of two maize homologs from the R2R3-MYB subfamily 4, namely ZmMYB31 and ZmMYB42, in *Arabidopsis* results in down-regulation of the lignin pathway and a patchy secondary cell wall deposition phenotype in fiber cells, which supports a repressive role for these proteins. In addition, there is molecular evidence showing that MYB4, MYB7, and MYB32 repress not only their own promoters but also the promoter of the secondary cell wall NAC master TF SND1/NST3 that regulates MYB46. Such negative regulations suggests that R2R3-MYB subfamily 4 may fine-tune the expressions and activities of secondary wall NAC-MYB-based transcriptional regulatory network for vascular xylem and fiber cells development.

The secondary cell wall master regulators in the endothecium of anthers include NST2, which is co-expressed with the SHN/WIN genes from ERF/AP2 subfamily B-6 and also with WRKY DNA-Binding Protein 12 (Wang et al., "Mutation of WRKY Transcription Factors Initiates Pith Secondary Wall Formation and Increases Stem Biomass in Dicotyledonous Plants," *Proc. Natl. Acad. Sci. U.S.A.* 107(51): 22338-43 (2010); Yang et al., "PtrWRKY19, a Novel WRKY Transcription Factor, Contributes to the Regulation of Pith Secondary Wall Formation in *Populus trichocarpa,*" *Sci. Rep.* 6:18643 (2016)) that are believed to be upstream transcriptional regulators. The OsSHN1 gene, a homolog of *Arabidopsis* AtSHN2 in rice, is also tightly co-expressed with TFs and biosynthetic genes associated with the formation of the secondary cell wall in xylem and fiber cells. Although both AtSHN2 and OsSHN1 genes are suggested to regulate wax and lipid biosynthesis, they can also (a) enhance cellulose synthase genes expression; and (b) suppress lignin biosynthetic gene expression when they are overexpressed in rice. Additional molecular evidence shows that AtSHN2 can bind the promoters of secondary cell wall NAC-MYB TFs in rice, indicating an upstream mechanism of transcriptional regulation by SHN gene family in monocots.

The expression modulation of the TFs for the fundamental studies, however, has been controlled by constitutive promoters, which often show detrimental effects as yield drag. The previously noted vascular xylem tissue-targeting overexpression with the above-mentioned promoters has not been applied to the TFs that can potentially act before the secondary wall NAC-MYB TFs.

The present invention seeks to cure these deficiencies through the combination of promoters which preferably target vascular xylem tissue and a series of DNA transcription factors (TFs) involved in the transcriptional regulation of developing vascular xylem cells to enhance multiple yield-related traits in plants.

SUMMARY

A first aspect of the present invention is directed to a nucleic acid construct that includes a polynucleotide encoding a transcription factor polypeptide and a heterologous, tissue-specific promoter operably linked to the polynucleotide encoding the transcription factor polypeptide, wherein the promoter specifically directs expression of the transcription factor polypeptide in vascular xylem tissue of a plant.

A second aspect of the present invention is directed to an expression vector that includes a nucleic acid construct of the present invention.

A third aspect of the present invention is directed to a recombinant host cell that includes a nucleic acid construct according to the first aspect of the invention or a recombinant expression vector according to the second aspect of the invention. In certain embodiments, the recombinant host cells are bacterial cells or plant cells.

A fourth aspect of the present invention is directed to a transgenic plant or transgenic plant seed that includes a nucleic acid construct according to the first aspect of the invention or a recombinant host cell according to the third aspect of the invention.

A fifth aspect of the present invention is directed to a plant having (i.e., including) a transgene that includes a heterologous, tissue-specific promoter operably linked to a polynucleotide encoding a transcription factor involved in vascular xylem cell development, wherein the promoter specifically directs expression of the transcription factor in vascular xylem tissue of the plant.

A sixth aspect of the present invention is directed to a rootstock, cutting, or seed obtained from a transgenic plant according to the fourth aspect of the invention or a plant according to the fifth aspect of the invention.

A seventh aspect of the invention is directed to a method of enhancing plant growth or yield by providing a transgenic plant or transgenic plant seed that is transformed with a nucleic acid construct according to the first aspect of the invention (which includes a transgenic plant or transgenic plant seed according to the fourth aspect of the invention). In one embodiment, the transgenic plant is provided, and then grown under conditions effective to permit the nucleic acid construct to express the transcription factor polypeptide in vascular xylem tissue of the transgenic plant, and thereby enhance plant growth or yield. In another embodiment, the transgenic plant seed is provided, planted in a growth medium, and a transgenic plant is then propagated from the transgenic plant seed to permit the nucleic acid construct to express the transcription factor polypeptide in vascular xylem tissue of the transgenic plant, and thereby enhance plant growth or yield.

An eighth aspect of the invention is directed to a method of enhancing plant growth or yield by providing a rootstock, cutting, or seed according to the sixth aspect of the invention, which rootstock, cutting, or seed is planted in a growth medium, and a transgenic plant is then propagated from the rootstock, cutting, or seed to permit the nucleic acid construct (or transgene) to express the transcription factor polypeptide in vascular xylem tissue of the transgenic plant, and thereby enhance plant growth or yield.

A ninth aspect of the invention is directed to a method of enhancing plant growth or yield by providing a plant according to the fifth aspect of the invention, and growing the plant under conditions effective to permit the transgene to express the transcription factor polypeptide in vascular xylem tissue of the transgenic plant, and thereby enhance plant growth or yield.

A tenth aspect of the present invention is directed to a method of planting, cultivating, or harvesting a part or all of a plant according to the first aspect of the invention or fifth aspect of the invention.

An eleventh aspect of the present invention is direct to a method of making a plant according to the fourth aspect of the invention or a plant according to the fifth aspect of the present invention. The method includes introducing a nucleic acid construct or transgene of the invention into a plant cell and propagating the plant from the plant cell.

A twelfth aspect of the present invention is directed to a method of enhancing degradability of plant biomass by providing a transgenic plant or transgenic plant seed that is transformed with a nucleic acid construct according to the first aspect of the invention (which includes a transgenic plant or transgenic plant seed according to the fourth aspect of the invention). In one embodiment, the transgenic plant is provided, and then grown under conditions effective to permit the nucleic acid construct to express the transcription factor polypeptide in vascular xylem tissue of the transgenic plant, and thereby enhance degradability of plant biomass. In another embodiment, the transgenic plant seed is provided, planted in a growth medium, and a transgenic plant is then propagated from the transgenic plant seed to permit the nucleic acid construct to express the transcription factor polypeptide in vascular xylem tissue of the transgenic plant, and thereby enhance degradability of plant biomass.

An thirteenth aspect of the invention is directed to a method of enhancing degradability of plant biomass by providing a rootstock, cutting, or seed according to the sixth aspect of the invention, which rootstock, cutting, or seed is planted in a growth medium, and a transgenic plant is then propagated from the rootstock, cutting, or seed to permit the nucleic acid construct (or transgene) to express the transcription factor polypeptide in vascular xylem tissue of the transgenic plant, and thereby enhance degradability of plant biomass.

A fourteenth aspect of the invention is directed to a method of enhancing degradability of plant biomass by providing a plant according to the fifth aspect of the invention, and growing the plant under conditions effective to permit the transgene to express the transcription factor polypeptide in vascular xylem tissue of the transgenic plant, and thereby enhance degradability of plant biomass.

The minimal cis-genic combination of (i) a promoter sequence that preferably targets vascular xylem tissues, and (ii) a TF polypeptides from an R2R3-MYB subfamily 4 or ERF/AP2 subfamily B-6 is unique. The accompanying Examples surprisingly demonstrate that multiple yield-related traits could be introduced into plant cells by the vascular xylem tissue-targeting overexpression of the TFs that are believed (a) to be upstream regulators of secondary cell wall NAC master TFs (i.e., SND1/NST3, NST1, NST2, VND6, VND7), and (b) to be involved in the vascular xylem cell development. The tissue-targeting manner of the TF overexpression also enables reduced lignin in only the vascular xylem tissue and maintains lignin in other tissue cells that are vital to the structural supports of the plant. This invention generated significantly improved crops with a combination of three beneficial traits: (1) accelerated root growth, (2) increased seeds/grains and vegetative biomass yields, and (3) enhanced degradability of inedible/lignocellulosic biomass. These traits may contribute to enhancing U.S. agricultural production, self-sustainability, the economy, food security, and bioenergy. The invention has wide applicability across plant species, including both monocots and dicots.

BRIEF DESCRIPTION OF THE DRAWINGS

FIG. 2 illustrates the map and nucleotide sequence for construct 002, pAtLAC4-AtMYB32-tRBS, which includes the promoter from AtLAC4, the open reading frame of AtMYB32 (shaded in sequence), and the 3' RBS transcription terminator.

FIG. 3 illustrates the map and nucleotide sequence for construct 003, pAtCesA4-AtMYB32-tRBS, which includes the promoter from AtCesA4, the open reading frame of AtMYB32 (shaded in sequence), and the 3' RBS transcription terminator.

FIG. 4 illustrates the map and nucleotide sequence for construct 004, pAtCesA8-AtMYB32-tRBS, which includes the promoter and 5' UTR from AtCesA8, the open reading frame of AtMYB32 (shaded in sequence), and the 3' RBS transcription terminator.

FIG. 6 illustrates the map and nucleotide sequence for construct 006, pAtCesA7-AtMYB32-tRBS, which includes the promoter and 5' UTR from AtCesA7, the open reading frame of AtMYB32 (shaded in sequence), and the 3' RBS transcription terminator.

FIG. 7 illustrates the map and nucleotide sequence for construct 007, pAtIRX9-AtMYB32-tRBS, which includes the promoter and 5' UTR from AtIRX9, the open reading frame of AtMYB32 (shaded in sequence), and the 3' RBS transcription terminator.

FIG. 8 illustrates the map and nucleotide sequence for construct 008, pAtCesA4-AtMYB4-tRBS, which includes the promoter from AtCesA4, the open reading frame of AtMYB4 (shaded in sequence), and the 3' RBS transcription terminator.

FIG. 9 illustrates the map and nucleotide sequence for construct 009, pAtCesA8-AtMYB4-tRBS, which includes the promoter and 5' UTR from AtCesA8, the open reading frame of AtMYB4 (shaded in sequence), and the 3' RBS transcription terminator.

FIG. 10 illustrates the map and nucleotide sequence for construct 010, pZmCesA12-ZmMYB31-tRBS, which includes the promoter from ZmCesA12, the open reading frame of ZmMYB31 (shaded in sequence), and the 3' RBS transcription terminator.

FIG. 11 illustrates the map and nucleotide sequence for construct 011, pZmCesA11-ZmMYB31-tRBS, which includes the promoter from ZmCesA11, the open reading frame of ZmMYB31 (shaded in sequence), and the 3' RBS transcription terminator.

FIG. 13 illustrates the map and nucleotide sequence for construct 013, pOsCesA7-ZmMYB31-tRBS, which includes the promoter from OsCesA7, the open reading frame of ZmMYB31 (shaded in sequence), and the 3' RBS transcription terminator.

FIG. 14 illustrates the map and nucleotide sequence for construct 014, pZmCesA12-ZmMYB42-tRBS, which includes the promoter from ZmCesA12, the open reading frame of ZmMYB42 (shaded in sequence), and the 3' RBS transcription terminator.

FIG. 15 illustrates the map and nucleotide sequence for construct 015, pZmCesA11-ZmMYB42-tRBS, which includes the promoter from ZmCesA11, the open reading frame of ZmMYB42 (shaded in sequence), and the 3' RBS transcription terminator.

FIG. 17 illustrates the map and nucleotide sequence for construct 017, pOsCesA7-ZmMYB42-tRBS, which includes the promoter from OsCesA7, the open reading frame of ZmMYB42 (shaded in sequence), and the 3' RBS transcription terminator.

FIG. 18 illustrates the map and nucleotide sequence for construct 018, pZmCesA12-PvMYB4-tRBS, which includes the promoter from ZmCesA12, the open reading frame of PvMYB4 (shaded in sequence), and the 3' RBS transcription terminator.

FIG. 19 illustrates the map and nucleotide sequence for construct 019, pZmCesA11-PvMYB4-tRBS, which includes the promoter from ZmCesA11, the open reading frame of PvMYB4 (shaded in sequence), and the 3' RBS transcription terminator.

FIG. 21 illustrates the map and nucleotide sequence for construct 021, pOsCesA7-PvMYB4-tRBS, which includes the promoter from OsCesA7, the open reading frame of PvMYB4 (shaded in sequence), and the 3' RBS transcription terminator.

FIG. 22 illustrates the map and nucleotide sequence for construct 022, pZmCesA12-OsSHN1-tRBS, which includes the promoter from ZmCesA12, the open reading frame of OsSHN1 (shaded in sequence), and the 3' RBS transcription terminator.

FIG. 23 illustrates the map and nucleotide sequence for construct 023, pZmCesA11-OsSHN1-tRBS, which includes the promoter from ZmCesA11, the open reading frame of OsSHN1 (shaded in sequence), and the 3' RBS transcription terminator.

FIG. 25 illustrates the map and nucleotide sequence for construct 025, pOsCesA7-OsSHN1-tRBS, which includes the promoter from OsCesA7, the open reading frame of OsSHN1 (shaded in sequence), and the 3' RBS transcription terminator.

DETAILED DESCRIPTION

Figure 1:
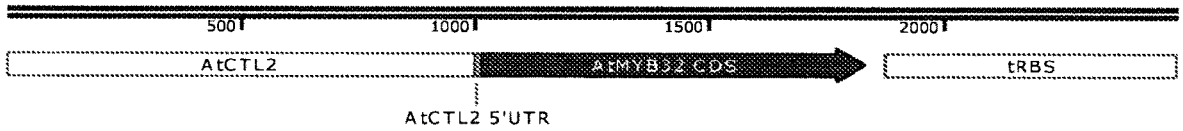
FIG. 1 illustrates the map and nucleotide sequence for construct 001, pAtCTL2-AtMYB32-tRBS, which includes the promoter and 5' UTR from AtCTL2, the open reading frame of AtMYB32 (shaded in sequence), and the 3' RBS transcription terminator.

The present invention is directed to recombinant nucleic acid constructs and transgenes as well as expression vectors and host cells useful for generating transgenic plants that preferentially express the transgenes in vascular xylem tissue of the plant. Transgenic plant parts are also encompassed by the present invention, as are various methods for making the transgenic plants and plant parts. Also encompassed by the present invention are methods that utilize the transgenic plants or plant parts, including methods for enhancing plant growth, enhancing plant yield, modifying plant lignin content, promoting earlier reproductive maturation, and enhancing degradability of plant biomass. These recombinant materials and their use in practicing the various methods are described below.

One aspect of the present invention is directed to a nucleic acid construct that includes a polynucleotide encoding a transcription factor ("TF") polypeptide and a heterologous, tissue-specific promoter operably linked to the polynucleotide encoding the TF polypeptide, wherein the promoter specifically directs expression of the TF polypeptide in vascular xylem tissue of a plant.

According to one embodiment, the nucleic acid construct takes the form of a transgene that includes a heterologous, tissue-specific promoter operably linked to a polynucleotide encoding the TF polypeptide involved in vascular xylem cell development, and a 3' transcription termination sequence that is operably linked to the polynucleotide encoding the TF, wherein the promoter specifically directs expression of the TF in vascular xylem tissue of the plant.

Thus, this invention involves the formation and use of synthetic oligonucleotides or nucleotide sequences. A synthetic sequence is one that is initially produced or reproduced in a laboratory setting. The structure of the synthetic sequence is altered or different from that found in the sequence that is directly isolated from its natural setting. A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety). "Operably linked" is intended to mean a functional linkage between two or more elements.

In these and other aspects of the invention, the TF polypeptide encoded by the nucleic acid construct, or transgene, is one that modulates expression of at least one gene, and possibly a series of genes (i.e., two or more), involved with cell wall and secondary metabolite biosynthetic pathways. Transcription factors are proteins that are involved in the process of transcribing DNA into RNA. Transcription factors have DNA-binding domains that allow them to bind to specific DNA sequences (e.g., promoter sequences, enhancer sequences, and silencers). In certain embodiment of the present invention, the TF polypeptide is a polypeptide that can act as an upstream transcriptional regulator to secondary wall master TFs as an upstream transcriptional regulator.

Suitable classes of TF polypeptides include, without limitation, an R2R3-MYB subfamily 4 TF polypeptide, an ERF/AP2 subfamily B-6 TF polypeptide, and combinations thereof (i.e., when co-expressed). Both R2R3-MYB subfamily 4 TFs and ERF/AP2 subfamily B-6 TFs are widely conserved among both monocots and dicots, and therefore it is contemplated that any of a variety of TFs from these classes can be utilized.

Non-limiting examples of both the R2R3-MYB subfamily 4 TF polypeptide and an ERF/AP2 subfamily B-6 TF polypeptide are provided in the examples, and include those listed below.

ERF/AP2 subfamily B-6 Transcription Factors: *Arabidopsis* AtSHN3 (SEQ ID NOS:1, 37); *Arabidopsis* AtSHN1/WIN1 (SEQ ID NOS: 2, 38); *Arabidopsis* AtSHN2 (SEQ ID NOS: 3, 39); rice OsSHN1 (OsEREB19) (SEQ ID NOS: 7, 43); rice OsSHN2 (OsEREB114) (SEQ ID NOS: 8, 44); sorghum SbEREB63 (SEQ ID NOS: 13, 49); sorghum SbEREB150 (SEQ ID NOS: 14, 50); and maize ZmEREB46 (SEQ ID NOS: 17, 53).

R2R3-MYB Subfamily 4 Transcription Factors: *Arabidopsis* AtMYB32 (SEQ ID NOS: 4, 40); *Arabidopsis* AtMYB4 (SEQ ID NOS: 5, 41); *Arabidopsis* MYB7 (SEQ ID NOS: 6, 42); rice OsMYB108-L (SEQ ID NOS: 9, 45); rice OsMYB108 (SEQ ID NOS: 10, 46); poplar PdMYB221 (SEQ ID NOS: 11, 47); poplar PdMYB156 (SEQ ID NOS: 12, 48); sorghum SbMYB86 (SEQ ID NOS: 15, 51); sorghum SbMYB23 (SEQ ID NOS: 16, 52); maize ZmMYB42 (SEQ ID NOS: 18, 54); maize ZmMYB31 (SEQ ID NOS: 19, 55); and switchgrass PvMYB4 (SEQ ID NOS: 20, 56).

As will be appreciated by persons of skill in the art, polynucleotides encoding homologous TFs can be isolated from other monocots and dicots. Such homologous TFs can be substantially similar to one another at the protein level, and polynucleotides encoding those TFs can be substantially identical at the nucleic acid level. "Substantially identical," as used in the context of two nucleic acids or polypeptides, refers to a sequence that has at least 60% sequence identity with a reference sequence. Alternatively, percent identity can be any integer from 60% to 100% inclusive. In some embodiments, this identity is at least: 60%, 65%, 70%, 75%, 80%, 85%, 90%, 91%, 92%, 93%, 94%, 95%, 96%, 97%, 98%, or 99% compared to a reference sequence using the programs described herein; preferably BLAST using standard parameters, as described below. Embodiments of the present invention provide for nucleic acids encoding polypeptides that are substantially identical to any of the provided TFs sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. The BLAST algorithm also performs a statistical analysis of the similarity between two sequences. One measure of similarity provided by the BLAST algorithm is the smallest sum probability, which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$ (0.00001), and most preferably less than about $10^{-10}$ (0.0000000001).

The polynucleotides encoding such TFs can also be used to isolate corresponding sequences from other plants. In this manner, methods such as PCR and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription activation or enhancer activities, and which hybridize under stringent conditions to the sequences disclosed herein, or to variants or fragments thereof, are encompassed by the present invention.

Variant sequences may also be identified by analysis of existing databases of sequenced genomes. In this manner, corresponding TF or enhancer sequences can be identified and used in the methods of the invention.

As noted above, the nucleic acid construct, or transgene, or the present invention includes tissue-specific promoters that specifically direct expression of the TF polypeptide in vascular xylem tissue of a plant, fiber tissues of a plant, or both.

A promoter is a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene, in this case the nucleic acid construct, or transgene, that includes a coding sequence for a TF of the type described above. A plant promoter is a promoter capable of initiating transcription in plant cells. Whereas a constitutive promoter is one that is capable of initiating transcription in nearly all tissue types, a tissue-specific promoter initiates transcription in one or a few particular tissue types, and a cell type-specific promoter initiates transcription only in one or a few particular cell types. As used herein, "tissue-specific" does not preclude the promoter from causing initiation of transcription in multiple different types of plant tissues. Rather, the term "tissue-specific" is intended to connote that the promoter causes preferential expression in one or more, but not all, plant tissues. In preferred embodiments, the tissue-specific promoter induces a high level of expression in the one or more plant tissues or, alternatively, where the tissue-specific promoter induces a high level of expression in the one or more plant tissues, the expression level is preferably elevated in vascular xylem and fiber tissues.

Expression levels of a TF can be increased (e.g., by up-regulation or overexpression) relative to the expression level of TF in a wild-type or control plant. With respect to the promoters of the present invention, "specifically directs expression in vascular xylem and fiber tissues" or "vascular xylem tissue-targeting expression" means that the promoter causes expression of a TF of the present invention that is at least 3-fold (e.g., 5-fold, 10-fold, 20-fold, 50-fold, etc.) greater in at least a portion of the vascular xylem tissue of a plant compared to other cell types (e.g., compared to epidermal or mesophyll cells). Vascular xylem tissues of a plant include plant procambium/cambium, xylem, and fiber cell types. In some embodiments, specific expression in plant vascular xylem tissues can be limited to a portion of the vasculature, e.g., above ground (aerial), below ground (roots), cambium cells only, xylem cells only, or both cambium and xylem cells. Further, in certain embodiment of the present invention, the tissue-specific promoter directs expression of the TF polypeptide in aerial parts of the plant, in roots of the plant, or in both the aerial parts and the roots of the plant.

The tissue-specific promoter directs expression of the TF polypeptide involved in developmental process of vascular xylem tissue cells that occurs before secondary wall thickening progresses with polysaccharide deposition and lignification.

The expression level of the TF may be measured, for example, by assaying for the level of the TF in the plant. Measurement of TF levels can be carried out directly using any of a variety of protein assays (e.g., by Western Blot) or indirectly by measuring the level of RNA transcripts (e.g., by northern blot).

Classes of suitable tissue-specific promoter include gene promoters for secondary cell wall development, an endomembrane protein gene promoter, or a secondary wall cellulose synthase (CesA) promoter. Exemplary tissue-specific promoters that induce elevated expression in vascular xylem and/or fiber tissues include, without limitation, *Arabidopsis* AtCTL2 promoter (SEQ ID NO:21); *Arabidopsis* AtLAC4 promoter (SEQ ID NO:22); *Arabidopsis* AtCesA4 promoter (SEQ ID NO:23); *Arabidopsis* AtCesA8 promoter (SEQ ID NO:24); *Arabidopsis* AtFLA11 promoter (SEQ ID NO:25); *Arabidopsis* AtCesA7 promoter (SEQ ID NO:26); *Arabidopsis* AtIRX9 promoter (SEQ ID NO:27); rice OsFLA9 promoter (SEQ ID NO:28); rice OsCTL1 promoter (SEQ ID NO:29); rice OsCesA4 promoter (SEQ ID NO:30); rice OcCesA7 promoter (SEQ ID NO:31); rice OsLac10 promoter (SEQ ID NO:32); rice OsGT43J promoter (SEQ ID NO:33); maize ZmCesA10 promoter (SEQ ID NO:34); maize ZmCesA12 promoter (SEQ ID NO:35); maize ZmCesA11 promoter (SEQ ID NO:36).

As will be appreciated by persons of skill in the art, promoters from homologous genes can be isolated from other monocots and dicots. Such homologous promoters can be substantially identical at the nucleic acid level as defined above.

Alternative tissue-specific promoters that induce elevated expression in vascular xylem and/or fiber tissues can be identified by examining native protein expression levels in the specified plant tissues over the course of development. See Oikawa et al., "An Integrative Approach to the Identification of *Arabidopsis* and Rice Genes Involved in Xylan and Secondary Wall Development," *PLoS ONE* 5(11): e15481 (2010), which is hereby incorporated by reference in its entirety.

As noted above, the nucleic acid construct, or transgenes, of the invention include 5' and 3' regulatory sequences operably linked to a TF polynucleotide.

As noted above, the nucleic acid construct, or transgene, also includes an operable 3' regulatory region, selected from among those which are capable of providing correct transcription termination and polyadenylation of mRNA for expression in the host cell of choice, operably linked to a modified trait nucleic acid molecule of the present invention. A number of 3' regulatory regions are known to be operable in plants, and any suitable 3' regulatory region can be used in accordance with the present invention.

Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety); and the pea Ribulose-1,5-Bisphosphate carboxylase/oxygenase Small subunit E9 ("RBS" or "E9") 3' regulatory region (Coruzzi et al., "Tissue-specific and light-regulated expression of a pea nuclear gene encoding the small subunit of ribulose-1,5-bisphosphate carboxylase," *EMBO J.* 3(8):1671-1679 (1984), which is hereby incorporated by reference in its entirety). Virtually any 3' regulatory region known to be operable in plants would be suitable for use in conjunction with the present invention.

Further aspects of the present invention include expression vectors including the nucleic acid constructs, or transgenes, described herein, as well as host cells, transgenic plants (plant cells and plant seeds produced from such transgenic plants), and transgenic plant seeds or plant parts transformed with the nucleic acid constructs described herein.

The nucleotide sequences used in the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pG-Cha, p35S-Cha, pBR322, pBR325, pACYC177, pACYC1084, pUC8, pUC9, pUC18, pUC19, pLG339, pR290, pKC37, pKC101, SV 40, pBluescript II SK+/− or KS+/−(see "Stratagene Cloning Systems" Catalog (1993) from Stratagene, La Jolla, CA, which is hereby incorporated by reference in its entirety), pQE, pIH821, pGEX, pET series (see Studier et al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation.

The DNA sequences are cloned into the vector using standard cloning procedures in the art, as described by Sambrook et al., *Molecular Cloning: A Laboratory Manual*, Second Edition, Cold Spring Harbor, NY: Cold Spring Harbor Press (1989), and Ausubel et al., *Current Protocols in Molecular Biology*, New York, N.Y: John Wiley & Sons (1989), which are hereby incorporated by reference in their entirety.

In preparing a nucleic acid construct for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall is characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," Nucleic Acids Res. 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Mol. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

The different components described above can be ligated together to produce the expression systems which contain the nucleic acid constructs used in the present invention, using well known molecular cloning techniques as described in Sambrook et al., *Molecular Cloning: A Laboratory Manual*, Second Edition Cold Spring Harbor, NY: Cold Spring Harbor Press (1989), and Ausubel et al. *Current Protocols in Molecular Biology*, New York, N.Y: John Wiley & Sons (1989), which are hereby incorporated by reference in their entirety.

Once the nucleic acid construct has been prepared, it is ready to be incorporated into a host cell. Basically, this method is carried out by transforming a host cell with the nucleic acid construct under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Spring Harbor Laboratory, Cold Spring Harbor, NY (1989), which is hereby incorporated by reference in its entirety. Suitable host cells are plant cells. Suitable host cells also include bacterial cells. Methods of transformation may result in transient or stable expression of the nucleic acid under control of the promoter. Stable transformation is intended to mean that the nucleotide construct introduced into a plant integrates into the genome of the plant and is capable of being inherited by the progeny thereof. Transient transformation is intended to mean that the nucleotide construct introduced into a plant is not stably integrated into the genome of the plant, but is maintained in the plant cell for a sufficient period of time to allow for the expression of the introduced genes. Preferably, the nucleic acid construct of the present invention is stably inserted into the genome of the recombinant plant cell as a result of the transformation, although transient expression can serve an important purpose, particularly when the plant under investigation is slow-growing.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," *Plant Cell* Reports 14:6-12 (1995), which are hereby incorporated by reference in their entirety.

In particle bombardment, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct of the present invention. As described supra, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., "Liposome-mediated Delivery of Tobacco Mosaic Virus RNA Into Tobacco Protoplasts: A Sensitive Assay for Monitoring Liposome-protoplast Interactions," *Proc. Natl. Acad. Sci. USA* 79:1859-63 (1982), which is hereby incorporated by reference in its entirety). The nucleic acid molecule may also be introduced into the plant cells by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention.

Yet a further method for introduction is by use of known techniques for genome editing or alteration. Such techniques for targeted genomic insertion involve, for example, inducing a double stranded DNA break precisely at one or more targeted genetic loci followed by integration of a chosen transgene or nucleic acid molecule (or construct) during repair. Such techniques or systems include, for example, zinc finger nucleases ("ZFNs") (Urnov et al., "Genome Editing with Engineered Zinc Finger Nucleases," *Nat Rev Genet.* 11: 636-646 (2010), which is hereby incorporated by reference in its entirety), transcription activator-like effector nucleases ("TALENs") (Joung & Sander, "TALENs: A Widely Applicable Technology for Targeted Genome Editing," *Nat Rev Mol Cell Biol.* 14: 49-55 (2013), which is hereby incorporated by reference in its entirety), clustered regularly interspaced short palindromic repeat ("CRISPR")-associated endonucleases (e.g., CRISPR/CRISPR-associated ("Cas") 9 systems) (Wiedenheft et al., "RNA-Guided Genetic Silencing Systems in Bacteria and Archaea," *Nat* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7): 397-405 (2013), each of which is hereby incorporated by reference in its entirety).

In certain embodiments, transformation described herein is carried out by microinjection, *Agrobacterium*-mediated transformation, direct gene transfer, ballistic particle acceleration, whisker method transformation, vacuum infiltration, biolistic transformation, electroporation, micro-injection, polyethylene-mediated transformation, or laser-beam transformation.

After transformation, the transformed plant cells must be regenerated. Plant regeneration from cultured protoplasts is described in Evans et al., *Handbook of Plant Cell Cultures*, Vol. 1, New York, New York: MacMillan Publishing Co. (1983); Vasil, ed., *Cell Culture and Somatic Cell Genetics of Plants*, Vol. I (1984) and Vol. III (1986), Orlando: Acad. Press; and Fitch et al., "Somatic Embryogenesis and Plant Regeneration from Immature Zygotic Embryos of *Papaya* (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferase II ("nptII") gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., "Vectors Containing a Prokaryotic Dihydrofolate Reductase Gene Transform *Drosophila* Cells to Methotrexate-resistance," *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: 3 Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, New York: Cold Spring Harbor Press (1989), which is hereby incorporated by reference in its entirety).

After a transgene containing a nucleic acid construct is stably incorporated in transgenic plants, the transgene can be transferred to other plants by sexual crossing. Any of a number of standard breeding techniques can be used, depending upon the species to be crossed. Once transgenic plants of this type are produced, the plants themselves can be transplanted to a suitable growth medium and cultivated in accordance with conventional procedure so that the nucleic acid construct is present in the resulting plants. Alternatively, transgenic seeds are recovered from the transgenic plants. These seeds can then be planted in a suitable growth medium and cultivated using conventional procedures to produce transgenic plants.

In these embodiments, suitable growth medium includes soil, soil-less particulate medium, or a liquid growth medium. Conditions for cultivating and harvesting may different depending on the type of growth medium and location, e.g., field, greenhouse, hydroponic environment, etc.

During subsequent growth and cultivation of the transgenic plants of the invention, it is also contemplated that individual plants may be selected based on their exhibiting one or more of the following properties: faster vegetative growth including that which leads to early maturation, increased biomass yields, enhanced root development, increased seed/grain production, improved nutrient contents in biomass, increased release of glucose saccharides, increased release of xylose saccharides, reduced lignin composition, and any combinations thereof.

The present invention may be used for transformation of any plant species, including, but not limited to, monocots and dicots. Examples of plant species of interest include, but are not limited to, the genus *Abies, Acacia, Acer, Aegilops, Aesculus, Agave, Ailanthus, Alnus, Amborella, Amelanchier, Arabidopsis, Arbutus, Arctostaphylos, Artemisia*, Asiminia, *Asparagus, Atriplex, Atropa, Aucuba, Avena, Berberis, Betula, Brachypodium, Brassica, Buddleia, Buxus, Calocedrus, Calotropis, Camellia, Camptotheca, Campsis, Cannabis, Capsicum, Capsella, Carpinus, Carya, Castanea, Catalpa, Ceanothus, Cedrus, Celastrus, Celtis, Cephalanthus, Cercidium, Cercis, Chaenomeles, Chamaecyparis, Chilopsis, Chionanthus, Chrysothamnus, Cicer, Cistus, Citrus, Citrullus, Cladrastis, Clematis, Coleogynia, Cornus, Corylus, Cotinus, Cotoneaster, Cowania, Crataegus, Crataegus, Cucumis, Cupressus, Cytisus, Daphne, Daucus, Deutzia, Diospyros, Dioscorea, Elaeagnus, Ephedra, Erythranthe, Escallonia, Eucalyptus, Euonymus, Eutrema, Fagus, Forsythia, Fragaria, Fraxinus, Gaultheria, Gelsemium, Genlisea, Ginkgo, Gleditsia, Glycine, Grevillea, Gymnocladus, Gossypium, Hamamelis, Hebe, Helianthus, Heliamphora, Hibiscus, Heterocallis, Hordeum, Hydrangea, Hyoscyamus, Hypericum, Lactuca, Linum, Lolium, Lycopersicon, Ilex, Ipomea, Juglans, Juniperus, Kalmia, Kerria, Koelreuteria, Lagerstroemia, Larix, Larrea, Libocedrus, Ligustrum, Liquidambar, Liriodendron, Lonicera, Lotus, Maclura, Magnolia, Mahonia, Malus, Manihot, Majorana, Medicago, Menispermum, Morus, Myrica, Nicotiana, Nyssa, Oryza, Osmanthus, Ostrya, Oxydendron, Panicum, Pannesetum, Parthenocissus, Papaver, Persea, Phaseolus, Philadelphus, Photinia, Physocarpus, Picea, Pisum, Pinus, Pittosporum, Platanus, Populus, Podophyllum, Prosopis, Prunus, Pseudotsuga, Ptelea, Purshia, Pyrus, Quercus, Raphanus, Rhamnus, Rhaphiolepis, Rhododendron, Rhus, Ribes, Ricinus, Robinia, Rosa, Rubus, Salix, Sambucus, Sassafras, Sequoia, Secale, Setaria, Senecio, Shepherdia, Smilax, Sinapis, Solanum, Sophora, Sorbus, Sorghum, Spiraea, Staphylea, Stevia, Stewartia, Symphoricarpos, Syringa, Taxodium, Taxus, Theobroma, Thuja, Tilia, Triticum, Trigonella, Tsuga, Ulmus, Umbellularia, Vaccinium, Viburnum, Vitis, Vigna, Zanthoxylum, Zea*, or *Zelkova*.

Further aspects of the invention relates to the planting, cultivating, or harvesting a part or all of a transgenic plant of the present invention.

In addition to transgenic plants, the present invention also relates to transgenic plant parts including plant seeds, rootstock, and cuttings removed from the transgenic plant (including both woody and herbaceous cuttings). In certain embodiments, the plant, plant seed, rootstock, or cutting is (or is from) a monocot, including but not limited to those identified above. In other embodiments, the plant, plant seed, rootstock, or cutting is (or is from) a dicot, including but not limited to those identified above.

The present invention is also directed to one or more methods of enhancing plant growth or plant yield. As used herein, "yield" is defined as the measurement of the amount of a crop that was harvested per unit of land area. Crop yield is the measurement often used for grains or cereals and is typically measured as the amount of plant harvested per unit area for a given time, i.e., metric tons per hectare or kilograms per hectare. Crop yield can also refer to the actual seed or biomass produced or generated by the plant. Thus, an "enhanced yield" refers to an increase in yield relative to a non-transgenic control plant. As used herein, "enhanced plant growth" encompasses a number of aspects including, without limitation, faster vegetative growth including that which leads to early maturation, increased biomass yields, enhanced root development, increased seed/grain production, improved nutrient contents in biomass, and any combinations thereof.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; or (d) the subject plant or plant cell itself, under conditions in which the gene of interest is not expressed. A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

According to one embodiment, this method is carried out by providing a transgenic plant transformed with a nucleic acid construct of the present invention and growing the plant under conditions effective to permit the nucleic acid construct to express the TF polypeptide in vascular xylem tissue of the transgenic plant, and thereby enhance plant growth or yield.

According to a second embodiment, this method is carried out by providing a transgenic plant seed transformed with a nucleic acid construct of the present invention, planting the transgenic plant seed in a growth medium, and propagating a transgenic plant from the transgenic plant seed to permit the nucleic acid construct to express the TF polypeptide in vascular xylem tissue of the transgenic plant, and thereby enhance plant growth or yield.

According to a third embodiment, this method is carried out by providing a rootstock, cutting, or seed from a transgenic plant of the present invention, introducing the rootstock, cutting, or seed into a growth medium; and propagating a transgenic plant from the rootstock, cutting, or seed to permit the nucleic acid construct to express the TF polypeptide in vascular xylem tissue of the transgenic plant, and thereby enhance plant growth or yield.

According to a fourth embodiment, this method is carried out by providing a plant comprising a transgene that includes a heterologous, tissue-specific promoter operably linked to a polynucleotide encoding a TF involved in vascular xylem cell development, wherein the promoter specifically directs expression of the TF in vascular xylem tissue of the plant, and growing the plant under conditions effective to permit the transgene to express the TF polypeptide in vascular xylem tissue of the transgenic plant, and thereby enhance plant growth or yield.

According to a fifth embodiment, this method is carried out by providing a rootstock, cutting, or seed obtained from a plant comprising a transgene that includes a heterologous, tissue-specific promoter operably linked to a polynucleotide encoding a TF involved in vascular xylem cell development, wherein the promoter specifically directs expression of the TF in vascular xylem tissue of the plant, introducing the rootstock, cutting, or seed into a growth medium, and propagating a plant from the rootstock, cutting, or seed to permit the transgene to express the TF polypeptide in vascular xylem tissue of the transgenic plant, and thereby enhance plant growth or yield.

The present invention is also directed to one or more methods of enhancing degradability of plant biomass. As used herein, enhanced degradability of plant biomass refers to the rate of biomass degradation when otherwise exposed to similar environmental conditions, using comparable amounts of plant biomass, as compared to the biomass of a control plant. Enhanced degradability may refer to any one or more of: (i) increased release of glucose saccharides, (ii) increased release of xylose saccharides, (iii) reduced lignin composition, and any combinations thereof.

According to one embodiment, this method is carried out by providing a transgenic plant of the present invention and growing the plant under conditions effective to permit the nucleic acid construct to express the TF polypeptide in vascular xylem tissue of the transgenic plant, and thereby enhance degradability of plant biomass.

According to a second embodiment, this method is carried out by providing a transgenic plant seed of the present invention, planting the transgenic plant seed in a growth medium, and propagating a transgenic plant from the transgenic plant seed to permit the nucleic acid construct to express the TF polypeptide in vascular xylem tissue of the transgenic plant, and thereby enhance degradability of plant biomass.

According to a third embodiment, this method is carried out by providing a rootstock, cutting, or seed of the present invention, introducing the rootstock, cutting, or seed into a growth medium, and propagating a transgenic plant from the rootstock, cutting, or seed to permit the nucleic acid construct to express the TF polypeptide in vascular xylem tissue of the transgenic plant, and thereby enhance degradability of plant biomass.

According to a fourth embodiment, this method is carried out by providing a plant of the present invention and growing the plant under conditions effective to permit the transgene to express the TF polypeptide in vascular xylem tissue of the transgenic plant, and thereby enhance degradability of plant biomass.

According to a fifth embodiment, this method is carried out by providing a rootstock, cutting, or seed of the present invention, introducing the rootstock, cutting, or seed into a growth medium, and propagating a plant from the rootstock, cutting, or seed to permit the transgene to express the TF polypeptide in vascular xylem tissue of the transgenic plant, and thereby enhance degradability of plant biomass.

EXAMPLES

The examples below are intended to exemplify the practice of embodiments of the disclosure but are by no means intended to limit the scope thereof.

Example 1—Gene Combinations of a Promoter and a TF

A series of simple gene cassettes comprising TFs driven by promoters active in the target tissues were generated (see Tables 1 and 2). The promoters in Table 2 were selected based on their expression profile corresponding to the development of xylem tissue (Oikawa et al., "An Integrative Approach to the Identification of *Arabidopsis* and Rice Genes Involved in Xylan and Secondary Wall Development," *PLoS ONE* 5(11):e15481 (2010), which is hereby incorporated by reference in its entirety).

TABLE 1

Examples of Transcription Factors for Gene Combination

| Referenced expression database[1] | Expression[2] | Gene name | SEQ ID NO | | TF family | Species | Gene ID |
| --- | --- | --- | --- | --- | --- | --- | --- |
| | | | AA | NT | | | |
| *Arabidopsis* root transcripts | 291.76 | AtSHN3 | 1 | 37 | ERF/AP2 subfamily B-6 | *Arabidopsis* | At5g25390 |

TABLE 1-continued

Examples of Transcription Factors for Gene Combination

| Referenced expression database[1] | Expression[2] | Gene name | SEQ ID NO AA | SEQ ID NO NT | TF family | Species | Gene ID |
|---|---|---|---|---|---|---|---|
| Arabidopsis root transcripts | 611.33 | AtSHN1/WIN1 | 2 | 38 | ERF/AP2 subfamily B-6 | Arabidopsis | At1g15360 |
| Arabidopsis root transcripts | N/A | AtSHN2 | 3 | 39 | ERF/AP2 subfamily B-6 | Arabidopsis | At5g11190 |
| Arabidopsis root transcripts | 448.22 | AtMYB32 | 4 | 40 | R2R3-MYB Subfamily 4 | Arabidopsis | At4g34990 |
| Arabidopsis root transcripts | 2052.79 | AtMYB4 | 5 | 41 | R2R3-MYB Subfamily 4 | Arabidopsis | At4g38620 |
| Arabidopsis root transcripts | 2630.65 | MYB7 | 6 | 42 | R2R3-MYB Subfamily 4 | Arabidopsis | At2g16720 |
| Rice mas transcripts | N/A | OsSHN1 (OsEREB19) | 7 | 43 | ERF/AP2 subfamily B-6 | Rice | LOC_Os02g10760/ Os02g0202000 |
| Rice mas transcripts | 5636.25 | OsSHN2 (OsEREB114) | 8 | 44 | ERF/AP2 subfamily B-6 | Rice | LOC_Os06g40150/ Os06g0604000 |
| Rice mas transcripts | N/A | OsMYB108-L | 9 | 45 | R2R3-MYB Subfamily 4 | Rice | Os08g0549000 |
| Rice mas transcripts | 3694.68 | OsMYB108 | 10 | 46 | R2R3-MYB Subfamily 4 | Rice | LOC_Os09g36730/ Os09g0538400 |
| Poplar development transcripts | 206.76 | PdMYB221 | 11 | 47 | R2R3-MYB Subfamily 4 | Poplar | POPTR_0004s18020 |
| Poplar development transcripts | 3436.2 | PdMYB156 | 12 | 48 | R2R3-MYB Subfamily 4 | Poplar | POPTR_0009s13640 |
| N/A | N/A | SbEREB63 | 13 | 49 | ERF/AP2 subfamily B-6 | Sorghum | Sb04g006970 |
| N/A | N/A | SbEREB150 | 14 | 50 | ERF/AP2 subfamily B-6 | Sorghum | Sb10g023600 |
| N/A | N/A | SbMYB86 | 15 | 51 | R2R3-MYB Subfamily 4 | Sorghum | Sb07g024890 |
| N/A | N/A | SbMYB23 | 16 | 52 | R2R3-MYB Subfamily 4 | Sorghum | Sb02g031190 |
| Maize leaf gradient transcripts | 23.74 | ZmEREB46 | 17 | 53 | ERF/AP2 subfamily B-6 | Maize | GRMZM2G085678 |
| Maize leaf gradient transcripts | 12.97 | ZmMYB42 | 18 | 54 | R2R3-MYB Subfamily 4 | Maize | GRMZM2G419239 |
| Maize leaf gradient transcripts | 64.76 | ZmMYB31 | 19 | 55 | R2R3-MYB Subfamily 4 | Maize | GRMZM2G050305 |
| N/A | N/A | PyMYB4 | 20 | 56 | R2R3-MYB Subfamily 4 | Switchgrass | Pavir.J16675.1 |

[1]The Bio-Analytic Resource for Plant Biology, available online at http://bar.utoronto.ca/ and described in Toufighi et al, "The Botany Array Resource: e-Northerns, Expression Angling, and Promoter Analyses," *The Plant Journal* 43: 153-63 (2005), each of which is hereby incorporated by reference in its entirety.
[2]Relative gene expression value in vascular tissues or xylem-related organ.

The sequences referenced in Table 1 are set forth below.

```
                                            SEQ ID NO: 1
Met Val His Ser Lys Lys Phe Arg Gly Val Arg Gln Arg Gln Trp Gly

Ser Trp Val Ser Glu Ile Arg His Pro Leu Leu Lys Arg Arg Val Trp

Leu Gly Thr Phe Asp Thr Ala Glu Thr Ala Ala Arg Ala Tyr Asp Gln

Ala Ala Val Leu Met Asn Gly Gln Ser Ala Lys Thr Asn Phe Pro Val

Ile Lys Ser Asn Gly Ser Asn Ser Leu Glu Ile Asn Ser Ala Leu Arg

Ser Pro Lys Ser Leu Ser Glu Leu Leu Asn Ala Lys Leu Arg Lys Asn

Cys Lys Asp Gln Thr Pro Tyr Leu Thr Cys Leu Arg Leu Asp Asn Asp

Ser Ser His Ile Gly Val Trp Gln Lys Arg Ala Gly Ser Lys Thr Ser

Pro Asn Trp Val Lys Leu Val Glu Leu Gly Asp Lys Val Asn Ala Arg

Pro Gly Gly Asp Ile Glu Thr Asn Lys Met Lys Val Arg Asn Glu Asp
```

-continued

```
Val Gln Glu Asp Asp Gln Met Ala Met Gln Met Ile Glu Glu Leu Leu
Asn Trp Thr Cys Pro Gly Ser Gly Ser Ile Ala Gln Val
                                                              SEQ ID NO: 2
Met Val Gln Thr Lys Lys Phe Arg Gly Val Arg Gln Arg His Trp Gly
Ser Trp Val Ala Glu Ile Arg His Pro Leu Leu Lys Arg Arg Ile Trp
Leu Gly Thr Phe Glu Thr Ala Glu Glu Ala Ala Arg Ala Tyr Asp Glu
Ala Ala Val Leu Met Ser Gly Arg Asn Ala Lys Thr Asn Phe Pro Leu
Asn Asn Asn Asn Thr Gly Glu Thr Ser Glu Gly Lys Thr Asp Ile Ser
Ala Ser Ser Thr Met Ser Ser Ser Thr Ser Ser Ser Ser Leu Ser Ser
Ile Leu Ser Ala Lys Leu Arg Lys Cys Cys Lys Ser Pro Ser Pro Ser
Leu Thr Cys Leu Arg Leu Asp Thr Ala Ser Ser His Ile Gly Val Trp
Gln Lys Arg Ala Gly Ser Lys Ser Asp Ser Ser Trp Val Met Thr Val
Glu Leu Gly Pro Ala Ser Ser Ser Gln Glu Thr Thr Ser Lys Ala Ser
Gln Asp Ala Ile Leu Ala Pro Thr Thr Glu Val Glu Ile Gly Gly Ser
Arg Glu Glu Val Leu Asp Glu Glu Glu Lys Val Ala Leu Gln Met Ile
Glu Glu Leu Leu Asn Thr Asn
                                                              SEQ ID NO: 3
Met Val His Ser Arg Lys Phe Arg Gly Val Arg Gln Arg Gln Trp Gly
Ser Trp Val Ser Glu Ile Arg His Pro Leu Leu Lys Arg Arg Val Trp
Leu Gly Thr Phe Glu Thr Ala Glu Ala Ala Ala Arg Ala Tyr Asp Gln
Ala Ala Leu Leu Met Asn Gly Gln Asn Ala Lys Thr Asn Phe Pro Val
Val Lys Ser Glu Glu Gly Ser Asp His Val Lys Asp Val Asn Ser Pro
Leu Met Ser Pro Lys Ser Leu Ser Glu Leu Leu Asn Ala Lys Leu Arg
Lys Ser Cys Lys Asp Leu Thr Pro Ser Leu Thr Cys Leu Arg Leu Asp
Thr Asp Ser Ser His Ile Gly Val Trp Gln Lys Arg Ala Gly Ser Lys
Thr Ser Pro Thr Trp Val Met Arg Leu Glu Leu Gly Asn Val Val Asn
Glu Ser Ala Val Asp Leu Gly Leu Thr Thr Met Asn Lys Gln Asn Val
Glu Lys Glu Glu Glu Glu Glu Ala Ile Ile Ser Asp Glu Asp Gln
Leu Ala Met Glu Met Ile Glu Glu Leu Leu Asn Trp Ser
                                                              SEQ ID NO: 4
Met Gly Arg Ser Pro Cys Cys Glu Lys Asp His Thr Asn Lys Gly Ala
Trp Thr Lys Glu Glu Asp Asp Lys Leu Ile Ser Tyr Ile Lys Ala His
Gly Glu Gly Cys Trp Arg Ser Leu Pro Arg Ser Ala Gly Leu Gln Arg
Cys Gly Lys Ser Cys Arg Leu Arg Trp Ile Asn Tyr Leu Arg Pro Asp
Leu Lys Arg Gly Asn Phe Thr Leu Glu Glu Asp Asp Leu Ile Ile Lys
Leu His Ser Leu Leu Gly Asn Lys Trp Ser Leu Ile Ala Thr Arg Leu
Pro Gly Arg Thr Asp Asn Glu Ile Lys Asn Tyr Trp Asn Thr His Val
Lys Arg Lys Leu Leu Arg Lys Gly Ile Asp Pro Ala Thr His Arg Pro
Ile Asn Glu Thr Lys Thr Ser Gln Asp Ser Ser Asp Ser Ser Lys Thr
Glu Asp Pro Leu Val Lys Ile Leu Ser Phe Gly Pro Gln Leu Glu Lys
Ile Ala Asn Phe Gly Asp Glu Arg Ile Gln Lys Arg Val Glu Tyr Ser
Val Val Glu Glu Arg Cys Leu Asp Leu Asn Leu Glu Leu Arg Ile Ser
```

```
                                                       -continued
Pro Pro Trp Gln Asp Lys Leu His Asp Glu Arg Asn Leu Arg Phe Gly
Arg Val Lys Tyr Arg Cys Ser Ala Cys Arg Phe Gly Phe Gly Asn Gly
Lys Glu Cys Ser Cys Asn Asn Val Lys Cys Gln Thr Glu Asp Ser Ser
Ser Ser Ser Tyr Ser Ser Thr Asp Ile Ser Ser Ser Ile Gly Tyr Asp
Phe Leu Gly Leu Asn Asn Thr Arg Val Leu Asp Phe Ser Thr Leu Glu
Met Lys SEQ ID NO: 5
Met Gly Arg Ser Pro Cys Cys Glu Lys Ala His Thr Asn Lys Gly Ala
Trp Thr Lys Glu Glu Asp Glu Arg Leu Val Ala Tyr Ile Lys Ala His
Gly Glu Gly Cys Trp Arg Ser Leu Pro Lys Ala Ala Gly Leu Leu Arg
Cys Gly Lys Ser Cys Arg Leu Arg Trp Ile Asn Tyr Leu Arg Pro Asp
Leu Lys Arg Gly Asn Phe Thr Glu Glu Glu Asp Glu Leu Ile Ile Lys
Leu His Ser Leu Leu Gly Asn Lys Trp Ser Leu Ile Ala Gly Arg Leu
Pro Gly Arg Thr Asp Asn Glu Ile Lys Asn Tyr Trp Asn Thr His Ile
Arg Arg Lys Leu Ile Asn Arg Gly Ile Asp Pro Thr Ser His Arg Pro
Ile Gln Glu Ser Ser Ala Ser Gln Asp Ser Lys Pro Thr Gln Leu Glu
Pro Val Thr Ser Asn Thr Ile Asn Ile Ser Phe Thr Ser Ala Pro Lys
Val Glu Thr Phe His Glu Ser Ile Ser Phe Pro Gly Lys Ser Glu Lys
Ile Ser Met Leu Thr Phe Lys Glu Glu Lys Asp Glu Cys Pro Val Gln
Glu Lys Phe Pro Asp Leu Asn Leu Glu Leu Arg Ile Ser Leu Pro Asp
Asp Val Asp Arg Leu Gln Gly His Gly Lys Ser Thr Thr Pro Arg Cys
Phe Lys Cys Ser Leu Gly Met Ile Asn Gly Met Glu Cys Arg Cys Gly
Arg Met Arg Cys Asp Val Val Gly Gly Ser Ser Lys Gly Ser Asp Met
Ser Asn Gly Phe Asp Phe Leu Gly Leu Ala Lys Lys Glu Thr Thr Ser
Leu Leu Gly Phe Arg Ser Leu Glu Met Lys SEQ ID NO: 6
Met Gly Arg Ser Pro Cys Cys Glu Lys Glu His Met Asn Lys Gly Ala
Trp Thr Lys Glu Glu Asp Glu Arg Leu Val Ser Tyr Ile Lys Ser His
Gly Glu Gly Cys Trp Arg Ser Leu Pro Arg Ala Ala Gly Leu Leu Arg
Cys Gly Lys Ser Cys Arg Leu Arg Trp Ile Asn Tyr Leu Arg Pro Asp
Leu Lys Arg Gly Asn Phe Thr His Asp Glu Asp Glu Leu Ile Ile Lys
Leu His Ser Leu Leu Gly Asn Lys Trp Ser Leu Ile Ala Ala Arg Leu
Pro Gly Arg Thr Asp Asn Glu Ile Lys Asn Tyr Trp Asn Thr His Ile
Lys Arg Lys Leu Leu Ser Lys Gly Ile Asp Pro Ala Thr His Arg Gly
Ile Asn Glu Ala Lys Ile Ser Asp Leu Lys Lys Thr Lys Asp Gln Ile
Val Lys Asp Val Ser Phe Val Thr Lys Phe Glu Glu Thr Asp Lys Ser
Gly Asp Gln Lys Gln Asn Lys Tyr Ile Arg Asn Gly Leu Val Cys Lys
Glu Glu Arg Val Val Val Glu Glu Lys Ile Gly Pro Asp Leu Asn Leu
Glu Leu Arg Ile Ser Pro Pro Trp Gln Asn Gln Arg Glu Ile Ser Thr
Cys Thr Ala Ser Arg Phe Tyr Met Glu Asn Asp Met Glu Cys Ser Ser
Glu Thr Val Lys Cys Gln Thr Glu Asn Ser Ser Ser Ile Ser Tyr Ser
```

-continued

Ser Ile Asp Ile Ser Ser Ser Asn Val Gly Tyr Asp Phe Leu Gly Leu

Lys Thr Arg Ile Leu Asp Phe Arg Ser Leu Glu Met Lys

SEQ ID NO: 7

Met Gly Gln Ser Lys Lys Lys Phe Arg Gly Val Arg Gln Arg His Trp

Gly Ser Trp Val Ser Glu Ile Arg His Pro Leu Leu Lys Arg Arg Val

Trp Leu Gly Thr Phe Glu Thr Ala Glu Glu Ala Ala Arg Ala Tyr Asp

Glu Ala Ala Ile Leu Met Ser Gly Arg Asn Ala Lys Thr Asn Phe Pro

Val Ala Arg Asn Ala Thr Gly Glu Leu Thr Pro Ala Ala Ala Val Ala

Gly Arg Asp Gly Arg Val Gly Gly Gly Ser Gly Ser Ser Ser Ser Met

Thr Ala Asn Gly Gly Gly Asn Ser Leu Ser Gln Ile Leu Ser Ala Lys

Leu Arg Lys Cys Cys Lys Thr Pro Ser Pro Ser Leu Thr Cys Leu Arg

Leu Asp Pro Glu Lys Ser His Ile Gly Val Trp Gln Lys Arg Ala Gly

Ala Arg Ala Asp Ser Ser Trp Val Met Thr Val Glu Leu Asn Lys Asp

Thr Ala Val Ser Ser Ala Ala The Val Ala Ala Ala Thr Ala Val Ser

Ser Ser Asp Gln Pro Thr Pro Ser Asp Ser Thr Val Thr Thr Thr Ser

Thr Ser Thr Thr Gly Ser Pro Ser Pro Pro Pro Ala Met Asp Asp

Glu Glu Arg Ile Ala Leu Gln Met Ile Glu Glu Leu Leu Gly Arg Ser

Gly Pro Gly Ser Pro Ser His Gly Leu Leu His Gly Gly Glu Gly Ser

Leu Val Ile

SEQ ID NO: 8

Met Gly Gln Ser Lys Lys Lys Phe Arg Gly Val Arg Gln Arg His Trp

Gly Ser Trp Val Ser Glu Ile Arg His Pro Leu Leu Lys Arg Arg Val

Trp Leu Gly Thr Phe Glu Thr Ala Glu Glu Ala Ala Arg Ala Tyr Asp

Glu Ala Ala Ile Leu Met Ser Gly Arg Asn Ala Lys Thr Asn Phe Pro

Val Ala Arg Asn Ala Thr Gly Glu Leu Thr Pro Ala Ala Ala Val Ala

Gly Arg Asp Gly Arg Val Gly Gly Gly Ser Gly Ser Ser Ser Ser Met

Thr Ala Asn Gly Gly Gly Asn Ser Leu Ser Gln Ile Leu Ser Ala Lys

Leu Arg Lys Cys Cys Lys Thr Pro Ser Pro Ser Leu Thr Cys Leu Arg

Leu Asp Pro Glu Lys Ser His Ile Gly Val Trp Gln Lys Arg Ala Gly

Ala Arg Ala Asp Ser Ser Trp Val Met Thr Val Glu Leu Asn Lys Asp

Thr Ala Val Ser Ser Ala Ala Thr Val Ala Ala Ala Thr Ala Val Ser

Ser Ser Asp Gln Pro Thr Pro Ser Asp Ser Thr Val Thr Thr Thr Ser

Thr Ser Thr Thr Gly Ser Pro Ser Pro Pro Pro Ala Met Asp Asp

Glu Glu Arg Ile Ala Leu Gln Met Ile Glu Glu Leu Leu Gly Arg Ser

Gly Pro Gly Ser Pro Ser His Gly Leu Leu His Gly Gly Glu Gly Ser

Leu Val Ile

SEQ ID NO: 9

Met Gly Arg Ser Pro Cys Cys Glu Lys Glu His Thr Asn Lys Gly Ala

Trp Thr Lys Glu Glu Asp Glu Arg Leu Val Ala Tyr Ile Arg Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Ala Asp Glu Asp Asp Leu Ile Ile Lys

Leu His Ser Leu Leu Gly Asn Lys Trp Ser Leu Ile Ala Ala Arg Leu
Pro Gly Arg Thr Asp Asn Glu Ile Lys Asn Tyr Trp Asn Thr His Ile
Arg Arg Lys Leu Leu Gly Arg Gly Ile Asp Pro Val Thr His Arg Pro
Val Asn Ala Ala Ala Ala Thr Ile Ser Phe His Pro Gln Pro Pro Pro
Thr Thr Lys Glu Glu Gln Leu Ile Leu Ser Lys Pro Pro Lys Cys Pro
Asp Leu Asn Leu Asp Leu Cys Ile Ser Pro Pro Ser Cys Gln Glu Glu
Asp Asp Asp Tyr Glu Ala Lys Pro Ala Met Ile Val Arg Ala Pro Glu
Leu Gln Arg Arg Arg Gly Gly Leu Cys Phe Gly Cys Ser Leu Gly Leu
Gln Lys Glu Cys Lys Cys Ser Gly Gly Gly Ala Gly Ala Gly Ala Gly
Asn Asn Phe Leu Gly Leu Arg Ala Gly Met Leu Asp Phe Arg Ser Leu
Pro Met Lys

SEQ ID NO: 10
Met Gly Arg Ser Pro Cys Cys Glu Lys Ala His Thr Asn Lys Gly Ala
Trp Thr Lys Glu Glu Asp Asp Arg Leu Ile Ala Tyr Ile Lys Ala His
Gly Glu Gly Cys Trp Arg Ser Leu Pro Lys Ala Gly Leu Leu Arg
Cys Gly Lys Ser Cys Arg Leu Arg Trp Ile Asn Tyr Leu Arg Pro Asp
Leu Lys Arg Gly Asn Phe Thr Glu Glu Glu Asp Glu Leu Ile Ile Lys
Leu His Ser Leu Leu Gly Asn Lys Trp Ser Leu Ile Ala Gly Arg Leu
Pro Gly Arg Thr Asp Asn Glu Ile Lys Asn Tyr Trp Asn Thr His Ile
Arg Arg Lys Leu Leu Ser Arg Gly Ile Asp Pro Val Thr His Arg Pro
Ile Asn Asp Ser Ala Ser Asn Ile Thr Ile Ser Phe Glu Ala Ala Ala
Ala Ala Ala Arg Asp Asp Lys Ala Ala Val Phe Arg Arg Glu Asp His
Pro His Gln Pro Lys Ala Val Thr Val Ala Gln Glu Gln Ala Ala
Ala Asp Trp Gly His Gly Lys Pro Leu Lys Cys Pro Asp Leu Asn Leu
Asp Leu Cys Ile Ser Leu Pro Ser Gln Glu Glu Pro Met Met Lys
Pro Val Lys Arg Glu Thr Gly Val Cys Phe Ser Cys Ser Leu Gly Leu
Pro Lys Ser Thr Asp Cys Lys Cys Ser Ser Phe Leu Gly Leu Arg Thr
Ala Met Leu Asp Phe Arg Ser Leu Glu Met Lys

SEQ ID NO: 11
Met Gly Arg Ser Pro Cys Cys Glu Lys Ala His Thr Asn Lys Gly Ala
Trp Thr Lys Glu Glu Asp Asp Arg Leu Ile Ala Tyr Ile Arg Thr His
Gly Glu Gly Cys Trp Arg Ser Leu Pro Lys Ala Gly Leu Leu Arg
Cys Gly Lys Ser Cys Arg Leu Arg Trp Ile Asn Tyr Leu Arg Pro Asp
Leu Lys Arg Gly Asn Phe Thr Glu Glu Glu Asp Glu Leu Ile Ile Lys
Leu His Ser Leu Leu Gly Asn Lys Trp Ser Leu Ile Ala Gly Arg Leu
Pro Gly Arg Thr Asp Asn Glu Ile Lys Asn Tyr Trp Asn Thr His Ile
Arg Arg Lys Leu Leu Asn Arg Gly Ile Asp Pro Ala Thr His Arg Pro
Leu Asn Glu Pro Ala Gln Glu Ala Ser Thr Thr Ile Ser Phe Ser Thr
Thr Thr Ser Val Lys Glu Glu Ser Leu Ser Ser Val Lys Glu Glu Ser
Asn Lys Glu Lys Ile Ile Ser Ala Ala Ala Phe Ile Cys Lys Glu Glu
Lys Thr Pro Val Gln Glu Arg Cys Pro Asp Leu Asn Leu Glu Leu Arg
Ile Ser Leu Pro Cys Gln Asn Gln Pro Asp Arg His Gln Ala Phe Lys

-continued

Thr Gly Gly Ser Thr Ser Leu Cys Phe Ala Cys Ser Leu Gly Leu Gln

Asn Ser Lys Asp Cys Ser Cys Ser Val Ile Val Gly Thr Ile Gly Ser

Ser Ser Ser Ala Gly Ser Lys Thr Gly Tyr Asp Phe Leu Gly Met Lys

Ser Gly Val Leu Asp Tyr Arg Gly Leu Glu Met Lys

SEQ ID NO: 12

Met Gly Arg Ser Pro Cys Cys Glu Lys Ala His Thr Asn Lys Gly Ala

Trp Thr Lys Glu Glu Asp Asp Arg Leu Val Ala Tyr Ile Arg Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Glu Ala Glu Asp Glu Leu Ile Ile Lys

Leu His Ser Leu Leu Gly Asn Lys Trp Ser Leu Ile Ala Gly Arg Leu

Pro Gly Arg Thr Asp Asn Glu Ile Lys Asn Tyr Trp Asn Thr His Ile

Arg Arg Lys Leu Leu Asn Arg Gly Ile Asp Pro Ala Thr His Arg Pro

Leu Asn Glu Pro Ala Val Gln Glu Ala Thr Thr Thr Ile Ser Phe Thr

Thr Thr Thr Thr Ser Val Leu Glu Glu Glu Ser Leu Gly Ser Ile Ile

Lys Glu Glu Asn Lys Glu Lys Ile Ile Ser Ala Thr Ala Phe Val Cys

Lys Glu Glu Lys Thr Gln Val Gln Glu Arg Cys Pro Asp Leu Asn Leu

Glu Leu Gly Ile Ser Leu Pro Ser Gln Asn Gln Pro Asp His His Gln

Pro Phe Lys Thr Gly Gly Ser Arg Ser Leu Cys Phe Ala Cys Ser Leu

Gly Leu Gln Asn Ser Lys Asp Cys Ser Cys Asn Val Ile Val Ser Thr

Val Gly Ser Ser Gly Ser Thr Ser Thr Lys Thr Gly Tyr Asp Phe Leu

Gly Met Lys Ser Gly Val Leu Asp Tyr Arg Ser Leu Glu Met Lys

SEQ ID NO: 13

Met Pro Thr Pro Thr Pro Thr Pro Thr Pro Thr Cys Gly Asp Gly Ser

Leu Ala Gly Phe Ala Leu Leu Leu Arg Gly Glu Lys Arg Val Ala Asn

Gly Ala Arg Gly Gly Arg Gly Ile Gly Gly Glu Arg Ala Lys Ile Ile

Arg Arg Arg His Ala Glu Lys Thr His Gly Arg Arg Glu Arg Gly Gly

His Arg Arg Ser His Arg Leu Ala Tyr Pro Leu Trp Val Leu Asp Ile

Arg Ser Pro Asn Gly Ile Met Leu Gly Ile Phe Arg Gly Ala Ala Leu

Trp Leu Trp Thr Leu Ala Trp His Met

SEQ ID NO: 14

Met Val Gln Ser Lys Lys Lys Phe Arg Gly Val Arg Gln Arg His Trp

Gly Ser Trp Val Ser Glu Ile Arg His Pro Leu Leu Lys Arg Arg Val

Trp Leu Gly Thr Phe Glu Thr Ala Glu Glu Ala Ala Arg Ala Tyr Asp

Glu Ala Ala Val Leu Met Ser Gly Arg Asn Ala Lys Thr Asn Phe Pro

Val Pro Arg Thr Ala Thr Gly Glu Leu Ala Pro Val Pro Ala Ala Arg

Asp Ala Arg Gly Gly Gly Gly Ser Ser Ser Ala Ala Ala Ala Pro Gly

Gly Gly Thr Ser Asn Leu Ser Gln Ile Leu Ser Ala Lys Leu Arg Lys

Cys Cys Lys Thr Pro Ser Pro Ser Leu Thr Cys Leu Arg Leu Asp Pro

Glu Lys Ser His Ile Gly Val Trp Gln Lys Arg Ala Gly Ala Arg Ala

Asp Ser Ser Trp Val Met Thr Val Gln Leu Asn Lys Asp Val Pro Pro

Pro Ala Ser Ser Ser Gly Glu Glu Pro Val Pro Ser Asp Gly Gly Ala

-continued

Ala Ala Thr Thr Pro Thr Ser Thr Ser Thr Ser Ser Thr Val Thr Thr
Thr Gly Ser Pro Pro Pro Ala Met Met Met Asp Asp Glu Glu Arg Ile
Ala Leu Gln Met Ile Glu Glu Leu Leu Gly Ser Ser His Ser His Gly
Met Phe Gln Gly Ala Ala Gly Ser Ile Val Ile

SEQ ID NO: 15
Met Gly Arg Ser Pro Cys Cys Glu Lys Ala His Thr Asn Lys Gly Ala
Trp Thr Lys Glu Glu Asp Asp Arg Leu Val Ala Tyr Ile Arg Ala His
Gly Glu Gly Cys Trp Arg Ser Leu Pro Lys Ala Ala Gly Leu Met Arg
Cys Gly Lys Ser Cys Arg Leu Arg Trp Ile Asn Tyr Leu Arg Pro Asp
Leu Lys Arg Gly Asn Phe Thr Ala Asp Glu Asp Leu Ile Ile Lys
Leu His Ser Leu Leu Gly Asn Lys Trp Ser Leu Ile Ala Ala Arg Leu
Pro Gly Arg Thr Asp Asn Glu Ile Lys Asn Tyr Trp Asn Thr His Ile
Arg Arg Lys Leu Leu Gly Arg Gly Ile Asp Pro Val Thr His Arg Pro
Ile Ala Asp Ala Gly Ala Gly Thr Val Thr Thr Ile Ser Phe Gln Pro
Asn Lys Pro Asn Ala Ala Val Ala Ala Gln Ala Pro Gln His Gln Pro
Ile Lys Ala Val Ala Thr Ala Val Val Lys Val Pro Arg Cys Pro Asp
Leu Asn Leu Asp Leu Cys Ile Ser Pro Pro Cys Gln Gln Lys Glu Asp
Glu Glu Leu Asp Leu Lys Pro Ala Val Val Val Lys Arg Glu Val Leu
Gln Ala Gly His Gly Gly Ser Leu Cys Phe Gly Cys Ser Leu Gly Ile
Gln Lys Gly Ala Pro Gly Cys Ser Cys Ser Ser Ser Asn Ser His His
Arg Phe Leu Gly Leu Arg Ser Gly Met Leu Asp Phe Arg Gly Leu Glu
Met Lys

SEQ ID NO: 16
Met Gly Arg Ser Pro Cys Cys Glu Lys Ala His Thr Asn Lys Gly Ala
Trp Thr Lys Glu Glu Asp Asp Arg Leu Val Ala Tyr Ile Lys Ala His
Gly Glu Gly Cys Trp Arg Ser Leu Pro Lys Ala Ala Gly Leu Leu Arg
Cys Gly Lys Ser Cys Arg Leu Arg Trp Ile Asn Tyr Leu Arg Pro Asp
Leu Lys Arg Gly Asn Phe Thr Glu Glu Glu Asp Glu Leu Ile Ile Lys
Leu His Ser Leu Leu Gly Asn Lys Trp Ser Leu Ile Ala Gly Arg Leu
Pro Gly Arg Thr Asp Asn Glu Ile Lys Asn Tyr Trp Asn Thr His Ile
Arg Arg Lys Leu Leu Ser Arg Gly Ile Asp Pro Val Thr His Arg Pro
Ile Asn Glu His Thr Ser Asn Ile Thr Ile Ser Phe Glu Ala Ala Ala
Ala Ala Arg Asp Arg Glu Glu Asn Lys Gly Ala Val Phe Arg Leu Glu
Glu His Asn Lys Ala Thr Ala Ala Ala Ala Ala Ile Gly Arg Asp
His His Gln Asn His His Pro Ala Gly Asp Trp Gly Gln Gly Lys Pro
Leu Lys Cys Pro Asp Leu Asn Leu Asp Leu Cys Ile Ser Pro Pro Ala
Ala Pro Cys Gln Glu Glu Lys Ala Met Val Thr Met Lys Pro Val Lys
Arg Glu Ala Gly Leu Cys Phe Ser Cys Ser Leu Gly Leu Pro Lys Ser
Ala Asp Cys Lys Cys Ser Asn Phe Leu Gly Leu Arg Thr Ala Met Leu
Asp Phe Arg Ser Leu Glu Met Lys

```
                                                              SEQ ID NO: 17
Met Thr Glu Asn Leu His Ser Arg Lys Met Val Gln Pro Lys Lys Phe

Arg Gly Val Arg Gln Arg His Trp Gly Ser Trp Val Ser Glu Ile Arg

His Pro Leu Leu Lys Arg Arg Val Trp Leu Gly Thr Phe Glu Thr Ala

Glu Glu Ala Ala Arg Ala Tyr Asp Glu Ala Ala Val Leu Met Ser Gly

Arg Asn Ala Lys Thr Asn Phe Pro Ile Gln Arg Ser Ser Thr Gly Glu

Pro Thr Pro Ala Ala Gly Arg Asp Ala Arg Ser Asn Phe Ser Ser Gly

Ser Ser Thr Thr Asn Leu Ser Gln Ile Leu Ser Ala Lys Leu Arg Lys

Cys Cys Lys Ala Pro Ser Pro Ser Leu Thr Cys Leu Arg Leu Asp Pro

Glu Lys Ser His Ile Gly Val Trp Gln Lys Arg Ala Gly Ala Arg Ala

Asp Ser Asn Trp Val Met Thr Val Glu Leu Asn Lys Asp Ala Ala Ser

Thr Asp Ala Ala Ser Gln Ser Thr Ser Ala Thr Thr Ala Pro Pro Ala

Thr Pro Met Asp Glu Glu Glu Arg Ile Ala Leu Gln Met Ile Glu Glu

Leu Leu Ser Ser Ser Ser Pro Ala Ser Pro Ser Asn Gly Asp Asp Gln

Gly Arg Phe Ile Ile

SEQ ID NO: 18
Met Gly Arg Ser Pro Cys Cys Glu Lys Ala His Thr Asn Arg Gly Ala

Trp Thr Lys Glu Glu Asp Glu Arg Leu Val Ala Tyr Val Arg Ala His

Gly Glu Gly Cys Trp Arg Ser Leu Pro Arg Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Ala Asp Glu Asp Asp Leu Ile Val Lys

Leu His Ser Leu Leu Gly Asn Lys Trp Ser Leu Ile Ala Ala Arg Leu

Pro Gly Arg Thr Asp Asn Glu Ile Lys Asn Tyr Trp Asn Thr His Ile

Arg Arg Lys Leu Leu Gly Ser Gly Ile Asp Pro Val Thr His Arg Arg

Val Ala Gly Gly Ala Ala Thr Thr Ile Ser Phe Gln Pro Ser Pro Asn

Thr Ala Val Ala Ala Ala Ala Glu Thr Ala Ala Gln Ala Pro Ile Lys

Ala Glu Glu Thr Ala Ala Val Lys Ala Pro Arg Cys Pro Asp Leu Asn

Leu Asp Leu Cys Ile Ser Pro Pro Cys Gln His Glu Asp Asp Gly Glu

Glu Glu Glu Glu Glu Leu Asp Leu Ile Lys Pro Ala Val Val Lys Arg

Glu Ala Leu Gln Ala Gly His Gly His Gly His Gly Leu Cys Leu Gly

Cys Gly Leu Gly Gly Gln Lys Gly Ala Gly Cys Ser Cys Ser Asn

Gly His His Phe Leu Gly Leu Arg Thr Ser Val Leu Asp Phe Arg Gly

Leu

SEQ ID NO: 19
Met Gly Arg Ser Pro Cys Cys Glu Lys Ala His Thr Asn Lys Gly Ala

Trp Thr Lys Glu Glu Asp Glu Arg Leu Val Ala His Ile Arg Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Glu Glu Glu Asp Glu Leu Ile Val Lys

Leu His Ser Val Leu Gly Asn Lys Trp Ser Leu Ile Ala Gly Arg Leu

Pro Gly Arg Thr Asp Asn Glu Ile Lys Asn Tyr Trp Asn Thr His Ile

Arg Arg Lys Leu Leu Ser Arg Gly Ile Asp Pro Val Thr His Arg Pro
```

-continued

Val Thr Glu His His Ala Ser Asn Ile Thr Ile Ser Phe Glu Thr Glu

Val Ala Ala Ala Ala Arg Asp Asp Lys Lys Gly Ala Val Phe Arg Leu

Glu Glu Glu Glu Glu Arg Asn Lys Ala Thr Met Val Val Gly Arg Asp

Arg Gln Ser Gln Ser Gln Ser His Ser His Pro Ala Gly Glu Trp Gly

Gln Gly Lys Arg Pro Leu Lys Cys Pro Asp Leu Asn Leu Asp Leu Cys

Ile Ser Pro Pro Cys Gln Glu Glu Glu Met Glu Glu Ala Ala Met

Arg Val Arg Pro Ala Val Lys Arg Glu Ala Gly Leu Cys Phe Gly Cys

Ser Leu Gly Leu Pro Arg Thr Ala Asp Cys Lys Cys Ser Ser Ser Ser

Phe Leu Gly Leu Arg Thr Ala Met Leu Asp Phe Arg Ser Leu Glu Met

Lys

SEQ ID NO: 20

Met Gly Arg Ser Pro Cys Cys Glu Lys Ala His Thr Asn Lys Gly Ala

Trp Thr Lys Glu Glu Asp Asp Arg Leu Val Ala Tyr Ile Arg Ala His

Gly Glu Gly Cys Trp Arg Ser Leu Pro Lys Ala Ala Gly Leu Leu Arg

Cys Gly Lys Ser Cys Arg Leu Arg Trp Ile Asn Tyr Leu Arg Pro Asp

Leu Lys Arg Gly Asn Phe Thr Ala Asp Glu Asp Asp Leu Ile Val Lys

Leu His Ser Leu Leu Gly Asn Lys Trp Ser Leu Ile Ala Ala Arg Leu

Pro Gly Arg Thr Asp Asn Glu Ile Lys Asn Tyr Trp Asn Thr His Ile

Lys Arg Lys Leu Leu Ser Arg Gly Ile Asp Pro Val Thr His Arg Pro

Ile Ala Asp Ala Ala Arg Asn Val Thr Ile Ser Phe Gln Pro Asp Ala

Pro Ser Gln Gln Gln Leu Ser Asp Asp Ala Glu Ala Pro Pro Pro

Pro Pro Gln Gln Gln Gln Gln Leu Lys Pro Pro Pro Arg Cys Pro Asp

Leu Asn Leu Asp Leu Cys Ile Ser Pro Pro Cys His Lys Glu Glu Glu

Asp Gln Glu Leu Val Lys Pro Ala Ala Val Lys Arg Glu Met Leu Gln

Ala Gly His Gly Thr Leu Gly Leu Cys Phe Gly Cys Ser Leu Gly Leu

Gln Lys Gly Ala Ala Gly Cys Thr Cys Ser Ser Asn Ser His Phe Leu

Gly Leu Arg Val Gly Met Leu Leu Asp Phe Arg Gly Leu Glu Met Lys

SEQ ID NO: 37 atg gta cat tcg aag aag ttc cga ggt gtc cgc cag cgt cag tgg ggt tct tgg gtt tct gag att cgt cat cct ctc ttg aag aga aga gtg tgg cta gga aca ttc gac acg gcg gaa aca gcg gct aga gcc tac gac caa gcc gcg gtt cta atg aac ggc cag agc gcg aag act aac ttc ccc gtc atc aaa tcg aac ggt tca aat tcc ttg gag att aac tct gcg tta agg tct ccc aaa tca tta tcg gaa cta ttg aac gct aag cta agg aag aac tgt aaa gac cag aca ccg tat ctg acg tgt ctc cgc ctc gac aac gac agc tca cac atc ggc gtc tgg cag aaa cgc gcc ggg tca aaa acg agt cca aac tgg gtc aag ctt gtt gaa cta ggt gac aaa gtt aac gca cgt ccc ggt ggt gat att gag act aat aag atg aag gta cga aac gaa gac gtt cag gaa gat gat caa atg gcg atg cag atg atc gag gag ttg ctt aac tgg acc tgt cct gga tct gga tcc att gca cag gtc taa

SEQ ID NO: 38

```
atg gta cag acg aag aag ttc aga ggt gtc agg caa cgc cat tgg ggt
tct tgg gtc gct gag att cgt cat cct ctc ttg aaa cgg agg att tgg
cta ggg acg ttc gag acc gca gag gag gca gca aga gca tac gac gag
gcc gcc gtt tta atg agc ggc cgc aac gcc aaa acc aac ttt ccc ctc
aac aac aac aac acc gga gaa act tcc gag ggc aaa acc gat att tca
gct tcg tcc aca atg tca tcc tca aca tca tct tca tcg ctc tct tcc
atc ctc agc gcc aaa ctg agg aaa tgc tgc aag tct cct tcc cca tcc
ctc acc tgc ctc cgt ctt gac aca gcc agc tcc cat atc ggc gtc tgg
cag aaa cgg gcc ggt tca aag tct gac tcc agc tgg gtc atg acg gtg
gag cta ggt ccc gca agc tcc tcc caa gag act act agt aaa gct tca
caa gac gct att ctt gct ccg acc act gaa gtt gaa att ggt ggc agc
aga gaa gaa gta ttg gat gag gaa gaa aag gtt gct ttg caa atg ata
gag gag ctt ctc aat aca aac taa
```

SEQ ID NO: 39

```
atg gta cat tcg agg aag ttc cga ggt gtc cgc cag cga caa tgg ggt
tct tgg gtc tct gag att cgc cat cct cta ttg aag aga aga gtg tgg
ctt gga act ttc gaa acg gca gaa gcg gct gca aga gca tac gac caa
gcg gct ctt cta atg aac ggc caa aac gct aag acc aat ttc cct gtc
gta aaa tca gag gaa ggc tcc gat cac gtt aaa gat gtt aac tct ccg
ttg atg tca cca aag tca tta tct gag ctt ttg aac gct aag cta agg
aag agc tgc aaa gac cta acg cct tct ttg acg tgt ctc cgt ctt gat
act gac agt tcc cac att gga gtt tgg cag aaa cgg gcc ggg tcg aaa
aca agt ccg act tgg gtc atg cgc ctc gaa ctt ggg aac gta gtc aac
gaa agt gcg gtt gac tta ggg ttg act acg atg aac aaa caa aac gtt
gag aaa gaa gaa gaa gaa gaa gaa gct att att agt gat gag gat cag
tta gct atg gag atg atc gag gag ttg ctg aat tgg agt tga
```

SEQ ID NO: 40

```
atg gga agg tct cct tgc tgt gag aaa gac cac aca aac aaa gga gct
tgg act aag gaa gaa gac gat aag ctc atc tct tac atc aaa gct cac
ggt gaa ggt tgt tgg cgt tct ctt cct aga tcc gcc ggt ctt caa cgt
tgc gga aaa agc tgt cgt ctc cga tgg att aac tat ctc cga cct gat
ctc aag agg ggt aac ttc acc ctc gaa gaa gat gat ctc atc atc aaa
cta cat agc ctt ctc ggt aac aag tgg tct ctt att gcg acg aga tta
cca gga aga aca gat aac gag att aag aat tac tgg aac aca cat gtt
aag agg aag cta tta aga aaa ggg att gat ccg gcg act cat cga cct
atc aac gag acc aaa act tct caa gat tcg tct gat tct agt aaa aca
gag gac cct ctt gtc aag att ctc tct ttt ggt cct cag ctg gag aaa
ata gca aat tcg ggg gac gag aga att caa aag aga gtt gag tac tca
gtt gtt gaa gaa aga tgt ctg gac ttg aat ctt gag ctt agg atc agt
cca cca tgg caa gac aag ctc cat gat gag agg aac cta agg ttt ggg
aga gtg aag tat agg tgc agt gcg tgc cgt ttt gga ttc ggg aac ggc
```

-continued aag gag tgt agc tgt aat aat gtg aaa tgt caa aca gag gac agt agt agc agt agt tat tct tca acc gac att agt agt agc att ggt tat gac ttc ttg ggt cta aac aac act agg gtt ttg gat ttt agc act ttg gaa atg aaa tga SEQ ID NO: 41
atg gga agg tca ccg tgc tgt gag aaa gct cac aca aac aaa gga gca tgg acg aaa gaa gag gac gag agg ctc gtc gcc tac att aaa gct cat gga gaa ggc tgc tgg aga tct ctc ccc aaa gcc gcc gga ctt ctt cgc tgt ggc aag agc tgc cgt ctc cgg tgg atc aac tat ctc cgg cct gac ctt aag cgt gga aac ttc acc gag gaa gaa gac gaa ctc atc atc aag ctc cat agc ctt ctt ggc aac aaa tgg tcg ctt att gcc ggg aga tta ccg gga aga aca gat aac gag ata aag aac tat tgg aac acg cat ata cga aga aag ctt ata aac aga ggg att gat cca acg agt cat aga cca atc caa gaa tca tca gct tct caa gat tct aaa cct aca caa cta gaa cca gtt acg agt aat acc att aat atc tca ttc act tct gct cca aag gtc gaa acg ttc atc gaa agt ata agc ttt ccg gga aaa tca gag aaa atc tca atg ctt acg ttc aaa gaa gaa aaa gat gag tgc cca gtt caa gaa aag ttc cca gat ttg aat ctt gag ctc aga atc agt ctt cct gat gat gtt gat cgt ctt caa ggg cat gga aag tca aca acg cca cgt tgt ttc aag tgc agc tta ggg atg ata aac ggc atg gag tgc aga tgc gga aga atg aga tgc gat gta gtc gga ggt agc agc aag ggg agt gac atg agc aat gga ttt gat ttt tta ggg ttg gca aag aaa gag acc act tct ctt ttg ggc ttt cga agc ttg gag atg aaa taa SEQ ID NO: 42
atg gga aga tct cct tgc tgc gag aaa gaa cac atg aac aaa ggt gct tgg act aaa gaa gaa gat gag aga cta gtc tct tac atc aag tct cac ggt gaa ggt tgt tgg cga tct ctt cct aga gcc gct ggt ctc ctt cgc tgc ggt aaa agc tgc cgt ctt cgg tgg att aac tat ctc cga cct gat ctc aaa aga gga aac ttt aca cat gat gaa gat gaa ctt atc atc aag ctt cat agc ctc cta ggc aac aag tgg tct ttg att gcg gcg aga tta cct gga aga aca gat aac gag atc aag aac tac tgg aac aca cat ata aag agg aag ctt ttg agc aaa ggg att gat cca gcc act cat aga ggg atc aac gag gca aaa att tct gat ttg aag aaa aca aag gac caa att gta aaa gat gtt tct ttt gtg aca aag ttt gag gaa aca gac aag tct ggg gac cag aag caa aat aag tat att cga aat ggg tta gtt gca aa gaa gag aga gtt gtt gtt gaa gaa aaa ata ggc cca gat ttg aat ctt gag ctt agg atc agt cca cca tgg caa aac cag aga gaa ata tct act tgc act gcg tcc cgt ttt tac atg gaa aac gac atg gag tgt agt agt gaa act gtg aaa tgt caa aca gag aat agt agc agc att agc tat tct tct att gat att agt agt agt aac gtt ggt tat gac ttc ttg ggt ttg aag aca aga att ttg gat ttt cga agc ttg gaa atg aaa taa -continued SEQ ID NO: 43
atg gta cag cca aag aag aag ttt cgt gga gtc agg cag cgg cac tgg
ggc tcc tgg gtc tct gag atc aga cac ccc ctc ctt aaa agg agg gtg
tgg ctg ggc acc ttt gag acg gcc gag gag gct gcg cga gcc tac gat
gag gct gct gtg ctg atg agt ggc cgc aac gcc aag acc aac ttc ccc
gtg cag agg aac tcc acc ggt gat ctc gcc acg gcc gca gac cag gac
gcc cgt agc aat ggc ggt agc agg aac tcc tcc gcg ggc aac ctg tca
cag att ctc agt gct aag ctc cgc aag tgc tgc aag gcg cca tct ccg
tcc tta acc tgc ctc cgc ctc gac ccc gag aag tcc cac att ggc gtg
tgg caa aag cgc gca ggg gcc cgt gct gac tcc aac tgg gtg atg acg
gtg gag ctc aac aaa gag gta gaa cca act gaa cct gca gct cag ccc
aca tca aca gca aca gct tcg caa gtg aca atg gat gat gag gaa aag
att gcg ctg caa atg atc gag gag ttg ctg agc agg agc agt cca gct
tca ccc tca cat gga gag gga gag ggt agc ttt gtc atc tga SEQ ID NO: 44
atg gga cag tcg aag aag aag ttc cgc gga gtc agg cag cgc cac tgg
ggc tcc tgg gtc tcc gag atc agg cac cct ctc ctt aag agg agg gtg
tgg ctg ggt acc ttt gag acg gcg gag gag gcg gcg cgg gcg tac gac
gag gcc gcc atc ctg atg agc ggc cgc aac gcc aag acc aac ttc cca
gtc gcg agg aac gcc acg ggg gag ctc aca ccg gcg gct gcg gtg gca
ggg cgg gat ggc cgt gtc ggc ggc ggc agc ggc agc tcg tcc tca atg
acg gcc aac ggc ggc ggg aac agc ctg tct cag atc ctc agc gcc aag
ctc cgc aag tgc tgc aag acg ccg tcg ccg tcg ctc acc tgc ctc cgc
ctt gac ccg gag aag tcc cac att ggc gtc tgg cag aag cgc gcc ggc
gca cgc gct gac tcc agc tgg gtc atg acc gtc gag ctc aac aag gac
acg gcc gtg tcg tcg gct gcg acg gtg gca gca gca aca gca gtg tcg
tcc agc gac cag ccg act ccg agt gac agc aca gtc aca acg acg tcc
acg tcc acc acg ggc tcg ccg tcg cca cca cct ccg gca atg gac gac
gag gag agg atc gcg ctg cag atg atc gag gag ctg ctg ggc agg agc
ggc ccg ggc tcg ccg tca cat ggg ctg ctg cac ggt ggt gaa ggt agc
ctc gtc atc tga SEQ ID NO: 45
atg ggg agg tcg ccg tgc tgc gag aag gag cac act aac aag ggc gcg
tgg acc aag gag gag gac gag cgc ctc gtc gcc tac atc cgc gcc cac
ggc gag ggc tgc tgg cgc tcg ctc ccc aag gcc gcc ggc ctc ctc cgc
tgc ggc aag agc tgc cgc ctc cgc tgg atc aac tac ctc cgc ccc gac
ctc aag cgc ggc aac ttc acc gcc gac gag gac gac ctc atc atc aag
ctc cac agc ctc ctc ggc aac aag tgg tct ctg atc gcg gcg agg ctg
ccg ggg agg acg gac aac gag atc aag aac tac tgg aac acg cac atc
cgc cgg aag ctt ctc ggc agg ggg atc gac ccc gtc acg cac cgc ccc
gtc aac gcc gcc gcc gcc acc atc tcc ttc cat ccc cag ccg ccg cca
acg acg aag gag gag cag ctc ata ctc agc aag ccg ccc aag tgc ccc -continued gac ctc aac ctg gac ctc tgc atc agc ccg ccg tcg tgc cag gaa gaa gac gat gac tat gag gcg aag ccg gcg atg atc gtg agg gcg ccg gag ctg cag cgc cgc cgc ggc ggc ctc tgc ttc ggc tgc agc ctc ggc ctc cag aag gag tgc aag tgc agc ggc ggc ggc gcc ggc gcc ggc gcc ggc aac aac ttc ctc ggc ctc agg gct ggc atg ctc gac ttc aga agc ctc ccc atg aaa tga

SEQ ID NO: 46 atg ggg agg tca ccg tgc tgc gag aag gca cac acc aac aag gga gca tgg acc aag gag gaa gat gac cgg ctc att gcc tac atc aag gcg cac ggc gaa ggt tgc tgg cga tcg ctg ccc aag gcc gcc ggc ctc ctc cgc tgt ggc aag agc tgc cgc ctc cgg tgg atc aac tac ctc cgg cct gac ctc aag cgc ggc aac ttc acc gag gag gag gat gag ctg atc atc aag ctt cac agc ctt tta ggc aac aaa tgg tct ctg ata gcc ggg agg ttg cca gga aga acg gac aac gag atc aag aac tac tgg aac acg cac atc agg agg aag ctg ctg agc cgt ggc atc gac ccg gtg aca cac cgg ccg atc aac gac agc gcg tcc aac atc acc ata tca ttc gag gcg gcc gcg gcg gcg gcg agg gac gac aag gcc gcc gtg ttc cgg cga gag gac cat cct cat cag ccg aag gcg gtg aca gtg gca cag gag cag cag gca gcc gcc gat tgg ggc cat ggg aag cca ctc aag tgc cct gac ctc aat ctg gac ctc tgc atc agc ctc cct tcc caa gaa gag ccc atg atg atg aag ccg gtg aag agg gag acc ggc gtc tgc ttc agc tgc agc ctg ggg ctc ccc aag agc aca gac tgc aag tgc agc agc ttc ctg gga ctc agg aca gcc atg ctc gac ttc aga agc ttg gaa atg aaa tga

SEQ ID NO: 47 atg gga agg tct cct tgc tgt gaa aaa gct cat aca aac aaa ggc gca tgg act aag gaa gaa gat gat cgc ctt att gct tac att aga acc cac ggt gaa ggt tgc tgg cgt tca ctt cct aaa gct gct ggc ctt cta aga tgc ggc aag agc tgc aga ctt cgt tgg atc aac tat tta aga cct gac ctt aaa cgt ggc aat ttt act gaa gaa gaa gat gag ctc att atc aaa ctc cat agt ctc ctc ggc aac aaa tgg tca ctt ata gcc gga agg tta cca ggg aga aca gat aat gag ata aag aat tat tgg aac aca cat ata aga agg aag ctc ttg aat aga ggc ata gat cct gcg act cat agg cca ctc aat gaa cca gcc caa gaa gct tca aca aca ata tct ttc agc act act acc tca gtt aaa gaa gag tcg ttg agt tct gtt aaa gag gaa agt aat aag gag aag ata att agc gca gct gct ttt ata tgc aaa gaa gag aaa acc cca gtt caa gaa agg tgt cca gac ttg aat ctt gaa ctt aga att agc ctt cct tgc caa aac cag cct gat cgt cac cag gca ttc aaa act gga gga agt aca agt ctt tgt ttt gct tgc agc ttg ggg cta caa aac agc aag gac tgc agt tgc agt gtc att gtg ggt act att gga agc agc agt agt gct ggc tcc aaa act ggc tat gac ttc tta ggg atg aaa agt ggt gtg ttg gat tat aga ggt ttg gag atg aaa tga

SEQ ID NO: 48

```
atg gga agg tct cct tgc tgt gaa aaa gcc cat aca aac aag ggt gcg
tgg acc aag gag gaa gac gat cgc ctt gtt gct tac att aga gct cac
ggt gaa ggt tgc tgg cgc tca ctt cct aaa gcc gct ggc ctt ctt aga
tgt ggc aag agt tgc aga ctt cgt tgg atc aac tat tta aga cct gac
ctt aaa cgt ggc aat ttc acc gaa gca gaa gat gag ctc att atc aaa
ctc cat agc ctc ctt gga aac aaa tgg tca ctc ata gct gga aga tta
cca ggg aga aca gat aat gag ata aag aat tat tgg aac aca cat ata
aga agg aag ctt ttg aac aga ggc ata gat ccc gca act cat agg cca
ctc aac gaa cca gca gta caa gaa gcc aca aca aca ata tct ttc acc
acg act act act tca gta ctt gaa gaa gag tct ctg ggt tct ata att
aaa gag gaa aat aaa gag aag ata att agc gca act gct ttc gta tgc
aaa gaa gag aaa acc caa gtt caa gaa agg tgt cca gac ttg aat ctc
gag ctt gga att agc ctt cct tcc caa aac cag cct gat cat cac cag
cca ttc aaa act gga gga agt aga agt ctt tgt ttt gct tgc agt ttg
ggg cta caa aac agc aag gat tgc agc tgc aat gtt att gtg agc act
gtt ggg agc agt ggc agc act agc aca aag act ggt tat gac ttc ttg
ggc atg aaa agt ggt gtt ttg gat tat aga agt tta gag atg aaa taa
```

SEQ ID NO: 49

```
atg aca gag aat ctc cac tcc aag aaa atg gta cag cca aag aag ttt
cgt gga gtc cgg cag cgc cac tgg ggt tcc tgg gtc tcc gag atc agg
cat ccc ctc ctt aag agg agg gtc tgg ctg ggc acc ttc gag acc gct
gag gag gca gcg aga gca tat gac gag gct gcc gtg ctg atg agc ggc
cgc aac gcc aag acc aac ttc ccg gtc caa agg agc agc aca ggg gag
cca acc cca gct gcg gga agg gac gct cac agc aac gcc ggc agc ggc
tcc tct acc gcc aac ctg tcc cag att ctc agt gcg aag ctc cgc aaa
tgc tgc aag gcg cca tcg ccc tcc ctg acc tgt ctc cgc ctt gac cct
gag aag tcc cac att ggt gtt tgg cag aag cgt gca gga gcc cgt gct
gac tcc aac tgg gtc atg acc gtg gag ctc aac aaa ggt gca gca tcc
act gat gct gca tca cag tcc aca tca gca aca act gct cca cca gcc
acc ccg atg gat gac gag gag agg atc gcc ctg caa atg atc gaa gag
ttg ctg agc agc agc agc cca gct tca ccc tcg cac gga gat gac caa
ggt cgc ttc atc atc tga
```

SEQ ID NO: 50

```
atg gtg caa tca aag aag aag ttc cgc ggc gtc agg cag cgc cac tgg
ggc tcc tgg gtc tcc gag atc agg cac ccg ctg ctt aag agg agg gtg
tgg ctg ggc acc ttc gag acg gca gag gag gcg gcg cgg gcg tac gac
gag gcc gcc gtc ctc atg agc ggc cgc aac gcc aag acc aac ttc ccc
gtc cca agg acc gcc acc ggg gag ctg gcc ccc gtg ccg gcg cgg
gac gca cgt ggc ggc ggc tcg tcc tcc gcg gca gca gcg ccc ggc
ggc ggc acc agc aac ctg tcg cag atc ctc agc gcc aag ctc cgc aag
tgc tgc aag acg ccg tcg ccg tcg ctc acc tgc ctc cgc ctc gac ccg
```

-continued gag aag tcc cac att ggc gtc tgg cag aag cgc gcg ggc gcg cgc gcc gac tcc agc tgg gtc atg acc gtc cag ctc aac aag gac gtg ccg ccg ccg gcg tcc tcc tcc ggc gag gag ccg gtg ccc agc gac gga ggc gca gcg gcc acc acg ccc acg tcc act tcc acg tcg tcc acg gtc acg acg acc ggc tcg cct cca cct gcg atg atg atg gac gac gag gag agg att gcg ctg cag atg atc gag gag ctg ctg ggc agc tcg cac tca cat ggg atg ttc cag ggt gca gcg ggc agc atc gtc atc tga

SEQ ID NO: 51 atg ggg cgg tcg ccg tgc tgc gag aag gcg cac acg aac aag ggc gcg tgg acc aag gag gag gac gac cgc ctg gtg gcg tac atc cgc gcg cac ggc gaa ggg tgc tgg cgg tcg ctg ccc aag gcg gcc gga ctg atg cgc tgc ggc aag agc tgc cgc ctc cgc tgg atc aac tac ctc cgc ccc gac ctc aag cgc ggc aac ttc acc gcc gac gag gac gac ctc atc atc aag ctc cac agc ctc ctc ggc aac aag tgg tcg ctc atc gcc gcg cgg ctc ccg ggg cgg acg gac aac gag atc aag aac tac tgg aac acg cac atc cgg cgg aag ctg ctt ggc agg ggc atc gac ccc gtc acg cac cgc ccc atc gcc gac gcc ggc gcc ggc acc gtc acc acc atc tcg ttc cag ccc aac aaa ccc aac gcc gcc gtc gca gcg cag gcg cca caa cat cag ccg atc aag gcg gtg gcg acg gcc gtc gtt aag gtg ccc agg tgc ccc gac ctc aac ctc gat ctc tgc atc agc ccg ccg tgc aaa cag aag gaa gac gag gag ctg gac ctc aag ccc gcc gtc gtc gtc aag cgg gag gtg ctg cag gcc ggc cat ggc ggc agc ctc tgc ttc ggc tgc agc ctg ggc atc caa aaa gga gcc ccc ggg tgc agc tgc agc agc agc aac agc cac cac cgc ttc ttg ggg ctc cgg tcc ggc atg ctc gac ttc aga ggc ctc gag atg aag tga

SEQ ID NO: 52 atg ggg agg tcg ccg tgc tgc gag aag gcg cac acc aac aag ggc gcg tgg acc aag gag gag gac gac cgc ctc gtg gcg tac atc aag gcg cac ggc gag ggt tgc tgg cgc tcg ctg ccc aag gcc gcc ggc ctc ctg cgc tgc ggc aag agc tgc cgc ctc cgg tgg atc aac tac ctc cgc ccc gac ctc aag cgc ggc aac ttc acg gaa gag gag gac gag ctc atc atc aag ctc cac agc ctc ctc ggc aac aaa tgg tcc ctg atc gct gga agg ctg ccg gga agg acg gac aac gag atc aag aac tac tgg aac acg cac atc cgg agg aag ctg ctg agc agg ggg atc gac ccg gtg aca cac cgc ccc atc aac gag cac acg tcc aac ata acc atc tcg ttc gag gcg gcg gcg gcc gcg cgt gac cgt gag gag aat aag ggc gcc gtg ttc cgg ctg gag gag cac aac aag gcg acg gcg gcg gcg gcc gcc gcg atc ggc cgc gat cat cat cag aac cac cac ccc gcc ggc gac tgg ggc cag ggg aag ccg ctc aag tgc ccc gac ctc aac ctg gac ctc tgc atc agc ccg ccg gcg gcg ccg tgc cag gag gag aag gcc atg gtg acg atg aag ccc gtg aag -continued

```
cgg gag gcc ggg ctc tgc ttc agc tgc agc ctg ggc ctc ccc aag agc gcc gac tgc aag tgc agc aac ttc ctc gga ctc agg acc gcc atg ctc gac ttc aga agc ctc gag atg aaa tga
```

SEQ ID NO: 53
```
atg aca gag aat ctc cac tcc agg aaa atg gta cag cca aag aag ttt cgt gga gtc cgg cag cgc cac tgg ggc tcc tgg gtc tct gag atc agg cat ccc ctc ctt aag agg agg gtc tgg ctg ggt acc ttt gag acg gct gag gag gca gcg aga gca tat gat gag gct gct gtg ctg atg agc gga cgc aac gcc aag acc aac ttc cca atc caa aga agc agc aca ggg gag cct acc cca gct gcg gga agg gac gcc cgc agc aac ttc agc agc ggc tcc tct acc acc aac ctg tcc cag att ctc agt gcg aag ctc cgc aaa tgc tgc aag gcg cca tca ccg tcc ctg acc tgt ctc cgc ctt gac cct gag aag tcc cac att ggt gtt tgg cag aag cgt gca gga gcc cgt gct gac tcc aac tgg gtc atg aca gtg gag ctc aac aaa gat gca gca tcc act gat gct gca tca cag tcc aca tca gca aca act gct cca cca gcc acg ccg atg gat gag gag gag agg atc gca ctg caa atg atc gaa gag ttg ctg agc agc agc agc cca gct tca ccc tca aac gga gat gac caa ggt cgc ttc atc atc tga
```

SEQ ID NO: 54
```
atg ggg cgg tcg ccg tgc tgc gag aag gcg cac acc aac agg ggc gcg tgg acc aag gag gag gac gag cgg ctg gtg gcc tac gtc cgc gcg cac ggc gaa ggg tgc tgg cgc tcg ctg ccc agg gcg gcg ggc ctg ctg cgc tgc ggc aag agc tgc cgc ctg cgc tgg atc aac tac ctc cgc ccg gac ctc aag cga ggc aac ttc acc gcc gac gag gac gac ctc atc gtc aag ctg cac agc ctc ctc ggg aac aag tgg tcg ctc atc gcc gcg cgg ctc ccg ggg cgg acg gac aac gag atc aag aac tac tgg aac acg cac atc cgg cgc aag ctg ctg ggc agc ggc atc gac ccc gtc acg cac cgc cgc gtc gcg ggg ggc gcc gcg acc acc atc tcg ttc cag ccc agc ccc aac tcc gcc gcc gcc gcc gcc gca gaa aca gca gcg cag gcg ccg atc aag gcc gag gag acg gcg gcc gtc aag gcg ccc agg tgc ccc gac ctc aac ctg gac ctc tgc atc agc ccg ccg tgc cag cat gag gac gac ggc gag gag gag gac gag gag ctg gac ctc aag ccc gcc ttc gtc aag cgg gag gcg ctg cag gcc ggc cac ggc cac ggc cac ggc ctc tgc ctc ggc tgc ggc ctg ggc gga cag aag gga gcg gcc ggg tgc agc tgc agc aac ggc cac cac ttc ctg ggg ctc agg acc agc gtg ctc gac ttc aga ggc ctg gag atg aag tga
```

SEQ ID NO: 55
```
atg ggg agg tcg ccg tgc tgc gag aag gcg cac acc aac aag ggc gcg tgg acc aag gag gag gac gag cgc ctg gtc gcg cac atc agg gcg cac ggc gag ggg tgc tgg cgc tcg ctg ccc aag gcc gcc ggc ctc ctg cgc tgc ggc aag agc tgc cgc ctc cgc tgg atc aac tac ctc cgc ccc gac ctc aag cgc ggc aac ttc acg gag gaa gag gac gag ctc atc gtc aag
```

```
ctg cac agc gtc ctc ggc aac aag tgg tcc ctg atc gcc gga agg ctg
ccc ggc agg acg gac aac gag atc aag aac tac tgg aac acg cac atc
cgg agg aag ctg ctg agc agg ggg atc gac ccg gtg acg cac cgc ccg
gtc acg gag cac cac gcg tcc aac atc acc ata tcg ttc gag acg gaa
gtg gcc gcc gct gcc cgt gat gat aag aag ggc gcc gtc ttc cgg ttg
gag gac gag gag gag gag gag cgc aac aag gcg acg atg gtc gtc ggc
cgc gac cgg cag agc cag agc cac agc cac agc cac ccc gcc ggc gag
tgg ggc cag ggg aag agg ccg ctc aag tgc ccc gac ctc aac ctg gac
ctc tgc atc agc ccg ccg tgc cag gag gag gag gag atg gag gag gct
gcg atg aga gtg aga ccg gcg gtg aag cgg gag gcc ggg ctc tgc ttc
ggc tgc agc ctg ggg ctc ccc agg acc gcg gac tgc aag tgc agc agc
agc agc ttc ctc ggg ctc agg acc gcc atg ctc gac ttc aga agc ctc
gag atg aaa tga
```

```
                                                        SEQ ID NO: 56
atg ggg cga tcg ccg tgc tgc gag aag gcg cac acg aac aag ggc gcc
tgg acc aag gag gag gac gac cgc ctc gtt gcc tac atc cgg gcg cac
ggc gag ggg tgc tgg cgc tcc ctc ccc aag gcc gcg ggc ctg ctg cgc
tgc ggc aag agc tgc cgc ctg cgc tgg atc aac tac ctc cgc ccg gac
ctc aag cgc ggc aac ttc acc gcc gac gag gac gac ctc atc gtc aag
ctc cac agc ctc ctc ggc aac aag tgg tcg ctc atc gcc gcg cgc ctc
ccc ggc cgc acc gac aac gag atc aag aac tac tgg aac acg cac atc
aag cgc aag ctc ctc agc cgc ggc atc gac ccc gtc aca cac cgc ccc
atc gcc gac gca gcc aga aac gtc acc atc tcc ttc cag ccc gac gcg
ccg tcg cag cag cag ctc agc gac gac gcc gag gcg ccg ccg ccg ccg
ccg ccg cag cag cag cag cag ctc aag ccg ccg ccc agg tgc ccc gac
ctc aat ctc gac ctc tgc atc agc ccg ccc tgc cac aag gaa gaa gag
gac cag gag ctc gtc aag ccc gcc gcc gtc aag cgc gag atg ctg cag
gcc ggc cac ggc act cta gga ctc tgc ttc ggc tgc agc ctg ggc ctc
cag aag ggc gcc gcc ggg tgc acc tgc agc agc aac agc cac ttc ctg
ggg ctc agg gtc ggc atg ctc ctc gac ttc aga ggc ctc gag atg aag
tga
```

TABLE 2

Examples of Vascular Xylem Tissue Targeting Promoters for Gene Combination

| Referenced expression database[1] | Expression[2] | Gene name | SEQ ID NO: | Sequence Feature and Location | Prot TABLE 2-continued Examples of Vascular Xylem Tissue Targeting Promoters for Gene Combination

| Referenced expression database[1] | Expression[2] | Gene name | SEQ ID NO: | Sequence Feature and Location | Protein family (Pfam) | Species | Gene ID |
|---|---|---|---|---|---|---|---|
| Arabidopsis root transcripts | 9693.64 | AtCesA4 | 23 | promoter (1) . . . (1000) | PF03552 | Arabidopsis | AT5G44030 |
| Arabidopsis root transcripts | 9591.84 | AtCesA8 | 24 | promoter (1) . . . (1000); 5'UTR (1001) . . . (1167) | PF03552 | Arabidopsis | AT4G18780 |
| Arabidopsis root transcripts | 8423.1 | AtFLA11 | 25 | promoter (1) . . . (1000); 5'UTR (1001) . . . (1019) | PF02469 | Arabidopsis | AT5G03170 |
| Arabidopsis root transcripts | 6779.81 | AtCesA7 | 26 | promoter (1) . . . (1000); 5'UTR (1001) . . . (1093) | PF03552 | Arabidopsis | AT5G17420 |
| Arabidopsis root transcripts | 6471.5 | AtIRX9 | 27 | promoter (1) . . . (1000); 5'UTR (1001) . . . (1146) | PF03360 | Arabidopsis | AT2G37090 |
| Rice mas transcripts | 15061.86 | OsFLA9 | 28 | promoter (1) . . . (948); 5'UTR (949) . . . (1000) | PF02469 | Rice | LOC_Os05g07060/ Os05g0163300 |
| Rice mas transcripts | 10893.78 | OsCTL1 | 29 | promoter (1) . . . (677); 5'UTR (678) . . . (1000) | PF00182 | Rice | LOC_Os09g32080/ Os09g0494200 |
| Rice mas transcripts | 8754.03 | OsCesA4 | 30 | promoter (1) . . . (1000); 5'UTR (1001) . . . (1141) | PF03552 | Rice | LOC_Os01g54620/ Os01g0750300 |
| Rice mas transcripts | 7977.04 | OcCesA7 | 31 | promoter (1) . . . (1000) | PF03552 | Rice | LOC_Os10g32980/ Os10g0467800 |
| Rice mas transcripts | 7972.41 | OsLac10 | 32 | promoter (1) . . . (845); 5'UTR (895) . . . (1000) | PF00394 | Rice | LOC_Os03g16610/ Os03g0273200 |
| Rice mas transcripts | 7099.66 | OsGT43J | 33 | promoter (1) . . . (1000); 5'UTR (1001) . . . (1247) | PF03360 | Rice | LOC_Os06g47340/ Os06g0687900 |
| Maize leaf gradient transcripts | 446.24 | ZmCesA10 | 34 | promoter (1) . . . (977); 5'UTR (978) . . . (1000) | PF03552 | Maize | GRMZM2G445905 |
| Maize leaf gradient transcripts | 123.92 | ZmCesA12 | 35 | promoter (1) . . . (1000) | PF03552 | Maize | GRMZM2G142898 |
| Maize leaf gradient transcripts | 44.89 | ZmCesA11 | 36 | promoter (1) . . . (1000) | PF03552 | Maize | GRMZM2G037413 |

[1]The Bio-Analytic Resource for Plant Biology, available online at http://bar.utoronto.ca/ and described in Toufighi et al, "The Botany Array Resource: e-Northerns, Expression Angling, and Promoter Analyses," *The Plant Journal* 43: 153-63 (2005), each of which is hereby incorporated by reference in its entirety.
[2]Relative gene expression value in vascular tissues or xylem-related organ.

The sequences referenced in Table 2 are set forth below.

```
                                                       SEQ ID NO: 21
acgtacctcg tgtccaccgg tgactctatc cccggcgtta gaagtgatga tagtctcgtt cccaagggaa atcagccttc gaattggaat tgatccctcc ggacattttg tgccgttcgt gtgccagact tgccatccat ataatgcatc ttcttctttt tttcccgcag atggcatgtc cgttggtctt tcctgtatca tttatttaca aaagaaaaat aaattaaaca tttattaagt tcccccgta  aaaaaaaat  atatatatat atatatatat aacacatgca tcataattgg tatgtccgta ggtgtttcct tatcataact gaaccattgg taaactatcg gttccgttaa agcataagac tagaaaaggc tcggtgcgac tcgctaccac gtttctaaag attttattta
```

```
gcaaattaac cccaatatat attttgctat gagggtctaa acaaactggt atatgagcca tttacttacc acttattagt tccaagtatt tattttttgg gttaattaat gtttaaatta ttggttgaca aaaaatataa aaataatggt taagttattg aaatgacttg agcaatctga tgcaactgcg gataacatga actcattcga agtgacgtcc caaatatttg attctttgtt tttattcctt tttgtcaagg tcaagattgg ccaaacattt tcaatatcta aatatattga cattcatagc ctggaaaaga aaaaatatat ggttaaatta gttccaaagt attctagcag caacaaaacc gctccaataa acgatttcca atttctatct caaacttgtt tcccaatcat tagttataat ccgtccccta aaccaaaaaa aaatctaatt gtaaaggtgt tgcaatagat taaccattt tattttattt tggtaaaata gattaaccat tttgttagaa aaatgaagtt taaaacattt acagttctac gtgtacatgc ttcgaccaat atgcttcgac caat
```

SEQ ID NO: 22

```
atacatgtca tgattttata attatgtata tataaatact aattgatgta tgaagtacgt agataatgtt acgatctatt aatctatta cattaacttt taattagtgt tgagtaggga aaattaacat ataaacttt agcagttggt tgtattatta aaaataattt gaacttaaaa tccaccttcg aaaagataaa tcaaacaagt ataaaaaatg ctataaatcc agaatattta cctaaggttt ttattcttct acttaataat gtaagataaa accggcacaa tacttgttac gtatgcatgg taggtaccgc aattgtgtaa gcaaatcggc acaatactaa ggttacatat actaactaaa taaaacaatc tgatttcagt gacaccgtat atctaacctt tattcaaatc caagggaaca tgacttgact tcttctgttg gaactaactc gatccctcaa ccatctccag ggatagaaga gttagtaaaa tcaaacttga agtgaggaag taagcagttt aacgactcca tatgactaca gttatataca aagttgggca caaagtacaa gtactaaata ctcaaagtca gataataatt ttaataagta caaactatat atatgcagta caattattga gtatatataa acgagactgg tgatttgggg cattgtccac caggggtgtta tatcccaatt gaaatttgaa aatttaagtg tgtgagtgtt acgacaaaaa aaagtgtgtg aattgtaggc gcggtgaaaa ggtaaattaa gattggaact agaaaaatag ttgaatatcc tttactaaaa gttgtcaatt ccggttttag taaaaaaaaa ttttaaaata gaaattttat ccaaaagact tcaaacacac atattcgcat ataacata agatatcatt ttttgtaaac agttaaaaag aaaaacacat gttttttttt ttaatttaga aaaaaacatg ttattataca aaacagagtt ttgcccactt ttaatatgtt atgaaaagaa aaatgatttt cttgggtttg gtcagagaga ttggttgtgg taagaatggg aatcttaatt acaaagaatt ggattttggg tcgacctacc acctaaaacg acgtcgcctc catctctggt ttccaaatct cttctcctc tcctttata agcttgcgtt ggccagtcgc tcatctcgaa aacagagaga aaaagactaa aaacacagtt taagaagaag gagagataga gagagaagag aaagatagag agggag
```

SEQ ID NO: 23

```
aactagaaca cttcagataa attttgtcgt tctgttgact tcatttattc tctaaacaca aagaactata gaccataatc gaaataaaaa ccctaaaaac caaatttatc tatttaaaac aaacattagc tatttgagtt tcttttaggt aagttattta aggttttgga gactttaaga tgttttcagc atttatggtt gtgtcattaa tttgtttagt ttagtaaaga aagaaaagat agtaattaaa gagttggttg tgaaatcata tttaaaacat taataggtat ttatgtctaa tttggggaca aaatagtgga attctttatc atatctagct agttcttatc gagtttgaac tcgggttatg attatgttac atgcattggt ccatataaat ctatgagcaa tcaatataat
```

-continued

```
tcgagcattt tggtataaca taatgagcca agtataacaa aagtatcaaa cctatgcagg ggagaagatg atgaaaagaa gagtgtgagc caatacaaag cagatttgag gacatggctt acaagtcttg ggtacagagt ttggggagtg atgggtgcac aatggaacag cttctctggt tgtccagttc ccaagagaac cttcaagctc cctaactcca tctactatgt cgcctgatta aatcttattt actaacaaaa caataagatc agagtttcat tctgattctt gagtcttttt tttctctctc cctcttttca tttctggttt atataaccaa ttcaaatgct tatgatccat gcatgaacca tgatcatctt tgtgttttt tttccttctg tattaccatt ttgggccttt gtgaaattga ttttgggctt ttgttatata atctcctctt tctctttctc tacctgattg gattcaagaa catagccaga tttggtaaag tttataagat acaaaatatt aagtaagact aaagtagaaa tacataataa cttgaaagct actctaagtt
```

SEQ ID NO: 24

```
tacatcagtt tcatcatcta tcttgtttct tatagaagct cacaatcttc ttcctggtcg agtttagaaa tgtcagagag agttgtttcc acagagacgt agaaacccat aactttagta ttcttcaacc cttacaactt atctgagcaa aatcagaagg tcgaatttga tggatggttt tgctgtattt ggtcaacggt tttatttgag acagtagacc agaggaaact cagatgtgat gatgcaaaga ctgaattggt taagagtgta gattgatttg ttctaacatt gcaaatgtag agtagaatta tgcaaaaaac gttaatgaac agagaagtga ttaagcagaa acaaaattag agaagtgata ttatatctca aaatttattt ttggtacagc taaagctcaa attgttatag agattagaga tattaaacca aatgacgagt gttttctta gtagtaaacg gtgaaaattc tcttctgaca aagacaatta aaatttaag tttaagactt taatatttgt cacaaattgt catttaccta aataaaaaaa aaactaaata ttttttag atacatatgt gtcttataat tttaactata aattttaatt ttatgtctta aataattgtt tacactataa atttaaatat tttaatgcta aaattaattt gattcaaaaa agtgatttta attcttattt ttcttataga aagttggtga ttgaaaagat ttacttaaaa attataacaa cttcaatggt gaataacccg acccgaataa accggatata acaacttcaa tgttagcttg atatagaaag tacggtgacg cttaggaggc aagcaagcta gtatctgccg ctggttagag acaaagaaca tgtgtcactc ctctcaacta aaactttcct tcactttccc gcaaaatcat ttcaaaaaag ctccaaattt agcttaccca tcagctttct cagaaaacca gtgaaagaaa cttctcaact tccgattttt cacaatccac caaactttt ttaataactt ttttcctct tattacaaaa cctccactct catggcttct caaacttgtt atccatccaa atctcaatcc ctaattaggg ttcatttctc tgtttctcca aacaggggaa ttcgaag
```

SEQ ID NO: 25

```
tcttcttgca tcaatgatat caacaacaat gggtaataaa gaagctactt cgaaattata tatttttcg tattctatat tgatcatcag tcttaagtgg tttggtttgt tgcagtgaag aagaactatg tatggatcta cgccaccgtt cagttcggtt ttgtggtcct tttcgctcag cttttctaca gagttgtaag atttgatgta atgtcacaga gaaaccttac tttgttgtca cagagaaacc ttactttgtt gaagagtttt tgattcctca cactctctct cattaacttg tgtgtaggtg aagcagccgg taatgtgcat tgtcttagcc actatgatcg gatttggact caccatgacc ggcacaacag ctattaacga gtatttgaaa tggaggagaa gcaattccca cctgccagaa gagccagcaa gtactcaggt ggtttgacag cagcgtagat cttttgagtg aagctagagt ccctaaaggg ttggatcggt tttcaattaa ccggtcggga ttcggttttc ggtttagctt taatcgactt gtctaggttg agatcagatt tggttttcaa tacttccaag
```

```
tcttttttttt tttgccaact aaaatataag gaatgatgat aggcacacac atgacacata aaatcataat gaacagtagt atgattagca atccatattt cttggataac acttcttcac agcttttttg acaggtcact ataacacctt tttcagttca ttttcatttt tcaatcctca cccacccaaa ctctcccttc aaagcaatgt ctctcctctc tctttctcaa ttcaaacaaa ctttattaaa cctaaaagaa acatttccaa tctctaatga cttagttgat agaatctcat ttagttacct agtaataatc ttcacactag taagagaatc ctactcttca ccaaactaca tctctctcta tataacaaac cccaaaacat ctcaacatac acacacaaca actacaaca
```

SEQ ID NO: 26
```
tgcgaacagt ttgattctgt ttttcttttt ccttttttg ggtaattttc ttataacttt tttcatagtt tcgattattt ggataaaatt ttcagattga ggatcatttt atttatttat tagtgtagtc taatttagtt gtataactat aaaattgttg tttgtttccg aatcataagt ttttttttt tttggttttg tattgatagg tgcaagagac tcaaaattct ggtttcgatg ttaacagaat tcaagtagct gcccacttga ttcgatttgt tttgtatttg gaaacaacca tggctggtca aggcccagcc cgttgtgctt ctgaacctgc ctagtcccat ggactagatc tttatccgca gactccaaaa gaaaaggat tggcgcagag gaattgtcat ggaaacagaa tgaacaagaa agggtgaaga agatcaaagg catatatgat ctttacattc tctttagctt atgtatgcag aaaattcacc taattaagga cagggaacgt aacttggctt gcactcctct caccaaacct taccccctaa ctaattttaa ttcaaaatta ctagtatttt ggccgatcac tttatataat aagataccag atttattata tttacgaatt atcagcatgc atatactgta tatagttttt tttttgttaa agggtaaaat aataggatcc ttttgaataa aatgaacata tataattagt ataatgaaaa cagaaggaaa tgagattagg acagtaagta aaatgagaga gacctgcaaa ggataaaaaa gagaagctta aggaaaccgc gacgatgaaa gaaagacatg tcatcagctg atggatgtga gtgatgagtt tgttgcagtt gtgtagaaat ttttactaaa acagttgttt ttacaaaaaa gaaataatat aaaacgaaag cttagcttga aggcaatgga gactctacaa caaactatgt accatacaga gagagaaact aaaagctttt cacacataaa aaccaaactt attcgtctct cattgatcac cgttttgttc tctcaagatc gctgctaatc tccggccgtc cct
```

SEQ ID NO: 27
```
tctctaattg tcaagtatct tagtctagag ttaattactt aaatactaaa aggctgtcga caaaatcaag cttgaatctc cttgtggtat cttcaactct tcgttgtctg cttacgagtg gtttactcag taattatcta taatatgtta ttttttttcc ctcatctttt agttgttgtt tcattacatt gaaaagcttg taatgtcttt atatggtata tatggatctt atgagtgagg caagatccat gatgttttg atcttagaat gtatatgatg atcttagaat gtatttgacc gcccacaaat tattgttcat tgggattata tctctagtcc aactccaagc aatcgaaatg ggtcctgctt ttaagaacaa cagtatatgt ttaagaataa taactttata tattctcgat tttaagatct tttgacaaaa cctccttttc gttaggagcg tactaatttc caagtgtttg attagtgggg tctccgtaaa tttatttaga gtttctatct atttattaat agctcaatta attaatctat actgtatcta aacatcaatt tatatattta ctcttgagac caaaactgtc aatttataac attggatagt ttcttaattc ttattatata tttttcaaac acttttcaag actaatctcc acattaggta ctctctctag agataaaaat atttatcaaa acattttta tttatttatt aagtagtaga taaactactg tggcaaaatc gtaaatgtct aaatgctgat
```

-continued

```
gaatttttttt tgctgctcca atctggttta gtgctccata tacatccacg gccaaaatga atctatggcg gcattaagat tcattagtaa gcaacgatta tattaatata attgttttta gcaatgattt tccgtaattt cccaaatatg tttcagttaa tgtgttccaa tcccaacaac tggttgttgc aaaagaccac caacgcaagc aatcatcaaa catcaaaata atcttacctt agcgaacaaa caataactac acaattctca taaagctctt atatatcact aacttcacac attttgtttt ccacaaaaat aaaaacggaa ctcactcaag aaaccttctt ccttgaagag agggtt
```

SEQ ID NO: 28
```
tacagggtct caagccagga tgacctcctt tgaaacgtac gagtggtaaa acagtacgaa gaacatcaaa ttttcatgag aattttcata ggagacaggt taagagagaa cttcaagaga ttggacccta tgttaacttc ttctagagat tggaccttat gttaactttc ttctataaaa tattagtgaa gtgaggaaac ttctaaaaca attatatgga gtgatgaaaa aaattatttg gtcagacggt aactatgagt actccataat ccgtataaga taataacatg gtaattctat taggcgttcg ccaacgaagc cccaagcagc cacccaaggt agctaggcgg tgcctttgtc cgtgtatcaa aaatctccat gcacgggagc cattccaaat aaaattttga agctccaagt ttttgttccg aaggatcaaa tagaaaaatt atccgtagaa attgaatcct aacaaaaatt ccccacaatt cctctaatta aaacgaggcc gaagcggctt cctgatcgga cggctggaag gccatacatg tcctggcatt aattatcact caccttagat tattacagct cggagctaga aagccctgca agttgcaatt aatggtgagt atgatctgat ctgcagcgaa atgatctatc gatgtcccta gttaagcagt cattgtgtcc cttacccacc taaatccacg agtgtcagag ctaagcgcga tcccgatcct taaaccccaa ccccactctc ttgctgctcc atcaagcaac caaccccaat ccacacacca tacataatta catactacca gctaattaat tactaataat gacttaatat tccatcatct cccagctcag ttatcacttc ttgatcacac cccctaccat tgattaacct cttccatctc actctacacg cctatataat tagcctaatg atctcacttt gcaaagcatc tcattgcact aaactgctca ctgcatttgc
```

SEQ ID NO: 29
```
actcgattcc attagattat tcacaaaccc atgtgaaccg tgactgtcag tcaggtgagg aaacagatat tccaaaaatc atattctttc cttttgtatt aaccaaattc acacaaaggt gatatttaaa actgacgaag atgaaaatta agttgacgca cgtaaaatga aaaagctatc ggcatatgat taattaaatt taattattac aaacttgata aatgaatata tttgatattt taaggcaact tctatataaa acttttttat atgaagagga ctgctacaaa acgggatccc gttgcaacgg gataaggcat attaactatt ctcttgcatg agtatcacag atatcaggcc ctaagtatca taggtaccag gtaacaggta tcacaggtat cgggtaccat acagctcgta ccacaacagg tatcaggtac tatctcataa aaggtaacgt gataccgttg tctaggtttt ctgttatatg aaacatattg tagttttaaaa acgtgccaa cgaaaataga gataaaaatc tgaatcttga tgagaaaatc atgcccaaat ttcaccctaa acagtcaat ttcccgcgaa aaaaagcaaa aaaaaaaaaa ctccagacag ttgttaaaag gggaaaaaaa aagacagaat gctcagccgt cgagacacac acaacggcaa cgtcttacca gctcggagct ctctcgcttg ctgcctcttc tcttcttcct cccgccaccg acaccacctc caccagcagc ttcgccttcg ccgcgtcggc atctgcagtt gccacttcgc tttcttccac tcctcctcc tcctcgctta cctcacactc ctccccccca atttcatccc ccacccacca ccagatcccc caccacctgc
```

-continued cgcattctcc cccccaagat ccagatcgcc ggtcacccccc acgaactcgc tcgagatcca gagagagaga gagaggcagt ttcttggttg attttcgagg

SEQ ID NO: 30

GAGTTAAATTGATATGGTTTTGTCTGTCAAGGTGCCGTTTCTATGGTTGGAGGAGGAAAA

TGAAATTAGGGGAATAGAACAGTCGCAATCCAAAAGCTATTGTTCTCTCTTCTACGGTAG

TTGATAGTTCGATACGTGTGTTTGATGTGAGAGACTGAGAGGAGTGCACGGTGCACCTGC

CCCGTAAGGACGCGGAACTACATTATCAGAGGCTAGGCCGGTACTGTTATACGCGACGTT

CACGAATCACGATGCGTAAAAAAGTGAAGCATGAAACAGTACTAGGCTCTCCACGGGCCA

CATCATGAAAAAACTGGTGCGACGCCACGCTTAACAATTTGTCGGTCGTAAACTCGTAAA

GTTAAAAGCCCCACGACATTGTCAACCAATATCTCAGCACATGAACTTCTCTAACGAGTA

CAACGAAACCGCATCCGCAAAAGCGCCGTGAACCAAAGCTCTTGCCGTGCTGTGCCGTGC

CGGTGGCCGTGAACATGTGGAACACGAAGAACTCTTGCGCGAGATCGGAGCACCTGACCT

CCCACCTCGCGTCCGGCCCGTCGCCGTCGCAGCAAGCGGGCTGTCAAAAACGACGCCACA

GCGCGAGCGCTCTCGCCGATCCGGCGGACCCACCCTCCTCACCTCGCGCACCAACCGCCC

GTTCGCTAGTCCGATCCCCCACCCCTCATCCCCCCTACGCCTTGCAGGTTACGCGCCTCG

CCGCGGCCAACGCAAACCAAACCAAATCCCCCGTCACCTTCGCTTCGAAACCCCGCAAAA

CCCCATGGAAGAAAACACCGAACACCTGCCGCGCGCACGCCTCCTCCTCCCCCGCCTCTC

CTCCTCTCTCCCGTTCCATGTCCGCTCAACCTTGCTTCCATTCTTTCCATCCACCCGCCG

ATCGACGCGATGCCGACGCCCCAACCCCACCCACCGCCTGCCAGCGCCACCCCACCTCGC

GCCTCTGCGGCTATGGCTATATCACCATGCCTCCAACCTCCGGTACGCTTAGCCTCTCTC

TCTCTCCCCCTCCCATTCTGCGCATTGCTCTCTGCGCGCGGTCGCGTGCTGCTGCTCGCG

GCGCCCCGGAGCGTCTCCTTTGGGGGAGAGGAGAGGAGAGGAGAGGAGAGGGGGGTGAGC

C

SEQ ID NO: 31 ttcaatgcag gatgacgcca agagggagaa accaagcaga ggtggacggt acaacgtgta agtcaccgca aaacgttgca gcttggatag tggccatcga gtggtgtgcc gataccggcg cctgttcttt acagcctcag ctagtgttgt tgtccgaggc aattttttccg acctattgtg ttgctttcct ctctgatagc ttatggtaaa agatacaaag atgttgagga gtttgtacgc cacttaattt tgctcgtaac atacattgac aatcaagagg agccatggca ttgcgatctg cttacacggc atattcttac tggatggtgt acactactta cccttttttaa tgcaagcatc aatccattgc ttttctcact gcacacctga ttcgtactga aaacgtgaaa cataaaaaaa aacaaaaatc tagctgatgt tggctctcgg ggcctcgagt ctagtttgtc ctagatggct aacctgatat gtgttggtca cgctcacgtt tgaaccgaga aagagtgtgt gtgtgtgtgt gtcggcgtgc tgctacacca gagcctccct gaatcgcaat gcgtgttaac gccagcatcg caggatttca tctcacttga caggttcaga tggccttcct cctaccgtct gccatttata cacgcagtga cttaacgctt acacgagccg gatggcccgg atctccccccc tgcaccatct caccagaaaa acggtgaggc gtcaccgcaa cccacccacc aaacacatcc acgtcccttc accgttggcc ttcgattttg cttcagctgc actacgaccc ctccaacaca tttccctcgc gtctcgttgc gatctcacct tacgacgatc tcgttccagc agcagcagca tcggcagcgg cggcttgctt ccgaagcgag caatgcatgg cgcgcgcggc cgcgtgcgtg cgtgccttgg cttgcgctct aatcaaaccg ggacgcccca actcacggtt -continued SEQ ID NO: 32
```
acaacccctg ttgcaccaaa cttgcttttt taagttttaa ctgaaattag gatagcaaag
agagtacttt aggcttcatg ctacgagctg cctacgacca tagacaggct taatcttgtc
ttatagttgt atcttgttga tcattaggtg cctaactgcc tacataggca taatgcatcc
tttcatctga tctttgtcac tgaccccatg tacagagtcc tataagttgc aatgttctaa
tccttgtttc gtcagtcatt tcgtacacat ggatgaaagt ctggggttta accaccgatg
cgatccaatc ttctcctaca gtcgatgata aggaaatcgt aacaaagaat gtgaattttt
ttgacgctac aaagaatgtg aatgatctga ccagtctatc tttcaccgaa ctgaagcata
tactctgaat gtctaagatc atacttagac tgaactatat actctgaata tctaaagatc
tcatacattc atacttacgc tgcaggttgc aaattctagt cattattaca ctcgagacct
aaattatgat tagtggggtg tactccgata gaacagttta cagttcagaa ctcaaaagct
acgaatgaat tcatgacaaa aggcgacaag tgatacgtat tcgagaataa atgtgtgaac
aaaggccgtc tcaaaaaaaa aaagaaaaa aaaaagaga tcccctttgc ctgcactcta
aaacccagcc cgacccaact ctttgtacat gaccagcaaa agcaccgtct gctgcgactt
tttttctctt gtgcaatcta ttgtcgggaa aaaagagagg agaattatca tatcatcacc
taataaattg caaccaccag aggtactgtc ctctctatat aactctttct cgggcatttt
gctggcactt gcctgttcta gtatctatag ctagctaact gttactgtac ctcctcccat
atatcatctt catattttg cagatcgata agcgagaaaa
```
SEQ ID NO: 33
```
CATACTTTACCTTGTTGTATAACTGCATGCATAAGAATCTGAGAGCCATTGCTCAATTCT
TTTCAACGAAGATGTGAACTGTTGGAAGGCAATGTAAAACGGGAAGCGCTGTATGAAAGA
ATATGACGCACATCGTCTTTTGTTTTTTAAGAATTGAGTATATATTCGTTGTGGGGAACA
GCCTGATGATGGGCCCCGGGAATTAACGCTCGAGCAACGTTGGACCATTCTGACATCGCG
TTTCCTGATTAGCACAATGTTTCGTTTTATTTGGAAATTGAATTGAATGTTTCTACTGTT
ATTAATTGCAGACAGTACACCAAACGACCAAATCTATCTGCAAACAATTAACCAAGACCA
ACTGGAGAATTTACAGATGAATCACTGTGTTACACCTGTAAACTGTGGCTCCTTTGAGAA
TTGAGTTACAACAAGAGTTTGGAGATGAACTTGTAGTTCATCTATATCATCTTAATTAAA
CAATAATATTTATTCAGGAATGCAGTTCAGAGACTGCTTAACACACACACACACAAAAAA
AAAACCTAAACCTGAGGCTTGTACTGGAACAAGGTCATTAGCAAGGTGTCCTCTAGACTC
CCGGACCGACACTACCCTTGGAAGTCAAACGCAGCTGGCACAAACAAACGGAGCCTCGGT
GACGCCGGTAAACCGCACCAATCATTGTTAAACCAAAAAACGTGAACAACAAACCAAAAA
GAAACTAAAAAACCGCTAAAAAGACGCAAAAGAGAGAGAAAAAAAATGAAAGAAGAAAAG
AAACGACGCGGACTCGCTGACGACCCGCGGCCCGGTCCAACCCAACCCCCACCGCCTCTC
TCGCCGACCCCGTCCACTCCGCCGAATTCCCCCCCAAACCCAAACCCAACGCGACCTCAC
CTCACCCGCACGACGACGGCACGACGCGACGCGTTGCCCGAGCTGACGGCTTGACGACGC
CTCCGTCCCCGTCCGGCACCAACCCATCCCAACCCAACGCTCCCCTTTTCCACTGACCAA
TTGATAGCCCAACCTCACCTCTCCTCTCCTCCTCCCCCCTCCTCTCCTCCTCGCCTCCGC
ACCAGCAGTTTCGTGCACCGCACTTCACCCACCTACCTCCCCCAACCTCCCCATCAAAAA
CTAGTAGTAGCAGTATCCACCCATCCACGCACGCGACCGAGCGCGATCGATTCGAGGCGG
CGGCGGCGGAGGAGGAGGAGGGGGAGTAGATCCGGCGGGCGGCAGCG
```

SEQ ID NO: 34
tttgtgctga gatcggcacc agctttcatt taatacagcc tcagcttacc tgaggcaatt
ttcgcacctg ttatgatgtt gttttgctct cagataggtt tatgtagcac aagaaagata
tgttggagac gttgacgatt ttgtatgcaa ctaaatttct atcttaatat gccccgattc
aacagcaccc agtcgagtca ttgcgttctg gagattcttg cagcgcattt ccatgtttaa
gaccttatta tgaaatgtct ggcattcgtg gatccactga gcttctttct gcgaatgtgc
catatcgtgg cattggccga agcaaccaaa catttgttgc ccttttgtgt cggtgtttta
taaagtacct caatgacgat acagcctcag ggcgcttcct gcttttgcac ttattcggag
ttcaggcgag ttaacgaagt tcagacggtt ctgaagagag gccgtgttgt gttttgtcgg
cgtggtatcg cgcaagcaca tgtgtctttg gtaagatggt ctggatggct gtcctaccac
ctgccattta tacacacact gacttcaccg tcacactggc acgacatgag ctcgccatcc
taccagaaac gctgagacgt caccggcaac cacccctctc gctcgctctg gcctctgctc
ctgatttgat ttggacagaa aactgggcag ggcagggcgc gctcagcacg tttgcttcgg
aaacactgcg agtgtgcgac acatttcccg gcttgatctc gaagcgagcc ctgatgtgtt
tgtcatgcac ctgcctgcct tggcttgtgc tctaatcaac gccggactcc ccaactcacg
gttggtgcgg gacgccaccc cgccaccttc ccgcccgcct cggcgcctca ccagtcacca
cacctcgcgc ctgccatcag ctatatcacc gtggccactt ccgtgtccct tcacggatac
ctcacccca cagcccccgg tcgatcgctc ggcaatcggc SEQ ID NO: 35
acatgtatat aagtattcaa tacataaatc agttctggta aagagtgaat taagttaatg
gacgtgctga aaatggtttg gcttagtctt gttgtgtttt atggaaaaat tgtgtaggtc
acgattactt ctcaatgcaa ttgagaaaag ttttaattgc aagccattta tggttattta
ttaaaaaaac aaggagtaac acgtcattgt tcaaggcgcc aagctaccac atcactatga
ttcaaagaac cacttcagat tttactcaag attggaaatt gaatggtttt gatatttaag
gttacttttt accgaaaaat attggaaacg atcagactga aatcgacttg atctagaaat
tatgatagaa tctcttgttt catagcgggt ccggtgggaa gacaaaatgt gtaatcccgt
cgatatgtgc tttctaaatg ctaaaaacga tccaatatac gacgtgtgct ttctagcctg
tttgtttgtc tttaatctgt actagtttct atgttttttt tctcattgaa ttacagctac
agtagtctaa caacagcgg gctttaattc gaagcgaaca cacctgctg agtaagcaaa
cccacgctga atagtttcag aaatgttttc tggatgaata gcaaaattgt agtagcaaca
ggatagacgg cgggaaagcc aagtctcggt tggtccggcc gtccggacgc agcctgacaa
gggcagcagc atagcaatag catcaggcgc aagccagcgc aggcggcttt cgcttcactt
agcggcaacg gggacgcagc gcccgcaccc aaccaacacg agctcctctc ctcacccgcc
gcgacacgcg cgcggctcca acgcctccat ctccatcgcg cgcaccaaat cgcactccgt
ccgcccgtc gatcgaacag ccaccgctca cctctctcac ccgccaaaac ctcctcccct
ggcctcctct catactcata tagctgagca gcccctgcca SEQ ID NO: 36
catgtatata agtattcaat acataaatca gttctggtaa agagtgaatt aagttaatgg
acgtgctgaa aatggtttgg cttagtcttg ttgtgtttta tggaaaaatt gtgtaggtca
cgattacttc tcaatgcaat tgagaaaagt tttaattgca agccatttat ggttatttat
taaaaaaaca aggagtaaca cgtcattgtt caaggcgcca agctaccaca tcactatgat
tcaaagaacc acttcagatt ttactcaaga ttggaaattg aatggttttg atatttaagg -continued

```
ttacttttta ccgaaaaata ttggaaacga tcagactgaa atcgacttga tctagaaatt atgatagaat ctcttgtttc atagcgggtc cggtgggaag acaaaatgtg taatcccgtc gatatgtgct ttctaaatgc taaaaacgat ccaatatacg acgtgtgctt tctagcctgt ttgtttgtct ttaatctgta ctagtttcta tgtttttttt ctcattgaat tacagctaca gtagtctaaa caacagcggg ctttaattcg aagcgaacaa cacctgctga gtaagcaaac ccacgctgaa tagtttcaga aatgttttct ggatgaatag caaaattgta gtagcaacag gatagacggc gggaaagcca agtctcggtt ggtccggccg tccggacgca gcctgacaag ggcagcagca tagcaatagc atcaggcgca agccagcgca ggcggctttc gcttcactta gcggcaacgg ggacgcagcg cccgcaccca accaacacga gctcctctcc tcacccgccg cgacacgcgc gcggctccaa cgcctccatc tccatcgcgc gcaccaaatc gcactccgtc cgccccgtcg atcgaacagc caccgctcac ctctctcacc cgccaaaacc tcctcccctg gcctcctctc atactcatat agctgagcag cccctgccac
```

Twenty-five independent plasmids suitable for *Agrobacterium*-mediated plant transformation were generated (see Table 3). Nine (9) combinations (construct 001 to construct 009 shown in Table 3) and one vector control were integrated into a dicot binary vector for alfalfa, canola, and other dicot transformation, and sixteen (16) combinations (construct 010 to construct 025 shown in Table 3) and one vector were generated into a monocot binary vector for sorghum, switchgrass, and other monocot transformation.

TABLE 3

List of Constructs

| Construct number | SEQ ID NO: | Promoter and 5'UTR | | | Coding sequence | | | |
|---|---|---|---|---|---|---|---|---|
| | | Gene name | SEQ ID NO: | Gene ID | Gene name | SEQ ID NO: AA | SEQ ID NO: NT | Gene ID |
| 001 | 57 | AtCTL2 | 21 | AT3G16920 | AtMYB32 | 4 | 40 | At4g34990 |
| 002 | 58 | AtLAC4 | 22 | AT2G38080 | AtMYB32 | 4 | 40 | At4g34990 |
| 003 | 59 | AtCesA4 | 23 | AT5G44030 | AtMYB32 | 4 | 40 | At4g34990 |
| 004 | 60 | AtCesA8 | 24 | AT4G18780 | AtMYB32 | 4 | 40 | At4g34990 |
| 005 | 61 | AtFLA11 | 25 | AT5G03170 | AtMYB32 | 4 | 40 | At4g34990 |
| 006 | 62 | AtCesA7 | 26 | AT5G17420 | AtMYB32 | 4 | 40 | At4g34990 |
| 007 | 63 | AtIRX9 | 29 | AT2G37090 | AtMYB32 | 4 | 40 | At4g34990 |
| 008 | 64 | AtCesA4 | 23 | AT5G44030 | AtMYB4 | 5 | 41 | At4g38620 |
| 009 | 65 | AtCesA8 | 24 | AT4G18780 | AtMYB4 | 5 | 41 | At4g38620 |
| 010 | 66 | ZmCesA12 | 35 | GRMZM2G142898 | ZmMYB31 | 19 | 55 | GRMZM2G050305 |
| 011 | 67 | ZmCesA11 | 36 | GRMZM2G037413 | ZmMYB31 | 19 | 55 | GRMZM2G050305 |
| 012 | 68 | OsCesA4 | 30 | LOC_Os01g54620/ Os01g0750300 | ZmMYB31 | 19 | 55 | GRMZM2G050305 |
| 013 | 69 | OcCesA7 | 31 | LOC_Os10g32980/ Os10g0467800 | ZmMYB31 | 19 | 55 | GRMZM2G050305 |
| 014 | 70 | ZmCesA12 | 35 | GRMZM2G142898 | ZmMYB42 | 19 | 55 | GRMZM2G419239 |
| 015 | 71 | ZmCesA11 | 36 | GRMZM2G037413 | ZmMYB42 | 19 | 55 | GRMZM2G419239 |
| 016 | 72 | OsCesA4 | 30 | LOC_Os01g54620/ Os01g0750300 | ZmMYB42 | 19 | 55 | GRMZM2G419239 |
| 017 | 73 | OcCesA7 | 31 | LOC_Os10g32980/ Os10g0467800 | ZmMYB42 | 19 | 55 | GRMZM2G419239 |
| 018 | 74 | ZmCesA12 | 35 | GRMZM2G142898 | PvMYB4 | 20 | 56 | Pavir.J16675 |
| 019 | 75 | ZmCesA11 | 36 | GRMZM2G037413 | PvMYB4 | 20 | 56 | Pavir.J16675 |
| 020 | 76 | OsCesA4 | 30 | LOC_Os01g54620/ Os01g0750300 | PvMYB4 | 20 | 56 | Pavir.J16675 |
| 021 | 77 | OcCesA7 | 31 | LOC_Os10g32980/ Os10g0467800 | PvMYB4 | 20 | 56 | Pavir.J16675 |
| 022 | 79 | ZmCesA12 | 35 | GRMZM2G142898 | OsSHN1 | 7 | 43 | LOC_Os06g40150/ Os06g0604000 |
| 023 | 79 | ZmCesA11 | 36 | GRMZM2G037413 | OsSHN1 | 7 | 43 | LOC_Os06g40150/ Os06g0604000 |
| 024 | 80 | OsCesA4 | 30 | LOC_Os01g54620/ Os01g0750300 | OsSHN1 | 7 | 43 | LOC_Os06g40150/ Os06g0604000 |
| 025 | 81 | OcCesA7 | 31 | LOC_Os10g32980/ Os10g0467800 | OsSHN1 | 7 | 43 | LOC_Os06g40150/ Os06g0604000 |

Figure 5:
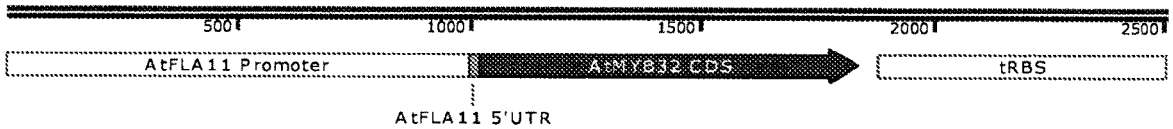
FIG. 5 illustrates the map and nucleotide sequence for construct 005, pAtFLA11-AtMYB32-tRBS, which includes the promoter and 5' UTR from AtFLA11, the open reading frame of AtMYB32 (shaded in sequence), and the 3' RBS transcription terminator.
Figure 26:
FIG. 26 is a map of an exemplary plasmid operable in dicots, which includes construct 003 shown in FIG. 3. Similar dicot-functional plasmids containing constructs 001, 002 and 004-009 were also prepared.

A similar approach was used for preparation of each of the constructs and plasmids. Briefly, approximately 1.0 kb of genome sequences upstream of the respective AtCTL2 (AT3G16920), AtLAC4 (AT2G38080), AtCesA4 (AT5G44030), AtCesA8 (AT4G18780), AtFLA11 (AT5G03170), AtCesA7 (AT5G17420), and AtTRX9 (AT2G37090) start codons were amplified by PCR from *Arabidopsis thaliana* genomic DNA; and the nucleotide sequences from start codon to stop codon of transcription factor AtMYB32 (At4g34990) and AtMYB4 (At4g38620) coding region were amplified by PCR from *Arabidopsis thaliana* cDNA derived from reverse transcription reaction using stem tissue RNA. The two nucleotide sequences (promoter and coding regions) were then combined with RBS terminator region into a commonly used binary vector plasmid (including Kanamycin selection marker) through Gibson cloning (Gibson et al., "Enzymatic Assembly of DNA Molecules up to Several Hundred Kilobases," *Nature Methods* 6(5):343-345 (2009), which is hereby incorporated by reference in its entirety). The result was assembly of constructs 001-009: pAtCTL2-AtMYB32-tRBS (FIG. 1), pAtLAC4-AtMYB32-tRBS (FIG. 2), pAtCesA4-AtMYB32-tRBS (FIG. 3), pAtCesA8-AtMYB32-tRBS (FIG. 4), pAtFLA11-AtMYB32-tRBS (FIG. 5), pAtCesA7-AtMYB32-tRBS (FIG. 6), pAtIRX9-AtMYB32-tRBS (FIG. 7), pAtCesA4-AtMYB4-tRBS (FIG. 8), and pAtCesA8-AtMYB4-tRBS (FIG. 9), respectively. A representative plasmid map for construct 003 is shown in FIG. 26. Similar dicot-functional plasmids containing constructs 001, 002 and 004-009 were also prepared.

Figure 12:
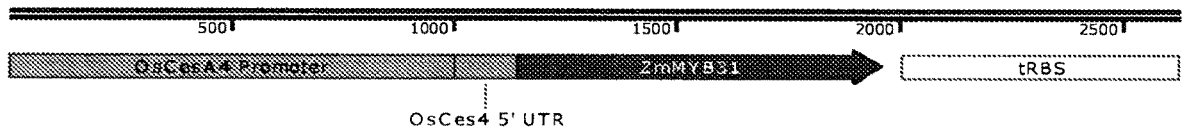
FIG. 12 illustrates the map and nucleotide sequence for construct 012, pOsCesA4-ZmMYB31-tRBS, which includes the promoter from OsCesA4, the open reading frame of ZmMYB31 (shaded in sequence), and the 3' RBS transcription terminator.
Figure 16:
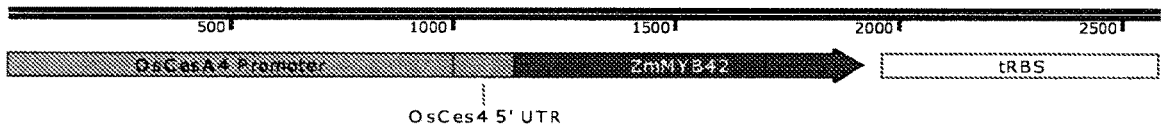
FIG. 16 illustrates the map and nucleotide sequence for construct 016, pOsCesA4-ZmMYB42-tRBS, which includes the promoter from OsCesA4, the open reading frame of ZmMYB42 (shaded in sequence), and the 3' RBS transcription terminator.
Figure 20:
FIG. 20 illustrates the map and nucleotide sequence for construct 020, pOsCesA4-PvMYB4-tRBS, which includes the promoter from OsCesA4, the open reading frame of PvMYB4 (shaded in sequence), and the 3' RBS transcription terminator.
Figure 24:
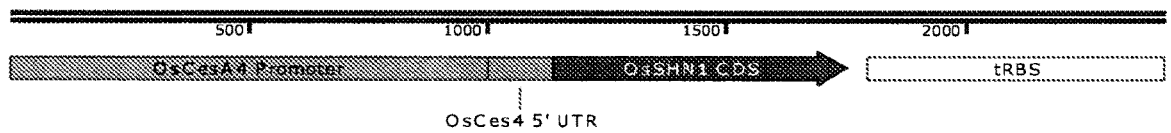
FIG. 24 illustrates the map and nucleotide sequence for construct 024, pOsCesA4-OsSHN1-tRBS, which includes the promoter from OsCesA4, the open reading frame of OsSHN1 (shaded in sequence), and the 3' RBS transcription terminator.
Figure 27:
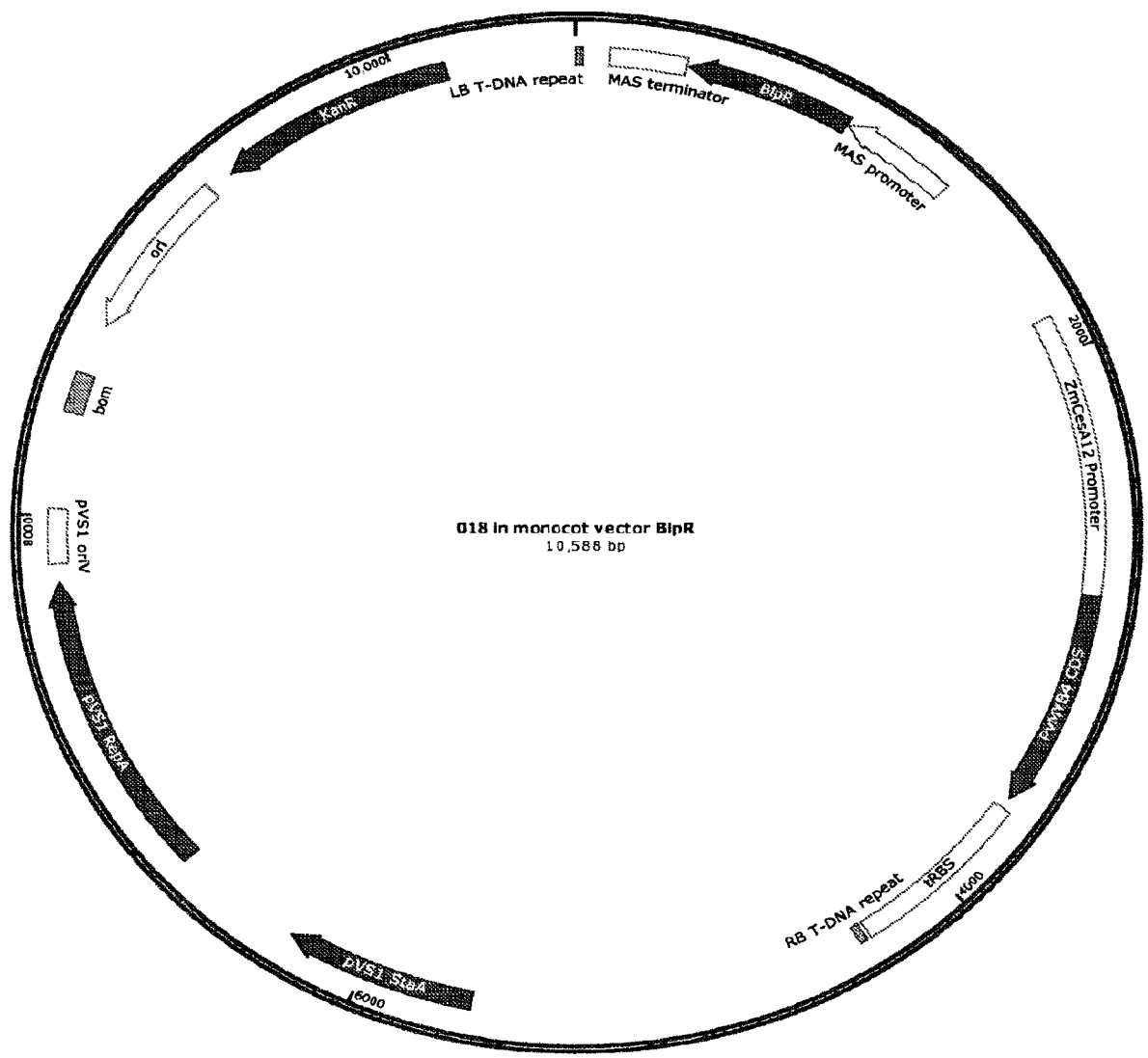
FIG. 27 is a map of an exemplary plasmid operable in monocots, which includes construct 018 shown in FIG. 18. Similar monocot-functional plasmids containing constructs 010-017 and 019-025 were also prepared.

Using this same approach, approximately 1.0 kb of genome sequences upstream of the respective ZmCesA12 (GRMZM2G142898) ZmCesA11 (GRMZM2G037413), OsCesA4 (LOC_Os01g54620), and OcCesA7 (LOC_Os10g32980) start codons were amplified by PCR from corn and rice genomic DNA; and the nucleotide sequences from start codon to stop codon of transcription factors ZmMYB31 (GRMZM2G050305), ZmMYB42 (GRMZM2G419239), PvMYB4 (Pavir.J16675), and OsSHN1 (LOC_Os06g40150) were amplified by PCR from corn, rice, and switchgrass cDNA derived from reverse transcription reaction using stem tissue RNA. The two nucleotide sequences (promoter and coding regions) were then combined with RBS terminator region into a commonly used binary vector plasmid (including Kanamycin selection marker) through Gibson cloning (Gibson et al., "Enzymatic Assembly of DNA Molecules up to Several Hundred Kilobases," *Nature Methods* 6(5):343-345 (2009), which is hereby incorporated by reference in its entirety). The result was assembly of constructs 010-025: pZmCesA12-ZmMYB31-tRBS (FIG. 10), pZmCesA11-ZmMYB31-tRBS (FIG. 11), pOsCesA4-ZmMYB31-tRBS (FIG. 12), pOsCesA7-ZmMYB31-tRBS (FIG. 13), pZmCesA12-ZmMYB42-tRBS (FIG. 14), pZmCesA11-ZmMYB42-tRBS (FIG. 15), pOsCesA4-ZmMYB42-tRBS (FIG. 16), pOsCesA7-ZmMYB42-tRBS (FIG. 17), pZmCesA12-PvMYB4-tRBS (FIG. 18), pZmCesA11-PvMYB4-tRBS (FIG. 19), pOsCesA4-PvMYB4-tRBS (FIG. 20), pOsCesA7-PvMYB4-tRBS (FIG. 21), pZmCesA12-OsSHN1-tRBS (FIG. 22), pZmCesA11-OsSHN1-tRBS (FIG. 23), pOsCesA4-OsSHN1-tRBS (FIG. 24), and pOsCesA7-OsSHN1-tRBS (FIG. 25). A representative plasmid map for construct 018 is shown in FIG. 27. Similar monocot-functional plasmids containing constructs 010-017 and 019-025 were also prepared.

Empty vectors corresponding to those shown in FIGS. 26 and 27, but lacking the constructs 001-025, were used as controls in the following molecular biology analysis and phenotypic analysis described in the following Examples.

Example 2—Introduction of Construct Nos. 003 and 008 into Alfalfa (*Medicago sativa* L. cv Regen S)

The vectors containing construct Nos. 003 and 008, along with the control vector, were used to generate transgenic alfalfa (*Medicago sativa* L. cv Regen S) using tissue culture and the *Agrobacterium*-mediated transformation method. After selection of primary transgenic plants using kanamycin, multiple events were obtained from the regeneration medium, cloned and propagated vegetatively, and transferred to soil after roots were developed. Introduction of the transgene cassette in the genome of the regenerated plants was confirmed by PCR using genomic DNA extracted from leaves.

Figure 28:
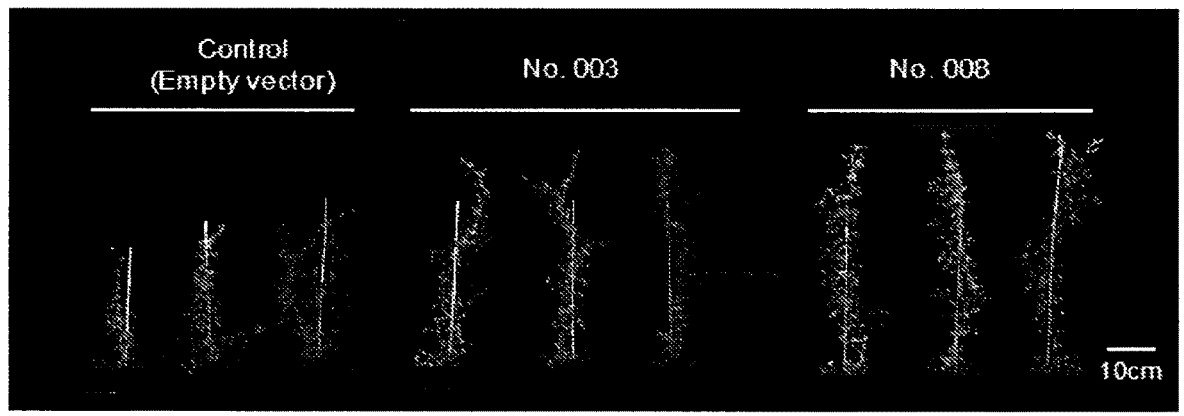
FIG. 28 is an image of representative control (empty vector) and vector-transformed alfalfa (*Medicago sativa* L. cv Regen S) using construct No. 003 (center) and construct 008 (right). The height difference between the control and transgenic plants is evident.

The experimentally confirmed and propagated plants were grown in individual pots inside growth chambers with 18/6-hour light/dark cycles. Table 4 shows biomass yield and stem internode length at approximately 250 days after propagation along with similar data for the control alfalfa plant with the construct. Engineered alfalfa shows approximately 15-18% longer internodes and 58-63% increased yields compared to the control plant. Representative images of control and inventive vector-transformed alfalfa plants are shown in FIG. 28.

TABLE 4

Biomass yield and stem length in alfalfa plants

| Construct | Events (n) | Stem length | Biomass yield (g) | |
| --- | --- | --- | --- | --- |
| | | | Fresh weight | Dry weight |
| Control | 8 (17) | 57.56 ± 5.42 | 11.42 ± 2.99 | 2.20 ± 0.51 |
| No. 008 | 8 (21) | 66.47 ± 7.77*** | 17.74 ± 5.80*** | 3.49 ± 1.10*** |
| No. 003 | 7 (16) | 68.37 ± 6.28*** | 17.47 ± 3.95*** | 3.60 ± 0.73*** |

***$p < 0.001$

RNA was extracted from the leaves and stems in the engineered alfalfa lines for quantitative RT-PCR. Results show that the expression level of the target TF was similar to that of the native UbiQ gene. Moreover, transcript levels of the target TF were approximately 50 times higher in stem-enriched tissues compared to leaves, which highlights the tissue-preferential expression pattern enabled by the promoter used to drive expression of the TF. During the course of propagation, engineered alfalfa No. 003 also showed better development not only in stems but also significantly in roots. Table 5 shows regeneration efficiency and root length of alfalfa control and engineered No. 003 at 13 days after initiation of the regeneration step using sectioned internodes.

TABLE 5

Regeneration efficiency of new roots from sectioned stems

| Construct | Prepared stem fragments (n) | Number of rooted stems | Rooting efficiency (%) | Regenerated root length (mm) |
|---|---|---|---|---|
| Control | 59 | 10 | 16.95 | 1.91 ± 2.47 (Max: 19.0) |
| No. 003 | 62 | 24 | 38.71 | 8.25** ± 5.90 (Max: 29.0) |

**$p < 0.01$

The construct No. 003 and No. 008 alfalfa lines also showed a reduction of insoluble lignin and ash content (Table 6) and changes in lignin monomeric composition (Table 7), which indicate the inventive constructs also enhance biomass degradability through reduced lignin composition. Moreover, 12% and 16% less insoluble lignin content and 20% and 38% less ash content were observed in the No. 003 and No. 008 alfalfa lines, respectively, compared to control lines.

TABLE 6

Ash and insoluble lignin content in cell wall biomass

| Construct | Events (n) | Insoluble lignin (%) | Ash (%) |
|---|---|---|---|
| Control | 8 (8) | 12.96 ± 1.94 | 0.26 ± 0.09 |
| No. 008 | 11 (11) | 10.93* ± 0.86 | 0.16 ± 0.04 |
| No. 003 | 10 (10) | 11.45* ± 0.57 | 0.21* ± 0.04 |

*$p < 0.05$

TABLE 7

Lignin monomeric composition in cell wall biomass

| Construct (events) | H unit (%) | G unit (%) | S unit (%) | S/G ratio |
|---|---|---|---|---|
| Control (3) | 1.77 ± 0.74 | 63.58 ± 1.24 | 34.65 ± 0.50 | 0.55 ± 0.02 |
| No. 008 (3) | 1.48 ± 0.34 | 48.39 ± 1.47 | 50.13 ± 1.76 | 1.04** ± 0.07 |
| No. 003 (3) | 1.48 ± 0.39 | 51.08 ± 3.28 | 46.99 ± 3.08 | 0.93* ± 0.11 |

**$p < 0.01$, *$p < 0.05$

Table 8 summarizes the composition of saccharide released from cell wall fraction in the control lines and construct No. 003 and No. 008 lines. After a mild thermochemical treatment, glucose, xylose, and arabinose saccharides from constructs No. 003 and No. 008 biomass cell wall fraction were released two to three times more efficiently than the control lines.

TABLE 8

Composition of saccharide released from cell wall biomass

| Construct (events) | Glucose (%) | Xylose (%) | Arabinose (%) |
|---|---|---|---|
| Control (11) | 4.71 ± 2.46 | 8.01 ± 3.32 | 1.56 ± 0.18 |
| No. 008 (11) | 14.14** ± 3.79 | 15.78** ± 3.57 | 1.82** ± 0.18 |
| No. 003 (11) | 14.11** ± 4.05 | 15.84** ± 3.48 | 1.98*** ± 0.23 |

*$p < 0.001$, $p < 0.01$

Example 3—Introduction of Construct No. 004 into Canola (*Brassica napus* L. cv Westar)

The vector containing construct No. 004 and the control vector were used to generate transgenic canola (*Brassica napus* L. cv Westar) using tissue culture and the *Agrobacterium*-mediated transformation method. After selection of primary transgenic plants using kanamycin, multiple events were obtained on the regeneration agar plates and transferred to soil after vegetative tissue and roots were developed and cloned by vegetative propagation.

Figure 29:
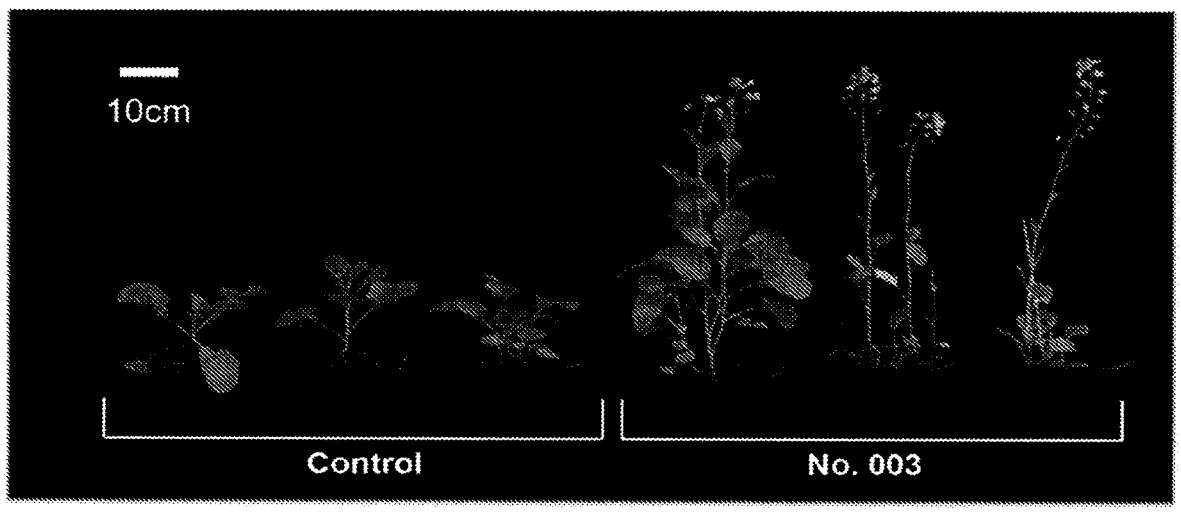
FIG. 29 is an image of representative control (empty vector) and vector-transformed canola (*Brassica napus* L. cv Westar) using construct No. 004. The height difference between the control and transgenic plants is evident.

Table 9 summarizes the measured heights of five (5) transformed control canola lines compared to the four (4) No. 004 lines. The height of the plants transformed with the inventive method is approximately two times taller than the height of the control plants at 130 days after regeneration. These results indicate the inventive constructs enhance stem internode development and may increase biomass yield. Representative images of control and inventive vector-transformed canola plants are shown in FIG. 29.

TABLE 9

Plant height over 30-day period after regeneration

| | | Days after regeneration | | | |
|---|---|---|---|---|---|
| Construct | Events (n) | 100 | 110 | 120 | 130 |
| Control | 5 (5) | 18.58 ± 1.78 | 19.52 ± 1.82 | 20.38 ± 1.70 | 2.26 ± 1.75 |
| No. 004 | 4 (4) | 18.90 ± 0.70 | 22.35* ± 1.43 | 27.48** ± 3.23 | 46.45*** ± 4.18 |

*p < 0.001, p < 0.01, *p < 0.05

The measured number of branches and flowers for five (5) control lines compared to the four (4) lines engineered with inventive constructs are shown in Table 10. Among the examined lines at day 150 after regeneration, two control lines and three No. 004 lines possessed grain pods, although grain in mature pods was observed in only No. 004 lines as shown in Table 11. All of the results indicate the inventive constructs enhance vegetative growth, root redevelopment as well as reproductive tissue development, and may increase overall yields.

TABLE 10

Numbers of Branch and Flower at 130 and 140 days after regeneration (DAR)

| | | Number of Branch | | Number of Flower | |
|---|---|---|---|---|---|
| Construct | Events (n) | 130 DAR | 140 DAR | 130 DAR | 140 DAR |
| Control | 5 (5) | 1.00 ± 0.00 | 1.40 ± 0.48 | 0.00 ± 0.00 | 0.00 ± 0.00 |
| No. 004 | 4 (4) | 4.00** ± 1.00 | 4.00* ± 1.00 | 12.00** ± 4.50 | 41.50*** ± 8.75 |

*p < 0.001, p < 0.01, *p < 0.05

TABLE 11

Number of seed pods and seeds at 150 days after regeneration

| Construct | Number of plant with grain pods | Number of grain pods per event | Diameter of pods (cm) | Number of grain per pod |
|---|---|---|---|---|
| Control | 2 (2) | 5.50 ± 1.50 | 1.60 ± 0.10 | 0.00 ± 0.00 |
| No. 004 | 3 (3) | 25.67** ± 15.6 | 3.17** ± 1.38 | 6.67** ± 4.44 |

**p < 0.01

Example 4—Introduction of Construct No. 018 into Sorghum (*Sorghum bicolor* P898012)

The vector containing construct No. 018 and the control vector were used to generate transgenic sorghum (*Sorghum bicolor* P898012) using tissue culture and the *Agrobacterium*-mediated transformation method. After selection of primary transgenic plants using glufosinate, multiple lines were obtained on the regeneration agar plates and transferred to soil after vegetative issue and roots were developed and cloned by vegetative propagation. Introduction of the transgene cassette was confirmed by PCR using genomic DNA extracted from the regenerated plant's leaves as the template.

Figure 30:
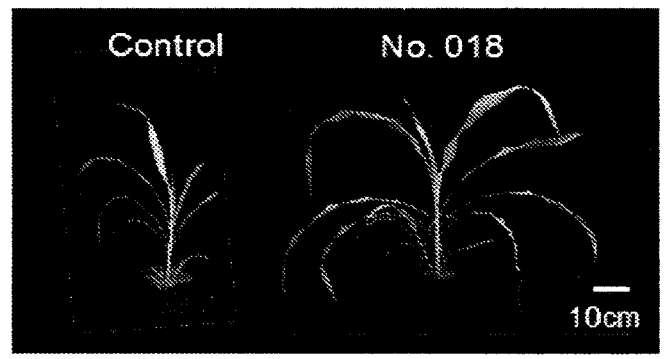
FIG. 30 is an image of representative control (empty vector) and vector-transformed sorghum (*Sorghum bicolor* P898012) using construct No. 018. The height difference between the control and transgenic plant is evident.

The experimentally confirmed and propagated plants were grown in individual pots inside the greenhouse with 18/6-hour light/dark cycles. Table 12 shows biomass yield, number of branches and plant height at approximately 250 days after propagation, along with similar data for sorghum control lines. The engineered sorghum lines showed approximately 80% more dry weight than the control lines, probably due to enhanced branching specific to the engineered lines. The obtained grain number and weight data, summarized in Table 13, indicate improved grain production. Representative images of control and inventive vector-transformed sorghum plants are shown in FIG. 30.

TABLE 12

Biomass yield and related-morphology data from engineered sorghum

| Construct | Events n) | Plant height (cm) | Number of branches | Biomass yield (Dry weight: g) |
|---|---|---|---|---|
| Control | 8 (8) | 128.81 ± 15.98 | 0.00 ± 0.00 | 100.94 ± 25.14 |
| No. 018 | 8 (8) | 134.29 ± 16.41 | 6.57*** ± 1.63 | 183.29*** ± 14.17 |

***p < 0.001

TABLE 13

Grains from engineered sorghum

| Construct | Events (n) | Number of grains | Average grain weight (mg) |
|---|---|---|---|
| Control (8) | 8 (8) | 975 ± 84 | 40 |
| No. 018 (8) | 8 (8) | 4082* ± 526 | 40 |

*$p < 0.05$

Example 5—Introduction of Construct No. 018 into Switchgrass (*Panicum* Virgatum Alamo)

The vector containing construct No. 018 and the empty vector control were used to generate transgenic switchgrass (*Panicum virgatum* Alamo) using tissue culture and the *Agrobacterium*-mediated transformation method. After selection of primary transgenic plants using hygromycin, multiple events were obtained on the regeneration agar plates and transferred to soil after vegetative tissue and roots were developed and cloned by vegetative propagation. Introduction of the transgene cassette was confirmed by PCR using genomic DNA extracted from the regenerated plant's leaves as the template.

The experimentally confirmed and propagated plants were grown in individual pots with 18/6 hours light/dark cycles at a green house facility. RNA was extracted from the engineered switchgrass leaves and stems for quantitative RT-PCR. The analysis confirmed the target TF genes are mainly expressed in the stem rather than the leaves, suggesting that the tissue-preferred expression was enabled by the used cellulose synthase gene promoters.

Figure 31:
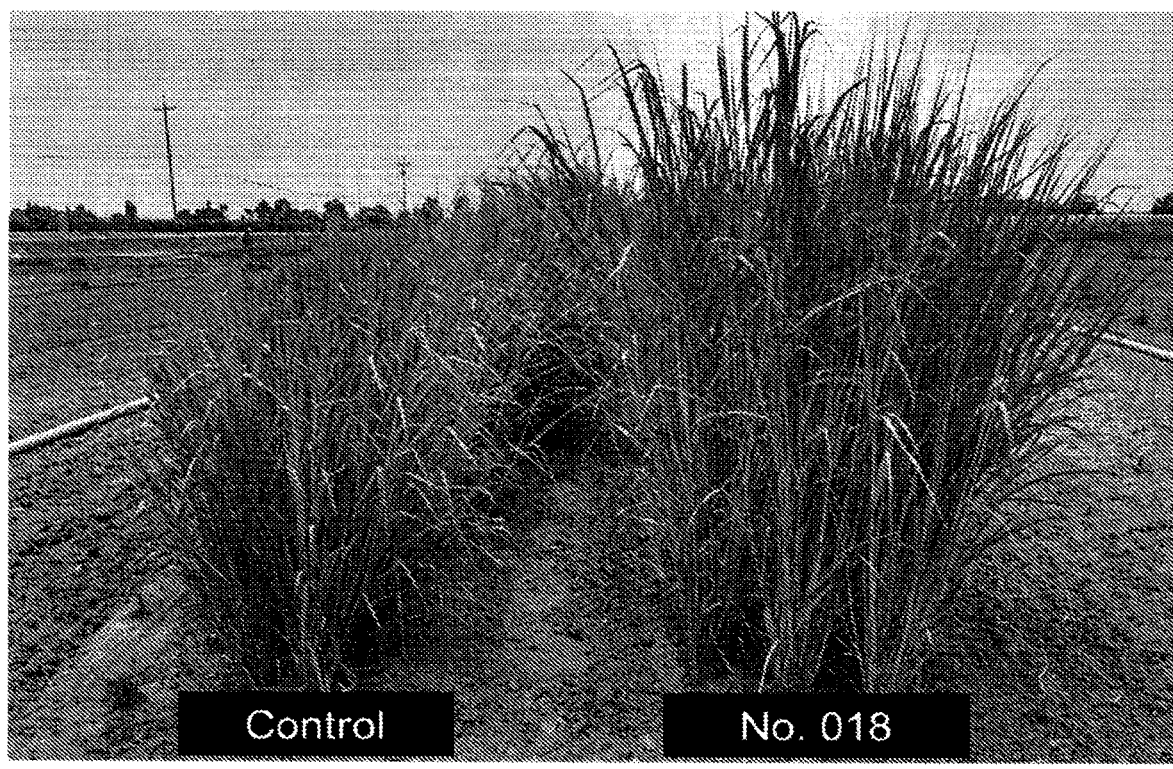
FIG. 31 is an image of representative control (empty vector) and vector-transformed switchgrass (*Panicum virgatum* Alamo) using construct No. 018. The height difference between the control and transgenic plants is evident.

During the course of transgenic plant generation, the engineered switchgrass with the gene cassette tended to show better differentiation and vegetative development. Table 14 compares plant height and number of tillers at 40 days after ratooning. In comparison to the control lines, approximately double the growth and 2-3× times more tillers were observed in the engineered lines. Representative images of control and inventive vector-transformed switchgrass plants are shown in FIG. 31.

TABLE 14

Plant height and number of tillers (40 days after ratooning)

| Construct | Event (n) | Plant height (cm) | Number of tillers |
|---|---|---|---|
| Control | 3 (3) | 83.00 ± 9.42 | 6.00 ± 2.83 |
| No. 010 | 5 (5) | 159.00** ± 18.14 | 22.80** ± 9.66 |
| No. 012 | 8 (8) | 178.00*** ± 10.09 | 32.88*** ± 8.33 |
| No. 013 | 5 (5) | 161.60*** ± 4.63 | 25.20** ± 10.72 |
| No. 020 | 7 (7) | 139.71** ± 23.14 | 24.00** ± 7.80 |
| No. 022 | 8 (8) | 164.13** ± 15.81 | 16.38** ± 4.47 |

*$p < 0.001$, $p < 0.01$

The switchgrass engineered by MYB TFs showed not only faster growth but also approximately 10-20% less insoluble lignin content (see Table 15: Constructs No. 010, No. 012, No. 013, and No. 020). Plants engineered by ERF TFs, however, maintained a similar amount of insoluble lignin (see Table 15: Construct No. 022), suggesting that the R2R3-MYB subfamily 4 and ERF/AP2 subfamily B-6 contribute to faster growth through distinguished mechanisms.

TABLE 15

Insoluble lignin content in upper and lower stem biomass

| | | Insoluble lignin content (%) | |
|---|---|---|---|
| Construct | Event (n) | Upper stem biomass | Lower stem biomass |
| WT | 6 | 17.46 ± 0.59 | 21.13 ± 0.46 |
| Control | 3 (11) | 17.06 ± 0.41 | 20.00 ± 0.90 |
| No. 010 | 5 (5) | 15.92** ± 0.32 | 18.62** ± 0.54 |
| No. 012 | 5 (5) | 15.95** ± 0.92 | 18.33** ± 0.90 |
| No. 013 | 4 (4) | 15.15** ± 0.25 | 17.44** ± 0.34 |
| No. 020 | 4 (4) | 15.51** ± 0.41 | 16.96** ± 0.16 |
| No. 022 | 7 (7) | 17.59 ± 1.47 | 21.18 ± 0.85 |

**$p < 0.01$

Faster development in the reproductive phase was also observed in the engineered lines. Mature seeds produced after the completion of reproductive development were harvested and quantitatively analyzed (Table 16). Among engineered lines, construct No. 012, No. 013, and No. 018 switchgrass produced large quantities of seeds, approximately 6-7× more seeds than the control lines.

TABLE 16

Number of mature seeds produced

| Construct | Event (n) | Number of seeds produced |
|---|---|---|
| Control | 11 (11) | 165.4 ± 39.9 |
| No. 012 | 12 (12) | 915.3** ± 153.7 |
| No. 013 | 5 (5) | 1012.0** ± 153.2 |
| No. 018 | 7 (7) | 1109.0* ± 451.4 |

**$p < 0.01$, *$p < 0.05$

Germinating efficiency from the obtained T1 seeds was examined by using a 96 well format system. Two containers that included pre-soaked sponges with 96 well halls were prepared for seed planting and used for the germination process in dark conditions at 25° C. Time-course observation of the germinated seedlings confirmed that the seeds from construct No. 012 and No. 018 switchgrass enhances not only the germination rate but also seedling development (seedling length) in comparison to the control lines (Table 17).

TABLE 17

Time course of T1 seedling length (cm)

| | Days after seed planting | | | | | | |
|---|---|---|---|---|---|---|---|
| Construct | 0 | 8 | 10 | 13 | 16 | 20 | 23 |
| Control Container 1 | 0.00 ±0.00 | 0.19 ±0.48 | 0.49 ±0.84 | 1.35 ±1.14 | 1.42 ±1.17 | 1.75 ±1.20 | 3.31 ±1.78 |

TABLE 17-continued

Time course of T1 seedling length (cm)

| Construct | 0 | 8 | 10 | 13 | 16 | 20 | 23 |
|---|---|---|---|---|---|---|---|
| Control | 0.00 | 0.00 | 0.29 | 1.13 | 1.45 | 2.06 | 3.76 |
| Container 2 | ±0.00 | ±0.00 | ±0.51 | ±1.32 | ±1.37 | ±1.50 | ±2.49 |
| No. 012 | 0.00 | 2.22** | 3.57** | 4.40** | 4.61** | 4.92** | 5.48** |
| Container 1 | ±0.00 | ±1.92 | ±2.36 | ±2.61 | ±2.70 | ±2.56 | ±2.43 |
| No. 012 | 0.00 | 2.22** | 3.25** | 4.03** | 4.19** | 4.78** | 5.74** |
| Container 2 | ±0.00 | ±1.57 | ±1.85 | ±1.34 | ±1.22 | ±0.99 | ±0.96 |
| No. 018 | 0.00 | 1.77** | 2.20** | 3.10** | 3.80** | 4.77** | 6.35** |
| Container 1 | ±0.00 | ±1.72 | ±2.32 | ±2.35 | ±2.52 | ±2.48 | ±2.94 |
| No. 018 | 0.00 | 2.07** | 2.61** | 3.37** | 4.16** | 5.06** | 6.50** |
| Container 2 | ±0.00 | ±1.97 | ±2.59 | ±2.63 | ±2.82 | ±2.67 | ±2.54 |

**$p < 0.01$

Growth and morphology of the engineered lines were also examined in a field environment. Switchgrass plantlets were grown under greenhouse conditions and transplanted to field plots with a total of 1,000 square feet. A total of 30 plantlets was distributed to each plot, and a total of 120 plantlets were planted per construct. Table 18 shows biomass data for constructs No. 012 and No. 018 switchgrass that yielded approximately 35% more than wild-type and control lines.

TABLE 18

Biomass yield (total dry weight) from the field test

| Construct | n per plot | Number of plots | Biomass yield (kg) from one plot |
|---|---|---|---|
| WT | 30 | 4 | 8.82 ± 1.04 |
| Control | 30 | 4 | 8.44 ± 1.09 |
| No. 012 | 30 | 4 | 12.14** ± 1.29 |
| No. 018 | 30 | 4 | 12.96** ± 1.21 |

**$p < 0.01$

Construct No. 012 and No. 018 plants grown in field conditions also showed cell wall characteristics similar to those observed in laboratory-grown plants. As shown in Table 19, the constructs had 10% less insoluble lignin content and higher S/G unit composition ratios in comparison to wild-type switchgrass, suggesting the engineered switchgrass could be useful as potential forage with better digestibility and/or as less recalcitrant feedstock for a cost-effective biorefinery process.

TABLE 19

Lignin characteristics from the field test.

| Construct | Insoluble lignin (%) | G unit (%) | S (%) | S/G ratio |
|---|---|---|---|---|
| WT | 22.74 ± 1.94 | 75.01 ± 0.05 | 24.99 ± 0.47 | 0.33 ± 0.0008 |
| No. 012 | 20.48** ± 1.58 | 69.47** ± 0.70 | 30.53** ± 0.53 | 0.44** ± 0.01 |
| No. 018 | 20.90** ± 0.78 | 65.49** ± 0.53 | 34.51** ± 0.54 | 0.53** ± 0.01 |

**$p < 0.01$

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of producing a transgenic plant having improved traits as compared to a non-transgenic or wild-type control plant of the same plant species, the method comprises:

a) introducing into a plant cell a nucleic acid construct consisting of a heterologous plant tissue-specific promoter as set forth in SEQ ID NO: 23 which is operably linked to a polynucleotide encoding a transcription factor polypeptide as set forth in SEQ ID NO: 04 and obtaining transformed plant cells;

b) obtaining transgenic plants expressing said polypeptide from the transformed plant cells of step a); and c) selecting a transgenic plant from said transgenic plants of step b) that expresses said polypeptide, and wherein expression of said polypeptide in said selected transgenic plant results in said improved traits comprising i) at least 5% increased plant height, ii) at least 5% increased number of tillers/branches;, iii) at least 20% increased biomass yield, iv) at least 50% enhanced root development, v) at least 5% lower insoluble lignin content, vi) at least 20% increased ratio of syringyl to guaiacyl monomeric units in lignin,; and vii) at least 10% increased saccharide release from plant cell wall.

2. The method according to claim 1, wherein the nucleic acid construct further comprises a 3' transcription termination site, wherein the 3' transcription termination site is operably linked to said polynucleotide.

3. The method according to claim 1, wherein the nucleic acid construct is present on a plasmid capable of being transformed into a plant.

4. The method according to claim 1, wherein the nucleic acid construct is present in *Agrobacterium* for plant transformation.

5. The method according to claim 1, wherein the nucleic acid construct is introduced into said plant cell by infective transformation, electroporation, direct uptake, microinjection, or biolistic transformation.

6. The method according to claim 1, wherein the nucleic acid construct is introduced into said plant cell by transfection.

7. The method according to claim 1, wherein the nucleic acid construct is introduced into said plant cell by transfection into a bacterium for plant transformation.

* * * * *

SEQUENCE LISTING

```
Sequence total quantity: 81
SEQ ID NO: 1         moltype = AA  length = 189
FEATURE              Location/Qualifiers
PEPTIDE              1..189
source               1..189
                     mol_type = protein
                     organism = Arabidopsis thaliana
```

```
SEQUENCE: 1
MVHSKKFRGV RQRQWGSWVS EIRHPLLKRR VWLGTFDTAE TAARAYDQAA VLMNGQSAKT    60
NFPVIKSNGS NSLEINSALR SPKSLSELLN AKLRKNCKDQ TPYLTCLRLD NDSSHIGVWQ   120
KRAGSKTSPN WVKLVELGDK VNARPGGDIE TNKMKVRNED VQEDDQMAMQ MIEELLNWTC   180
PGSGSIAQV                                                          189

SEQ ID NO: 2            moltype = AA   length = 199
FEATURE                 Location/Qualifiers
source                  1..199
                        mol_type = protein
                        organism = Arabidopsis thaliana
SEQUENCE: 2
MVQTKKFRGV RQRHWGSWVA EIRHPLLKRR IWLGTFETAE EAARAYDEAA VLMSGRNAKT    60
NFPLNNNNTG ETSEGKTDIS ASSTMSSSTS SSSLSSILSA KLRKCCKSPS PSLTCLRLDT   120
ASSSHIGVWQK RAGSKSDSSW VMTVELGPAS SSQETTSKAS QDAILAPTTE VEIGGSREEV  180
LDEEEKVALQ MIEELLNTN                                               199

SEQ ID NO: 3            moltype = AA   length = 189
FEATURE                 Location/Qualifiers
PEPTIDE                 1..189
source                  1..189
                        mol_type = protein
                        organism = Arabidopsis thaliana
SEQUENCE: 3
MVHSRKFRGV RQRQWGSWVS EIRHPLLKRR VWLGTFETAE AAARAYDQAA LLMNGQNAKT    60
NFPVVKSEEG SDHVKDVNSP LMSPKSLSEL LNAKLRKSCK DLTPSLTCLR LDTDSSHIGV   120
WQKRAGSKTS PTWVMRLELG NVVNESAVDL GLTTMNKQNV EKEEEEEEAI ISDEDQLAME   180
MIEELLNWS                                                          189

SEQ ID NO: 4            moltype = AA   length = 274
FEATURE                 Location/Qualifiers
PEPTIDE                 1..274
source                  1..274
                        mol_type = protein
                        organism = Arabidopsis thaliana
SEQUENCE: 4
MGRSPCCEKD HTNKGAWTKE EDDKLISYIK AHGEGCWRSL PRSAGLQRCG KSCRLRWINY    60
LRPDLKRGNF TLEEDDLIIK LHSLLGNKWS LIATRLPGRT DNEIKNYWNT HVKRKLLRKG   120
IDPATHRPIN ETKTSQDSSD SSKTEDPLVK ILSFGPQLEK IANFGDERIQ KRVEYSVVEE   180
RCLDLNLELR ISPPWQDKLH DERNLRFGRV KYRCSACRFG FGNGKECSCN NVKCQTEDSS   240
SSSYSSTDIS SSIGYDFLGL NNTRVLDFST LEMK                              274

SEQ ID NO: 5            moltype = AA   length = 282
FEATURE                 Location/Qualifiers
PEPTIDE                 1..282
source                  1..282
                        mol_type = protein
                        organism = Arabidopsis thaliana
SEQUENCE: 5
MGRSPCCEKA HTNKGAWTKE EDERLVAYIK AHGEGCWRSL PKAAGLLRCG KSCRLRWINY    60
LRPDLKRGNF TEEEDELIIK LHSLLGNKWS LIAGRLPGRT DNEIKNYWNT HIRRKLINRG   120
IDPTSHRPIQ ESSASQDSKP TQLEPVTSNT INISFTSAPK VETFHESISF PGKSEKISML   180
TFKEEKDECP VQEKFPDLNL ELRISLPDDV DRLQGHGKST TPRCFKCSLG MINGMECRCG   240
RMRCDVVGGS SKGSDMSNGF DFLGLAKKET TSLLGFRSLE MK                     282

SEQ ID NO: 6            moltype = AA   length = 269
FEATURE                 Location/Qualifiers
PEPTIDE                 1..269
source                  1..269
                        mol_type = protein
                        organism = Arabidopsis thaliana
SEQUENCE: 6
MGRSPCCEKE HMNKGAWTKE EDERLVSYIK SHGEGCWRSL PRAAGLLRCG KSCRLRWINY    60
LRPDLKRGNF THDEDELIIK LHSLLGNKWS LIAARLPGRT DNEIKNYWNT HIKRKLLSKG   120
IDPATHRGIN EAKISDLKKT KDQIVKDVSF VTKFEETDKS GDKQNKYIR NGLVCKEERV    180
VVEEKIGPDL NLELRISPPW QNQREISTCT ASRFYMENDM ECSSETVKCQ TENSSSISYS   240
SIDISSSNVG YDFLGLKTRI LDFRSLEMK                                    269

SEQ ID NO: 7            moltype = AA   length = 243
FEATURE                 Location/Qualifiers
PEPTIDE                 1..243
source                  1..243
                        mol_type = protein
                        organism = Oryza sativa
SEQUENCE: 7
MGQSKKKFRG VRQRHWGSWV SEIRHPLLKR RVWLGTFETA EEAARAYDEA AILMSGRNAK    60
TNFPVARNAT GELTPAAAVA GRDGRVGGGS GSSSSMTANG GGNSLSQILS AKLRKCCKTP   120
```

```
SPSLTCLRLD PEKSHIGVWQ KRAGARADSS WVMTVELNKD TAVSSAATVA AATAVSSSDQ    180
PTPSDSTVTT TSTSTTGSPS PPPPAMDDEE RIALQMIEEL LGRSGPGSPS HGLLHGGEGS    240
LVI                                                                 243

SEQ ID NO: 8            moltype = AA   length = 243
FEATURE                 Location/Qualifiers
PEPTIDE                 1..243
source                  1..243
                        mol_type = protein
                        organism = Oryza sativa
SEQUENCE: 8
MGQSKKKFRG VRQRHWGSWV SEIRHPLLKR RVWLGTFETA EEAARAYDEA AILMSGRNAK    60
TNFPVARNAT GELTPAAAVA GRDGRVGGGS GSSSSMTANG GGNSLSQILS AKLRKCCKTP    120
SPSLTCLRLD PEKSHIGVWQ KRAGARADSS WVMTVELNKD TAVSSAATVA AATAVSSSDQ    180
PTPSDSTVTT TSTSTTGSPS PPPPAMDDEE RIALQMIEEL LGRSGPGSPS HGLLHGGEGS    240
LVI                                                                 243

SEQ ID NO: 9            moltype = AA   length = 243
FEATURE                 Location/Qualifiers
PEPTIDE                 1..243
source                  1..243
                        mol_type = protein
                        organism = Oryza sativa
SEQUENCE: 9
MGRSPCCEKE HTNKGAWTKE EDERLVAYIR AHGEGCWRSL PKAAGLLRCG KSCRLRWINY    60
LRPDLKRGNF TADEDDLIIK LHSLLGNKWS LIAARLPGRT DNEIKNYWNT HIRRKLLGNF    120
IDPVTHRPVN AAAATISFHP QPPPTTKEEQ LILSKPPKCP DLNLDLCISP PSCQEEDDDY    180
EAKPAMIVRA PELQRRRGGL CFGCSLGLQK ECKCSGGGAG AGAGNNFLGL RAGMLDFRSL    240
PMK                                                                 243

SEQ ID NO: 10           moltype = AA   length = 251
FEATURE                 Location/Qualifiers
PEPTIDE                 1..251
source                  1..251
                        mol_type = protein
                        organism = Oryza sativa
SEQUENCE: 10
MGRSPCCEKA HTNKGAWTKE EDDRLIAYIK AHGEGCWRSL PKAAGLLRCG KSCRLRWINY    60
LRPDLKRGNF TEEEDELIIK LHSLLGNKWS LIAGRLPGRT DNEIKNYWNT HIRRKLLSRG    120
IDPVTHRPIN DSASNITISF EAAAAAARDD KAAVFRREDH PHQPKAVTVA QEQQAAADWG    180
HGKPLKCPDL NLDLCISLPS QEEPMMMKPV KRETGVCFSC SLGLPKSTDC KCSSFLGLRT    240
AMLDFRSLEM K                                                        251

SEQ ID NO: 11           moltype = AA   length = 268
FEATURE                 Location/Qualifiers
PEPTIDE                 1..268
source                  1..268
                        mol_type = protein
                        organism = Populus trichocarpa
SEQUENCE: 11
MGRSPCCEKA HTNKGAWTKE EDDRLIAYIR THGEGCWRSL PKAAGLLRCG KSCRLRWINY    60
LRPDLKRGNF TEEEDELIIK LHSLLGNKWS LIAGRLPGRT DNEIKNYWNT HIRRKLLNRG    120
IDPATHRPLN EPAQEASTTI SFSTTTSVKE ESLSSVKEES NKEKIISAAA FICKEEKTPV    180
QERCPDLNLE LRISLPCQNQ PDRHQAFKTG GSTSLCFACS LGLQNSKDCS CSVIVGTIGS    240
SSSAGSKTGY DFLGMKSGVL DYRGLEMK                                      268

SEQ ID NO: 12           moltype = AA   length = 271
FEATURE                 Location/Qualifiers
PEPTIDE                 1..271
source                  1..271
                        mol_type = protein
                        organism = Populus trichocarpa
SEQUENCE: 12
MGRSPCCEKA HTNKGAWTKE EDDRLVAYIR AHGEGCWRSL PKAAGLLRCG KSCRLRWINY    60
LRPDLKRGNF TEAEDELIIK LHSLLGNKWS LIAGRLPGRT DNEIKNYWNT HIRRKLLNRG    120
IDPATHRPLN EPAVQEATTT ISFTTTTTSV LEEESLGSII KEENKEKIIS ATAFVCKEEK    180
TQVQERCPDL NLEGISLPS QNQPDHHQPF KTGGSRSLCF ACSLGLQNSK DCSCNVIVST    240
VGSSGSTSTK TGYDFLGMKS GVLDYRSLEM K                                  271

SEQ ID NO: 13           moltype = AA   length = 105
FEATURE                 Location/Qualifiers
PEPTIDE                 1..105
source                  1..105
                        mol_type = protein
                        organism = Sorghum bicolor
SEQUENCE: 13
MPTPTPTPTP TCGDGSLAGF ALLLRGEKRV ANGARGGRGI GGERAKIIRR RHAEKTHGRR    60
ERGGHRRSHR LAYPLWVLDI RSPNGIMLGI FRGAALWLWT LAWHM                   105
```

```
SEQ ID NO: 14            moltype = AA  length = 235
FEATURE                  Location/Qualifiers
PEPTIDE                  1..235
source                   1..235
                         mol_type = protein
                         organism = Sorghum bicolor
SEQUENCE: 14
MVQSKKKFRG VRQRHWGSWV SEIRHPLLKR RVWLGTFETA EEAARAYDEA AVLMSGRNAK   60
TNFPVPRTAT GELAPVPAAR DARGGGGSSS AAAAPGGGTS NLSQILSAKL RKCCKTPSPS  120
LTCLRLDPEK SHIGVWQKRA GARADSSWVM TVQLNKDVPP PASSSGEEPV PSDGGAAATT  180
PTSTSTSSTV TTTGSPPPAM MMDDEERIAL QMIEELLGSS HSHGMFQGAA GSIVI       235

SEQ ID NO: 15            moltype = AA  length = 258
FEATURE                  Location/Qualifiers
PEPTIDE                  1..258
source                   1..258
                         mol_type = protein
                         organism = Sorghum bicolor
SEQUENCE: 15
MGRSPCCEKA HTNKGAWTKE EDDRLVAYIR AHGEGCWRSL PKAAGLMRCG KSCRLRWINY   60
LRPDLKRGNF TADEDDLIIK LHSLLGNKWS LIAARLPGRT DNEIKNYWNT HIRRKLLGRG  120
IDPVTHRPIA DAGAGTVTTI SFQPNKPNAA VAAQAPQHQP IKAVATAVVK VPRCPDLNLD  180
LCISPPCQQK EDEELDLKPA VVVKREVLQA GHGGSLCFGC SLGIQKGAPG CSCSSSNSHH  240
RFLGLRSGML DFRGLEMK                                                258

SEQ ID NO: 16            moltype = AA  length = 264
FEATURE                  Location/Qualifiers
PEPTIDE                  1..264
source                   1..264
                         mol_type = protein
                         organism = Sorghum bicolor
SEQUENCE: 16
MGRSPCCEKA HTNKGAWTKE EDDRLVAYIK AHGEGCWRSL PKAAGLLRCG KSCRLRWINY   60
LRPDLKRGNF TEEEDELIIK LHSLLGNKWS LIAGRLPGRT DNEIKNYWNT HIRRKLLSRG  120
IDPVTHRPIN EHTSNITISF EAAAAARDRE ENKGAVFRLE EHNKATAAAA AAIGRDHHQN  180
HHPAGDWGQG KPLKCPDLNL DLCISPPAAP CQEEKAMVTM KPVKREAGLC FSCSLGLPKS  240
ADCKCSNFLG LRTAMLDFRS LEMK                                         264

SEQ ID NO: 17            moltype = AA  length = 213
FEATURE                  Location/Qualifiers
PEPTIDE                  1..213
source                   1..213
                         mol_type = protein
                         organism = Zea mays
SEQUENCE: 17
MTENLHSRKM VQPKKFRGVR QRHWGSWVSE IRHPLLKRRV WLGTFETAEE AARAYDEAAV   60
LMSGRNAKTN FPIQRSSTGE PTPAAGRDAR SNFSSGSSTL NLSQILSAKL RKCCKAPSPS  120
LTCLRLDPEK SHIGVWQKRA GARADSNWVM TVELNKDAAS TDAASQSTSA TTAPPATPMD  180
EEERIALQMI EELLSSSSPA SPSNGDDQGR FII                               213

SEQ ID NO: 18            moltype = AA  length = 257
FEATURE                  Location/Qualifiers
PEPTIDE                  1..257
source                   1..257
                         mol_type = protein
                         organism = Zea mays
SEQUENCE: 18
MGRSPCCEKA HTNRGAWTKE EDERLVAYVR AHGEGCWRSL PRAAGLLRCG KSCRLRWINY   60
LRPDLKRGNF TADEDDLIVK LHSLLGNKWS LIAARLPGRT DNEIKNYWNT HIRRKLLSRG  120
IDPVTHRRVA GGAATTISFQ PSPNTAVAAA AETAAQAPIK AEEETAAVKAP RCPDLNLDLC  180
ISPPCQHEDD GEEEEELDL IKPAVVKREA LQAGHGHGHG LCLGCGLGGQ KGAAGCSCSN   240
GHHFLGLRTS VLDFRGL                                                 257

SEQ ID NO: 19            moltype = AA  length = 273
FEATURE                  Location/Qualifiers
PEPTIDE                  1..273
source                   1..273
                         mol_type = protein
                         organism = Zea mays
SEQUENCE: 19
MGRSPCCEKA HTNKGAWTKE EDERLVAHIR AHGEGCWRSL PKAAGLLRCG KSCRLRWINY   60
LRPDLKRGNF TEEEDELIVK LHSVLGNKWS LIAGRLPGRT DNEIKNYWNT HIRRKLLSRG  120
IDPVTHRPVT EHHASNITIS FETEVAAAAR DDKKGAVFRL EEEEERNKAT MVVGRDRQSQ  180
SQSHSHPAGE WGQGKRPLKC PDLNLDLCIS PPCQEEEEME EAAMRVRPAV KREAGLCFGC  240
SLGLPRTADC KCSSSSFLGL RTAMLDFRSL EMK                               273

SEQ ID NO: 20            moltype = AA  length = 256
FEATURE                  Location/Qualifiers
PEPTIDE                  1..256
```

```
source                  1..256
                        mol_type = protein
                        organism = Panicum virgatum
SEQUENCE: 20
MGRSPCCEKA HTNKGAWTKE EDDRLVAYIR AHGEGCWRSL PKAAGLLRCG KSCRLRWINY    60
LRPDLKRGNF TADEDDLIVK LHSLLGNKWS LIAARLPGRT DNEIKNYWNT HIKRKLLSRG   120
IDPVTHRPIA DAARNVTISF QPDAPSQQQL SDDAEAPPPP PPQQQQQLKP PPRCPDLNLD   180
LCISPPCHKE EEDQELVKPA AVKREMLQAG HGTLGLCFGC SLGLQKGAAG CTCSSNSHFL   240
GLRVGMLLDF RGLEMK                                                   256

SEQ ID NO: 21           moltype = DNA   length = 1014
FEATURE                 Location/Qualifiers
regulatory              1..1000
                        note = tissue specific promoter
                        regulatory_class = promoter
5'UTR                   1001..1014
source                  1..1014
                        mol_type = genomic DNA
                        organism = Arabidopsis thaliana
SEQUENCE: 21
acgtacctcg tgtccaccgg tgactctatc cccggcgtta gaagtgatga tagtctcgtt    60
cccaagggaa atcagccttc gaattggaat tgatccctcc ggacattttg tgccgttcgt   120
gtgccagact tgccatccat ataatgcatc ttcttctttt tttcccgcag atggcatgtc   180
cgttggtctt tcctgtatca tttatttaca aagaaaaat aaattaaaca tttattaagt   240
tccccccgta aaaaaaaat atatatat atatatat aacacatgca tcataattgg       300
tatgtccgta ggtgttttcct tatcataact gaaccattgg taaactatcg gttccgttaa   360
agcataagac tagaaaaggc tcggtgcgac tcgctaccac gttctaaag attttatta   420
gcaaattaac cccaatatat attttgctat gagggtctaa acaaactggt atatgagcca   480
tttacttacc acttattagt tccaagtatt tattttttgg gttaattaat gtttaaatta   540
ttggttgaca aaaaatataa aaataatggt taagttattg aaatgacttg agcaatctga   600
tgcaactgcg gataacatga actcattcga agtgacgtcc caaatatttg attctttgtt   660
tttattcctt tttgtcaagg tcaagattgg ccaaacattt tcaatatcta aatatattga   720
cattcatagc ctgaaaagaa aaaaatatat ggttaaatta gttccaaagt attctagcag   780
caacaaaacc gctccaataa acgatttcca atttctatct caaactttgt tcccaatcat   840
tagttataat ccgtcccta aaccaaaaaa aaatctaatt gtaaaggtgt tgcaatagat   900
taaccattttt tattttattt tggtaaaata gattaaccat tttgttagaa aaatgaagtt   960
taaaacattt acagttctac gtgtacatgc ttcgaccaat atgcttcgac caat        1014

SEQ ID NO: 22           moltype = DNA   length = 1296
FEATURE                 Location/Qualifiers
regulatory              1..1000
                        note = tissue specific promoter
                        regulatory_class = promoter
5'UTR                   1000..1296
source                  1..1296
                        mol_type = genomic DNA
                        organism = Arabidopsis thaliana
SEQUENCE: 22
atacatgtca tgattttata attatgtata tataaatact aattgatgta tgaagtacgt    60
agataatgtt acgatctatt aatctatta cattaacttt taattagtgt tgagtaggga   120
aaattaacat ataaacctt agcagttggt tgtattatta aaaataattt gaacttaaaa   180
tccaccttcg aaaagataaa tcaaacaagt ataaaaatg ctataaatcc agaatatta   240
cctaaggttt ttattcttct acttaataat gtaagataaa accggcacaa tacttgttac   300
gtatgcatgt taggtaccgc aattgtgtaa gcaaatcggc acaatactaa ggttacatat   360
actaactaaa taaaacaatc tgatttcagt gacaccgtat atctaacctt tattcaaatc   420
caagggaaca tgacttgact tcttctgttg gaactaactc gatccctcaa ccatctccaa   480
ggatagaaga gttagtaaaa tcaaacttga agtgaggaag taagcagttt aacgactcca   540
tatgactaca gttatataca aagttgggca caaagtacaa gtactaaata ctcaaagtca   600
gataataatt ttaataagta caaactatat atatgcagta caattattga gtatatataa   660
acgagactgg tgatttgggg cattgtccac cagggtgtta tatcccaatt gaaatttgaa   720
aatttaagtg tgtgagtgtt acgacaaaaa aaagtgtgtg aattgtaggc gcggtgaaaa   780
ggtaaattaa gattggaact agaaaaatag ttgaatatcc tttactaaaa gttgtcaatt   840
ccggtttttag taaaaaaaaa tttaaaaata gaaatttata ccaaaagact tcaaacacac   900
atattcgcat atataacata agatatcatt ttttgtaaac agttaaaaag aaaaacacat   960
gtttttttt taatttaga aaaaacatg ttattataca aaacagagtt tgcccacttt      1020
ttaatatgtt atgaaaagaa aaatgatttt cttgggtttg gtcagagaga ttggttgtgg   1080
taagaatggg aatcttaatt acaaagaatt ggatttggg tcgacctacc acctaaaacg   1140
acgtcgcctc catctctggt ttccaaatct cttttctcctc tccctttata agcttgcgtt   1200
ggccagtcgc tcatctcgaa aacagagaga aaaagactaa aaacacagtt taagaagaag   1260
gagagataga gagagaagag aaagatagag agggag                             1296

SEQ ID NO: 23           moltype = DNA   length = 1000
FEATURE                 Location/Qualifiers
regulatory              1..1000
                        note = tissue specific promoter
                        regulatory_class = promoter
source                  1..1000
                        mol_type = genomic DNA
                        organism = Arabidopsis thaliana
```

```
SEQUENCE: 23
aactagaaca cttcagataa attttgtcgt tctgttgact tcatttattc tctaaacaca    60
aagaactata gaccataatc gaaataaaaa ccctaaaaac caaatttatc tatttaaaac   120
aaacattagc tatttgagtt tcttttaggt aagttattta aggttttgga gactttaaga   180
tgttttcagc atttatggtt gtgtcattaa tttgtttagt ttagtaaaga aagaaaagat   240
agtaattaaa gagttggttg tgaaatcata tttaaaacat taataggtat ttatgtctaa   300
tttggggaca aaatagtgga attctttatc atatctagct agttcttatc gagtttgaac   360
tcggggtatg attatgttac atgcattggt ccatataaat ctatgagcaa tcaatataat   420
tcgagcattt tggtataaca taatgagcca agtataacaa aagtatcaaa cctatgcagg   480
ggagaagatg atgaaaagaa gagtgtgagc caatacaaag cagatttgag gacatggctt   540
acaagtcttg ggtacagagt ttggggagtg atgggtgcac aatggaacag cttctctggt   600
tgtccagttc ccaagagaac cttcaagctc cctaactcca tctactatgt cgcctgatta   660
aatcttattt actaacaaaa caataagatc agagtttcat tctgattctt gagtcttttt   720
tttctctctc cctcttttca tttctggttt atataaccaa ttcaaatgct tatgatccat   780
gcatgaacca tgatcatctt tgtgtttttt tttccttctg tattaccatt ttgggccttt   840
gtgaaattga ttttgggctt ttgttatata atctcctctt tctctttctc tacctgattg   900
gattcaagaa catagccaga tttggtaaag tttataagat acaaaatatt aagtaagact   960
aaagtagaaa tacataataa cttgaaagct actctaagtt                        1000

SEQ ID NO: 24        moltype = DNA   length = 1167
FEATURE              Location/Qualifiers
regulatory           1..1000
                     note = tissue specific promoter
                     regulatory_class = promoter
5'UTR                1000..1167
source               1..1167
                     mol_type = genomic DNA
                     organism = Arabidopsis thaliana
SEQUENCE: 24
tacatcagtt tcatcatcta tcttgtttct tatagaagct cacaatcttc ttcctggtcg    60
agtttagaaa tgtcagagag agttgtttcc acagagacgt agaaacccat aactttagta   120
ttcttcaacc cttacaactt atctgagcaa aatcagaagg tcgaatttga tggatggttt   180
tgctgtattt ggtcaacggt tttatttgag acagtagacc agaggaaact cagatgtgat   240
gatgcaaaga ctgaattggt taagagtgta gattgatttg ttctaacatt gcaaatgtag   300
agtagaatta tgcaaaaaac gttaatgaac agagaagtga ttaagcagaa acaaaattag   360
agaagtgata ttatatctca aaatttattt ttggtacagc taaagctcaa attgttatag   420
agattagaga tattaaacca aatgacgagt gttttcttta gtagtaaacg gtgaaaattc   480
tcttctgaca aagacaatta aaatttttagg tttaagactt taatacatatgt cacaaattgt   540
catttaccta aataaaaaaa aaactaaata ttttttttag atacatatgt gtcttataat   600
tttaactata aattttaatt ttatgtctta ataattgtt tacactataa atttaaatat   660
tttaatgcta aaattaattt gattcaaaaa agtgatttta attcttattt ttcttataga   720
aagttggtga ttgaaaagat ttacttaaaa attataacaa cttcaatggt gaataacccg   780
acccgaataa accggatata acaacttcaa tgttagcttg aatagaaag tacggtgacg   840
cttaggaggc aagcaagcta gtatctgccg ctggttagag acaaagaaca tgtgtcactc   900
ctctcaacta aaactttcct tcactttccc gcaaaatcat ttcaaaaaag ctccaaattt   960
agcttaccca tcagctttct cagaaaacca gtgaagaaa cttctcaact tccgattttt  1020
cacaatccac caaactttt ttaataactt ttttcctct tattacaaaa cctccactct  1080
catggcttct caaacttgtt atccatccaa atctcaatcc ctaattaggg ttcatttctc  1140
tgtttctcca aacaggggaa ttcgaag                                     1167

SEQ ID NO: 25        moltype = DNA   length = 1019
FEATURE              Location/Qualifiers
regulatory           1..1000
                     note = tissue specific promoter
                     regulatory_class = promoter
5'UTR                1000..1019
source               1..1019
                     mol_type = genomic DNA
                     organism = Arabidopsis thaliana
SEQUENCE: 25
tcttcttgca tcaatgatat caacaacaat gggtaataaa gaagctactt cgaaattata    60
tatttttcg tattctatat tgatcatcag tcttaagtgg tttggtttgt tgcagtgaag   120
aagaactatg tatggatcta cgccaccgtt cagttcggtt ttgtggtcct tttcgctcag   180
cttttctaca gagttgtaag atttgatgta atgtcacaga gaaaccttac tttgttgtca   240
cagagaaacc ttactttgtt gaagagtttt tgattcctca cactctctct cattaacttg   300
tgtgtaggtg aagcagccgg taatgtgcat tgtcttagcc actatgatcg gatttggact   360
caccatgacc ggcacaacag ctattaacga gtatttgaaa tggaggagaa gcaattccca   420
cctgccagaa gagccagcaa gtactcaggt ggtttgacag cagcgtagat ctttttgagtg   480
aagctagagt ccctaaaggg ttggatcggt tttcaattaa ccggtcgggt ttcggtttc   540
ggtttagctt taatcgactt gtctaggttg agatcagatt tggttttcaa tacttccaag   600
tcttttttttt tttgccaact aaaatataag gaatgatgat aggcacacac atgacacata   660
aaatcataat gaacagtagt atgattagca atccatattt cttggataac acttcttcac   720
agctttttg acaggtcact ataacacctt tttcagttca tttttcattt tcaatcctca   780
cccacccaaa ctctccctttc aaagcaattgt ctctcctcct tctttctcaa ttcaaacaaa   840
ctttattaaa cctaaagaa acatttccaa tctctaatga cttagttgat agaatctcat   900
ttagttacct agtaataatc ttcacactag taagagaatc ctactcttca ccaaactaca   960
tctctctcta tataacaaac cccaaaacat ctcaacatac acacacaaca actacaaca  1019

SEQ ID NO: 26        moltype = DNA   length = 1093
```

| FEATURE | Location/Qualifiers |
|---|---|
| regulatory | 1..1000 |
| | note = tissue specific promoter |
| | regulatory_class = promoter |
| 5'UTR | 1000..1093 |
| source | 1..1093 |
| | mol_type = genomic DNA |
| | organism = Arabidopsis thaliana |

SEQUENCE: 26

```
tgcgaacagt ttgattctgt ttttcttttt cctttttttg ggtaattttc ttataacttt   60
tttcatagtt tcgattattt ggataaaatt ttcagattga ggatcatttt atttatttat  120
tagtgtagtc taatttagtt gtataactat aaaattgttg tttgtttccg aatcataagt  180
ttttttttt tttggttttg tattgatagg tgcaagagac tcaaaattct ggtttcgatg  240
ttaacagaat tcaagtagct gcccacttga ttcgatttgt tttgtatttg gaaacaaca  300
tggctggtca aggcccagcc cgttgtgctt ctgaacctgc ctagtcccat ggactagatc  360
tttatccgca gactccaaaa gaaaaggat tggcgcagag gaattgtcat ggaaacagaa  420
tgaacaagaa agggtgaaga agatcaaagg catatatgat ctttacattc tctttagctt  480
atgtatgcag aaaattcacc taattaagga cagggaacgt aacttggctt gcactcctct  540
caccaaacct taccccctaa ctaattttaa ttcaaaatta ctagtatttt ggccgatcac  600
tttatataat aagataccag atttattata tttacgaatt atcagcatgc atatactgta  660
tatagttttt tttttgttaa agggtaaaat aataggatcc ttttgaataa aatgaacata  720
tataattagt ataatgaaaa cagaaggaaa tgagattagg acagtaagta aaatgagaga  780
gacctgcaaa ggataaaaaa gagaagctta aggaaaccgc gacgatgaaa gaaagacatg  840
tcatcagctg atggatgtga gtgatgagtt tgttgcagtt gtgtagaaat ttttactaaa  900
acagttgttt ttacaaaaaa gaaataatat aaaacgaaag cttagcttga aggcaatgga  960
gactctacaa caaactatgt accatacaga gagagaaact aaaagcttt cacacataaa  1020
aaccaaactt attcgtctct cattgatcac cgttttgttc tctcaagatc gctgctaatc  1080
tccggccgtc cct                                                   1093
```

| SEQ ID NO: 27 | moltype = DNA  length = 1146 |
|---|---|
| FEATURE | Location/Qualifiers |
| source | 1..1146 |
| | mol_type = genomic DNA |
| | organism = Arabidopsis thaliana |

SEQUENCE: 27

```
tctctaattg tcaagtatct tagtctagag ttaattactt aaatactaaa aggctgtcga   60
caaaatcaag cttgaatctc cttgtggtat cttcaactct tcgttgtctg cttacgagtg  120
gtttactcag taattatcta taatatgtta ttttttttcc ctcatctttt agttgttgtt  180
tcattacatt gaaaagcttg taatgtcttt atatggtata tggatctt atgagtgagg   240
caagatccat gatgttttg atcttagaat gtatatgatg atcttagaat gtatttgacc  300
gcccacaaat tattgttcat tgggattata tctctagtcc aactccaagc aatcgaaatg  360
ggtcctgctt ttaagaacaa cagtatatgt ttaagaataa taactttata tattctcgat  420
tttaagatct tttgacaaaa cctccttttc gttaggagcg tactaatttc caagtgtttg  480
attagtgggg tctccgtaaa tttatttaga gtttctatct atttattaat agctcaatta  540
attaatctat actgtatcta aacatcaatt tatatattta ctcttgagac caaaactgtc  600
aatttataac attggatagt ttcttaattc ttattatata ttttcaaac acttttcaag  660
actaatctcc acattaggta ctctctctag agataaaaat atttatcaaa aacattttta  720
tttatttatt aagtagtaga taaactactg tggcaaaatc gtaaatgtct aaatgctgat  780
gaattttttt tgctgctcca atctggttta gtgctccata tacatccacg gccaaaatga  840
atctatggcg gcattaagat tcattagtaa gcaacgatta tattaatata attgttttta  900
gcaatgattt tccgtaattt cccaaatatg tttcagttaa tgtgttccaa tcccaacaac  960
tggttgttgc aaaagaccac caacgcaagc aatcatcaaa catcaaaata atcttacctt  1020
agcgaacaaa caataactac acaattctca taaagctctt atatatcact aacttcacac  1080
atttgttttt ccacaaaaat aaaaacggaa ctcactcaag aaaccttctt ccttgaagag  1140
agggtt                                                            1146
```

| SEQ ID NO: 28 | moltype = DNA  length = 1000 |
|---|---|
| FEATURE | Location/Qualifiers |
| source | 1..1000 |
| | mol_type = genomic DNA |
| | organism = Oryza sativa |

SEQUENCE: 28

```
tacagggtct caagccagga tgacctcctt tgaaacgtac gagtggtaaa acagtacgaa   60
gaacatcaaa ttttcatgag aattttcata ggagacaggt taagagagaa cttcaagaga  120
ttggacctta tgttaacttc ttctagagat tggaccttat gttaactttc ttctataaaa  180
tattagtgaa gtgaggaaac ttctaaaaca attatatgga gtgatgaaaa aaattatttg  240
gtcagacggt aactatgagt actccataat ccgtataaga taataacatg gtaattctat  300
taggcgttcg ccaacgaagc cccaagcagc cacccaaggt agctaggcgg tgcctttgtc  360
cgtgtatcaa aaatctccat gcacgggagc cattccaaat aaaattttga agctccaagt  420
ttttgttccg aaggatcaaa tagaaaaatt atccgtagaa attgaatcct aacaaaaatt  480
ccccacaatt cctctaatta aaacgaggcc gaagcggctt cctgatcgga cggctggaag  540
gccatacatg tcctggcatt aattatcact caccttagat tattacagct cggagctaga  600
aagccctgca agttgcaatt aatggtgagt atgatctgat ctgcagcgaa atgatctatc  660
gatgtcccta gttaagcagt cattgtgtcc cttacccacc taaatccacg agtgtcagag  720
ctaagcgcga tcccgatcct taaacccaa ccccactctc ttgctgctcc atcaagcaac  780
caaccccaat ccacacacca tacataatta catactacca gctaattaat tactaataat  840
gacttaatat tccatcatct cccagctcag ttatcacttc ttgatcacac ccctaccat   900
tgattaacct cttccatctc actctacacg cctatataat tagcctaatg atctcacttt  960
gcaaagcatc tcattgcact aaactgctca ctgcatttgc                       1000
```

```
SEQ ID NO: 29           moltype = DNA  length = 1000
FEATURE                 Location/Qualifiers
source                  1..1000
                        mol_type = genomic DNA
                        organism = Oryza sativa
SEQUENCE: 29
actcgattcc attagattat tcacaaaccc atgtgaaccg tgactgtcag tcaggtgagg    60
aaacagatat tccaaaaatc atattctttc cttttgtatt aaccaaattc acacaaaggt   120
gatatttaaa actgacgaag atgaaaatta agttgacgca cgtaaaatga aaaagctatc   180
ggcatatgat taattaaatt taattattac aaacttgata aatgaatata tttgatattt   240
taaggcaact tctatataaa acttttttat atgaagagga ctgctacaaa acgggatccc   300
gttgcaacgg gataaggcat attaactatt ctcttgcatg agtatcacag atatcaggcc   360
ctaagtatca taggtaccag gtaacaggta tcacaggtat cgggtaccat acagctcgta   420
ccacaacagg tatcaggtac tatctcataa aaggtaacgt gataccgttg tctaggtttt   480
ctgttatatg aaacatattg tagtttaaaa aacgtgccaa cgaaaataga gataaaaatc   540
tgaatcttga tgagaaaatc atgcccaaat ttcaccctaa aacagtcaat ttcccgcgaa   600
aaaaagcaaa aaaaaaaaaa ctccagacag ttgttaaaag gggaaaaaaa aagacagaat   660
gctcagccgt cgagacacac acaacggcaa cgtcttacca gctcggagct ctctcgcttg   720
ctgcctcttc tcttcttcct cccgccaccg acaccacctc caccagcagc ttcgccttcg   780
ccgcgtcggc atctgcagtt gccacttcgc tttcttccac tccctcctcc tcctcgctta   840
cctcacactc ctccccccca atttcatccc ccacccacca ccagatcccc caccacctgc   900
cgcattctcc cccccaagat ccagatcgcc ggtcacccc acgaactcgc tcgagatcca    960
gagagagaga gagaggcagt ttcttggttg attttcgagg                        1000

SEQ ID NO: 30           moltype = DNA  length = 1141
FEATURE                 Location/Qualifiers
source                  1..1141
                        mol_type = genomic DNA
                        organism = Oryza sativa
SEQUENCE: 30
gagttaaatt gatatggttt tgtctgtcaa ggtgccgttt ctatggttgg aggaggaaaa    60
tgaaattagg ggaatagaac agtcgcaatc caaaagctat tgttctctct tctacggtag   120
ttgatagttc gatacgtgtg tttgatgtga gagactgaga ggatgcacg gtgcacctga   180
cccgtaagga cgcggaacta cattatcaga ggctaggccg gtactgttat acgcgacgtt   240
cacgaatcac gatgcgtaaa aaagtgaagc atgaaacagt actaggctct ccacgggcca   300
catcatgaaa aaactggtgc gacgccacgc ttaacaattt gtcggtcgta aactcgtaaa   360
gttaaaagcc ccacgacatt gtcaaccaat atctcagcac atgaacttct ctaacgagta   420
caacgaaacc gcatccgcaa aagcgccgtg aaccaaagct cttgccgtgc tgtgccgtgc   480
cggtggccgt gaacatgtgg aacacgaaga actcttgcgc gagatcggag cacctgacct   540
cccacctcgc gtccggcccg tcgccgtcgc agcaagcggg ctgtcaaaaa cgacgccaca   600
gcgcgagcgc tctcgccgat ccggcggacc caccctcctc acctgcgca ccaaccgccc    660
gttcgctagt ccgatccccc accctcatc cccctcagct caggtt acgcgcctcg       720
ccgcggccaa cgcaaaccaa accaaatccc ccgtcacctt cgcttcgaaa ccccgcaaaa   780
ccccatggaa gaaaacaccg aacacctgcc gcgcgcacgc ctcctcctcc ccgcctctc    840
ctcctctctc ccgttccatg tccgctcaac cttgcttcca ttctttccat ccacccgccg   900
atcgacgcga tgccgacgcc caacccac ccaccgccgc cagccgccac cccaccctgc    960
gcctctgcgg ctatggctat atcaccatgc ctccaacctc cggtacgctt agcctctctc  1020
tctctcccc tcccattctg cgcattgctc tctgcgcgcg gtgcgcgtgct gctgctcgcg  1080
gcgccccgga gcgtctcctt tggggagag gagaggagag gagaggagag ggggtgagc   1140
c                                                                 1141

SEQ ID NO: 31           moltype = DNA  length = 1000
FEATURE                 Location/Qualifiers
source                  1..1000
                        mol_type = genomic DNA
                        organism = Oryza sativa
SEQUENCE: 31
ttcaatgcag gatgacgcca agagggagaa accaagcaga ggtggacggt acaacgtgta    60
agtcaccgca aaacgttgca gcttggatag tggccatcga gtggtgtgcc gataccggcg   120
cctgttcttt acagcctcag ctagtgttgt tgtccgaggc aattttttccg acctattgtg   180
ttgctttcct ctctgatagc ttatggtaaa agatacaaag atgttgagga gtttgtacgc   240
cacttaattt tgctcgtaac atacattgac aatcaagagg agccatggca ttgcgatctg   300
cttacacggc atattcttac tggatggtgt acactactta cccttttta tgcaagcatc    360
aatccattgc ttttctcact gcacacctga ttcgtactga aaacgtgaaa cataaaaaaa   420
aacaaaaatc tagctgatgt tggctctcgg ggcctcgagt ctagtttgtc ctagatggct   480
aacctgatat gtgttggtca cgctcacgtt tgaaccgaga aagagtgtgt gtgtgtgtgt   540
gtcggcgtgc tgctacacca gagcctccct gaatcgcaat gcgtgttaac gccagcatcg   600
caggatttca tctcacttga caggttcaga tggccttcct cctacgtct gccatttata    660
cacgcagtga cttaacgctt acacgagccg gatggcccgg atctcccccc tgcaccatct   720
caccagaaaa acgtgaggc gtcaccgcaa cccacccacc aaacacatcc acgtcccttc    780
accgttggcc ttcgattttg cttcagctgc actacgaccc ctcaacaca tttccctcgc    840
gtctcgttgc gatctcacct tacgacgatc tcgttccagc agcagcagca tcggcagcgg   900
cggcttgctt ccgaagcgag caatgcatgg cgcgcgcggc gcgtgcgtg cgtgccttgg    960
cttgcgctct aatcaaaccg ggacgcccca actcacggtt                        1000

SEQ ID NO: 32           moltype = DNA  length = 1000
FEATURE                 Location/Qualifiers
```

```
source              1..1000
                    mol_type = genomic DNA
                    organism = Oryza sativa
SEQUENCE: 32
acaacccctg ttgcaccaaa cttgctttt taagttttaa ctgaaattag gatagcaaag    60
agagtacttt aggcttcatg ctacgagctg cctacgacca tagacaggct taatcttgtc   120
ttatagttgt atcttgttga tcattaggtg cctaactgcc tacataggca taatgcatcc   180
tttcatctga tctttgtcac tgaccccatg tacagagtcc tataagttgc aatgttctaa   240
tccttgtttc gtcagtcatt tcgtacacat ggatgaaagt ctggggttta accaccgatg   300
cgatccaatc ttctcctaca gtcgatgata aggaaatcgt aacaaagaat gtgaattttt   360
ttgacgctac aaagaatgtg aatgatctga ccagtctatc tttcaccgaa ctgaagcata   420
tactctgaat gtcaagatc atacttagac tgaactatat actctgaata tctaaagatc    480
tcatacattc atacttacgc tgcaggttgc aaattctagt cattattaca ctcgagacct   540
aaattatgat tagtggggtg tactccgata gaacagttca cagttcagaa ctcaaaagct   600
acgaatgaat tcatgacaaa aggcgacaag tgatacgtat tcgagaataa atgtgtgaac   660
aaaggccgtc tcaaaaaaaa aaagaaaaa aaaaaagaga atcccttgc ctgcactcta     720
aaacccagcc cgacccaact ctttgtacat gaccagcaaa agcaccgtct gctgcgactt   780
ttttctctt gtgcaatcta ttgtcggaa aaagagagg agaattatca tatcatcacc      840
taataaattg caaccaccag aggtactgtc ctctctatat aactcttct cgggcatttt    900
gctggcactt gcctgttcta gtatctatag ctagctaact gttactgtac ctcctcccat   960
atatcatctt catatttttg cagatcgata agcgagaaaa                        1000

SEQ ID NO: 33       moltype = DNA   length = 1247
FEATURE             Location/Qualifiers
source              1..1247
                    mol_type = genomic DNA
                    organism = Oryza sativa
SEQUENCE: 33
catactttac cttgttgtat aactgcatgc ataagaatct gagagccatt gctcaattct    60
tttcaacgaa gatgtgaact gttggaaggc aatgtaaaac gggaagcgct gtatgaaaga   120
atatgacgca catcgtcttt tgttttttaa gaattgagta tatattcgtt gtggggaaca   180
gcctgatgat gggccccggg aattaacgct cgagcaacgt tggaccattc tgacatcgcg   240
tttcctgatt agcacaatgt ttcgttttat ttggaaattg aattgaatgt ttctactgtt   300
attaattgca gacagtacac caaacgacca aatctatctg aaacaatta accaagacca    360
actggagaat ttacagatga atcactgtgt tacacctgta aactgtggct cctttgagaa   420
ttgagttaca acaagagttt ggagatgaac ttgtagttca tctatatcat cttaattaaa   480
caataatatt tattcaggaa tgcagttcag agactgctta acacacacac acacaaaaaa   540
aaaacctaaa cctgaggctt gtactggaac aaggtcatta gcaaggtgtc ctctagactc   600
ccggaccgac actaccettg gaagtcaaac gcagctggca caaacaaacg gagcctcggt   660
gacgccggta aaccgcacca atcattgtta aaccaaaaaa cgtgaacaac aaaccaaaaa   720
gaaactaaaa aaccgctaaa aagacgcaaa agagagagaa aaaaatgaa agaagaaaag    780
aaacgacgcg gactcgctga cgacccgcgg cccggtccaa cccaacccc accgcctctc    840
tcgccgaccc cgtccactcc gccgaattcc cccccaaacc caaaccccaac gcgacctcac    900
ctcacccgca cgacgacggc acgacgcgac gcgttgcccg agctgacggc ttgacgacgc   960
ctccgtcccc gtccggcacc aacccatccc aacccaacgc tccccttttc cactgaccaa  1020
ttgatagccc aacctcacct ctcctctcct cctccccct cctctcctcc tcgcctccgc   1080
accagcagtt tcgtgcaccg cacttcaccc acctacctcc cccaacctcc ccatcaaaaa  1140
ctagtagtag cagtatccac ccatccacgc acgcgaccga gcgcgatcga ttcgaggcgg  1200
cggcggcgga ggaggaggag ggggagtaga tccggcgggc ggcagcg                1247

SEQ ID NO: 34       moltype = DNA   length = 1000
FEATURE             Location/Qualifiers
source              1..1000
                    mol_type = genomic DNA
                    organism = Zea mays
SEQUENCE: 34
tttgtgctga gatcggcacc agctttcatt taatacagcc tcagcttacc tgaggcaatt    60
ttcgcacctg ttatgatgtt gttttgctct cagataggtt tatgtagcac aagaaagata   120
tgttggagac gttgacgatt ttgtatgcaa ctaaatttct atcttaatat gccccgattc   180
aacagcaccc agtcgagtca ttgcgttctg gagattcttg cagcgcattt ccatgtttaa   240
gaccttatta tgaaatgtct ggcattcgtg gatccactga gcttcttct gcgaatgtgc    300
catatcgtgg cattggccga agcaaccaaa catttgttgc ccttttgtgt cggtgtttta   360
taaagtacct caatgacgat acagcctcag ggcgcttcct gcttttgcac ttattcggag   420
ttcaggcgag ttaacgaagt tcagacggtt ctgaagagag gccgtgttgt gttttgtcag   480
cgtggtatcg cgcaagcaca tgtgtctttg gtaagatggt ctggatggct gtcctaccac   540
ctgccatta tacacacact gacttcaccg tcacactggc acgacatgag ctcgccatcc    600
taccagaaac gctgagacgt caccggcaac caccctctc gctcgctctg gctctgtctc    660
ctgattttgat ttggacagaa aactgggcag ggcagggcgc gctcagcacg tttgcttcgg   720
aaacactgcg agtgtcgac acatttcccg gcttgatctc gaagcgagcc ctgatgtgtc   780
tgtcatgcac ctgcctgcct tggcttgtgc tctaatcaac gccggactcc ccaactcacg   840
gttggtgcgg gacgccaccc cgccacctta ccgcccgcct cggcgcctca ccagtcacca   900
cacctcgcgc ctgccatcag ctatatcacc gtggccactt ccgtgtccct tcacggatac   960
ctcaccccca cagcccccgg tcgatcgctc ggcaatcggc                        1000

SEQ ID NO: 35       moltype = DNA   length = 1000
FEATURE             Location/Qualifiers
source              1..1000
                    mol_type = genomic DNA
                    organism = Zea mays
```

```
SEQUENCE: 35
aggcggggcc ggaggagggc accagagagg ctgctcagga gagagaaata atagaatatg    60
tggtatagag taaacatgag tgcggatgat tgtggtatag agtaaagaat tttgctgact   120
aggacagaat attcttttta gggtagaaat ttagagtact atgagtgcgg atagcctaag   180
gaccacttta aatttgacac aatattgaaa tttgaatggt tttaacattt gaaggctgaa   240
aaccaaaata ctttgtagct aagtgttgga aacccgactc ggccaataag tcgacagacc   300
gtaaaataag gtcaatctaa actttatgat aaatattctt gtttgatagc aatagcattg   360
caggaccagg acccaaggga agagaagatg ccaaatccca tcgaggctaa agcaaaaacg   420
atccaattta tgagcaaacc cacactgaag ttttcaaaatt gttttctgaa aaaaaagtaa   480
ccagcaagtt aaaaaatgag atggcgggaa agccaagtct cggttggtcg agggggttggt   540
tggggcgcag cctgacaagt gacaacggca gcaggatagt agcatcaggc gcaagccagc   600
gcaggcggca gcgcgaggat ttcgcttcac ttagcggcaa cggagacgct gcacccaacc   660
aacacgagct ccccctcacc cgctgcgacg cgcgcgtccc acgagcggaa gccccccgcg   720
ccgacgcgag cgcggggggct cgaccgaccg acccaacgcc tccatctcca ccgccgcgcag  780
caaatcgcac tcccgtccgc cccgccgatc gaacagccac cgctcacctc tcccaccccgc  840
caaaaacctc cggcctcctc tcatattcat atagctagcc cctgccacaa ggtagagcgt   900
cgctcacacc tgcgtcgccc tgcctcgcaa tcgcgaatct gtcgagcacc tgaggggtcg   960
gaggccgaga gctagcctag cacgccggcc tccgcgcgcg                         1000

SEQ ID NO: 36          moltype = DNA   length = 1000
FEATURE                Location/Qualifiers
source                 1..1000
                       mol_type = genomic DNA
                       organism = Zea mays
SEQUENCE: 36
catgtatata agtattcaat acataaatca gttctggtaa agagtgaatt aagttaatgg    60
acgtgctgaa aatggtttgg cttagtcttg ttgtgtttta tggaaaaatt gtgtaggtca   120
cgattacttc tcaatgcaat tgagaaaagt tttaattgca agccatttat ggttatttat   180
taaaaaaaca aggagtaaca cgtcattgtt caaggcgcca agctaccaca tcactatgat   240
tcaaagaacc acttcagatt ttactcaaga ttggaaattg aatggttttg atatttaagg   300
ttactttttta ccgaaaaata ttggaaacga tcagactgaa atcgacttga tctagaaatt   360
atgatagaat ctcttgtttc atagcgggtc cggtgggaag acaaaatgtg taatcccgtc   420
gatatgtgct ttctaaatgc taaaaacgat ccaatatacg acgtgtgctt tctagcctgt   480
ttgtttgtct ttaatctgta ctagtttcta tgttttttt ctcattgaat tacagctaca   540
gtagtctaaa caacagcggg ctttaattcg aagcgaacaa cacctgctga gtaagcaaac   600
ccacgctgaa tagtttcaga aatgttttct ggatgaatag caaaattgta gtagcaacag   660
gatagacggc gggaaagcca agtctcggtt ggtccggccg tccggacgca gcctgacaag   720
ggcagcagca tagcaatagc atcaggcgca agccagcgca ggcggctttc gcttcactta   780
gcggcaacgg ggacgcagcg cccgcaccca accaacacga gctcctctcc tcacccgccg   840
cgacacgcgc gcggctccaa cgcctccatc tccatcgcgc gcaccaaatc gcactccgtc   900
cgccccgtcg atcgaacagc caccgctcac ctctctcacc cgccaaaacc tcctcccctg   960
gcctcctctc atactcatat agctgagcag ccctgccac                         1000

SEQ ID NO: 37          moltype = DNA   length = 570
FEATURE                Location/Qualifiers
source                 1..570
                       mol_type = genomic DNA
                       organism = Arabidopsis thaliana
SEQUENCE: 37
atggtacatt cgaagaagtt ccgaggtgtc cgccagcgtc agtggggttc ttgggtttct    60
gagattcgtc atcctctctt gaagagaaga gtgtggctag gaacattcga cacggcggaa   120
acagcggcta gagcctacga ccaagccgcg gttctaatga acggccagag cgcgaagact   180
aacttccccg tcatcaaatc gaacggttca aattccttgg agattaactc tgcgttaagg   240
tctcccaaat cattatcgga actattgaac gctaagctaa ggaagaactg taaagaccag   300
acaccgtatc tgacgtgtct ccgcctcgac aacgacagct cacacatcgg cgtctggcag   360
aaacgcgccg ggtcaaaaac gagtccaaac tgggtcaagc ttgttgaact aggtgacaaa   420
gttaacgcac gtcccggtgg tgatattgag actaataaga tgaaggtacg aaacgaagac   480
gttcaggaag atgatcaaat ggcgatgcag atgatcgagg agttgcttaa ctggacctgt   540
cctggatctg gatccattgc acaggtctaa                                     570

SEQ ID NO: 38          moltype = DNA   length = 600
FEATURE                Location/Qualifiers
source                 1..600
                       mol_type = genomic DNA
                       organism = Arabidopsis thaliana
SEQUENCE: 38
atggtacaga cgaagaagtt cagaggtgtc aggcaacgcc attggggttc ttgggtcgct    60
gagattcgtc atcctctctt gaaacggagg atttggctag gacgttcga ccgcgcagag    120
gaggcgcaa gagcatacga cgaggccgcc gttttaatga cgaggccgca cgccaaaacc   180
aactttcccc tcaacaacaa caaccaccgga gaaacttccg agggcaaaac cgatatttca   240
gcttcgtcca caatgtcatc ctcaacatca tcttcatcgc tctcttccat cctcagcgcc   300
aaactgagga aatgctgcaa gtctccttcc ccatccctca cctgcctccg tcttgacaca   360
gccagctccc atatcggcgt ctggcagaaa cgggccggtt caaagtctga ctccagctgg   420
gtcatgacgg tggagctagg tcccgcaagc tcctcccaag agactactag taaagcttca   480
caagacgcta ttcttgctcc gaccactgaa gttgaaattg gtggcagcag agaagaagta   540
ttggatgagg aagaaaaggt tgcttttgcaa atgatagagg agcttctcaa tacaaactaa   600

SEQ ID NO: 39          moltype = DNA   length = 570
FEATURE                Location/Qualifiers
```

```
source                  1..570
                        mol_type = genomic DNA
                        organism = Arabidopsis thaliana
SEQUENCE: 39
atggtacatt cgaggaagtt ccgaggtgtc cgccagcgac aatgggggttc ttgggtctct    60
gagattcgcc atcctctatt gaagagaaga gtgtggcttg aactttcga acggcagaa     120
gcggctgcaa gagcatacga ccaagcggct cttctaatga acggccaaaa cgctaagacc   180
aatttccctg tcgtaaaatc agaggaaggc tccgatcacg ttaaagatgt taactctccg   240
ttgatgtcac caaagtcatt atctgagctt ttgaacgcta agctaaggaa gagctgcaaa   300
gacctaacgc cttctttgac gtgtctccgt cttgatactg acagttccca cattggagtt   360
tggcagaaac gggccgggtc gaaaacaagt ccgacttggg tcatgcgcct cgaacttggg   420
aacgtagtca acgaaagtgc ggttgactta gggttgacta cgatgaacaa acaaaacgtt   480
gagaaagaag aagaagaaga agaagctatt attagtgatg aggatcagtt agctatggag   540
atgatcgagg agttgctgaa ttggagttga                                    570

SEQ ID NO: 40           moltype = DNA   length = 825
FEATURE                 Location/Qualifiers
source                  1..825
                        mol_type = genomic DNA
                        organism = Arabidopsis thaliana
SEQUENCE: 40
atgggaaggt ctccttgctg tgagaaagac cacacaaaca aaggagcttg gactaaggaa    60
gaagacgata agctcatctc ttacatcaaa gctcacggtg aaggttgttg gcgttctctt   120
cctagatccg ccggtcttca acgttgcgga aaaagctgtc gtctccgatg gattaactat   180
ctccgacctg atctcaagag gggtaacttc accctcgaag aagatgatct catcatcaaa   240
ctacatagcc ttctcggtaa caagtggtct cttattgcag cgagattacc aggaagaaca   300
gataacgaga ttaagaatta ctggaacaca catgttaaga ggaagctatt aagaaaaggg   360
attgatccgg cgactcatcg acctatcaac gagaccaaaa cttctcaaga ttcgtctgat   420
tctagtaaaa cagaggaccc tcttgtcaag attctctctt tggtcctca gctggagaaa    480
atagcaaatt tcggggacga gagaattcaa aagagagttg agtactcagt tgttgaagaa   540
agatgtctgg acttgaatct tgagcttagg atcagtccac catggcaaga caagctccat   600
gatgagagga acctaaggtt tgggagagtg aagtataggt gcagtgcgtg ccgttttgga   660
ttcgggaacg gcaaggagtg tagctgtaat aatgtgaaat gtcaaacaga ggacagtagt   720
agcagcagtt attcttcaac cgacattagt agtagcattg gttatgactt cttgggtcta   780
aacaacacta gggttttgga ttttagcact ttggaaatga aatga                    825

SEQ ID NO: 41           moltype = DNA   length = 849
FEATURE                 Location/Qualifiers
source                  1..849
                        mol_type = genomic DNA
                        organism = Arabidopsis thaliana
SEQUENCE: 41
atgggaaggt caccgtgctg tgagaaagct cacacaaaca aaggagcatg gacgaaagaa    60
gaggacgaga ggctcgtcgc ctacattaaa gctcatggag aaggctgctg gagatctctc   120
cccaaagccg ccggacttct tcgctgtggc aagagctgcc gtctccggtg gatcaactat   180
ctccggcctg accttaagcg tggaaacttc accgaggaag aagacgaact catcatcaag   240
ctccatagcc ttcttggcaa caaatggtcg cttattgccg cgagattacc gggaagaaca   300
gataacgaga taaagaacta ttggaacacg catatacgaa gaaagcttat aaacagaggg   360
attgatccaa cgagtcatag accaatccaa gaatcatcag cttctcaaga ttctaaacct   420
acacaactag aaccagttac gagtaatacc attaatatct cattcacttc tgctccaaag   480
gtcgaaacgt tccatgaaag tataagcttt ccgggaaaat cagagaaaat ctcaatgctt   540
acgttcaaag aagaaaaaga tgagtgccca gttcaagaaa agttcccaga tttgaatctt   600
gagctcagaa tcagtcttcc tgatgatgtt gatcgtcttc aagggcatgg aaagtcaaca   660
acgccacgtt gtttcaagtg cagcttaggg atgataaacg gcatggagtg cagatgcgga   720
agaatgagat gcgatgtagt cggaggtagc agcaagggga gtgacatgag caatggattt   780
gatttttag ggttggcaaa gaaagagacc acttctcttt gggctttcg aagcttggag     840
atgaaataa                                                            849

SEQ ID NO: 42           moltype = DNA   length = 810
FEATURE                 Location/Qualifiers
source                  1..810
                        mol_type = genomic DNA
                        organism = Arabidopsis thaliana
SEQUENCE: 42
atgggaagat ctccttgctg cgagaaagaa cacatgaaca aggtgcttg gactaaagaa     60
gaagatgaga gactagtctc ttacatcaag tctcacggtg aaggttgttg gcgatctctt   120
cctagagccg ctggtctcct tcgctgcggt aaaagctgcc gtcttcggtg gattaactat   180
ctccgacctg atctcaaaag aggaaacttt acacatgatg agaaagaact tatcatcaag   240
cttcatagcc tcctaggcaa caagtggtct ttgattgcgg cgagattacc tggaagaaca   300
gataacgaga tcaagaacta ctggaacaca catataaaga ggaagctttt gagcaaaggg   360
attgatccag ccactcatag agggatcaac gaggcaaaaa tttctgattt gaagaaaaca   420
aaggaccaaa ttgtaaaaga tgtttctttt gtgacaaagt tgaggaaac agacaagtct    480
ggggaccaga agcaaaataa gtatattcga aatgggttag tttgcaaaga agagagagtt   540
gttgttgaag aaaaaaatag gcccagattg aatcttgagc ttaggatcag tccaccatgg   600
caaaaccaga gagaaatatc tacttgcact gcgtccgtt tttacatgga aaacgacatg     660
gagtgtagta gtgaaactgt gaatgtcaa acagagaata gtagcagcat tagctattct    720
tctattgata ttagtagtag taacgttggt tatgacttct gggtttgaa gacaagaatt    780
ttggattttc gaagcttgga aatgaaataa                                    810
```

```
SEQ ID NO: 43            moltype = DNA  length = 618
FEATURE                  Location/Qualifiers
source                   1..618
                         mol_type = genomic DNA
                         organism = Oryza sativa
SEQUENCE: 43
atggtacagc caaagaagaa gtttcgtgga gtcaggcagc ggcactgggg ctcctgggtc    60
tctgagatca gacaccccct ccttaaaagg agggtgtggc tgggcacctt tgagacggcc   120
gaggaggctg cgcgagccta cgatgaggct gctgtgctga tgagtggccg caacgccaag   180
accaacttcc ccgtgcagag gaactccacc ggtgatctcg ccacggccgc agaccaggac   240
gcccgtagca atggcggtag caggaactcc tccgcgggca acctgtcaca gattctcagt   300
gctaagctcc gcaagtgctg caaggcgcca tctccgtcct taacctgcct ccgcctcgac   360
cccgagaagt cccacattgg cgtgtggcaa aagcgcgcag gggcccgtgc tgactccaac   420
tgggtgatga cggtggagct caacaaagag gtagaaccaa ctgaacctgc agctcagccg   480
acatcaacag caacagcttc gcaagtgaca atggatgatg aggaaaagat tgcgctgcaa   540
atgatcgagg agttgctgag caggagcagt ccagcttcac cctcacatgg agagggagag   600
ggtagctttg tcatctga                                                 618

SEQ ID NO: 44            moltype = DNA  length = 732
FEATURE                  Location/Qualifiers
source                   1..732
                         mol_type = genomic DNA
                         organism = Oryza sativa
SEQUENCE: 44
atgggacagt cgaagaagaa gttccgcgga gtcaggcagc gccactgggg ctcctgggtc    60
tccgagatca ggcaccctct ccttaagagg agggtgtggc tgggtaccct tgagacggcg   120
gaggaggcgg cgcgggcgta cgacgaggcc gccatcctga tgagcggccg caacgccaag   180
accaacttcc cagtcgcgag gaacgccacg ggggagctca ccggcggccg tgcggtggca   240
gggcgggatg ccgtgtcgg cggcggcagc ggcagctcgt cctcaatgac ggccaacggc   300
ggcgggaaca gcctgtctca gatcctcagc gccaagctcc gcaagtgctg caagcgcccg   360
tcgccgtcgc tcacctgcct ccgccttgac ccggagaagt cccacattgg cgtctgcag   420
aagcgcgccg gcgcacgcgc tgactccagc tgggtcatga ccgtcgagct caacaaggac   480
acggccgtgt cgtcggctgc gacggtggca gcagcaacag cagtgtcgtc cagcgaccag   540
ccgactccga gtgacagcac agtcacaacg acgtccacgt ccaccacggg ctcgccgtcg   600
ccaccacctc cggcaatgga cgacgaggag aggatcgcgc tgcagatgat cgaggagctg   660
ctgggcagga gcggcccggg ctcgccgtca catgggctgc tgcacggtgg tgaaggtagc   720
ctcgtcatct ga                                                       732

SEQ ID NO: 45            moltype = DNA  length = 732
FEATURE                  Location/Qualifiers
source                   1..732
                         mol_type = genomic DNA
                         organism = Oryza sativa
SEQUENCE: 45
atggggaggt cgccgtgctg cgagaaggag cacactaaca agggcgcgtg gaccaaggag    60
gaggacgagc gcctcgtcgc ctacatccgc gcccacggcg agggctgctg gcgctcgctc   120
cccaaggccg ccggcctcct ccgctgcggc aagagctgcc gcttccgctg gatcaactac   180
ctccgccccg acctcaagcg cggcaacttc accgccgacg aggacgacct catcatcaag   240
ctccacagcc tcctcggcaa caagtggtct ctgatcgcgg cgaggctgcc ggggaggacg   300
gacaacgaga tcaagaacta ctggaacacg cacatccgcc ggaagcttct cggcaggggg   360
atcgaccccg tcacgcaccg ccccgtcaac gccgcccgc ccaccatctc cttccatccc   420
cagccgccgc caacgacgaa ggaggagcag ctcatactca gcaagccgcc caagtgcccc   480
gacctcaacc tggacctctg catcagcccg ccgtcgtgcc aggaagaaga cgatgactat   540
gaggcgaagc cggcgatgat cgtgagggcg ccggagctgc agcgccgccg cggcggcctc   600
tgcttcggct gcagcctcgg cctccagaag gagtgcaagt gcagcggcgg cggcgccggc   660
gccggcgccg gcaacaactt cctcggcctc agggctggca tgctcgactt cagaagcctc   720
cccatgaaat ga                                                       732

SEQ ID NO: 46            moltype = DNA  length = 756
FEATURE                  Location/Qualifiers
source                   1..756
                         mol_type = genomic DNA
                         organism = Oryza sativa
SEQUENCE: 46
atggggaggt caccgtgctg cgagaaggca cacaccaaca agggagcatg gaccaaggag    60
gaagatgacc ggctcattgc ctacatcaag gcgcacggcg aaggttgctg gcgatcgctg   120
cccaaggccg ccggcctcct ccgctgtggc aagagctgcc gcttccgtg gatcaactac   180
ctccggcctg acctcaagcg cggcaacttc accgaggagg aggatgagct gatcatcaag   240
cttcacagcc ttttaggcaa caaatggtct ctgatagccg gaggttgcc aggaagaacg   300
gacaacgaga tcaagaacta ctggaacacg cacatcagga ggaagctgct gagccgtggc   360
atcgacccgg tgacacaccg gccgatcaac gacagcgcgt caacatcac catatcattc   420
gaggcggccg cggcggcggc gagggacgac aaggccgccg tgttccggcg agaggaccat   480
cctcatcagc cgaaggcggt gacagtggca caggagcagc aggcagccgc cgattgggc   540
catggaagc cactcaagtg ccctgacctc aatctgacc tctgcatcag cctccctcc   600
caagaagagc ccatgatgat gaagccggtg aagagggaga ccggcgtctg cttcagctgc   660
agcctggggc tccccaagag cacagactgc aagtgcagca gcttcctggg actcaggaca   720
gccatgctcg acttcagaag cttggaaatg aaatga                              756

SEQ ID NO: 47            moltype = DNA  length = 807
```

```
FEATURE              Location/Qualifiers
source               1..807
                     mol_type = genomic DNA
                     organism = Populus trichocarpa
SEQUENCE: 47
atgggaaggt ctccttgctg tgaaaaagct catacaaaca aaggcgcatg gactaaggaa   60
gaagatgatc gccttattgc ttacattaga acccacggtg aaggttgctg gcgttcactt  120
cctaaagctg ctggccttct aagatgcggc aagagctgca gacttcgttg gatcaactat  180
ttaagacctg accttaaacg tggcaatttt actgaagaag aagatgagct cattatcaaa  240
ctccatagtc tcctcggcaa caatggtca cttatagccg gaaggttacc agggagaaca  300
gataatgaga taaagaatta ttggaacaca catataagaa ggaagctctt gaatagaggc  360
atagatcctg cgactcatag gccactcaat gaaccagccc aagaagcttc aacaacaata  420
tctttcagca ctactacctc agttaaagaa gagtcgttga gttctgttaa agaggaaagt  480
aataaggaga agataattag cgcagctgct tttatatgca aagaagagaa aaccccagtt  540
caagaaaggt gtccagactt gaatcttgaa cttagaatta gccttccttg ccaaaaccag  600
cctgatcgtc accaggcatt caaaactgga ggaagtacaa gtctttgttt tgcttgcagc  660
ttggggctac aaaacagcaa ggactgcagt tgcagtgtca ttgtgggtac tattggaagc  720
agcagtagtg ctggctccaa aactggctat gacttcttag gatgaaaag tggtgtgttg  780
gattatagag gtttggagat gaaatga                                      807

SEQ ID NO: 48        moltype = DNA  length = 816
FEATURE              Location/Qualifiers
source               1..816
                     mol_type = genomic DNA
                     organism = Populus trichocarpa
SEQUENCE: 48
atgggaaggt ctccttgctg tgaaaaagcc catacaaaca agggtgcgtg gaccaaggag   60
gaagacgatc gccttgttgc ttacattaga gctcacggtg aaggttgctg gcgctcactt  120
cctaaagccg ctggccttct tagatgtggc aagagttgca gacttcgttg gatcaactat  180
ttaagacctg accttaaacg tggcaatttc accgaagcag aagatgagct cattatcaaa  240
ctccatagcc tccttggaaa caatggtca ctcatagctc gaagattacc agggagaaca  300
gataatgaga taaagaatta ttggaacaca catataagaa ggaagctttt gaacagaggc  360
atagatcccg caactcatag gccactcaac gaaccagcag tacaagaagc cacaacaaca  420
atatctttca ccacgactac tacttcagta cttgaagaag agtctctggg ttctataatt  480
aaagaggaaa ataagagaa gataattagc gcaactgctt tcgtatgcaa agaagagaaa  540
acccaagttc aagaaaggtg tccagacttg aatctcgagc ttggaattag ccttccttcc  600
caaaaccagc ctgatcatca ccagccattc aaaactggag gaagtagaag tctttgtttt  660
gcttgcagtt tgggctacaa aacagcaag gattgcagct gcaatgttat tgtgagcact  720
gttgggagca gtgcagcac tagcacaaag actggttatg acttcttggg catgaaaagt  780
ggtgttttgg attatagaag tttagagatg aaataa                            816

SEQ ID NO: 49        moltype = DNA  length = 642
FEATURE              Location/Qualifiers
source               1..642
                     mol_type = genomic DNA
                     organism = Sorghum bicolor
SEQUENCE: 49
atgacagaga atctccactc caagaaaatg gtacagccaa gaagtttcg tggagtccgg    60
cagcgccact ggggttcctg ggtctccgag atcaggcatc ccctccttaa gaggagggtc  120
tggctgggca ccttcgagac cgctgaggag gcagcgagag catatgacga ggctgccgtg  180
ctgatgagcg gccgcaacgc caagaccaac ttcccggtcc aaaggagcag cacagggggag  240
ccaaccccag ctgcgggaag ggacgctcac agcaacgccg gcagcggctc ctctaccgcc  300
aacctgtccc agattctcag tgcgaagctc cgcaaatgct gcaaggcgcc atcgccctcc  360
ctgacctgtc tccgccttga ccctgagaag tcccacattg tgtttggca gaagcgtgca  420
ggagcccgtg ctgactccaa ctgggtcatg accgtgagc tcaacaaagg tgcagcatcc  480
actgatgctg catcacagtc cacatcagca acaactgctc caccagccac cccgatggat  540
gacgaggaga ggatcgccct gcaaatgatc gaagagttgc tgagcagcag cagcccagct  600
tcaccctcgc acggagatga ccaaggtcgc ttcatcatct ga                     642

SEQ ID NO: 50        moltype = DNA  length = 708
FEATURE              Location/Qualifiers
source               1..708
                     mol_type = genomic DNA
                     organism = Sorghum bicolor
SEQUENCE: 50
atggtgcaat caagaagaa gttccgcggc gtcaggcagc gccactgggg ctcctgggtc    60
tccgagatca ggcacccgct gcttaagagg agggtgtggc tgggcacctt cgagacggca  120
gaggaggcgg cgcgggcgta cgacgaggcc gccgtcctca tgagcggccg caacgccaag  180
accaacttcc ccgtcccaag gaccgccacc ggggagctgg ccgccgtgcg gcgcgggcgg  240
gacgcacgtg gcggcggcgg ctcgtcctcc gcggcagcag cgcccggcgg cggcaccagc  300
aacctgtcgc agatcctcag cgccaagctc cgcaagtgct gcaagacgcc gtcgccgtcg  360
ctcacctgcc tccgcctcga cccggagaag tcccacattg gcgtctggca gaagcgcgcg  420
ggcgcgcgcg ccgactccag ctgggtcatg accgtgcagc tcaacaagga cgtgccgccg  480
ccggcgtcct cctccgcga ggagccggtg cccagcgacg gaggcgccac gccaccacg   540
cccacgtcca cttccacgtc gtccacggtc acgacgaccg gctcgcctcc acctggtgatg  600
atgatggacg acgaggagag gattgcgctg cagatgatcg aggagctgct ggcagctcg  660
cactcacatg gatgttccc gggtgcagcg ggcagcatcc tcatctga                708

SEQ ID NO: 51        moltype = DNA  length = 777
```

```
FEATURE              Location/Qualifiers
source               1..777
                     mol_type = genomic DNA
                     organism = Sorghum bicolor
SEQUENCE: 51
atggggcggt cgccgtgctg cgagaaggcg cacacgaaca agggcgcgtg gaccaaggag    60
gaggacgacc gcctggtggc gtacatccgc gcgcacggcg aagggtgctg gcggtcgctg   120
cccaaggcgg ccggactgat cgctgcggc aagagctgcc gcctccgctg gatcaactac    180
ctccgccccg acctcaagcg cggcaacttc accgccgacg aggacgacct catcatcaag   240
ctgcacagcc tcctcggcaa caagtggtcg ctcatcgccg cgcggctccc ggggcggacg   300
gacaacgaga tcaagaacta ctggaacacg cacatccggc ggaagctgct tggcaggggc   360
atcgaccccg tcacgcaccg ccccatcgcc gacgccggcg ccggcaccgt caccaccatc   420
tcgttccagc ccaacaaacc caacgccgcc gtcgcagcgc aggcgccaca acatcagccg   480
atcaaggcag tggcgacggc cgtcgttaag gtgcccaggt gccccgacct caacctcgat   540
ctctgcatca gcccgccgtg ccaacagaag gaagacgagg agctggacct caagcccgcc   600
gtcgtcgtca gcgggaggt gctgcaggcc ggccatggcg gcagcctctg cttcggctgc   660
agcctgggca tccaaaaagg agcccccggg tgcagctgca gcagcagcaa cagccaccac   720
cgcttcttgg ggctccggtc cggcatgctc gacttcagag gcctcgagat gaagtga      777

SEQ ID NO: 52        moltype = DNA   length = 795
FEATURE              Location/Qualifiers
source               1..795
                     mol_type = genomic DNA
                     organism = Sorghum bicolor
SEQUENCE: 52
atggggaggt cgccgtgctg cgagaaggcg cacaccaaca agggcgcgtg gaccaaggag    60
gaggacgacc gcctcgtggc gtacatcaag gcgcacggcg agggttgctg gcgctcgctg   120
cccaaggccg ccggcctcct gcgctgcggc aagagctgcc gcctccgtg gatcaactac    180
ctccgccccg acctcaagcg cggcaacttc acggaagagg aggacgagct catcatcaag   240
ctcccagcc tcctcggcaa caaatggtcc ctgatcgctg cgaaggctgcc gggaaggacg   300
gacaacgaga tcaagaacta ctggaacacg cacatccgga ggaagctgct gagcaggggac   360
atcgacccgg tgacacaccg ccccatcaac gagcacacgt ccaacataac catctcgttc   420
gaggcggcgg cggccgcgcg tgaccgtgag gagaataagg gcgccgtgtt ccggctggag   480
gagcacaaca aggcgacggc ggcggcggcc gccgcgatcg gccgcgatca tcatcagaac   540
caccaccccg ccggcgactg gggccagggg aagccgctca agtgccccga cctcaacctg   600
gacctctgca tcagcccgcc ggcggcgccg tgccaggagg agaaggccat ggtgacgatg   660
aagcccgtga gcgggaggc cgggctctgt ttcagctgca gcctgggcct ccccaagagc   720
gccgactgca agtgcagcaa cttcctcgga ctcaggaccg ccatgctcga cttcagaagc   780
ctcgagatga aatga                                                    795

SEQ ID NO: 53        moltype = DNA   length = 642
FEATURE              Location/Qualifiers
source               1..642
                     mol_type = genomic DNA
                     organism = Zea mays
SEQUENCE: 53
atgacagaga atctccactc caggaaaatg gtacagccaa agaagtttcg tggagtccgg    60
cagcgccact ggggctcctg ggtctctgag atcaggcatc cctcccttaa gaggagggtc   120
tggctgggta cctttgagac ggctgaggag gcagcgagag catatgatga ggctgctgtg   180
ctgatgagcg gacgcaacgc caagaccaac ttcccaatcc aaagaagcag cacaggggag   240
cctacccag ctgcgggaag ggacgcccgc agcaacttca ccagcggctc ctctaccacc    300
aacctgtccc agattctcag tgcgaagctc cgcaaatgct gcaaggcgcc atcaccgtca   360
ctgacctgtc tccgccttga ccctgagaag tcccacattg tgtttggca gaagcgtgca   420
ggagcccgtg ctgactccaa ctgggtcatg acagtggagc tcaacaaaga tgcagcatcc   480
actgatgctg catcacagtc cacatcagca caaactgctc caccagccac gccgatggat   540
gaggaggaga ggatcgcact gcaaatgatc gaagagttgc tgagcagcag cagcccagct   600
tcaccctcaa acggagatga ccaaggtcgc ttcatcatct ga                      642

SEQ ID NO: 54        moltype = DNA   length = 783
FEATURE              Location/Qualifiers
source               1..783
                     mol_type = genomic DNA
                     organism = Zea mays
SEQUENCE: 54
atggggcggt cgccgtgctg cgagaaggcg cacaccaaca ggggcgcgtg gaccaaggag    60
gaggacgagc ggctggtggc ctacgtccgc gcgcacggcg aagggtgctg gcgctcgctg   120
cccagggcgg cgggcctgct gcgctgcggc aagagctgcc gcctgcgctg gatcaactac   180
ctccgcccgg acctcaagcg aggcaacttc accgccgacg aggacgacct catcgtcaag   240
ctgcacagcc tcctcgggaa caagtggtcg ctcatcgccg cgcggctccc ggggcggacg   300
gacaacgaga tcaagaacta ctggaacacg cacatccggc gcaagctgct gggcagcggc   360
atcgaccccg tcacgcaccg ccgcgtcgcg ggggcgccg cgaccaccat ctcgttccag    420
cccagcccca actccgccgc cgccgccgcc gccgcagaaa cagcagcgca ggcgccgatc   480
aaggccgagg agacggcggc cgtcaaggcg cccaggtgcc ccgacctcaa cctggacctc   540
tgcatcagcc cgccgtgcca gcatgaggac gacggcgagg aggaggacga ggagctggac   600
ctcaagcccg ccttcgtcaa gcgggaggcg ctgcaggccg gccacggcca cggccacggc   660
ctctgcctcg gctgcggcct gggcggacag aagggagcgg ccgggtgcag ctgcagcaac   720
ggccaccact cctgggggct caggaccagc gtgctcgact tcagaggcct ggagatgaag   780
tga                                                                 783
```

| SEQ ID NO: 55 | moltype = DNA length = 828 |
| --- | --- |
| FEATURE | Location/Qualifiers |
| source | 1..828 |
| | mol_type = genomic DNA |
| | organism = Zea mays |

SEQUENCE: 55

```
atggggaggt cgccgtgctg cgagaaggcg cacaccaaca agggcgcgtg gaccaaggag    60
gaggacgagc gcctggtcgc gcacatcagg gcgcacggcg aggggtgctg gcgctcgctg   120
cccaaggccg ccggcctcct gcgctgcggc aagagctgcc gcctccgctg gatcaactac   180
ctccgccccg acctcaagcg cggcaacttc acggaggaag aggacgagct catcgtcaag   240
ctgcacagcg tcctcggcaa caagtggtcc ctgatcgccg gaaggctgcc cggcaggacg   300
gacaacgaga tcaagaacta ctggaacacg cacatccgga ggaagctgct gagcagggggg   360
atcgacccgt gacgcaccg cccggtcacg gagcaccacg cgtccaacat caccatatcg   420
ttcgagacgg aagtggccgc cgctgcccgt gatgataaga agggcgccgt cttccggttg   480
gaggacgagg aggaggagga gcgcaacaag gcgacgatgg tcgtcggccg cgaccggcag   540
agccagagcc acagccacag ccaccccgcc ggcgagtggg gccaggggaa gaggccgctc   600
aagtgccccg acctcaacct ggacctctgc atcagcccgc cgtgccagga ggaggaggag   660
atggaggagg ctgcgatgag agtgagaccg gcggtgaagc ggggtgccgg gctctgcttc   720
ggctgcagcc tggggctccc caggaccgcg gactgcaagt gcagcagcag cagcttcctc   780
gggctcagga ccgccatgct cgacttcaga agcctcgaga tgaaatga              828
```

| SEQ ID NO: 56 | moltype = DNA length = 771 |
| --- | --- |
| FEATURE | Location/Qualifiers |
| source | 1..771 |
| | mol_type = genomic DNA |
| | organism = Panicum virgatum |

SEQUENCE: 56

```
atggggcgat cgccgtgctg cgagaaggcg cacacgaaca agggcgcctg gaccaaggag    60
gaggacgacc gcctcgttgc ctacatccgg gcgcacggcg aggggtgctg gcgctccctc   120
cccaaggccg cgggcctgct gcgctgcggc aagagctgcc gcctcgcctg gatcaactac   180
ctccgcccgg acctcaagcg cggcaacttc accgccgacg aggacgacct catcgtcaag   240
ctccacagcc tcctcggcaa caagtggtcg ctcatcgccg cgcgcctccc cggccgcacc   300
gacaacgaga tcaagaacta ctggaacacg cacatcaagc gcaagctcct cagccgcggc   360
atcgacccgt cacacaccg cccatcgcc gacgcagcca gaaacgtcac catctccttc   420
cagcccgacg cgccgtcgca gcagcagctc agcgacgacg ccgaggcgcc gccgccgccg   480
ccgccgcagc agcagcagca gctcaagccg ccgcccaggt gccccgacct caatctcgac   540
ctctgcatca gcccgccctg ccacaaggaa gaagaggacc aggagctcgt caagcccgcc   600
gccgtcaagc gcgagatgct gcaggccggc cacggcactc taggactctg cttcggctgc   660
agcctggggc tccagaaggg gcgccgcggg tgcacctgca gcagcaacag ccacttcctg   720
gggctcaggg tcggcatgct cctcgacttc agaggcctcg agatgaagtg a            771
```

| SEQ ID NO: 57 | moltype = DNA length = 2496 |
| --- | --- |
| FEATURE | Location/Qualifiers |
| misc_feature | 1..2496 |
| | note = Construct No. 001 |
| source | 1..2496 |
| | mol_type = other DNA |
| | organism = synthetic construct |

SEQUENCE: 57

```
acgtacctcg tgtccaccgg tgactctatc cccggcgtta gaagtgatga tagtctcgtt    60
cccaagggaa atcagccttc gaattggaat tgatccctcg ggacattttg tgccgtcgt   120
gtgccagact tgccatccat ataatgcatc ttcttctttt tttcccgcag atggcatgtc   180
cgttggtctt tcctgtatca tttatttaca aagaaaaat aaattaaaca tttattaagt   240
tccccccgta aaaaaaaat atatatatat atatatatat aacacatgca tcataattgg   300
tatgtccgta ggtgtttcct tatcataact gaaccattgg taaactatcg gttccgttaa   360
agcataagac tagaaaaggc tcggtgcgac tcgctaccac gtttctaaag atttttattta  420
gcaaattaac cccaatatat attttgctat gagggtctaa acaaactggt atatgagcca   480
tttacttacc acttattagt tccaagtatt tattttttgg gttaattaat gtttaaatta   540
ttggttgaca aaaaatataa aaataatggt taagttattg aaatgacttg agcaatctga   600
tgcaactgcg gataacatga actcattcga agtgacgtcc caaatatttg attctttgtt   660
tttattcctt tttgtcaagg tcaagattgg ccaaacattt tcaatatcta aatatattga   720
cattcatagc ctggaaaaga aaaaatatat ggttaaatta gttccaaagt attctagcag   780
caacaaaacc gctccaataa acgatttcca atttctatct caaacttgtt tcccaatcat   840
tagttataat ccgtccccta aaccaaaaaa aaatctaatt gtaaaggtgt tgcaatagat   900
taaccatttt tattttattt tggtaaaata gattaaccat tttgttagaa aaatgaagtt   960
taaaacattt acagttctac gtgtacatgc ttcgaccaat atgcttcgac caatatggca  1020
aggtctcctt gctgtgagaa agaccacaca acaaaggag cttggactaa ggaagaagac  1080
gataagctca tctcttacat caaagctcac ggtgaaggtt gttggcgttc tcttcctaga  1140
tccgccggtc ttcaacgttg cggaaaaagc tgtcgtctcc gatggattaa ctatctccga  1200
cctgatctca agagggtaa cttcaccctc gaagaagatg atctcatcat caaactacat  1260
agccttctcg gtaacaagtg gtctcttatt gcgacgagat taccaggaag aacagataac  1320
gagattaaga attactggaa cacacatgtt aagaggaagc tattaagaaa agggattgat  1380
ccggcgactc atcgacctat caacgagacc aaaacttctc aagattcgtc tgattctagt  1440
aaaacaggg accctcttgt caagattctc tcttttgctg ctcagctgga gaaaatagca  1500
aattcgggg acgagagaat tcaaagagaa gttgagtact cagttgttga agaaagatgt  1560
ctggacttga atcttgagct taggatcagt ccaccatggc aagacaagct ccatgatgag  1620
aggaacctaa ggtttgggag agtgaagtat aggtgcagtg cgtgccgttt tggattcggg  1680
aacggcaagg agtgtagctg taataatgtg aaatgtcaaa cagaggacag tagtagcagc  1740
agttattctt caaccgacat tagtagtagc attggttatg acttcttggg tctaaacaac  1800
```

-continued

```
actagggttt tggatttttag cactttggaa atgaaatgac acgtgtgaat tacaggtgac  1860
cagctcgaat ttccccgata gctttcgttc gtatcatcgg tttcgacaac gttcgtcaag  1920
ttcaatgcat cagtttcatt gcgcacacac cagaatccta ctgagttcga gtattatggc  1980
attgggaaac atgtttttct tgtaccattt gttgtgcttg taatttactg tgttttttat  2040
tcggttttcg ctatcgaact gtgaaatgga aatggatgga gaagagttaa tgaatgatat  2100
ggtccttttg ttcattctca aattaatatt atttgttttt tctcttattt gttgtgtgtt  2160
gaatttgaaa atataagaga tatgcaaaca ttttgttttg agtaaaaatg tgtcaaatcg  2220
tggcctctaa tgaccgaagt taatatgagg agtaaaacac ttgtagttgt accattatgc  2280
ttattcacta ggcaacaaat atattttcag acctagaaaa gctgcaaatg ttactgaata  2340
caagtatgtc ctcttgtgtt ttagacattt atgaactttc ctttatgtaa ttttccagaa  2400
tccttgtcag attctaatca ttgctttata attatagtta tactcatgga tttgtagttg  2460
agtatgaaaa tattttttaa tgcattttat gacttg                              2496
```

SEQ ID NO: 58          moltype = DNA  length = 2778
FEATURE             Location/Qualifiers
misc_feature      1..2778
                     note = Construct No. 002
source              1..2778
                     mol_type = other DNA
                     organism = synthetic construct
SEQUENCE: 58

```
atacatgtca tgattttata attatgtata tataaatact aattgatgta tgaagtacgt    60
agataatgtt acgatctatt aatctatttta cattaactttt taattagtgt tgagtaggga   120
aaattaacat ataaacctttt agcagttggt tgtattatta aaaataatttt gaacttaaaa   180
tccaccttcg aaaagataaa tcaaacaagt ataaaaaatg ctataaatcc agaatattta   240
cctaaggttt ttattcttct acttaataat gtaagataaa accggcacaa tacttgttac   300
gtatgcatgg taggtaccgc aattgtgtaa gcaaatcggc acaatactaa ggttacatat   360
actaactaaa taaacaatc tgatttcagt gacaccgtat atctaacctt tattcaaatc    420
caagggaaca tgacttgact tcttctgttg gaactaactc gatccctcaa ccatctccag   480
ggatagaaga gttagtaaaa tcaaacttga agtgaggaag taagcagttt aacgactcca   540
tatgactaca gttatataca aagttgggca caaagtacaa gtactaaata ctcaaagtca   600
gataataatt ttaataagta caaactatat atatgcagta caattattga gtatatataa   660
acgagactgt tgatttgggg cattgtccac cagggtgtta tatcccaatt gaaatttgaa   720
aatttaagtg tgtgagtgtt acgacaaaaa aaagtgtgtg aattgtaggc gcggtgaaaa   780
ggtaaattaa gattggaact agaaaaatag ttgaatatcc tttactaaaa gttgtcaatt   840
ccggttttag taaaaaaaaa ttttaaaata gaaattttat ccaaaagact tcaaacacac   900
atattcgcat ataacata agatatcatt ttttgtaaac agttaaaaag aaaaacacat    960
gtttttttt taattagga aaaacatg ttattataca aaacagagtt ttgcccactt      1020
ttaatatgtt atgaaaagaa taagatttt cttgggtttg gtcagagaga ttggttgtgg   1080
taagaatggg aatcttaatt acaaagaatt ggattttggg tcgacctacc acctaaaacg   1140
acgtcgcctc catctctggt ttccaaatct cttctcctc tccctttata agcttgcgtt   1200
ggccagtcgc tcatctcgaa aacagagaga aaaagactaa aaacacagtt taagaagaag   1260
gagagataga gagagaagag aaagatagag agggagatgg caagtctcc ttgctgtgag   1320
aaagaccaca caaacaaagg agcttggact aaggaagaag acgataagct catctcttac   1380
atcaaagctc acggtgaagg ttgttggcgt tctcttccta gatccgccgg tcttcaacgt   1440
tgcgaaaaa gctgtcgtct ccgatggatt aactatctcc gacctgatct caagaggggt   1500
aacttccacc tcgaagaaga tgatctcatc atcaaactac atagccttct cggtaacaag   1560
tggtctctta ttgcgacgag attaccagga agaacagata acgagattaa gaattactga   1620
aacacacatg ttaagaggaa gctattaaga aaagggattg atccggcgac tcatcgacct   1680
atcaacgaga ccaaaacttc tcaagattcg tctgattcta gtaaaacaga ggaccctctt   1740
gtcaagattc tctcttttgg tcctcagctg gagaaaatag caaattttcgg ggacgagaga   1800
attcaaaaga gagttgagta ctcagttgtt gaagaaaagat gtctggactt gaatcttgag   1860
cttaggatca gtccaccatg gcaagacaag ctccatgatg agaggaacct aaggtttggg   1920
agagtgaagt ataggtgcag tgcgtgccgt tttggattcg ggaacggcaa ggagtgtagc   1980
tgtaataatg tgaaaatgtca aacagaggac agtagtagca gcagttattc ttcaaccgac   2040
attagtagta gcattggtta tgacttcttg ggtctaaaca acactagggt tttggatttt   2100
agcactttgg aaatgaaatg acacgtgtga attacaggtg accagctcga atttccccga   2160
tagctttcgt tcgtatcatc ggtttcgaca acgttcgtca agttcaatgc atcagtttca   2220
ttgcgcacac accagaatcc tactgagttc gagtattatg gcattgggaa acatgttttc   2280
cttgtaccat tgttgtgctt gtaatttac tgtgttttt attcggtttt cgctatcgaa   2340
ctgtgaaatg gaaatggatg gagaagagtt aatgaatgat atggtccttt tgttcattct   2400
caaattaata ttatttgttt tttctcttat tgttgtgtg ttgaatttga aaatataaga   2460
gatatgcaaa cattttgttt tgagtaaaaa tgtgtcaaat cgtggcctct aatgaccgaa   2520
gttaatatga ggagtaaaac acttgtagtt gtaccattat gcttattcac taggcaacaa   2580
atatattttc agacctagaa aagctgcaaa tgttactgaa tacaagtatg tcctcttgtg   2640
ttttagacat tatgaactt tccttatgt aattttccag aatccttgtc agattctaat   2700
cattgcttta taattatagt tatactcatg gatttgtagt tgagtatgaa aatattttt   2760
aatgcatttt atgacttg                                                 2778
```

SEQ ID NO: 59          moltype = DNA  length = 2482
FEATURE             Location/Qualifiers
misc_feature      1..2482
                     note = Construct No. 003
source              1..2482
                     mol_type = other DNA
                     organism = synthetic construct
SEQUENCE: 59

```
aactagaaca cttcagataa attttgtcgt tctgttgact tcatttattc tctaaacaca    60
aagaactata gaccataatc gaaataaaaa ccctaaaaac caaatttatc tatttaaaac   120
```

```
aaacattagc tatttgagtt tcttttaggt aagttattta aggttttgga gactttaaga    180
tgttttcagc atttatggtt gtgtcattaa tttgtttagt ttagtaaaga aagaaaagat    240
agtaattaaa gagttggttg tgaaatcata tttaaaacat taataggtat ttatgtctaa    300
tttggggaca aaatagtgga attctttatc atatctagct agttcttatc gagtttgaac    360
tcgggttatg attatgttac atgcattggt ccatataagt ctatgagcaa tcaatataat    420
tcgagcattt tggtataaca taatgagcca agtataacaa aagtatcaaa cctatgcagg    480
ggagaagatg atgaaaagaa gagtgtgagc caatacaaag cagatttgag gacatggctt    540
acaagtcttg ggtacagagt ttggggagtg atgggtgcac aatggaacag cttctctggt    600
tgtccagttc ccaagagaac cttcaagctc cctaactcca tctactatgt cgcctgatta    660
aatcttattt actaacaaaa caataagatc agagtttcat tctgattctt gagtcttttt    720
tttctctctc cctcttttca tttctggttt ataaccaa ttcaaatgct tatgatccat    780
gcatgaacca tgatcatctt tgtgttttt tttccttctg tattaccatt ttgggccttt    840
gtgaaattga ttttgggctt ttgttatata atctcctctt tctctttctc tacctgattg    900
gattcaagaa catagccaga tttggtaaag tttataagat acaaaatatt aagtaagact    960
aaagtagaaa tacataataa cttgaaagct actctaagtt atggcaaggt ctccttgctg   1020
tgagaaagac cacacaaaca aaggagcttg gactaaggaa gaagacgata agctcatctc   1080
ttacatcaaa gctcacggtg aaggttgttg gcgttctctt cctagatccg ccggtcttca   1140
acgttgcgga aaaagctgtc gtctccgatg gattaactat ctccgacctg atctcaagag   1200
gggtaacttc accctcgaag aagatgatct catcatcaaa ctacatagcc ttctcggtaa   1260
caagtggtct cttattgcga cgagattacc aggaagaaca gataacgaga ttaagaatta   1320
ctggaacaca catgttaaga ggaagctatt aagaaaggg attgatccgg cgactcatcg   1380
acctatcaac gagaccaaaa cttctcaaga ttcgtctgat tctagtaaaa cagaggaccg   1440
tcttgtcaag attctctctt ttggtcctca gctggagaaa atagcaaatt tcggggacga   1500
gagaattcaa aagagagttg agtactcagt tgttgaagaa agatgtctgg acttgaatct   1560
tgagcttagg atcagtccac catggcaaga caagctccat gatgagagga acctaaggtt   1620
tggagagtg aagtataggt gcagtgcgtg ccgtttgga ttcgggaacg gcaaggagtg   1680
tagctgtaat aatgtgaaat gtcaaacaga ggacagtagt agcagcagtt attcttcaac   1740
cgacattagt agtagcattg ttatgactt cttgggtcta aacaacacta gggttttgga   1800
ttttagcact ttggaaatga aatgacacgt gtgaattaca ggtgaccagc tcgaatttcc   1860
ccgatagctt tcgttcgtat catcggtttc gacaacgttc gtcaagttca atgcatcagt   1920
ttcattgcgc acacaccaga atcctactga gttcgagtat tatggcattg ggaaacatgt   1980
ttttcttgta ccatttgttg tgcttgtaat ttactgtgtt tttattcgg ttttcgctat   2040
cgaactgtga aatggaaatg gatggagaag agttaatgaa tgatatgtc cttttgttca   2100
ttctcaaatt aatattttt gttttttctc ttatttgttg tgtgttgaat ttgaaaatat   2160
aagagatatg caaacatttt gttttgagta aaaatgtgtc aaatcgtggc ctctaatgac   2220
cgaagttaat atgaggagta aaacacttgt agttgtacca ttatgcttat tcactaggca   2280
acaaatatat tttcagacct agaaaagctg caaatgttac tgaatacaag tatgtcctct   2340
tgtgttttag acatttatga actttccttt atgtaatttt ccagaatcct tgtcagattc   2400
taatcattgc tttataatta tagttatact catgatttg tagttgagta tgaaaatatt   2460
ttttaatgca tttttatgact tg                                            2482
SEQ ID NO: 60           moltype = DNA  length = 2546
FEATURE                 Location/Qualifiers
misc_feature            1..2546
                        note = Construct No. 004
source                  1..2546
                        mol_type = other DNA
                        organism = synthetic construct
SEQUENCE: 60
aacccataac tttagtattc ttcaacccct acaacttatc tgagcaaaat cagaaggtcg     60
aatttgatgg atggttttgc tgtatttggt caacggtttt atttgagaca gtagaccagt    120
ggaaactcag atgtgatgat gcaaagactg aattggttaa gagtgtagat tgatttgttc    180
taacattgca aatgtagagt agaattatgc aaaaaacgtt aatgaacaga gaagtgatta    240
agcagaaaca aaattagaga agtgatatta tatctcaaaa tttattttg gtacagctaa    300
agctcaaatt gttatagaga ttagagatat taaaccaagt gacgagtgtt ttcttttagta   360
gtaaacggtg aaaattctct tctgacaaag acaattaaaa ttttaggttt aagactttaa   420
tatttgtcac aaattgtcat ttacctaaat aaaaaaaaaa ctaaatattt tttttagata   480
catatgtgtc ttataatttt aactataaat tttaatttta tgtcttaaat aattgtttac   540
actataaatt taaatatttt aaatgctaaaa ttaatttgat tcaaaaaagt gattttaatt   600
cttattttc ttatagaaag ttggtgattg aaaagattta cttaaaaatt ataacaactt    660
caatggtgaa taacccgacc cgaataaacc ggatataaca acttcaatgt tagcttgata   720
tagaaagtac ggtgacgctt aggaggcaag caagctagta tctgccgctg ttagagaca    780
aagaacatgt gtcactcctc tcaactaaaa ctttccttca ctttcccgca aaatcatttc   840
aaaaaagctc caaatttagc ttacccatca gctttctcag aaaaccagtg aaagaaactt   900
ctcaacttcc gattttttcac aatccaccaa actttttta ataacttttt ttcctcttat   960
tacaaaacct ccactctcat ggcttctcaa acttgttatc catccaaatc tcaatcccta  1020
attagggttc atttctctgt ttctccaaac aggggaattc gaagatggca aggtctcctt  1080
gctgtgagaa agaccacaca aacaaaggag cttggactaa ggaagaagac gataagctca  1140
tcttacat caaagctcac ggtgaaggtt gttggcgttc tcttcctaga tccgccggtca  1200
ttcaacgttg cggaaaaagc tgtcgtctcc gatggattaa ctatctccga cctgatctca  1260
agaggggtaa cttcacccct cgaagaagatg atctcatcat caaactacat agccttctcg  1320
gtaacaagtg gtctcttatt gcgacgagat taccaggaag aacagataac gagattaaga  1380
attactggaa cacacatgtt aagaggaagc tattaagaaa agggattgat ccggcgactc  1440
atcgacctat caacgagacc aaaacttctc aagattcgtc tgattctagt aaaacagagg  1500
accctcttgt caagattctc tcttttggtc ctcagctgga gaaaatagca aatttcgggg  1560
acgagagaat tcaaaagaga gttgagtact cagttgttga agaaagatgt ctggacttga  1620
atcttgagct taggatcagt ccaccatggc aagacaagct ccatgatgag aggaacctaa  1680
ggtttgggag agtgaagtat aggtgcagtg cgtgccgttt ggattcgggg aacggcaagg  1740
agtgtagctg taataatgtg aaatgtcaaa cagaggacag tagtagcagc agttattctt  1800
```

```
caaccgacat tagtagtagc attggttatg acttcttggg tctaaacaac actagggttt   1860
tggattttag cactttggaa atgaaatgac acgtgtgaat tacaggtgac cagctcgaat   1920
ttccccgata gctttcgttc gtatcatcgg tttcgacaac gttcgtcaag ttcaatgcat   1980
cagtttcatt gcgcacacac cagaatccta ctgagttcga gtattatggc attgggaaac   2040
atgttttttct tgtaccattt gttgtgcttg taatttactg tgttttttat tcggttttcg   2100
ctatcgaact gtgaaatgga aatggatgga gaagagttaa tgaatgatat ggtccttttg   2160
ttcattctca aattaatatt attttgttttt tctcttattt gttgtgtgtt gaatttgaaa   2220
atataagaga tatgcaaaca ttttgttttg agtaaaaatg tgtcaaatcg tggcctctaa   2280
tgaccgaagt taatatgagg agtaaaacac ttgtagttgt accattatgc ttattcacta   2340
ggcaacaaat atattttcag acctagaaaa gctgcaaatg ttactgaata caagtatgtc   2400
ctcttgtgtt ttagacattt atgaactttc ctttatgtaa ttttccagaa tccttgtcag   2460
attctaatca ttgctttata attatagtta tactcatgga tttgtagttg agtatgaaaa   2520
tattttttaa tgcattttat gacttg                                        2546

SEQ ID NO: 61          moltype = DNA   length = 2501
FEATURE                Location/Qualifiers
misc_feature           1..2501
                       note = Construct No. 005
source                 1..2501
                       mol_type = other DNA
                       organism = synthetic construct
SEQUENCE: 61
tcttcttgca tcaatgatat caacaacaat gggtaataaa gaagctactt cgaaattata     60
tattttttcg tattctatat tgatcatcag tcttaagtgg tttggtttgt tgcagtgaag    120
aagaactatg tatggatcta cgccaccgtt cagttcggtt ttgtggtcct tttcgctcag    180
cttttctaca gagttgtaag atttgatgta atgtcacaga gaaaccttac tttgttgtca    240
cagagaaacc ttactttgtt gaagagtttt tgattcctca cactctctct cattaacttg    300
tgtgtaggtg aagcagccgg taatgtgcat tgtcttagcc actatgatcg gatttggact    360
caccatgacc ggcacaacag ctattaacga gtatttgaaa tggaggagaa gcaattccca    420
cctgccagaa gagccagcaa gtactcaggt ggtttgacag cagcgtagat cttttgagtg    480
aagctagagt ccctaaaggg ttggatcggt tttcaattaa ccgtcgggaa ttcggttttc    540
ggtttagctt taatcgactt gtctaggttg agatcagatt tggttttcaa tacttccaag    600
tcttttttttt tttgccaact aaaatataag gaatgatgat aggcacacac atgcacata    660
aaatcataat gaacagtagt atgattagca atccatattt cttggataac acttcttcac    720
agctttttttg acaggtcact ataacacctt tttcagttca tttttcattt tcaatcctca    780
cccacccaaa ctctcccttc aaagcaatgt ctctcctctc tctttctcaa ttcaaacaaa    840
ctttattaaa cctaaaagaa acatttccaa tctctaatga cttagttgat agaatctcat    900
ttagttacct agtaataatc ttcacactag taagagaatc ctactcttca ccaaactaca    960
tctctctcta tataacaaac cccaaaacat ctcaacatac acacacaaca actacaacaa   1020
tggcaaggtc tccttgctgt gagaaagacc acacaaacaa aggagcttgg actaaggaag   1080
aagacgataa gctcatctct tacatcaaag ctcacggtga aggttgttgg cgttctcttc   1140
ctagatccgc cggtcttcaa cgttgcgaaa aaagctgtcg tctccgatgg attaactatc   1200
tccgacctga tctcaagagg ggtaacttca cctcgaagga atgatcatcc atcatcaaac   1260
tacatagcct tctcggtaac aagtggtctc ttattgcgac gagattacca ggaagaacag   1320
ataacgagat taagaattac tggaacacac atgttaagag gaagctatta agaaaaggga   1380
ttgatccggc gactcatcga cctatcaacg agaccaaaac ttctcaagat tcgtctgatt   1440
ctagtaaaac agaggaccct cttgtcaaga ttctctcttt tggtcctcag ctggagaaaa   1500
tagcaaattt cggggacgag agaattcaaa agagagttga gtactcagtt gttgaagaaa   1560
gatgtctgga cttgaatctt gagcttagga tcagtccacc atggcaagac aagctccatg   1620
atgagaggaa cctaaggttt gggagagtga agtataggtg cagtgcgtgc cgttttggat   1680
tcgggaacgg caaggagtgt agctgtaata atgtgaaatg tcaaacagag cagcagtagta   1740
gcagcagtta ttcttcaacc gacattagta gtagcattgg ttatgacttc ttgggtctaa   1800
acaacactag ggttttggat tttagcactt tggaaatgaa atgacacgtg tgaattacag   1860
gtgaccagct cgaatttccc cgatagcttt cgttcgtatc atcggtttcg acaacgttcg   1920
tcaagttcaa tgcatcagtt tcattgcgca cacaccagaa tcctactagg ttcgagtatt   1980
atggcattgg gaaacatgtt ttcttgtac catttgttgt gcttgtaatt tactgtgttt   2040
tttattcggt tttcgctatc gaactgtgaa atggaaatgg atgagaaga gttaatgaat   2100
gatatggtcc ttttgttcat tctcaaatta atattatttg tttttttctct tatttgttgt   2160
gtgttgaatt tgaaaatata agagatatgc aaacattttg ttttgagtaa aaatgtgtca   2220
aatcgtggcc tctaatgacc gaagttaata tgaggagtaa acacttgta gttgtaccat   2280
tatgcttatt cactaggcaa caaatatatt ttcagaccta gaaaagctgc aaatgttact   2340
gaatacaagt atgtcctctt gtgtttaga catttatgaa ctttccttta tgtaattttc   2400
cagaatcctt gtcagattct aatcattgct ttataattat agttatactc atggatttgt   2460
agttgagtat gaaaatattt ttaatgcat ttatgactt g                         2501

SEQ ID NO: 62          moltype = DNA   length = 2575
FEATURE                Location/Qualifiers
misc_feature           1..2575
                       note = Construct No. 006
source                 1..2575
                       mol_type = other DNA
                       organism = synthetic construct
SEQUENCE: 62
tgcgaacagt tgattctgt tttctttttt cctttttttg ggtaattttc ttataacttt      60
tttcatagtt tcgattattt ggataaaatt ttcagattga ggtcattttt atttatttat    120
tagtgtagtc taatttagtt gtataactat aaaattgttg tttgtttccg aatcataagt    180
tttttttttt tttggttttg tattgatagg tgcaagagac tcaaaattct ggtttcgatg    240
ttaacagaat tcaagtagct gcccacttga ttcgattgt tttgtatttg gaaacaacca    300
tggctggtca aggcccagcc cgttgtgctt ctgaacctgc ctagtcccat ggactagatc    360
```

```
tttatccgca gactccaaaa gaaaaaggat tggcgcagag gaattgtcat ggaaacagaa    420
tgaacaagaa agggtgaaga agatcaaagg catatatgat ctttacattc tctttagctt    480
atgtatgcag aaaattcacc taattaagga cagggaacgt aacttggctt gcactcctct    540
caccaaacct tacccctaa ctaattttaa ttcaaaatta ctagtatttt ggccgatcac     600
tttatataat aagataccag atttattata tttacgaatt atcagcatgc atatactgta    660
tatagttttt tttttgttaa agggtaaaat aataggatcc ttttgaataa aatgaacata    720
tataattagt ataatgaaaa cagaaggaaa tgagattagg acagtaagta aaatgagaga    780
gacctgcaaa ggataaaaaa gagaagctta aggaaaccgc gacgatgaaa gaaagacatg    840
tcatcagctg atggatgtga gtgatgagtt tgttgcagtt gtgtagaaat ttttactaaa    900
acagttgttt ttacaaaaaa gaataatat aaaacgaaag cttagcttga aggcaatgga     960
gactctacaa caaactatgt accatacaga gagagaaact aaaagctttt cacacataaa   1020
aaccaaactt attcgtctct cattgatcac cgttttgttc tctcaagatc gctgctaatc   1080
tccggccgtc cctatggcaa ggtctccttg ctgtgagaaa gaccacacaa acaaaggagc   1140
tggactaag gaagaagacg ataagctcat ctcttacatc aaagctcacg gtgaaggttg    1200
ttggcgttct cttcctagat ccgccggtct tcaacgttgc ggaaaaagct gtcgtctccg   1260
atggattaac tatctccgac ctgatctcaa gagggtaac ttcaccctcg aagaagatga    1320
tctcatcatc aaactacata gccttctcgg taacaagtgg tctcttattg cgacgagatt   1380
accaggaaga acagataacg agattaagaa tactggaac acacatgtta aggaagct     1440
attaagaaaa gggattgatc cggcgactca tcgacctatc aacgagacca aaacttctca   1500
agattcgtct gattcagtta aaacagagga ccctcttgtc aagattctct cttttggtcc   1560
tcagctggag aaaatagcaa atttcgggga cgagagaatt caaagagag ttgagtactc    1620
agttgttgaa gaaagatgtc tggacttgaa tcttgagctc aggatcagtc caccatggca   1680
agacaagctc catgatgaga ggaacctaag gtttgggaga gtgaagtata ggtgcagtgc   1740
gtgccgtttt ggattcggga acggcaagga gtgtagctgt aataatgtga aatgtcaaac   1800
agaggacagt agtagcagca gttattcttc aaccgacatt agtagtagca ttggttatga   1860
cttcttgggt ctaaacaaca ctaggggttt ggattttagc actttggaaa tgaaatgaca   1920
cgtgtgaatt acaggtgacc agctcgaatt tccccgatag cttccgttcg tatcatcggt   1980
ttcgacaacg ttcgtcaagt tcaatgcatc agtttcattg cgcacacacc agaatcctac   2040
tgagttcgag tattatggca ttgggaaaca tgttttttctt gtaccatttg ttgtgcttgt   2100
aatttactgt gttttttatt cggttttcgc tatcgaactg tgaaatggaa atggatggag   2160
aagagttaat gaatgatatg gtccttttgt tcattctcaa attaatatta tttgttttt    2220
ctcttatttg ttgtgtgttg aatttgaaaa tataagagat atgcaaacat tttgttttga   2280
gtaaaaatgt gtcaaatcgt ggcctctaat gaccgaagtt aatatgagga gtaaaacact   2340
tgtagttgta ccattatgct tattcactag gcaacaaata tattttcaga cctagaaaag   2400
ctgcaaatgt tactgaatac aagtatgtcc tcttgtgttt tagacattta tgaactttcc   2460
tttatgtaat tttccagaat ccttgtcaga ttccaatcat tgcttataa ttatagttat    2520
actcatggat ttgtagttga gtatgaaaat atttttaat gcattttatg acttg         2575

SEQ ID NO: 63         moltype = DNA  length = 2628
FEATURE               Location/Qualifiers
misc_feature          1..2628
                      note = Construct No. 007
source                1..2628
                      mol_type = other DNA
                      organism = synthetic construct
SEQUENCE: 63
tctctaattg tcaagtatct tagtctagag ttaattactt aaatactaaa aggctgtcga    60
caaaatcaag cttgaatctc cttgtgtat cttcaactct tcgttgtctg cttacgagtg    120
gtttactcag taattatcta taatatgtta ttttttttcc ctcatctttt agttgttgtt   180
tcattacatt gaaaagcttg taatgtcttt atatggtata tatggatctt atgagtgagg   240
caagatccat gatgttttg atcttagaat gtatatgatg atcttagaat gtatttgtat   300
gcccacaaat tattgttcat tgggattata tctctagtcc aactccaagc aatcgaaatg    360
ggtcctgctt ttaagaacaa cagtatatgt ttaagaataa taactttata tattctcgat   420
tttaagatct tttgacaaaa cctccttttc gttaggagcg tactaatttc caagtgtttg   480
attagtgggg tctccgtaaa tttatttaga gtttctatct atttattaat agctcaatta   540
attaatctat actgtatcta aacatcaatt tatatatta ctcttgagac caaaactgtc    600
aatttataac attggatagt ttcttaattc ttattatata ttttcaaac acttttcaag    660
actaatctcc acattaggta ctctctctag agataaaaat atttatcaaa aacattttta   720
tttatttatt aagtagtaga taaactactg tggcaaaatc gtaaatgtct aaatgctgat   780
gaatttttt tgctgctcca atctggttta gtgctccata tacatccacg gccaaaatga    840
atctatggcg gcattaagat tcattagtaa gcaacgatta tattaatata attgttttta   900
gcaatgattt tccgtaattt cccaaatatg tttcagttaa tgtgttccaa tcccaacaac   960
tggttgttgc aaaagaccac caacgcaagc aatcatcaaa catcaaaata atcttacctt   1020
agcgaacaaa caataactac acaattctca taagctctt atatatcact aacttcacac   1080
attttgttt ccacaaaaat aaaaacggaa ctcactcaag aaacctttctt ccttgaaaag   1140
aggggttatgg caaggtctcc ttgctgtgag aaagaccaca caaacaaagg agcttggact   1200
aaggaagaag acgataagct catctcttac atcaaagctc acggtgaagg ttgttggcgt   1260
tctcttccta gatccgccgg tcttcaacgt tgcggaaaaa gctgtcgtct ccgatggatt   1320
aactatctcc gacctgatct caagaggggt aacttcaccc tcgaagaaga tgatcatc    1380
atcaaactac atagccttct cggtaacaag tggtctctta ttgcgacgag attaccagga   1440
agaacagata acgagattaa gaattactgg aacacacatg ttaagaggaa gctattaaga   1500
aaagggattg atccggcgac tcatcgacct atcaacgaga ccaaaactct caagattcg    1560
tctgattcta gtaaaacaga ggaccctctt gtcaagattc tctcttttgg tcctcagctg   1620
gagaaaatag caaatttcgg ggacgagaga attcaaaaga gagttgagta ctcagttgtt   1680
gaagaaagat gtctggactt gaatcttgag cttaggatca gtccaccatg gcaagacaag   1740
ctccatgatg agaggaacct aaggtttggg agagtgaagt ataggtgcag tgcgtgccgt   1800
tttggattcg ggaacggcaa ggagtgtagc tgtaataatg tgaaatgtca aacagaggac   1860
agtagtagca gcagttattc ttcaaccgac attagtagta gcattggtta tgacttcttg   1920
ggtctaaaca acactagggt tttggatttt agcactttgg aaatgaaatg acacgtgtga   1980
```

```
attacaggtg accagctcga atttccccga tagctttcgt tcgtatcatc ggtttcgaca   2040
acgttcgtca agttcaatgc atcagtttca ttgcgcacac accagaatcc tactgagttc   2100
gagtattatg gcattgggaa acatgttttt cttgtaccat tgttgtgct tgtaatttac    2160
tgtgttttt attcggtttt cgctatcgaa ctgtgaaatg gaaatggatg gagaagagtt    2220
aatgaatgat atggtccttt tgttcattct caaattaata ttatttgttt tttctcttat   2280
ttgttgtgtg ttgaatttga aaatataaga gatatgcaaa cattttgttt tgagtaaaaa   2340
tgtgtcaaat cgtggcctct aatgaccgaa gttaatatga ggagtaaaac acttgtagtt   2400
gtaccattat gcttattcac taggcaacaa atatattttc agacctagaa aagctgcaaa   2460
tgttactgaa tacaagtatg tcctcttgtg ttttagacat ttatgaactt tccttttatgt  2520
aattttccag aatcctttgtc agattctaat cattgcttta taattatagt tatactcatg   2580
gatttgtagt tgagtatgaa aatatttttt aatgcatttt atgacttg                2628

SEQ ID NO: 64           moltype = DNA   length = 2506
FEATURE                 Location/Qualifiers
misc_feature            1..2506
                        note = Construct No. 008
source                  1..2506
                        mol_type = other DNA
                        organism = synthetic construct SEQUENCE: 64
aactagaaca cttcagataa attttgtcgt tctgttgact tcatttattc tctaaacaca   60
aagaactata gaccataatc gaaataaaaa ccctaaaaac caaatttatc tatttaaaac   120
aaacattagc tatttgagtt tcttttaggt aagttattta aggttttgga gactttaaga   180
tgttttcagc atttatggtt gtgtcattaa tttgttagt ttagtaaaga aagaaaagat    240
agtaattaaa gagttggttg tgaaatcata tttaaaacat taataggtat ttatgtctaa   300
tttggggaca aaatagtgga attctttatc atatctagtc agttcttatc gagtttgaac   360
tcgggttatg attatgttac atgcattggt ccatataaat ctatgagcaa tcaatataat   420
tcgagcattt tggtataaca taatgagcca agtataacaa aagtatcaaa cctatgcagg   480
ggagaagatg atgaaaagaa gagtgtgagc aatacaaag cagatttgag gacatggctt   540
acaagtcttg ggtacagagt ttgggagtg atgggtgcaa aatggaacag cttctctggt   600
tgtccagttc ccaagagaac cttcaagctc cctaactcca tctactatgt cgcctgatta   660
aatcttattt actaacaaaa caataagatc agagtttcat tctgattctt gagtcttttt   720
tttctctctc cctcttttca tttctggttt ataataccaa ttcaaatgct tatgatccat   780
gcatgaacca tgatcatctt tgtgtttttt ttccttctg tattaccatt ttgggcctt   840
gtgaaattga ttttgggctt ttgttatata atctcctctt tctctttctc tacctgattg   900
gattcaagaa catagccaga tttggtaaag tttataagat acaaaatatt aagtaagact   960
aaagtagaaa tacataataa cttgaaagct actctaagtt atgggaaggt caccgtgctg  1020
tgagaaagct cacacaaaca aaggagcatg acgaaagaa gaggacgaga ggctcgtcgc   1080
ctacattaaa gctcatgag aaggctgctg gagatcctcc cccaaagccg ccggacttct   1140
tcgctgtggc aagagctgcc gtctccggtg atcaactat ctccggcctg acctttaagcg  1200
tggaaacttc accgaggaag aagacgaact catcatcaag ctccatagcc ttcttggcaa   1260
caaatggtcg cttattgccg ggagattacc gggaagaaca gataacgaga taagaacta    1320
ttggaacacg catatacgaa gaaagcttat aaacagaggg attgatccaa tgactcatag    1380
accaatccaa gaatcatcag cttctcaaga ttctaaacct acacaactag aaccagttac   1440
gagtaatacc attaatatct cattcacttc tgctccaaag gtcgaaacgt tccatgaaag   1500
tataagcttt ccgggaaaat cagagaaaat ctcaatgctt acgttcaaag aagaaaaaga   1560
tgagtgccca gttcaagaaa agttcccaga tttgaatctt gagctcagaa tcagtcttcc   1620
tgatgatgtt gatcgtcttc aagggcatgg aaagtcaaca acgccacgtt gtttcaagtg   1680
cagcttaggg atgataaacg gcatggagtg cagatgcgga agaatgagat gcgatgtagt   1740
cggaggtagc agcaaggga gtgacatgag caatggattt gatttttag ggttggcaaa    1800
gaaagacc acttctcttt tgggctttcg aagcttggag atgaaataac acgtgtgaat    1860
tacaggtgac cagctcgaat ttccccgata gctttcgttc gtatcatcgg tttcgacaac   1920
gttcgtcaag ttcaatgcat cagtttcatt gcgcacacac cagaatccta ctgagtcga    1980
gtattatggc attgggaaac atgttttct tgtaccattt gttgtgcttg taatttactg   2040
tgtttttat tcggttttcg ctatcgaact gtgaaatgga aatggatgga gaagagttaa    2100
tgaatgatat ggtcccttttg ttcattctca aattaatatt atttgttttt tctcttattt    2160
gttgtgtgtt gaatttgaaa ataagaga tatgcaaaca ttttgtttg agtaaaaatg     2220
tgtcaaatcg tggcctctaa tgaccgaagt taatatgagg agtaaaacac ttgtagttgt    2280
accattatgc ttattcacta ggcaacaaat atatttcag acctagaaaa gctgcaaatg    2340
ttactgaata caagtatgtc ctcttgtgtt ttagacattt atgaacttt ctttatgtaa    2400
ttttccagaa tcctttgtcag attctaatca ttgctttata attatagtta tactcatgga   2460
tttgtagtta gtatgaaaa tattttttaa tgcattttat gacttg                   2506

SEQ ID NO: 65           moltype = DNA   length = 2570
FEATURE                 Location/Qualifiers
misc_feature            1..2570
                        note = Construct No. 009
source                  1..2570
                        mol_type = other DNA
                        organism = synthetic construct SEQUENCE: 65
aacccataac tttagtattc ttcaacccctt acaacttatc tgagcaaaat cagaaggtcg   60
aatttgatgg atggttttgc tgtatttggt caacggtttt atttgagaca gtagaccaga   120
ggaaactcag atgtgatgat gcaaagactg aattggttaa gagtgtagat tgatttgttc   180
taacattgca aatgtagagt agaattatgc aaaaaacgtt aatgaacaga gaagtgatta   240
agcagaaaca aaattagaga agtgatatta tatctcaaaa ttatttttg gtacagctaa    300
agctcaaatt gttatagaga ttagagatat taaaccaaat gacgagtgtt tctttagta    360
gtaaacggtg aaaattctct tctgacaaag acaattaaaa ttttaggttt aagactttaa   420
tatttgtcac aaattgtcat ttacctaaat aaaaaaaaaa ctaaatatttt ttttagata   480
```

```
catatgtgtc ttataatttt aactataaat tttaatttta tgtcttaaat aattgtttac    540
actataaatt taaatatttt aatgctaaaa ttaatttgat tcaaaaagt gatttttaatt    600
cttattttc ttatagaaag ttggtgattg aaaagattta cttaaaaatt ataacaactt     660
caatggtgaa taacccgacc cgaataaacc ggatataaca acttcaatgt tagcttgata    720
tagaaagtac ggtgacgctt aggaggcaag caagctagta tctgccgctg gttagagaca    780
aagaacatgt gtcactcctc tcaactaaaa ctttccttca ctttcccgca aaatcatttc    840
aaaaaagctc caaatttagc ttacccatca gctttctcag aaaaccagtg aaagaaactt    900
ctcaacttcc gattttttcac aatccaccaa acttttttta ataactttt ttcctcttat    960
tacaaaacct ccactctcat ggcttctcaa acttgttatc catccaaatc tcaatccta   1020
attagggttc atttctctgt ttctccaaac aggggaattc gaagatggga aggtcaccgt   1080
gctgtgagaa agctcacaca aacaaaggag catggacgaa agaagaggac gagaggctcg   1140
tcgcctacat aaagctcat ggagaaggct gctggagatc tctccccaaa gccgccggac   1200
ttcttcgctg tggcaagagc tgccgtctcc ggtggatcaa ctatctccgg cctgacctta   1260
agcgttggaa cttcaccgag gaagaagacg aactcatcat caagctccat agccttcttg   1320
gcaacaaatg gtcgcttatt gccgggagat taccggaag aacagataac gagataaaga   1380
actattggaa cacgcatata cgaagaaagc ttataaacag agggattgat ccaacgagtc   1440
atagaccaat ccaagaatca tcagcttctc aagattctaa acctacacaa ctagaaccag   1500
ttacgagtaa taccattaat atctcattca ctttctgctcc aaaggtcgaa acgttccatg   1560
aaagtataag ctttccggga aaatcagaga aaatctcaat gcttacgttc aaagaagaaa   1620
aagatgagtg cccagttcaa gaaaagttcc cagatttgaa tcttgagctc agaatcagtc   1680
ttcctgatga tgttgatcgt cttcaagggc atggaaagtc aacaacgcca cgttgtttca   1740
agtgcagctt agggatgata aacggcatgg agtgcagatg cggaagaatg agtgcgatg   1800
tagtcggagg tagcagcaag gggagtgaca tgagcaatgg atttgatttt ttagggttga   1860
caaagaaaga gaccacttct cttttgggct ttcgaagctt ggagatgaaa taacacgtgt   1920
gaattacagg tgaccagctc gaatttcccc gatagctttc gttcgtatca tcggtttcga   1980
caacgttcgt caagttcaat gcatcagttt cattgcgcac aaccagaat cctactgagt   2040
tcgagtatta tggcattggg aaacatgttt ttcttgtacc atttgttgtg cttgtaattt   2100
actgtgtttt ttattcggtt ttcgctatcg aactgtgaaa tggaaatgga tggagaagag   2160
ttaatgaatg atatggtcct tttgttcatt ctcaaattaa tattatttgt ttttctctt    2220
attttgttgtg tgttgaattt gaaaatataa gagatatgca aacattttgt tttgagtaaa   2280
aatgtgtcaa atcgtggcct ctaatgaccg aagttaatat gaggagtaaa acacttgtag   2340
ttgtaccatt atgcttattc actaggcaac aaatatattt tcagacctag aaaagctgca   2400
aatgttactg aatacaagta tgtcctcttg tgttttagac atttatgaac tttcctttat   2460
gtaattttcc agaatccttg tcagattcta atcattgctt tataattata gttatactca   2520
tggatttgta gttgagtatg aaaatatttt ttaatgcatt ttatgacttg              2570
```

SEQ ID NO: 66        moltype = DNA  length = 2485
FEATURE              Location/Qualifiers
misc_feature       1..2485
                      note = Construct No. 010
source              1..2485
                      mol_type = other DNA
                      organism = synthetic construct
SEQUENCE: 66

```
aggcggggcc ggaggagggc accagagagg ctgctcagga gagagaaata atagaatatg     60
tggtatagag taaacatgag tgcggatgat tgtggtatag agtaaagaat tttgctgact    120
aggacagaat attcttttta gggtagaaat ttagagtact atgagtgcgg atagcctaag    180
gaccacttta aatttgacac aatattgaaa tttgaatggt tttaacattt gaaggctgaa    240
aaccaaaata ctttgtagct aagtgttgga aacccgactc ggccaataag tcgacagacc    300
gtaaaataag gtcaatctaa actttatgat aaatattctt gtttgatagc aatagcattg    360
caggacgag acccaaggga agagaagatg ccaaatccca tcgaggctaa agcaaaaacg    420
atccaattta tgagcaaacc cacactgaag tttcaaaatt gttttctgaa aaaaagtaa    480
ccagcaagtt aaaaaatgag atggcgggaa agccaagtct cggttggtcg aggggttggt    540
tggggcgcag cctgacaagt gacaacggca gcaggatagt agcatcaggc gcaagccagc    600
gcagcggca gcgcgaggat ttcgcttcac ttagcggcaa cggagacgtc gcacccaacc    660
aacacgagct cccctcacc cgctgcgacg cgcgcgtccc acgagcggaa gccccccgcg    720
ccgacgcgag cgcgggggct cgaccgaccg acccaacgcc tccatctcca ccgcgcgcac    780
caaatcgcac tccgtccgc cccgccgatc gaacagccac cgctcacctc tcccacccgc    840
caaaaacctc cggcctcctc tcatattcat atagctagcc cctgccacaa ggtagagcgt    900
cgctcacacc tgcgtcgccc tgcctcgcaa tcgcgaatct gtcgagcacc tgaggggtcg    960
gaggccgaga gctagcctag cacgccggcc tccgcgcgcg atgggaggt cgccgtgctg   1020
cgagaaggcg cacaccaaca agggcgcgtg gaccaaggag gaggacgagc gctggtcgc   1080
gcacatcagg gcgcacggcg aggggtgctg gcgctcgctg cccaaggccg ccggcctcct   1140
gcgctgcggc aagagctgcc gcctccgctg gatcaactac ctccgccccg acctcaagcg   1200
cggcaacttc acggaggaag aggacgagct catcgtcaag ctgcacagcg tcctcggcaa   1260
caagtggtcc ctgatcgccg aaggctgcc cggcaggacg gacaacgaga tcaagaacta   1320
ctggaacacg cacatccgga ggaagctgct gagcaggggg atcgacccgg tgacgcaccg   1380
cccggtcacg gagcaccacg cgtccaacat caccatatcg ttcgagacgg aagtggccgc   1440
cgctgcccgt gatgataaga agggcgccgt cttccggttg gaggacgggg aggagggaga   1500
gcgcaacaag gcgacgatgg tcgtcggccg cgaccggcag agccagagcc acagccacag   1560
ccaccccgcc ggcgagtggg gccagggaa gaggccgctc aagtgccccg acctcaacct   1620
ggacctctgc atcagcccgc cgtgccagga ggaggaggga atggaggagg ctgcgatgag   1680
agtgagaccg gcgggtgaagc gggaggccgg gctctgcttc ggctgcagcc tggggctccc   1740
caggacgcg gactgcaagt gcagcagcag cagcttcctc ggctcagga cgccatgct   1800
cgacttcaga agcctcgaga tgaaatgaca cgtgtgaatt acaggtgacc agctcgaatt   1860
tccccgatag ctttcgttcg tatcatcggt ttcgacaacg ttcgtcaagt tcaatgcatc   1920
agtttcattg cgcacacacc agaatcctac tgagttcgag tattatggca ttgggaaaca   1980
tgttttcctt gtaccatttg ttgtgcttgt aatttactgt gttttttatt cggttttcgc   2040
tatcgaactg tgaaatggaa atggatggag aagagttaat gaatgatatg gtccttttgt   2100
```

```
tcattctcaa attaatatta tttgttttt ctcttatttg ttgtgtgttg aatttgaaaa    2160
tataagagat atgcaaacat tttgttttga gtaaaatgt gtcaaatcgt ggcctctaat    2220
gaccgaagtt aatatgagga gtaaaacact tgtagttgta ccattatgct tattcactag   2280
gcaacaaata tattttcaga cctagaaaag ctgcaaatgt tactgaatac aagtatgtcc   2340
tcttgtgttt tagacattta tgaactttcc tttatgtaat tttccagaat ccttgtcaga   2400
ttctaatcat tgctttataa ttatagttat actcatggat ttgtagttga gtatgaaaat   2460
attttttaat gcattttatg acttg                                          2485

SEQ ID NO: 67           moltype = DNA   length = 2485
FEATURE                 Location/Qualifiers
misc_feature            1..2485
                        note = Construct No. 011
source                  1..2485
                        mol_type = other DNA
                        organism = synthetic construct
SEQUENCE: 67
atactgaaca ttatgttgca taacatgtag ataaggacac gaaaacatag aaagtttctc    60
agttatattt acccatcaac atgaaataaa aaacaacaaa gatgtcatag tgatgtttgt   120
ttcaacttac caagggtgac catgtcgtat ttataataat attatatatt tatatcgtca   180
atagaatatt agtgttacgg tgatatttta gcacaccgat ttttttatatc atactcgatgt 240
ttatcgtttt gtatctatat tttatatttg ttttataata atattagata tttatttcgt   300
caatagaata ttaatgttat gatgatactt tactatatty attttacata tgatagtgat   360
gttactcctt ccgtatctat attttatatt agttttttatc tcctggcaac acggtcacaa  420
cagaagagaa gttttttcaga ccgattccag gatcgatttt tttttatat ctgggctaag  480
acatcaggta gagattgttt aacctttgcg gctttccgca ctgacggacc caccccacc    540
gcatcaacgg aacctaccaa ccacccccgt gctccgaccc ccatctgcc cgtcttccag   600
gttacgcccc gcgcggccgc gcgcgcggaa gctgtatcac cccacccgtc gacgtcgtct   660
tcgcttcgaa accccgcaaa accccgcgga aaaacccac ctgctgcacg cacgcacccc   720
ctccctctcc ctccccatgg cgcctcccct cacccaactc tttgcttcca ttctttccat   780
ccaccgcca atgcgacgcc gacgccgcaa ctccacccac cgctgccag cgccacctca   840
ccgcaccgct tccatcaccc cgcgatcatg ggctaccgct atatcaccac gcctccaacc   900
tccggcacgc ttagcctctc tctcccattc tctcacaccc aacacccagc tatcacaccc   960
tgatccccga ggccgcgcgt cggggtgagg aggaggggcc atgggggagt cgccgtgctg  1020
cgagaaggcg cacaccaaca agggcgcgtg gaccaaggag gaggacgagc gcctggtcgc  1080
gcacatcagg gcgcacggcg aggggtgctg gcgctcgctc cccaaggcg ccggcctcct   1140
gcgctgcggc aagagctgcc gcctccgctg gatcaactac ctccgccccg acctcaagcg  1200
cggcaacttc acggaggaag aggacgagct catcgtcaag ctgcacagcg tcctcggcaa  1260
caagtggtcc ctgatcgccg gaaggctgcc cggcaggacg gacaacgaga tcaagaacta  1320
ctggaacacg cacatccgga ggaagctgct gagcagggg atcgaccgg tgacgcaccg   1380
cccggtcacg gagcaccacg cgtccaacat caccatatcg ttcgagacgg aagtggccgc  1440
cgctgcccgt gatgataaga agggcgccgt cttccggttg gaggacgagg aggaggagga  1500
gcgcaacaag gcgacgatgg tcgtcggccg cgaccggcag agccagagcc acagccacag  1560
ccacccgcc ggcgagtggg gccagggaa gaggccccgc aagtgccccg acctcaacct   1620
ggacctctgc atcagcccgc cgtgccagga ggaggaggag atggaggagg ctgcgatgag  1680
agtgagaccg gcggtgaagc gggaggccgg gctctgcttc ggctgcagcc tggggctccc  1740
caggaccgcg gactgcaagt gcagcagcag cagcttcctc gggctcagga ccgccatgct  1800
cgacttcaga agcctcgaga tgaaatgaca cgtgtgaatt acaggtgacc agctcgaatt  1860
tccccgatag ctttcgttcg tatcatcggg ttcgacaacg ttcgtcaagt tcaatgcatc  1920
agtttcattg cgcacacacc agaatcctac tgagttcgag tattatggca ttgggaaaca  1980
tgttttttctt gtaccatttg ttgtgcttgt aatttactgt gttttttatt cggttttcgc  2040
tatcgaactg tgaaatggaa atggatggag aagagttaat gaatgatatg gtcctttgtg  2100
tcattctcaa attaatatta tttgttttt ctcttatttg ttgtgtgttg aatttgaaaa   2160
tataagagat atgcaaacat tttgttttga gtaaaatgt gtcaaatcgt ggcctctaat   2220
gaccgaagtt aatatgagga gtaaaacact tgtagttgta ccattatgct tattcactag   2280
gcaacaaata tattttcaga cctagaaaag ctgcaaatgt tactgaatac aagtatgtcc   2340
tcttgtgttt tagacattta tgaactttcc tttatgtaat tttccagaat ccttgtcaga   2400
ttctaatcat tgctttataa ttatagttat actcatggat ttgtagttga gtatgaaaat   2460
attttttaat gcattttatg acttg                                          2485

SEQ ID NO: 68           moltype = DNA   length = 2626
FEATURE                 Location/Qualifiers
misc_feature            1..2626
                        note = Construct No. 012
source                  1..2626
                        mol_type = other DNA
                        organism = synthetic construct
SEQUENCE: 68
gagttaaatt gatatggttt tgtctgtcaa ggtgccgttt ctatggttgg aggaggaaaa    60
tgaaattagg ggaatagaac agtcgcaatc caaaagctat tgttctctct tctacggtag   120
ttgatagttc gatacgtgtg tttgatgtga gagactgaga ggagtgcacg gtgcacctgc   180
cccgtaagga cgcggaacta cattatcaga ggctaggccg gtactgttat acgcgacgtt   240
cacgaatcac gatgcgtaaa aaagtgaagc atgaaacagt actaggctct ccacgggcca   300
catcatgaaa aaactggtgc gacgccacgc ttaacaattt gtcggtcgta aactcgtaaa   360
gttaaaagcc ccacgacatt gtcaaccaat atctcagcac atgaacttct ctaacgagta   420
caacgaaacc gcatccgcaa aagcgccgtg aaccaaagct cttgccgtgc tgtgccgtgc   480
cggtggccgt gaacatgtgg aacacgaaga actcttgcgc gagatcggag cacctgacct   540
cccacctcgc gtccggcccg tcgccgtcgc agcaagcggg ctgtcaaaaa cgacgccaca   600
gcgcgagcgc tctcgccgat ccggcggacc caccctcctc acctcgcgca caaccgccc    660
gttcgctagt ccgatccccc accctcatc ccccctacgc cttgcaggtt acgcgcctcg   720
```

```
ccgcggccaa cgcaaaccaa accaaatccc ccgtcacctt cgcttcgaaa ccccgcaaaa    780
ccccatggaa gaaaacaccg aacacctgcc gcgcgcacgc ctcctcctcc cccgcctctc    840
ctcctctctc ccgttccatg tccgctcaac cttgcttcca ttctttccat ccacccgccg    900
atcgacgcga tgccgacgcc ccaacccac ccaccgcctg ccagcgccac cccacctcgc     960
gcctctgcgg ctatggctat atcaccatgc ctccaacctc cggtacgctt agcctctctc   1020
tctctcccc tcccattctg cgcattgctc tctgcgcgcg gtcgcgtgct gctgctcgcg    1080
gcgcccgga gcgtctcctt tgggggagag gagaggagag gagaggagag ggggtgagc    1140
catggggagg tcgccgtgct gcgagaaggc gcacaccaac aagggcgcgt ggaccaagga   1200
ggaggacgag cgcctggtcg cgcacatcag ggcgcacggc gaggggtgct ggcgctcgct   1260
gcccaaggcc gccggcctcc tgcgctgcgg caagagctgc cgcctccgcc ggatcaacta   1320
cctccgcccc gacctcaagc gcggcaactt cacggaggaa gaggacgagc tcatcgtcaa   1380
gctgcacagc gtcctcggca caagtggtc cctgatcgcc ggaaggctgc ccggcaggac   1440
ggacaacgag atcaagaact actggaacac gcacatccgg aggaagctgc tgagcagggg   1500
gatcgacccg gtgacgcacc gcccggtcac ggagcaccac gcgtccaaca tcaccatatc   1560
gttcgagacg gaagtggccg ccgctgcccg tgatgataag aagggcgccg tcttccggtt   1620
ggaggacgag gaggaggagg agcgcaacaa ggcgacgatg gtcgtcggcc gcgaccggca   1680
gagccagagc cacagccaca gccacccgc cggcgagtgg ggccagggga agaggccgct    1740
caagtgcccc gacctcaacc tggacctctg catcagcccg ccgtgccagg aggaggaga   1800
gatggaggag gctgcgatga gagtgagacc ggcggtgaag cgggaggccg ggctctgctt   1860
cggctgcagc ctggggctcc ccaggaccgc ggactgcaag tgcagcagca gcagcttcct   1920
cgggctcagg accgccatgc tcgacttcag aagcctcgag atgaaatgac acgtgtgaat   1980
tacaggtgac cagctcgaat ttccccgata gctttcgttc gtatcatcgg tttcgacaac   2040
gttcgtcaag ttcaatgcat cagtttcatt gcgcacacac cagaatccta ctgagttcga   2100
gtattatggc attgggaaac atgttttct tgtaccattt gttgtgcttg taatttactg    2160
tgtttttat tcggttttcg ctatcgaact gtgaaatgga aatggatgga gaagagttaa    2220
tgaatgatat ggtcctttg ttcattctca aattaatatt atttgttttt tctcttattt    2280
gttgtgtgtt gaatttgaaa atataagaga tatgcaaaca ttttgttttg agtaaaaatg   2340
tgtcaaatcg tggcctctaa tgaccgaagt taatatgagg agtaaaacac ttgtagttgt   2400
accattatgc ttattcacta ggcaacaaat atattttcag acctagaaaa gctgcaaatg   2460
ttactgaata caagtatgtc ctcttgtgtt ttagacattt atgaactttc ctttatgtaa   2520
ttttccagaa tccttgtcag attctaatca ttgcttatta attatagtta tactcatgga   2580
tttgtagttg agtatgaaaa tatttttaa tgcattttat gacttg                   2626

SEQ ID NO: 69           moltype = DNA   length = 2485
FEATURE                 Location/Qualifiers
misc_feature            1..2485
                        note = Construct No. 013
source                  1..2485
                        mol_type = other DNA
                        organism = synthetic construct SEQUENCE: 69
ttcaatgcag gatgacgcca agagggagaa accaagcaga ggtggacggt acaacgtgta     60
agtcaccgca aaacgttgca gcttggatag tggccatgga gtggtgtgcc gatacggacg    120
cctgttcttt acagcctcag ctagtgttgt tgtccgaggc aatttttccg acctattgtg    180
ttgcttttcct ctctgatagc ttatggtaaa agatacaaag atgttgagga gtttgtacgc   240
cacttaattt tgctcgtaac atacattgac aatcaagagg agccatggca ttgcgatctg    300
cttacacggc atattcttac tggatggtgt acactactta cccttttaa tgcaagcatc     360
aatccattgc ttttctcact gcacacctga ttcgtactga aaacgtgaaa cataaaaaaa    420
aacaaaaatc tagctgatgt tggctctcgg ggcctcgagt ctagtttgtc ctagatggct    480
aacctgatat gtgttggtca cgctcacgtt tgaaccgaga aagagtgtgt gtgtgtgtgt    540
gtcggcgtgc tgctacacca gagcctccct gaatcgcaat gcgtgttaac gcagcatcgg    600
caggatttca tctcacttga caggttcaga tggccttcct cctaccgtct gccatttata    660
cacgcagtga cttaacgctt acacgagccg gatggcccgg atctcccccc tgcaccatct    720
caccagaaaa acgtgaggc gtcaccgcaa cccacccacc aaaacatcc acgtcccttc     780
accgttggcc ttcgattttg cttcagctgc actacgaccg ctccaacaca tttccctgcg    840
gtctcgttgc gatctcacct tacgacgatc tcgttccagc agcagcagca tcggcagcgg    900
cggcttgctt ccgaagcgag caatgcatgg cgcgcgcggc cgcgtgcgtg cgtgccttgg    960
cttgcgctct aatcaaaccg ggacgcccca actcacggtt atggggaggt cgccgtgctg   1020
cgagaaggcg cacaccaaca agggcgcgt gaccaaggga gaggacgagc gcctggtcgc    1080
gcacatcagg gcgcacggcg aggggtgctg gcgctgctg cccaaggccg ccggcctcct    1140
gcgctgcggc aagagctgcc gcctccgctg atcaactac ctccgccccg acctcaagcg    1200
cggcaacttc acggaggaag aggacgagct catcgtcaag ctgcacagcg tcctcggcaa   1260
caagtggtcc ctgatcgccg gaaggctgcc cggcaggacg gacaacgaga tcaagaacta   1320
ctggaacacg cacatccgga ggaagctgct gagcagcacg tgacgcaccg cccggtcacg   1380
gagcaccacg cgtccaacat caccatatcg ttcgagacgg aagtggccgc cgctgcccgt   1440
gatgataaga agggcgccgt cttccggttg gaggacgagg aggaggagga gcgcaacaag   1500
gcgacgatgg tcgtcggccg cgaccggcag agccagagcc acagccacag ccacccgcc    1560
ggcgagtggg gccaggggaa gaggccgctc aagtgccccg acctcaacct ggacctctgc   1620
atcagcccgc cgtgccagga ggaggagagg atggaggagg ctgcgatgag agtgagaccg   1680
gcggtgaagc gggaggccgg gctctgcttc ggctgcagca tggggctccc caggaccgcg   1740
gactgcaagt gcagcagcag cagcttcctc gggctcagga ccgccatgct cgacttcaga   1800
agcctcgaga tgaaatgaca cgtgtgaatt acaggtgacc agctcgaatt tccccgatag   1860
ctttcgttcg tatcatcggt tcgacaacg ttcgtcaagt tcaatgcatc agtttcattg    1920
cgcacacacc agaatcctac tgagttcgag tattatggca ttgggaaaca tgttttct    1980
tgtaccattt gttgtgcttg taatttactg tgttttttatt cggttttcgc tatcgaactg   2040
tgaaatggaa atggatggag aagagttaa gaatgatatg gtccttttgt tcattctcaa    2100
attaatatta tttgttttttt ctcttatttg ttgtgtgttg aatttgaaaa               2160
tataagagat atgcaaacat tttgttttga gtaaaaatgt gtcaaatcgt ggcctctaat    2220
gaccgaagtt aatatgagga gtaaaacact tgtagttgta ccattatgct tattcactag    2280
```

```
gcaacaaata tattttcaga cctagaaaag ctgcaaatgt tactgaatac aagtatgtcc  2340
tcttgtgttt tagacattta tgaacttttcc tttatgtaat tttccagaat ccttgtcaga  2400
ttctaatcat tgctttataa ttatagttat actcatggat tgtagttga gtatgaaaat  2460
atttttaat gcattttatg acttg                                           2485
```

| SEQ ID NO: 70 | moltype = DNA  length = 2440 |
|---|---|
| FEATURE | Location/Qualifiers |
| misc_feature | 1..2440 |
| | note = Construct No. 014 |
| source | 1..2440 |
| | mol_type = other DNA |
| | organism = synthetic construct |

```
SEQUENCE: 70
aggcggggcc ggaggagggc accagagagg ctgctcagga gagagaaata atagaatatg   60
tggtatagag taaacatgag tgcggatgat tgtggtatag agtaaagaat tttgctgact  120
aggacagaat attcttttta gggtagaaat ttagagtact atgagtgcgg atagcctaag  180
gaccacttta aatttgacac aatattgaaa tttgaatggt tttaacattt gaaggctgaa  240
aaccaaaata ctttgtagct aagtgttgga aacccgactc ggccaataag tcgacagacc  300
gtaaaataag gtcaatctaa actttatgat aaatattctt gtttgatagc aatagccattg  360
caggaccagg acccaaggga agagaagatg ccaaatccca tcgaggctaa agcaaaaacg  420
atccaattta tgagcaaacc cacactgaag tttcaaaatt gttttctgaa aaaaaagtaa  480
ccagcaagtt aaaaaatgag atggcgggaa agccaagtct cggttggtcg aggggttggt  540
tggggcgcag cctgacaagt gacaacggca gcaggatagt agcatcaggc gcaagccagc  600
gcaggcggca gcgacaggat ttcgcttcac ttagcggcaa cggagacgct gcacccaacc  660
aacacgagct ccccctcacc cgctgcgacg cgcgcgtccc acgagcggaa gccccccgcg  720
ccgacgcgag cgcggggggct cgaccgaccg acccaacgcc tccatctcca ccgcgcgcac  780
caaatcgcac tcccgtccgc cccgccgatc gaacagccac cgctcacctc tcccaccgc   840
caaaaacctc cggcctcctc tcatattcat atagctagcc cctgccacaa ggtagagcgt   900
cgctcacacc tgcgtcgccc tgcctcgcaa tcgcgaatct gtcgagcacc tgaggggtcg   960
gaggcgcgaga gctagcctag cacgccggcc tccgcgcggg atgggcggt cgccgtgctg  1020
cgagaaggcg cacaccaaca ggggcgcgtg gaccaaggag gaggacgagc ggctggtggc  1080
ctacgtccgc gcgcacggcg aagggtgctg gcgctcgctg cccagggcgg cgggcctgct  1140
gcgctgcggc aagagctgcc gcctgcgctg gatcaactac ctccgcccgg acctcaagcg  1200
aggcaacttc accgccgacg aggacgacct catcgtcaag ctgcacagcc tcctcgggaa  1260
caagtggtcg ctcatcgccg cgcggctccc ggggcggacg gacaacgaga tcaagaacta  1320
ctggaacacg cacatccggc gcaagctgct gggcagcggc atcgaccccg tcacgcaccg  1380
ccgcgtcgcg ggggcgccg cgaccaccat ctcgttccag cccagcccca actccgccgc  1440
cgccgccgcc gccgcagaaa cagcagcgca ggcgccgatc aaggccgagg agacggcggc  1500
cgtcaaggcg cccaggtgcc ccgacctcaa cctggacctc tgcatcagcc cgccgtgcca  1560
gcatgaggac gacggcgagg aggaggacga ggagctggac ctcaagcccg ccttcgtcaa  1620
gcgggaggcg ctgcaggccg gccacggcca cggccacggc ctctgcctcg gctgcggcct  1680
gggcggacag aaggagcgg ccgggtgcag ctgcagcaac ggccaccact tcctgggcgt  1740
caggaccagc gtgctcgact tcagaggcct ggagatgaag tgacacgtgt gaattacagg  1800
tgaccagctc gaatttcccc gatagctttc gttcgtatca tcggtttcga caacgttcgt  1860
caagttcaat gcatcagttt cattgcgcac acaccagaat cctactgagt tcgagtatta  1920
tggcattggg aaacatgttt tcttgtacc atttgttgtg cttgtaattt actgtgtttt  1980
ttattcggtt ttcgctatcg aactgtgaaa tggaaatgga tggagaagag ttaatgaatg  2040
atatggtcct tttgttcatt ctcaaattaa tattatttgt tttttctctt atttgttgtg  2100
tgttgaattt gaaaatataa gagatatgca aacattttgt tttgagtaaa aatgtgtcaa  2160
atcgtggcct ctaatgaccg aagttaatat gaggagtaaa acacttgtag ttgtaccatt  2220
atgcttattc actaggcaac aaaatatattt tcagacctag aaaagctgca aatgttactg  2280
aatacaagta tgtcctcttg tgttttagac attttatgaac tttcctttat gtaattttcc  2340
agaatccttg tcagattcta atcattgctt tataattata gttatactca tggatttgta  2400
gttgagtatg aaaatatttt ttaatgcatt ttatgacttg                         2440
```

| SEQ ID NO: 71 | moltype = DNA  length = 2440 |
|---|---|
| FEATURE | Location/Qualifiers |
| misc_feature | 1..2440 |
| | note = Construct No. 015 |
| source | 1..2440 |
| | mol_type = other DNA |
| | organism = synthetic construct |

```
SEQUENCE: 71
atactgaaca ttatgttgca taacatgtag ataaggacac gaaaacatag aaagtttctc   60
agttatattt acccatcaac atgaaataaa aacaacaaa gatgtcatag tgatgtttgt  120
ttcaacttac caagggtgac catgtcgtat ttataataat attatatatt tatatcgtca  180
atagaatatt agtgttacgg tgatattta gcacaccgat ttttatatc atactgatgt  240
ttatcgtttt gtatctatat tttatatttg ttttataata atattagata tttatttcgt  300
caatagaata ttaatgttat gatgatactt tactatattg attttacata tgatagtgat  360
gttactcctt ccgtatctat attttatatt agttttatc tcctggcaac acggtcacaa  420
cagaagagaa gttttttcaga ccgattccag gatcgatttt tttttatat ctgggctaag  480
acatcaggta gagattgttt aacctttgcg gcttccgca ctgacggacc caccccacc   540
gcatcaacgg aacctaccaa ccaccccgt gctccgaccc ccatctgcc cgtcttcag   600
gttacgcccc gcgcggccgc gcgcgcggaa gctgtatcac cccacccgtc gacgtcgtct   660
tcgcttcgaa acccgcaaa accccgcgga aaaacccac ctgctgcacg cacgcacccc   720
ctccctctcc ctcccccatgg cgcctcccct cacccaactc tttgcttcca ttcttttccat  780
ccacccgcca atgcgacgcc gacgccgcaa ctccaccccac cgctgccag cgccacctca  840
ccgcaccgct tccatcaccc cgcgatcatg ggctaccgct atatcaccac gcctccaacc  900
tccggcacgc ttagcctctc tctcccattc tctcacaccc aacaccccagc tatcacaccc  960
```

-continued

```
tgatccccga ggccgcgcgt cggggtgagg aggaggggcc atggggcggt cgccgtgctg 1020
cgagaaggcg cacaccaaca ggggcgcgtg gaccaaggag gaggacgagc ggctggtggc 1080
ctacgtccgc gcgcacggcg aagggtgctg cgctcgctg cccagggcgg cgggcctgct 1140
gcgctgcggc aagagctgcc gcctgcgctg gatcaactac ctccgcccgg acctcaagcg 1200
aggcaacttc accgccgacg aggacgacct catcgtcaag ctgcacagcc tcctcgggaa 1260
caagtggtcg ctcatcgccc gcggctccc ggggcggacg gacaacgaga tcaagaacta 1320
ctggaacacg cacatccggc gcaagctgct gggcagcggc atcgaccccg tcacgcaccg 1380
ccgcgtcgcg gggggcgccg cgaccaccat ctcgttccag cccagcccca actccgccgc 1440
cgccgccgcc gccgcagaaa cagcagcgca ggcgccgatc aaggccgagg agacggcggc 1500
cgtcaaggcg cccaggtgcc ccgacctcaa cctggacctc tgcatcagcc cgccgtgcca 1560
gcatgaggac gacggcgagg aggaggacga ggagctggac ctcaagcccg ccttcgtcaa 1620
gcgggaggcg ctgcaggccg ccacggcca cggccacggc ctctgcctcg gctgcggcct 1680
gggcggacag aagggagcgg ccgggtgcag ctgcagcaac ggccaccact tcctgggggct 1740
caggaccagc gtgctcgact tcagaggcct ggagatgaag tgacacgtgt gaattacagg 1800
tgaccagctc gaatttcccc gatagctttc gttcgtatca tcggtttcga caacgttcgt 1860
caagttcaat gcatcagttt cattgcgcac acaccagaat cctactgagt tcgagtatta 1920
tggcattggg aaacatgttt ttcttgtacc atttgttgtg cttgtaattt actgtgtttt 1980
ttattcggtt ttcgctatcg aactgtgaaa tggaaatgga ttgagaagag ttaatgaatg 2040
atatggtcct tttgttcatt ctcaaattaa tattatttgt ttttttctct atttgttgtg 2100
tgttgaattt gaaaatataa agagatatgca aacatttttgt tttgagtaaa aatgtgtcaa 2160
atcgtggcct ctaatgaccg aagttaatat gaggagtaaa acacttgtag ttgtaccatt 2220
atgcttattc actaggcaac aaaatatattt tcagacctag aaaagctgca aatgttactg 2280
aatacaagta tgtcctcttg tgttttagac atttatgaac tttcctttat gtaattttcc 2340
agaatccttg tcagattcta atcattgctt tataattata gttatactca tggattttgta 2400
gttgagtatg aaaatatttt ttaatgcatt ttatgacttg 2440

SEQ ID NO: 72         moltype = DNA   length = 2581
FEATURE               Location/Qualifiers
misc_feature          1..2581
                      note = Construct No. 016
source                1..2581
                      mol_type = other DNA
                      organism = synthetic construct
SEQUENCE: 72
gagttaaatt gatatggttt tgtctgtcaa ggtgccgttt ctatggttgg aggaggaaaa 60
tgaaattagg ggaatagaac agtcgcaatc caaaagctat tgttctctct tctacggtag 120
ttgatagttc gatacgtgtg tttgatgtga gagactgaga ggagtgcacg gtgcacctgc 180
cccgtaagga cgcggaacta cattatcaga ggctaggccg gtacgttat acgcgacgtt 240
cacgaatcac gatgcgtaaa aaagtgaagc atgaaacagt actaggctct ccacgggcca 300
catcatgaaa aaactggtgc gacgccacgc ttaacaattt gtcggtcgta aactcgtaaa 360
gttaaaagcc ccacgacatt gtcaaccaat atctcagcac atgaacttct ctaacgagta 420
caacgaaacc gcatccgcaa aagcgccgtg aaccaaagct cttgccgtgc tgtgccgtgc 480
cggtggccgt gaacatgtgg aacacgaaga actcttgcgg gagatcggag cacctgacct 540
cccacctcgc gtccgcccg tcgccgtcgc agcaagcggg ctgtcaaaaa cgacgccaca 600
gcgcgagcgc tctcgccgat ccggcggacc caccctcctc acctcgcgca ccaaccgccc 660
gttcgctagt ccgatccccc accccctcatc ccccctacgc cttgcaggtt acgcgcctcg 720
ccgcggccaa cgcaaaccaa accaaatccc ccgtcacctt cgcttcgaaa ccccgcaaaa 780
ccccatggaa gaaaacaccg aacacctgcc gcgcgcacgc ctcctcctcc ccgcctctc 840
ctcctctctc ccgttccatg tccgctcaac cttgcttcca ttctttccat ccacccgccg 900
atcgacgcga tgccgacgcc caaccccac ccaccgcctg ccagcgccac cccacctcgc 960
gcctcgtcgg ctatgctat atcaccatgc ctccaaccttc cggtacgctt agcctctctc 1020
tctctcccc tcccattctg cgcattgctc tctgcgcgcg gtcgcgtgct gctgctcgcg 1080
gcgccccgga gcgtctcctt tgggggagag gagaggagag gagaggagag gggggtgagc 1140
catggggcgg tcgccgtgct gcgagaaggc gcacaccaac aggggcgcgt ggaccaagga 1200
ggaggacgag cggctggtgg cctacgtccg cgcgcacggc gaaagggtgtg ggcgctcgct 1260
gcccagggcg gcgggcctgc tgcgctgcgg caagagctgc cgcctgcgct ggatcaacta 1320
cctccgcccg gacctcaagc gaggcaactt caccgccgac gaggacgacc tcatcgtcaa 1380
gctgcacagc ctcctcggga caagtggtc gctcatcgcc gcgcggctcc cggggcggac 1440
ggacaacgag atcaagaact actggaacac gcacatccgg cgcaagctgc tgggcagcgg 1500
catcgacccc gtcacgcacc gccgcgtcgc gggggggcgccg cgaccaccat ctcgttccag 1560
cccagccccc aactccgccg ccgccgccgc cgccgcagaa acagcagcgc aggcgccgat 1620
caaggccgag gagacggcgg ccgtcaaggc gcccaggtgc cccgacctca acctggacct 1680
ctgcatcagc ccgccgtgcc agcatgagga cgacggcgag gaggaggacg aggagctgga 1740
cctcaagccc gccttcgtca agcgggaggc gctgcaggcc gctgcacggcc acggccacgg 1800
cctctgcctc ggctgcggcc tgggcggaca gaagggagcg gccgggtgca gctgcagcaa 1860
cggccaccac ttcctggggc tcaggaccag cgtgctcgac ttcagaggcc tggagatgaa 1920
gtgacacgtg tgaattacag gtgaccagct cgaatttccc cgatagcttt cgttcgtatc 1980
atcggtttcg acaacgttcg tcaagttcaa tgcatcagtt tcattgcgca cacaccagaa 2040
tcctactgag ttcgagtatt atggcattgg gaaacatgtt tttcttgtac catttgttgt 2100
gcttgtaatt tactgtgttt ttattcggtt ttcgctatc gaactgtgaa atggaaatgg 2160
atggagaaga gttaatgaat gatatggtcc ttttgttcat tctcaaatta atattatttg 2220
ttttttctct tatttgttgt gtgttgaatt tgaaaatata agagatatgc aaacatttttgt 2280
ttttgagtaa aatgtgtca atcgtggcc tctaatgacc gaagttaata tgaggagtaa 2340
aacacttgta gttgtaccat tatgcttatt cactaggcaac caaatatatt ttcagaccta 2400
gaaaagctgc aaatgttact gaatacaagt atgtcctctt gtgttttaga catttatgaa 2460
ctttcctttta tgtaattttc cagaatcctt gtcagattct aatcattgct ttataattat 2520
agttatactc atggatttgt agttgagtat gaaaatattt ttaatgcatt ttatgactt 2580
g                                                                 2581
```

| SEQ ID NO: 73 | moltype = DNA length = 2440 |
|---|---|
| FEATURE | Location/Qualifiers |
| misc_feature | 1..2440 |
| | note = Construct No. 017 |
| source | 1..2440 |
| | mol_type = other DNA |
| | organism = synthetic construct |

SEQUENCE: 73

```
ttcaatgcag gatgacgcca agagggagaa accaagcaga ggtggacggt acaacgtgta    60
agtcaccgca aaacgttgca gcttggatag tggccatcga gtggtgtgcc gataccggcg   120
cctgttcttt acagcctcag ctagtgttgt tgtccgaggc aatttttccg acctattgtg   180
ttgctttcct ctctgatagc ttatggtaaa agatacaaag atgttgagga gtttgtacgc   240
cacttaattt tgctcgtaac atacattgac aatcaagagg agccatggca ttgcgatctg   300
cttacacggc atattcttac tggatggtgt acactactta cccttttaa tgcaagcatc    360
aatccattgc ttttctcact gcacacctga ttcgtactga aaacgtgaaa cataaaaaaa   420
aacaaaaatc tagctgatgt tggctctcgg ggcctcgagt ctagtttgtc ctagatggct   480
aacctgatat gtgttggtca cgctcacgtt tgaaccgaga aagagtgtgt gtgtgtgtgt   540
gtcggcgtgc tgctacacca gagcctccct gaatcgcaat gcgtgttaac gccagcatcg   600
caggatttca tctcacttga caggttcaga tggccttcct cctaccgtct gccatttata   660
cacgcagtga cttaacgctt acacgagccg gatggcccgg atctccccc  tgcaccatct   720
caccagaaaa acgtgaggc gtcaccgcaa cccacccacc aaacacatcc acgtcccttc   780
accgttggcc ttcgattttg cttcagctgc actacgaccg ctccaacaca tttccctcgc   840
gtctcgttgc gatctcacct tacgacgatc tcgttccagc agcagcagca tcggcagcgg   900
cggcttgctt ccgaagcgag caatgcatgg cgcgcgcggc cgcgtgcgtg cgtgccttgg   960
cttgcgctct aatcaaaccg ggacgcccca actcacggtt atggggcggt cgccgtgctg  1020
cgagaaggcg cacaccaaca ggggcgcgtg gaccaaggag gggacgagc ggctggtggc   1080
ctacgtccgc gcgcacggcg aagggtgctg gcgctcgctg cccagggcgg cgggcctgct  1140
gcgctgcggc aagagctgcc gcctgcgctg gatcaactac ctccgcccgg acctcaagcg  1200
aggcaacttc accgccgacg aggacgacct catcgtcaag ctgcacagcc tcctcgggaa  1260
caagtggtcg ctcatcgccg cgcggctccc ggggcgaggg gacaacgaga tcaagaacta  1320
ctggaacacg cacatccggc gcaagctgct gggcagcggc atcgacccg  tcacgcaccg  1380
ccgcgtcgcg gggggcgccg cgaccaccat ctcgttccag cccagcccca actccgccgc  1440
cgccgccgcc gccgcagaaa cagcagcgca ggcgccgatc aaggccgagg agacggcggc  1500
cgtcaaggcg cccaggtgcc ccgacctcaa cctggacctc tgcatcagcc cgcccgtgcc  1560
gcatgaggac gacggcgagg aggaggacga ggagctggac ctcaagcccg ccttcgtcaa  1620
gcgggaggcg ctgcaggccg ccacggcca  cggccacggc ctctgcctcg gctgcggcct  1680
gggcggacag aagggagcgg ccgggtgcag ctgcagcaac ggccaccact tcctgggggct  1740
caggaccagc gtgctcgact tcagaggcct ggagatggac tgacacgtgt gaattacagg  1800
tgaccagctc gaatttcccc gatagctttc gttcgtatca tcggttttcga caacgttcgt  1860
caagttcaat gcatcagttt cattgcgcac acaccagaat cctactgagt tcgagtatta  1920
tggcattggg aaacatgttt ttcttgtacc atttgttgtg cttgtaattt actgtgtttt  1980
ttattcggtt ttcgctatcg aactgtgaaa tggaaatgga tggagaagag ttaatgaatg  2040
atatggtcct tttgttcatt ctcaaattaa tattatttgt ttttcttcttt  atttgttgtg 2100
tgttgaattt gaaatataa  agatatgca  aacattttgt tttgagtaaa aatgtgtcaa  2160
atcgtggcct ctaatgaccg aagttaatat gaggagtaaa acacttgtag ttgtaccatt  2220
atgcttattc actaggcaac aaatatattt tcagacctag aaaagctgca aatgttactg  2280
aatacaagta tgtcctcttg tgttttagac atttatgaat tttcctttat gtaatttttcc  2340
agaatccttg tcagattcta atcattgctt tataattata gttatactca tggatttgta  2400
gttgagtatg aaaatatttt ttaatgcatt ttatgacttg                         2440
```

| SEQ ID NO: 74 | moltype = DNA length = 2428 |
|---|---|
| FEATURE | Location/Qualifiers |
| misc_feature | 1..2428 |
| | note = Construct No. 018 |
| source | 1..2428 |
| | mol_type = other DNA |
| | organism = synthetic construct |

SEQUENCE: 74

```
aggcggggcc ggaggagggc accagagagg ctgctcagga gagagaaata atagaatatg    60
tggtatagag taaacatgag tgcggatgat tgtggtatag agtaaagaat tttgctgact   120
aggacagaat attcttttta gggtagaaat ttagagtact atgagtgcgg atagcctaag   180
gaccacttta aatttgacac aatattgaaa tttgaatggt tttaacattt gaaggctgaa   240
aaccaaaata ctttgtagct aagtgttgga aacccgactc ggccaataag tcgacagacc   300
gtaaaataag gtcaatctaa acttttatgat aaatattctt gtttgatagc aatagcattg  360
caggaccagg acccaaggga agagaagatg ccaaatccca tcgaggctaa agcaaaaacg   420
atccaattta tgagcaaacc cacactgaag tttcaaaatt gttttctgaa aaaaagtaa   480
ccagcaagtt aaaaaatgag atggcgggaa agccaagtct cggttggtcg aggggttggt   540
tggggcgcag cctgacaagt gacaacggca gcaggatagt agcatcaggc gcaagccagc   600
gcaggcggca gcgcggaggat ttcgcttcac ttagcggcaa gggagacgct gcacccaacc   660
aacacgagct cccctcacc  cgctgcgacg cgcgcgtccc acgagcggaa gccccccgcg   720
ccgacgcgag cgcgggggct cgaccgaccg acccaacgcc tccatctcca ccgcgcgcac   780
caaatcgcac tccgtccgc  cccgcgatc  gaacagccac cgctcacctc tcccacccgc   840
caaaaacctc cggcctcctc tcatattcat atagctagcc cctgccacaa ggtagagcgt   900
cgctcacacc tgcgtcgccc tgcctcgcaa tcgcgaatct gtcgaactg  cgaggggtcg    960
gaggccgaga gctagcctag cacgccggcc tccgcgcgcg atgggcgat  cgccgtgctg  1020
cgagaaggcg cacacgaaca agggcgcctg gaccaaggag gaggacgacc gctcgttgc   1080
ctacatccgg gcgcacggcg aggggtgctg gcgctccctc ccaaggccg  cgggcctgct  1140
gcgctgcggc aagagctgcc gcctgcgctg gatcaactac ctccgcccgg acctcaagcg  1200
cggcaacttc accgccgacg aggacgacct catcgtcaag ctccacagcc tcctcggcaa  1260
```

-continued

```
caagtggtcg ctcatcgccg cgcgcctccc cggccgcacc gacaacgaga tcaagaacta   1320
ctggaacacg cacatcaagc gcaagctcct cagccgcggc atcgacccg tcacacaccg    1380
ccccatcgcc gacgcagcca gaaacgtcac catctccttc cagcccgacg cgccgtcgca   1440
gcagcagctc agcgacgacg ccgaggcgcc gccgccgccg ccgccgcagc agcagcagca   1500
gctcaagccg ccgcccaggt gccccgacct caatctcgac ctctgcatca gcccgccctg   1560
ccacaaggaa gaagaggacc aggagctcgt caagcccgcc gccgtcaagc gcgagatgct   1620
gcaggccggc cacggcactc taggactctg cttcggctgc agcctgggcc tccagaaggg   1680
cgccgccggg tgcacctgca gcagcaacag ccacttcctg gggctcaggg tcggcatgct   1740
cctcgacttc agaggcctcg agatgaagtg acacgtgtga attacaggtg accagctcga   1800
atttccccga tagctttcgt tcgtatcatc ggtttcgaca acgttcgtca agttcaatgc   1860
atcagtttca ttgcgcacac accagaatcc tactgagttc gagtattatg cattgggaa    1920
acatgttttt cttgtaccat ttgttgtgct tgtaatttac tgtgtttttt attcggtttt   1980
cgctatcgaa ctgtgaaatg gaaatggatg gagaagagtt aatgaatgat atggtccttt   2040
tgttcattct caaattaata ttatttgttt tttctcttat ttgttgtgtg ttgaatttga   2100
aaatataaga gatatgcaaa catttttgttt tgagtaaaaa tgtgtcaaat cgtggcctct   2160
aatgaccgaa gttaatatga ggagtaaaac acttgtagtt gtaccattat gcttattcac   2220
taggcaacaa atatattttc agacctagaa aagctgcaaa tgttactgaa tacaagtatg   2280
tcctcttgtg ttttagacat ttatgaactt tcctttatgt aattttccag aatccttgtc   2340
agattctaat cattgcttta taattatagt tatactcatg gatttgtagt tgagtatgaa   2400
aatatttttt aatgcatttt atgacttg                                     2428
```

| SEQ ID NO: 75 | moltype = DNA  length = 2428 |
|---|---|
| FEATURE | Location/Qualifiers |
| misc_feature | 1..2428 |
| | note = Construct No. 019 |
| source | 1..2428 |
| | mol_type = other DNA |
| | organism = synthetic construct |

SEQUENCE: 75

```
atactgaaca ttatgttgca taacatgtag ataaggacac gaaaacatag aaagtttctc    60
agttatattt acccatcaac atgaaataaa aacaacaaa gatgtcatag tgatgtttgt    120
ttcaacttac caagggtgac catgtcgtat ttataataat attatatatt tatatcgtca   180
atagaatatt agtgttacgg tgatatttta gcacaccgat ttttatatc atactgatgt    240
ttatcgtttt gtatctatat ttttataatt ttttataata atattagata ttttatttcgt  300
caatagaata ttaatgttat gatgatactt tactatattg attttacata tgatagtgat   360
gttactcctt ccgtatctat attttatatt agttttatc tcctggcaac acgtcacaa     420
cagaagagaa gttttcaga ccgattccag gatcgatttt ttttttatat ctgggctaag    480
acatcaggta gagattgttt aacctttgcg gcttccgca ctgacggacc caccccacc     540
gcatcaacgg aacctaccaa ccacccccgt gctccgaccc ccatctgcc cgtcttccag    600
gttacgcccc gcgcggccgc gcgcgcgaa gctgtatcac cccacccgtc gacgtcgtct    660
tcgcttcgaa accccgcaaa accccgcgga aaaaacccac ctgctgcacg cacgcacccc   720
ctccctctcc ctccccatgg cgcctcccct caccccaactc tttgcttcca ttctttccat  780
ccaccgccaa atgcgacgcc gacgccgcaa tccacccac ttgttgctca cgccacctca    840
ccgcaccgct tccatcaccc cgcgatcatg ggctaccgct atatcaccac gcctccaacc   900
tccggcacgc ttagcctctc tctcccattc tctcacaccc aacacccagc tatcacaccc   960
tgatccccga ggccgcgcgt cggggtgagg aggaggggcc atgggcgat cgccgtgctg   1020
cgagaaggcg cacacgaaca agggcgcctg gaccaaggag gaggacgaacc gcctcgttgc 1080
ctacatccgg gcgcacggcg aggggtgctg gcgctccctc cccaaggccg cgggcctgct  1140
gcgctgcggc aagagctgcc gcctgcgctg gatcaactac ctccgcccgg acctcaagcg  1200
cggcaacttc accgccgacg aggacgacct catcgtcaag ctccacagcc tcctcggcaa  1260
caagtggtcg ctcatcgccg cgcgcctccc cggccgcacc gacaacgaga tcaagaacta  1320
ctggaacacg cacatcaagc gcaagctcct cagccgcggc atcgacccg tcacacaccg   1380
ccccatcgcc gacgcagcca gaaacgtcac catctccttc cagcccgacg cgccgtcgca  1440
gcagcagctc agcgacgacg ccgaggcgcc gccgccgccg ccgccgcagc agcagcagca  1500
gctcaagccg ccgcccaggt gccccgacct caatctcgac ctctgcatca gcccgccctg  1560
ccacaaggaa gaagaggacc aggagctcgt caagcccgcc gccgtcaagc gcgagatgct  1620
gcaggccggc cacggcactc taggactctg cttcggctgc agcctgggcc tccagaaggg  1680
cgccgccggg tgcacctgca gcagcaacag ccacttcctg gggctcaggg tcggcatgct  1740
cctcgacttc agaggcctcg agatgaagtg acacgtgtga attacaggtg accagctcga  1800
atttccccga tagctttcgt tcgtatcatc ggtttcgaca acgttcgtca agttcaatgc  1860
atcagtttca ttgcgcacac accagaatcc tactgagttc gagtattatg cattgggaa   1920
acatgttttt cttgtaccat ttgttgtgct tgtaatttac tgtgtttttt attcggtttt  1980
cgctatcgaa ctgtgaaatg gaaatggatg gagaagagtt aatgaatgat atggtccttt  2040
tgttcattct caaattaata ttatttgttt tttctcttat ttgttgtgtg ttgaatttga  2100
aaatataaga gatatgcaaa catttttgttt tgagtaaaaa tgtgtcaaat cgtggcctct 2160
aatgaccgaa gttaatatga ggagtaaaac acttgtagtt gtaccattat gcttattcac  2220
taggcaacaa atatattttc agacctagaa aagctgcaaa tgttactgaa tacaagtatg  2280
tcctcttgtg ttttagacat ttatgaactt tcctttatgt aattttccag aatccttgtc  2340
agattctaat cattgcttta taattatagt tatactcatg gatttgtagt tgagtatgaa  2400
aatatttttt aatgcatttt atgacttg                                    2428
```

| SEQ ID NO: 76 | moltype = DNA  length = 2569 |
|---|---|
| FEATURE | Location/Qualifiers |
| misc_feature | 1..2569 |
| | note = Construct No. 020 |
| source | 1..2569 |
| | mol_type = other DNA |
| | organism = synthetic construct |

```
SEQUENCE: 76
gagttaaatt gatatggttt tgtctgtcaa ggtgccgttt ctatggttgg aggaggaaaa    60
tgaaattagg ggaatagaac agtcgcaatc caaaagctat tgttctctct tctacggtag   120
ttgatagttc gatacgtgtg tttgatgtga gagactgaga ggagtgcacg gtgcacctgc   180
cccgtaagga cgcggaacta cattatcaga ggctaggccg gtactgttat acgcgacgtt   240
cacgaatcac gatgcgtaaa aaagtgaagc atgaaacagt actaggctct ccacgggcca   300
catcatgaaa aaactggtgc gacgccacgc ttaacaattt gtcggtcgta aactcgtaaa   360
gttaaaagcc ccacgacatt gtcaaccaat atctcagcac atgaacttct ctaacgagta   420
caacgaaacc gcatccgcaa aagcgccgtg aaccaaagct cttgccgtgc tgtgccgatc   480
cggtggccgt gaacatgtgg aacacgaaga actcttgcgc gagatcggag cacctgacct   540
cccacctcgc gtccggcccg tcgccgtcgc agcaagcggg ctgtcaaaaa cgacgccaca   600
gcgcgagcgc tctcgccgat ccggcggacc caccctcctc acctcgcgca caaccgccc    660
gttcgctagt ccgatccccc accccctcatc cccctacgc cttgcaggtt acgcgcctcg   720
ccgcggccaa cgcaaaccaa accaaatccc ccgtcaccctt cgcttcgaaa ccccgcaaaa   780
ccccatggaa gaaacaccg aacacctgcc gcgcgcacgc ctcctcctcc ccgcctctc    840
ctcctctctc ccgttccatg tccgctcaac cttgcttcca ttctttccat ccacccgccg   900
atcgacgcga tgccgacgcc caaccccac ccaccgcctg ccagccgcca cccacctcgc   960
gcctctgcgg ctatggctat atcaccatgc ctccaacctc cggtacgctt agcctctctc  1020
tctctccccc tcccattctg cgcattgctc tctgcgcgcg gtcgcgtgct gctgctcgcg  1080
gcgcccggaa gcgtctcctt tggggggagag gagaggagag gagaggagag ggggggtgagc  1140
catggggcga tcgccgtgct gcgagaaggc gcacacgaac aagggcgcct ggaccaagga  1200
ggaggacgac cgcctcgttg cctacatccg ggcgcacggc gagggtgcc ggcgctccct   1260
ccccaaggcc gcgggcctgc tgcgctgcgg caagagctgc cgcctgcgct ggatcaacta  1320
cctccgcccg gacctcaagc gcggcaactt caccgccgac gaggacgacc tcatcgtcaa  1380
gctccacagc ctcctcggca caagtggtc gctcatcgcc gcgcgcctcc ccggccgcac  1440
cgacaacgag atcaagaact actggaacac gcacatcgaa cgcaagctcc tcagccgccg  1500
catcgacccc gtcacacacc gcccatcgc cgacgcagcg agaaacgtca ccatctcttt  1560
ccagcccgac gcgccgtcgc agcagcagct cagcgacgac gccgaggcgc cgcgccgcc   1620
gccgccgcag cagcagcagc agctcaagcc gccgcccagg tgccccgacc tcaatctcga  1680
cctctgcatc agcccgccct gccacaagga agaagaggac caggagctcg tcaagccgcc  1740
cgccgtcaag cgcgagatgc tgcaggccgc ccacggcact ctaggactct gcttcggctg  1800
cagcctgggc ctccagaagg gcgcgcgcgg gtgcacctgc agcagcaaca gccacttcct  1860
gggcgtcagg gtcggcatgc tcctcgactt cagaggcctc gagatgaagt gacacgtgtg  1920
aattacaggt gaccagctcg aatttccccg atagctttcg ttcgtatcat cggtttcgat  1980
aacgttcgtc aagttcaatg catcagttc attgcgcaca caccagaatc ctactgagtt  2040
cgagtattat ggcattggga aacatgtttt tcttgtacca tttgttgtgc ttgtaattta  2100
ctgtgttttt tattcggttt tcgctatcga actgtgaaat ggaatggat ggagaagagt   2160
taatgaatga tatggtccctt tgttcattc tcaaattaat attatttgtt ttttctctta  2220
tttgttgtgt gttgaattg aaaaaataag agatatgcaa acattttgtt ttgagtaaaa  2280
atgtgtcaaa tcgtggcctc taatgaccga agttaatatg aggagtaaaa cacttgtagt  2340
tgtaccatta tgcttattca ctaggcaaca aatatatttt cagacctaga aaagctgcaa  2400
atgttactga atacaagtat gtcctcttgt gttttagaca tttatgaact ttcctttatg  2460
taattttcca gaatccttgt cagattctaa tcattgcttt ataattatag ttatactcat  2520
ggatttgtag ttgagtatga aaatatttt taatgcattt tatgacttg              2569

SEQ ID NO: 77         moltype = DNA   length = 2428
FEATURE               Location/Qualifiers
misc_feature          1..2428
                      note = Construct No. 021
source                1..2428
                      mol_type = other DNA
                      organism = synthetic construct
SEQUENCE: 77
ttcaatgcag gatgacgcca agagggagaa accaagcaga ggtggacggt acaacgtgta    60
agtcaccgca aaacgttgca gcttggatag tggccatcga gtggtgtgcc gataccggcg   120
cctgttcttt acagcctcag ctagtgttgt tgtccgagcc aatttttccg acctattgtg   180
ttgctttcct ctctgatagc ttatggtaaa agatacaaag atgttgagga gtttgtacgc   240
cacttaattt tgctcgtaac atacattgac aatcaagagg agccatggca ttgcgatctg   300
cttacacggc atattcttac tggatggtgt acactactta cccttttaa tgcaagcatc   360
aatccattgc ttttctcact gcacacctga ttcgtactga aaacgtgaaa cataaaaaaa   420
aacaaaaatc tagctgatgt tggctctcgg ggcctcgagt ctagtttgtc ctagatggct   480
aacctgatat gtgttggtca cgctcacgtt gaaccgaga aagagtgtgt gtgtgtgtgt   540
gtcggcgtgc tgctacacca gagcctccct gaatcgcaat gcgtgttaac gccagcatcg   600
caggatttca tctcacttga caggttcaga tggccttata cctaccgtct gccatttata   660
cacgcagtga cttaacgctt acacgagccg gatggcccgg atctcccccc tgccaccatc   720
caccagaaaa acgtgaggc gtcaccgcaa cccacccacc aaacacatcc acgtcccttc   780
accgttggcc ttcgattttg cttcagctgc actacgaccc ctccaacaca tttccctcgc   840
gtctcgttgc gatctcacct tacgacgatc tcgttccagc agcagcagca tcgcagcgg   900
cggcttgctt ccgaagcgag caatgcatgg cgcgcgcggc gcgcgcgtg cgtgccttgg   960
cttgcgctct aatcaaaccg ggacgcccca actcacggtt atggggcgat cgccgtgctg  1020
cgagaaggcg cacacgaaca agggcgcctt gaccaaggag gaggacgacc gctcgttgc  1080
ctacatccgg gcgcacggcg aggggtgctg gcgctcctc ccaagggccg ggggcctgct  1140
gcgctgcggg aagagctgcc gctgcgctg atcaactac ctccgcccgg acctcaagcg  1200
cggcaacttc accgccgacg aggacgacct catcgtcaag ctccacagcc tcctcggcaa  1260
caagtggtcg ctcatcgccg cgcgcctccc cggccgcacc gacaacgaga tcaagaacta  1320
ctggaacacg cacatcaagc gcaagctcct cagccgcggc atcgacccgt cacacaccg  1380
ccccatcgcc gacgcagcca gaaacgtcac catctccttc cagcccgacg cgccgtcgca  1440
gcagcagctc agcgacgacg ccgaggcgcc gccgccgccg ccgccgcagc agcagcagca  1500
gctcaagccg ccgcccaggt gccccgacct caatctcgac ctctgcatca gcccgccctg  1560
```

```
ccacaaggaa gaagaggacc aggagctcgt caagcccgcc gccgtcaagc gcgagatgct  1620
gcaggccggc cacggcactc taggactctg cttcggctgc agcctgggcc tccagaaggg  1680
cgccgccggg tgcacctgca gcagcaacag ccacttcctg gggctcaggg tcggcatgct  1740
cctcgacttc agaggcctcg agatgaagtg acacgtgtga attacaggtg accagctcga  1800
atttcccga tagctttcgt tcgtatcatc ggtttcgaca acgttcgtca agttcaatgc  1860
atcagtttca ttgcgcacac accagaatcc tactgagttc gagtattatg gcattgggaa  1920
acatgttttt cttgtaccat tgttgtgct tgtaatttac tgtgtttttt attcggtttt   1980
cgctatcgaa ctgtgaaatg gaaatggatg gagaagagtt aatgaatgat atggtccttt   2040
tgttcattct caaattaata ttatttgttt tttctcttat tgttgtgtg ttgaatttga    2100
aaatataaga gatatgcaaa catttttgttt tgagtaaaaa tgtgtcaaat cgtggcctct   2160
aatgaccgaa gttaatatga ggagtaaaac acttgtagtt gtaccattat gcttattcac   2220
taggcaacaa atatattttc agacctagaa aagctgcaaa tgttactgaa tacaagtatg   2280
tcctcttgtg ttttagacat ttatgaactt cctttatgt aattttccag aatccttgtc    2340
agattctaat cattgcttta taattatagt tatactcatg gatttgtagt tgagtatgaa    2400
aatattttt aatgcatttt atgacttg                                       2428

SEQ ID NO: 78          moltype = DNA   length = 2275
FEATURE                Location/Qualifiers
misc_feature           1..2275
                       note = Construct No. 022
source                 1..2275
                       mol_type = other DNA
                       organism = synthetic construct
SEQUENCE: 78
aggcggggcc ggaggagggc accagagagg ctgctcagga gagagaaata atagaatatg   60
tggtatagag taaacatgag tgcggatgat tgtggtatga agtaaagaat tttgctgact   120
aggacagaat attcttttta gggtagaaat ttagagtact atgagtgcgg atagcctaag   180
gaccacttta aatttgacac aatattgaaa tttgaatggt tttaacattt gaaggctgaa   240
aaccaaaata ctttgtagct aagtgttgga aacccgactc ggccaataag tcgacagacc   300
gtaaaataag gtcaatctaa actttatgat aaatattctt gtttgatagc aatagcattg   360
caggaccagg acccaaggga agagaagatg ccaaatccca tcgaggctaa agcaaaaacg   420
atccaattta tgagcaaacc cacactgaag tttcaaaatt gttttctgaa aaaaagtaa    480
ccagcaagtt aaaaaatgag atggcgggaa agccaagtct cggttggtcg aggggttggt   540
tggggcgcag cctgacaagt gacaacggca gcaggatagt agcatcaggc gcaagccagc   600
gcaggcggca gcgcgaggat ttcgcttcac ttagcgcaa cggagacgct gcacccaacc    660
aacacgagct cccccctcac cgctgcgacg cgcgcgtccc acgagcggaa gcccccgcg    720
ccgacgcgag cgcgggggct cgaccgaccg acccaacgcc tccatctcca ccgcgcgcac   780
caaatcgcac tcccgtccgc cccgcgatc gaacagccac cgctcacctc tcccaccgc    840
caaaaacctc cggcctcctc tcatattcat atagctagcc cctgccacaa ggtagagcgt   900
cgctcacacc tgcgtcgccc tgcctcgcaa tcgcgaatct gtcgagcacc tgaggggtcg   960
gaggccgaga gctagcctag cacgccggcc tccgcgcgcg atggtacagc caagaagaa   1020
gtttcgtgga gtcaggcagc ggcactgggg ctcctgggtc tctgagatca gacaccccct  1080
ccttaaaagg agggtgtggc tgggcacctt tgagacggcc aggaggctg cgcgagccta   1140
cgatgaggct gctgtgctga tgagtggccg caacgccaag accaacttcc ccgtgcagag   1200
gaactccacc ggtgatctcg ccacggccga agaccaggac gcccgtagca atggcggtag   1260
caggaactcc tccgcgggca acctgtcaca gattctcagt gctaagctcc gcaagtgctg   1320
caaggcgcca tctccgtcct taacctgcct ccgcctcgac cccgagaagt cccacattgg   1380
cgtgtggcaa aagcgcgcag gggcccgtgc tgactccaac tgggtgatga cggtggagct  1440
caacaaagag gtagaaccaa ctgaacctgc agctcagccc acatcaacag caacagcttc   1500
gcaagtgaca atggatgatg aggaaaagat tgcgctgcaa atgatcgagg agttgctgag   1560
caggagcagt ccagcttcac cctcacatgg agagggagg ggtagctttg tcatctgaca  1620
cgtgtgaatt acaggtgacc agctcgaatt tccccgatag ctttcgttcg tatcatcggt   1680
tcgacaacg ttcgtcaagt tcaatgcatc agtttcattg cgcacacacc agaatcctac    1740
tgagttcgag tattatggca ttgggaaaca tgttttcctt gtaccattg ttgtgcttgt    1800
aatttactgt gttttttatt cggttttcgc tatcgaactg tgaaatggaa atggatggag   1860
aagagttaat gaatgatatg gtccttttgt tcattctcaa attaatatta tttgtttttt   1920
ctcttatttg ttgtgtgttg aatttgaaaa tataagagat atgcaaacat tttgttttga   1980
gtaaaaatgt gtcaaatcgt ggcctctaat gaccgaagtt aatatgagga gtaaaacact   2040
tgtagttgta ccattatgct tattcactag gcaacaaata tatttcaga cctagaaaag    2100
ctgcaaatgt tactgaatac aagtatgtcc tcttgtgttt tagacattta tgaactttcc   2160
tttatgtaat tttccagaat ccttgtcaga ttctaatcat tgctttataa ttatagttat   2220
actcatggat ttgtagttga gtatgaaaat attttaat gcattttatg acttg          2275

SEQ ID NO: 79          moltype = DNA   length = 2275
FEATURE                Location/Qualifiers
misc_feature           1..2275
                       note = Construct No. 023
source                 1..2275
                       mol_type = other DNA
                       organism = synthetic construct
SEQUENCE: 79
atactgaaca ttatgttgca taacatgtag ataaggacac gaaaacatag aaagtttctc   60
agttatattt acccatcaac atgaaataaa aaacaacaaa gatgtcatag tgatgtttgt  120
ttcaacttac caagggtgac catgtcgtat ttataataat attatatatt tatatcgtca   180
atagaatatt agtgttacgg tgatatttta gcacaccgat ttttttatc atactgatgt    240
ttatcgtttt gtatctatat tttatatttg ttttataata atattagata tttatttcgt   300
caatagaata ttaatgttat gatgatactt tactatattg attttacata tgatagtgat   360
gttactcctt ccgtatctat attttatatt agttttatc tcctgcaac acggtcacaa    420
cagaagagaa gtttttcaga ccgattccag gatcgatttt tttttttatat ctgggctaag  480
```

-continued

```
acatcaggta gagattgttt aacctttgcg gctttccgca ctgacggacc caccccacc    540
gcatcaacgg aacctaccaa ccaccccgt gctccgaccc cccatctgcc cgtcttccag    600
gttacgcccc gcgcggccgc gcgcgcggaa gctgtatcac cccacccgtc gacgtcgtct   660
tcgcttcgaa accccgcaaa accccgcgga aaaacccac ctgctgcacg cacgcacccc    720
ctccctctcc ctccccatgg cgcctcccct cacccaactc tttgcttcca ttcttttccat  780
ccacccgcca atgcgacgcc gacgccgcaa ctcccccac cgcctgccag cgccacctca    840
ccgcaccgct tccatcaccc cgcgatcatg ggctaccgct atatcaccac gcctccaacc   900
tccggcacgc ttagcctctc tctcccattc tctcacaccc aacacccagc tatcacaccc   960
tgatccccga ggccgcgcgt cggggtgagg aggaggggcc atggtacagc caaagaagaa  1020
gtttcgtgga gtcaggcagc ggcactgggg ctcctgggtc tctgagatca gacacccct   1080
ccttaaaagg agggtgtggc tgggcacctt tgagacggcc gaggaggctg cgcgagccta  1140
cgatgaggct gctgtgctga tgagtggccg caacgccaag accaacttcc ccgtgcagag  1200
gaactccacc ggtgatctcg ccacggccgc agaccaggac gcccgtagca atggcggtag  1260
caggaactcc tccgcgggca acctgtcaca gattctcagt gctaagctcc gcaagtgctg  1320
caaggcgcca tctccgtcct taacctgcct ccgcctcgac cccgagaagt cccacattgg  1380
cgtgtggcaa aagcgcgcag gggccgtgc tgactccaac tgggtgatga cggtggagct   1440
caacaaagag gtagaaccaa ctgaacctgc agctcagccc acatcaacag caacagcttc  1500
gcaagtgaca atggatgatg aggaaaagat tgcgctgcaa atgatcgagg agttgctgag  1560
caggagcagt ccagcttcac cctcacatgg agagggagag ggtagctttg tcatctgaca  1620
cgtgtgaatt acaggtgacc agctcgaatt tccccgatag ctttcgttcg tatcatcggt  1680
ttcgacaacg ttcgtcaagt tcaatgcatc agtttcattg cgcacacacc agaatcctac  1740
tgagttcgag tattatggca ttgggaaaca tgttttttctt gtaccatttg ttgtgcttgt  1800
aatttactgt gttttttatt cggttttcgc tatcgaactg tgaaatggaa atggatggag  1860
aagagttaat gaatgatatg gtccttttgt tcattctcaa attaatatta tttgtttttt  1920
ctcttatttg ttgtgtgttg aatttgaaaa tataagagat atgcaaacat tttgttttga  1980
gtaaaaatgt gtcaaatcgt ggcctctaat gaccgaagtt aatatgagga gtaaaacact  2040
tgtagttgta ccattatgct tattcactag gcaacaaata tattttcaga cctagaaaag  2100
ctgcaaatgt tactgaatac aagtatgtcc tcttgtgttt tagacattta tgaacttttcc 2160
tttatgtaat tttccagaat ccttgtcaga ttctaatcat tgcttataa ttatagttat    2220
actcatggat ttgtagttga gtatgaaaat attttttaat gcattttatg acttg        2275
```

```
SEQ ID NO: 80          moltype = DNA   length = 2416
FEATURE                Location/Qualifiers
misc_feature           1..2416
                       note = Construct No. 024
source                 1..2416
                       mol_type = other DNA
                       organism = synthetic construct
SEQUENCE: 80
gagtaaaatt gatatggttt tgtctgtcaa ggtgccgttt ctatggttgg aggaggaaaa    60
tgaaattagg ggaatagaac agtcgcaatc caaaagctat tgttctctct tctacgtag   120
ttgatagttc gatacgtgtg tttgatgtga gagactgaga ggagtgcacg gtgcacctgc   180
cccgtaagga cgcggaacta cattatcaga ggctaggccg gtactgttat acgcgacgtt   240
cacgaatcac gatgcgtaaa aaagtgaagc atgaaacagt actaggctct ccacgggcca   300
catcatgaaa aaactggtgc gacgccacgc ttaacaattt gtcggtcgta aactcgtaaa   360
gttaaaagcc ccacgacatt gtcaaccaat atctcagcac atgaacttct ctaacgagta   420
caacgaaacc gcatccgcaa aagcgccgtg aaccaaagct cttgccgtgc tgtgccgtgc   480
cggtggccgt gaacatgtgg aacacgaaga actcttgcgc gagatcggag cacctgacct   540
cccacctcgc gtccggcccg tcgccgtcgc agcaagcggg ctgtcaaaaa cgacgccaca   600
gcgcgagcgc tctcgccgat ccggcggacc caccctcctc acctgcgca ccaaccgccc    660
gttcgctagt ccgatccccc acccctcatc ccccctacgc cttgcaggtt acgcgcctcg   720
ccgcggccaa cgcaaaccaa accaaatccc ccgtcaacctt cgcttcgaaa cccccgcaaa  780
ccccatggaa gaaaacaccg aacacctgcc gcgcgcacgc ctcctcctcc ccgcctctc   840
ctcctctctc ccgttccatg tccgtcaac cttgcttcca ttctttccat ccacccgccg    900
atcgacgcga tgccgacgcc caaccccac ccaccgcctg ccagcgccac cccacctcgc    960
gcctctgcgg ctatggctat atcaccatgc tccaacctc cggtacgctt agcctctctc   1020
tctctccccc tccattctg cgcattgctc tctgcgcgcg gtcgcgtgct gctgctcgcg   1080
gcgcccggga gcgtccctt tggggggagag gagaggagag gagaggagag ggggtgagc  1140
catggtacag ccaaagaaga agtttcgtgg agtcaggcag cggcactggg gctcctgggt  1200
ctctgagatc agacaccccc tccttaaaag gagggtgtgg ctgggcacct ttgagacggc   1260
cgaggaggct gcgcgagcct acgatgaggc tgctgtgctg atgagtggcc gcaacgccaa   1320
gaccaacttc cccgtgcaga ggaactccac cggtgatctc gccacggccg cagaccagga   1380
cgcccgtagc aatggcggta gcaggaactc ctccgcgggc aacctgtcac agattctcag   1440
tgctaagctc cgcaagtgct gcaaggcgcc atctccgtcc ttaacctgcc tccgcctcga   1500
ccccgagaag tcccacattg gcgtgtggca aaagcgcgca ggggcccgtg ctgactccaa   1560
ctgggtgatg acgtggagc tcaacaaaga ggtagaacca actgaacctg cagctcagcc   1620
cacatcaaca gcagcagctt cgcaagtgac aatggatgat gaggaaaaga ttgcgctgca   1680
aatgatcgag gagttgctga gcaggagcag tccagcttca cctcacatg agagggaga    1740
gggtagcttt gtcatctgac acgtgtgaat tacaggtgac cagctcgaat tccccgata    1800
gctttcgttc gtatcatcgg tttcgacaac gttcgtcaag ttcaatgcat cagtttcatt   1860
gcgcacacac cagaatccta ctgagttcga gtattatggc attgggaaac atgttttct    1920
tgtaccattt gttgtgcttg taatttactg tgtttttat tcggttttcg ctatcgaact    1980
gtgaaatgga aatgatggga gaagagttaa tgaatgatat ggtccttttg ttcattctca   2040
aattaatatt atttgttttt tctcttattt gttgtgtgtt gaatttgaaa atataagaga   2100
tatgcaaaca ttttgttttg agtaaaaatg tgtcaaatcg tggcctctaa tgaccgaagt   2160
taatatgagg agtaaaacac ttgtagttgt accattatgc ttattcacta ggcaacaaat   2220
atattttcag acctagaaaa gctgcaaatg ttactgaata caagtatgtc tcttgtgtt   2280
ttagacattt atgaactttc ctttatgtaa ttttccagaa tccttgtcag attctaatca   2340
```

```
                                                        -continued
ttgctttata attatagtta tactcatgga tttgtagttg agtatgaaaa tattttttaa  2400
tgcattttat gacttg                                                  2416

SEQ ID NO: 81           moltype = DNA  length = 2275
FEATURE                 Location/Qualifiers
misc_feature            1..2275
                        note = Construct No. 025
source                  1..2275
                        mol_type = other DNA
                        organism = synthetic construct
SEQUENCE: 81
ttcaatgcag gatgacgcca agagggagaa accaagcaga ggtggacggt acaacgtgta   60
agtcaccgca aaacgttgca gcttggatag tggccatcga gtggtgtgcc gataccggcg  120
cctgttcttt acagcctcag ctagtgttgt tgtccgaggc aattttccg acctattgtg   180
ttgctttcct ctctgatagc ttatggtaaa agatacaaag atgttgagga gtttgtacgc  240
cacttaattt tgctcgtaac atacattgac aatcaagagg agccatggca ttgcgatctg  300
cttacacggc atattcttac tggatggtgt acactactta ccctttttaa tgcaagcatc  360
aatccattgc ttttctcact gcacacctga ttcgtactga aaacgtgaaa cataaaaaaa  420
aacaaaaatc tagctgatgt tggctctcgg ggcctcgagt ctagtttgtc ctagatggct  480
aacctgatat gtgttggtca cgctcacgtt tgaaccgaga aagagtgtgt gtgtgtgtgt  540
gtcggcgtgc tgctacacca gagcctccct gaatcgcaat gcgtgttaac gccagcatcg  600
caggatttca tctcacttga caggttcaga tggcttcct cctaccgtct gccatttata   660
cacgcagtga cttaacgctt acacgagccg gatggcccgg atctcccccc tgcaccatct  720
caccagaaaa acggtgaggc gtcaccgcaa cccacccacc aaacacatcc acgtcccttc  780
accgttggcc ttcgattttg cttcagctgc actacgaccc ctccaacaca tttccctcgc  840
gtctcgttgc gatctcacct tacgacgatc tcgttccagc agcagcagca tcggcagcgg  900
cggcttgctt ccgaagcgag caatgcatgg cgcgcgcggc cgcgtgcgtg cgtgccttgg  960
cttgcgctct aatcaaaccg ggacgcccca actcacggtt atggtacagc caaagaagaa 1020
gtttcgtgga gtcaggcagc ggcactgggg ctcctgggtc tctgagatca gacaccccct 1080
ccttaaaagg agggtgtggc tgggcacctt tgagacggcc gaggaggctg cgcgagccta 1140
cgatgaggct gctgtgctga tgagtggccg caacgccaag accaacttcc ccgtgcagag 1200
gaactccacc ggtgatctcg ccacggccgc agaccaggac gcccgtagca atggcggtag 1260
caggaactcc tccgcgggca acctgtcaca gattctcagt gctaagctcc gcaagtgctg 1320
caaggcgcca tctccgtcct taacctgcct ccgcctcgac cccgagaagt cccacattgg 1380
cgtgtggcaa aagcgcgcag gggcccgtgc tgactccaac tgggtgatga cggtgggagct 1440
caacaaagag gtagaaccaa ctgaacctgc agctcagccc acatcaacag caacagcttc 1500
gcaagtgaca atggatgatg aggaaaagat tgcgctgcaa atgatcgagg agttgctgag 1560
caggagcagt ccagcttcac cctcacatgg agagggagag ggtagctttg tcatctgaca 1620
cgtgtgaatt acaggtgacc agctcgaatt tccccgatag ctttcgttcg tatcatcggt 1680
ttcgacaacg ttcgtcaagt tcaatgcatc agtttcattg cgcacacacc agaatcctac 1740
tgagttcgag tattatggca ttgggaaaca tgttttttctt gtaccatttg ttgtgcttgt 1800
aatttactgt gtttttttatt cggttttcgc tatcgaactg tgaaatggaa atggatggag 1860
aagagttaat gaatgatatg gtccttttgt tcattctcaa attaatatta tttgttttttt 1920
ctcttatttg ttgtgtgttg aatttgaaaa tataagagat atgcaaacat tttgtttttga 1980
gtaaaaatgt gtcaaatcgt ggcctctaat gaccgaagtt aatatgagga gtaaaacact 2040
tgtagttgta ccattatgct tattcactag gcaacaaata tattttcaga cctagaaaag 2100
ctgcaaatgt tactgaatac aagtatgtcc tcttgtgttt tagacattta tgaactttcc 2160
tttatgtaat tttccagaat ccttgtcaga ttctaatcat tgctttataa ttatagttat 2220
actcatggat ttgtagttga gtatgaaaat atttttttaat gcattttatg acttg      2275
```